United States Patent
Guegler et al.

(12)

(10) Patent No.: US 6,620,607 B1
(45) Date of Patent: Sep. 16, 2003

(54) ISOLATED HUMAN PROTEASE PROTEINS, NUCLEIC ACID MOLECULES ENCODING HUMAN PROTEASE PROTEINS, AND USES THEREOF

(75) Inventors: Karl Guegler, Menlo Park, CA (US); Marion Webster, San Francisco, CA (US); Chunhua Yan, Boyds, MD (US); Wei Shao, Frederick, MD (US); Karen A. Ketchum, Germantown, MD (US); Valentina Di Francesco, Rockville, MD (US); Ellen M. Beasley, Darnestown, MD (US)

(73) Assignee: Applera Corporation, Norwalk, CT (US)

( * ) Notice: Subject to any disclaimer, the term of this patent is extended or adjusted under 35 U.S.C. 154(b) by 0 days.

(21) Appl. No.: 10/160,187

(22) Filed: Jun. 4, 2002

Related U.S. Application Data

(62) Division of application No. 09/741,150, filed on Dec. 21, 2000, now Pat. No. 6,436,689.
(60) Provisional application No. 60/252,410, filed on Nov. 22, 2000.

(51) Int. Cl.⁷ ............................. C12N 9/50; C12Q 1/37; C07K 17/00; C12P 21/06; C07H 21/04
(52) U.S. Cl. ..................... 435/226; 435/23; 435/69.1; 435/219; 536/23.2; 530/350; 424/94.63
(58) Field of Search .................. 435/23, 69.1, 219, 435/226; 536/23.2; 530/350; 424/94.63

*Primary Examiner*—Rebecca E. Prouty
*Assistant Examiner*—Delia Ramirez
(74) *Attorney, Agent, or Firm*—Celera Genomics; Lin Sun-Hoffman

(57) ABSTRACT

The present invention provides amino acid sequences of peptides that are encoded by genes within the human genome, the protease peptides of the present invention. The present invention specifically provides isolated peptide and nucleic acid molecules, methods of identifying orthologs and paralogs of the protease peptides, and methods of identifying modulators of the protease peptides.

4 Claims, 42 Drawing Sheets

```
   1 GTGCGAAAGG CTGCCAGCAT GTCATCAGTG AGCCCCATCC AGATCCCCAG
  51 TGGCCTCCCG CTGCTGCTCA CCCACGAGGG CGTCCTGCTG CCCGGCTCCA
 101 CCATGCGCAC CAGCGTGGAC TGGCCCACA ACCTGCAGCT GGTGCGGAGC
 151 CGCCTTCTGA AGGGCACGTC GCTGCAAAGC ACCATCCTGG GCGTCATCCC
 201 CAACACGCCT GACCCCGCCA GCGACGCGCA GGACTGCCCG CCGCTGCACA
 251 GGATTGCCAC AGCTGCACTG GCCGTTCAGG TTGTGGGCAG TAACTGGCCC
 301 AAGCCCCACT ACACTCTGTT GATTACAGGC CTATGCCGTT TCCAGATTGT
 351 ACAGGTCTTA AAAGAGAAGC CATATCCCAT TGCTGAAGTG GAGCAGTTGG
 401 ACCGACTTGA GGAGTTTCCC AACACCTGTA AAATGAGGGA GGAGCTAGGA
 451 GAACTATCAG AGCAGTTTTA CAAATATGCA GTACAATTGG TTGAAATGTT
 501 GGATATGTCT GTCCCTGCAG TTGCTAAATT GAGACGTCTT TTAGATAGTC
 551 TTCCAAGGGA AGCTTTACCA GACATCTTGA CATCAATTAT CCGAACAAGC
 601 AACAAAGAGA AACTCCAGAT TTTAGATGCT GTGAGCCTAG AGGAGCGGTT
 651 CAAGATGACT ATACCACTGC TTGTCAGACA AATTGAAGGC CTGAAATTGC
 701 TTCAAAAAAC CAGAAAACCC AAGCAAGATG ATGATAAGAG GGTTATAGCA
 751 ATACGCCCTA TTAGGAGAAT TACACATATC TCAGGTACTT TAGAAGATGA
 801 AGATGAAGAT GAAGATAATG ATGACATTGT CATGCTAGAG AAAAAAATAC
 851 GAACATCTAG TATGCCAGAG CAGGCCCATA AAGTCTGTGT CAAAGAGATA
 901 AAGAGACTCA AAAAAATGCC TCAGTCAATG CCAGAATATG CTCTGACTAG
 951 AAATTATTTG GAACTTATGG TAGAACTTCC TGGAACAAA AGTACAACTG
1001 ACCGCCTGGA CATTAGGGCA GCCCGGATTC TTCTGGATAA TGACCATTAC
1051 GCCATGGAAA AATTGAAGAA AAGAGTACTG GAATACTGG CTGTCAGACA
1101 GCTCAAAAAT AACCTGAAGG GCCCAATCCT ATGCTTTGTT GGCCCTCCTG
1151 GAGTTGGTAA AACAAGTGTG GGAAGATCAG TGGCCAAGAC TCTAGGTCGA
1201 GAGTTCCACA GGATTGCACT TGGAGGAGTA TGTGATCAGT CTGACATTCG
1251 AGGACACAGG CGCACCTATG TTGGCAGCAT GCCTGGTCGC ATCATCAACG
1301 GCTTGAAGAC TGTGGGAGTG AACAACCCAG TGTTCCTATT AGATGAGGTT
1351 GACAAACTGG AAAAAGTCT ACAGGGTGAT CCAGCAGCAG CTCTGCTTGA
1401 GGTGTGGGAT CCTGAACAAA ACCATAACTT CACAGATCAT TATCTAAATG
1451 TGGCCTTTGA CCTTTCTCAA GTTCTTTTTA TAGCTACTGC CAACACCACT
1501 GCTACCATTC CAGCTGCCT GTTGGACAGA ATGGAGATCA TTCAGGTTCC
1551 AGGTTATACA CAGGAGGAGA AGATAGAGAT TGCCCATAGG CACTTGATTC
1601 CCAAGCAGCT GGAACAACAT GGGCTGACTC CACAGCAGAT TCAGATACCC
1651 CAGGTCACCA CTCTTGACAT CATCACCAGG TATACCAGAG AGGCAGGGGT
1701 TCGTTCTCTG GATAGAAAAC TTGGGCCAT TGCCGAGCT GTGGCCGTGA
1751 AGGTGGCAGA AGGACAGCAT AAGGAAGCCA AGTTGGACGG TTCTGATGTG
1801 ACTGAGAGAG AAGGTTGCAG AGAACACATC TTAGAAGATG AAAAACCTGA
1851 ATCTATCAGT GACACTACTG ACTTGGCTCT ACCACCTGAA ATGCCGATTT
1901 TGATTGATTT CCATGCTCTG AAAGACATCC TTGGGCCCC GATGTATGAA
1951 ATGGAGGTAT CTCAGCGTTT GAGTCAGCCA GGAGTAGCAA TAGGTTTGGC
2001 TTGGACTCCC TTAGGTGGAG AAATCATGTT CGTGGAGGCG AGTCGAATGG
2051 ATGGCGAGGG CCAGTTAACT CTGACCGGCC AGCTGGGGA CGTGATGAAG
2101 GAGTCCGCC ACCTGCTAT CAGCTGGCTC CGCAGCAACG CAAAGAAGTA
2151 CCAGCTGACC AATGCTTTTG GAAGTTTTGA TCTTCTTGAC AACACAGACA
2201 TCCATCTGCA CTTCCCAGCT GGAGCTGTCA CAAAAGATGG ACCATCTGCT
2251 GGAGTTACCA TAGTAACCTG TCTCGCCTCA CTTTTAGTG GCGGCTGGT
2301 ACGTTCAGAT GTAGCCATGA CTGGAGAAAT TACACTGAGA GGTCTTGTTC
2351 TTCCAGTGGG TGGAATTAAA GACAAAGTGC TGGCGGCACA CAGAGCGGGA
2401 CTGAAGCAAG TCATTATTCC TGGAGAAAAT GAAAAGACC TTGAGGGAAT
2451 CCCAGGCAAC GTACGACAGG ATTTAAGTTT TGTCACAGCA AGCTGCCTGG
2501 ATGAGGTTCT TAATGCAGCT TTTGATGGTG GCTTTACTGT CAAGACCAGA
2551 CCTGGTCTGT TAAATAGCAA ACTGTAGGTC CAAATCTCAA TTTT (SEQ ID NO:1)
```

FIGURE 1A

FEATURES:
5'UTR:        1 - 18
Start Codon:  19
Stop Codon:   2575
3'UTR:        2578

Homologous proteins:
Top 10 BLAST Hits

|  | Score | E |
|---|---|---|
| gi\|3914005\|sp\|P93647\|LON1_MAIZE MITOCHONDRIAL LON PROTEASE HOMO... | 713 | 0.0 |
| gi\|3914002\|sp\|O64948\|LON1_ARATH MITOCHONDRIAL LON PROTEASE HOMO... | 706 | 0.0 |
| gi\|3913996\|sp\|O04979\|LON1_SPIOL MITOCHONDRIAL LON PROTEASE HOMO... | 689 | 0.0 |
| gi\|547861\|sp\|P36774\|LON2_MYXXA ATP-DEPENDENT PROTEASE LA 2 >gi\|... | 665 | 0.0 |
| gi\|625653\|pir\|\|A36894 ATP-dependent proteinase BsgA - Myxococcu... | 661 | 0.0 |
| gi\|10175672\|dbj\|BAB06769.1\| (AP001517) ATP-dependent proteinase... | 581 | e-165 |
| gi\|547865\|sp\|P36772\|LON_BACBR ATP-DEPENDENT PROTEASE LA >gi\|980... | 573 | e-162 |
| gi\|585415\|sp\|P37945\|LON1_BACSU ATP-DEPENDENT PROTEASE LA 1 >gi\|... | 570 | e-161 |
| gi\|547860\|sp\|P36773\|LON1_MYXXA ATP-DEPENDENT PROTEASE LA 1 >gi\|... | 557 | e-157 |
| gi\|7471170\|pir\|\|B75530 ATP-dependent proteinase LA - Deinococcu... | 550 | e-155 |

EST:

|  | Score | E |
|---|---|---|
| gi\|9129501 /dataset=dbest /taxon=9606... | 1191 | 0.0 |
| gi\|9150157 /dataset=dbest /taxon=9606... | 1154 | 0.0 |
| gi\|9333228 /dataset=dbest /taxon=960... | 1074 | 0.0 |
| gi\|10365587 /dataset=dbest /taxon=960... | 1035 | 0.0 |
| gi\|9122839 /dataset=dbest /taxon=9606... | 997 | 0.0 |
| gi\|9336891 /dataset=dbest /taxon=960... | 969 | 0.0 |
| gi\|2669286 /dataset=dbest /taxon=9606 ... | 890 | 0.0 |
| gi\|3836333 /dataset=dbest /taxon=9606 ... | 767 | 0.0 |

EXPRESSION INFORMATION FOR MODULATORY USE:
library source:
gi\|9129501   Eye, retinoblastoma
gi\|9150157   Skin, melanotic melanoma
gi\|9333228   Uterus, endometrium adenocarcinoma
gi\|10365587  Ovary adenocarcinoma
gi\|2669286   Schizophrenic brain
gi\|3836333   Kidney Tissue Expression:
Human Heart

FIGURE 1B

```
  1 MSSVSPIQIP SRLPLLLTHE GVLLPGSTMR TSVDSAHNLQ LVRSRLLKGT
 51 SLQSTILGVI PNTPDPASDA QDLPPLHRIG TAALAVQVVG SNWPKPHYTL
101 LITGLCRFQI VQVLKEKPYP IAEVEQLDRL EEFPNTCKMR EELGELSEQF
151 YKYAVQLVEM LDMSVPAVAK LRRLLDSLPR EALPDILTSI IRTSNKEKLQ
201 ILDAVSLEER FKMTIPLLVR QIEGLKLLQK TRKPKQDDK RVIAIRPIRR
251 ITHISGTLED EDEDEINDDI VMLEKKIRTS SMPEQAHKVC VKEIKRLKKM
301 PQSMPEYALT RNYLEIMVEL PWNKSTTDRL DIRAARILLD NDHYAMEKLK
351 KRVLEYLAVR QLKNNLKGPI LCFVGPPGVG KTSVGRSVAK TLGREFHRIA
401 LGGVCDQSDI RGHRRTYVGS MPGRIINGLK TVGVNNPVFL LDEVDKLGKS
451 LQGDPAAALL EVLDPEQNHN FIDHYLNVAP DLSQVLFIAT ANTTATIPAA
501 LLDRMEIIQV PGYTQEEKIE IAHRHLIPKQ LEQHGLITPQQ IQIPQVTTLD
551 IITRYTREAG VRSLDRKLGA ICRAVAVKVA EGQHKEAKLD RSDVTEREGC
601 REHILEDEKP ESISDTIDLA LPPEMPILID FHALKDILGP PMYEMEVSQR
651 LSQPGVAIGL AWTPLGGEIM FVEASRMDGE GQLTLTGQLG DVMKESAHLA
701 ISWLRSNAKK YQLINAFGSF DLLDNIDIHL HFPAGAVTKD GPSAGVTIVT
751 CLASLFSGRL VRSDVAMIGE ITLRGLVLPV GGIKDKVLAA HRAGLKQVII
801 PRRNEKDLEG IPGNVRQDLS FVTASCLDEV LNAAFDGGFT VKIRPGLLNS
851 KL (SEQ ID NO:2)
```

FEATURES:
Functional domains and key regions:
[1] PDOC00001 PS00001 ASN_GLYCOSYLATION
N-glycosylation site Number of matches: 3
    1    323-326 NKST
    2    470-473 NFID
    3    492-495 NTTA

[2] PDOC00004 PS00004 CAMP_PHOSPHO_SITE
cAMP- and cGMP-dependent protein kinase phosphorylation site 249-252 RRIT

[3] PDOC00005 PS00005 PKC_PHOSPHO_SITE
Protein kinase C phosphorylation site

Number of matches: 11
    1     28-30  TMR
    2     35-37  SAR
    3    136-138 TCK
    4    194-196 SNK
    5    231-233 TRK
    6    327-329 TDR
    7    595-597 TER
    8    648-650 SQR
    9    757-759 SGR
   10    772-774 TLR
   11    840-842 TVK

FIGURE 2A

[4] PDOC00006 PS00006 CK2_PHOSPHO_SITE
Casein kinase II phosphorylation site

Number of matches: 13
```
    1      31-34   TSVD
    2     194-197  SNKE
    3     206-209  SLEE
    4     257-260  TLED
    5     281-284  SMPE
    6     303-306  SMPE
    7     281-284  SMPE
    8     303-306  SMPE
    9     325-328  STTD
   10     514-517  TQEE
   11     547-550  TTLD
   12     595-598  TERE
   13     612-615  SISD
```

[5] PDOC00007 PS00007 TYR_PHOSPHO_SITE
Tyrosine kinase phosphorylation site

```
        336-344  RILLDNDHY
```

[6] PDOC00008 PS00008 MYRISTYL
N-myristoylation site

Number of matches: 6
```
    1      58-63   GVIPNT
    2     378-383  GVGKTS
    3     419-424  GSMPGR
    4     655-660  GVAIGL
    5     810-815  GIPGNV
    6     846-851  GLLNSK
```

[7] PDOC00299 PS00342 MICROBODIES_CTER
Microbodies C-terminal targeting signal

```
        850-852  SKL
```

[8] PDOC00017 PS00017 ATP_GTP_A
ATP/GTP-binding site motif A (P-loop)

```
        375-382  GPPGVGKT
```

[9] PDOC00803 PS01046 LON_SER
ATP-dependent serine proteases, lon family, serine active site

```
        740-748  DGPSAGVTI
```

<u>Membrane spanning structure and domains:</u>
Candidate membrane-spanning segments:
```
   Helix Begin   End   Score  Certainity
     1    371    391   0.652  Putative
     2    488    508   1.280  Certain
     3    658    678   1.117  Certain
     4    747    767   1.430  Certain
```

BLAST Alignment to Top Hit:
>gi|3914005|sp|P93647|LON1_MAIZE MITOCHONDRIAL LON PROTEASE HOMOLOG
    1 PRECURSOR >gi|7428224|pir||T04321 endopeptidase La
    homolog (EC 3.4.21.-) LON1 precursor, mitochondrial -
    maize >gi|1816586|gb|AAC50011.1| (U85494) LON1 protease
    [Zea mays]

FIGURE 2B

```
         Length = 885

Score = 713 bits (1821), Expect = 0.0
Identities = 401/897 (44%), Positives = 562/897 (61%), Gaps = 65/897 (7%)

Query:   3 SVSPIQIPSRLPLLLTHEGVLLPGSIMRTSVDSARNLQLVRSRLLKGTSLQSTILGVIPN  62
           S SP+++PSRL +L    VLLPG+ +R  + +++LV L +    + ++GV+P
Sbjct:   2 SDSPVELPSRLAVLPFRNKVLLPGAIVRIRCINPSSVKLVEQELWQKE--EKGLIGVLPV  59

Query:  63 -----------TPDPASDA---------------QDLP----PLH--RIGTAAIAVQV   88
              +P    SD+             QD       P+H    G AA A+ +
Sbjct:  60 RDSEATAVGSLLSPGVGSDSGEGGSKVGGSAVESSKQDTKNGKEPIHWHSKGVAARALHL 119

Query:  89 V-GSNWPKPH--YTLLITGLCRFQIVQVLKEKPYPIAEVEQLDRLEEFPNTCKMREELGE 145
             G   P      Y +++ GLCRF + ++   PY +A V +LD +       + +L
Sbjct: 120 SRGVEKPSGRVTYIVVLEGLCRFSVQELSARGPYHVARVSRLDMTKTELEQAEQDPLLIA 179

Query: 146 LSEQFYKYAVQLVEMLDMSVPAVAKLRRLLDSLPREALPDILTSIIRTSNKEKLQILDAV 205
           LS QF  A++L+ +L+    V + +LLD++P L DI +  S +E+L +LD+V
Sbjct: 180 LSRQFKATAMELISVLEQKQKIVGRTKVLLDTVPVYRLADIFVASFEISFEEQLSMLDSV 239

Query: 206 SLEERFKMTIPLLVRQIEGL----KLLQKIRKPKQDDDKRVIAIRPIRRITHISGTLEDE 261
            L+ R      L+ R ++ +    K+ QK       K + ++R I      G
Sbjct: 240 HLKVRLSKATELVDRHLQSILVAEKTTQKVEGQLSKSQKEFLLRQQMRAIKEELG----- 294

Query: 262 DEDEDNDDIVMLEKKIRTSSMPEQAHKVCVKEIKRLKKMPQSMPEYALTRNYLELMVELP 321
           D D+D DD+ LE+K++ + MP    K +E++RL+KM   P Y+ +R YLEL+ +LP
Sbjct: 295 DNDDDEDDVAALERKMQNAGMPANIWKHAQREMRRLRKMPQQPGYSSSRAYLELLADLP 354

Query: 322 WNKSTIDR-LDIRAARILLDNDHYAMEKLKKRVLEYLAVRQLKNNLKGPILCFVGPPGVG 380
           W K  +R LD+R A+  LD DHY + K+K+R++EYLAVR+1K +  GP+LCFVGPPGVG
Sbjct: 355 WQKVSEEREIDLRVAKESLDQDHYGLTKVKQRIIEYLAVRKLKPDARGPVLCFVGPPGVG 414

Query: 381 KTSVGRSVAKTLGREFHRIALGGVCDQSDIRGHRRTYVGSMPGRIINGLKIVGVNNPVFL 440
           KTS+  S+AK L R+F RI+LGGV D++DIRGHRRTY+GSMPGR+I+GLK V V+NPV L
Sbjct: 415 KTSLASSIAKALNRKFIRISLGGVKDEADIRGHRRTYIGSMPGRLIDGLKRVSVSNPVML 474

Query: 441 LDEVDKLGKSLQGDPAAALLEVLDPEQNHNFTDHYLNVAFDLSQVLFIATANTTATIPAA 500
           +DE+DK G   ++GDPA+ALLEVLDPEQN  F DHYLNV FDLS+V+F+ATAN   IP
Sbjct: 475 LDEIDKIGSDVRGDPASALLEVLDPEQNKAFNDHYLNVPFDLSKVIFVATANRMQPIPPP 534

Query: 501 LLDRMEIIQVPGYTQEEKIEIAHRHLIPKQLEQHGLTPQQIQIPQVTTLDIITRYTREAG 560
           LLDRMEII++PGYT EEK++IA +HLIP+ LEQHGL+  +QIP+   +I RYTREAG
Sbjct: 535 LLDRMEIIELPGYTPEEKLKIAMKHLIPRVLEQHGLSTINLQIPEAMVKLVIERYTREAG 594

Query: 561 VRSLDRKLGAICRAVAVKVAEGQHKEAKLDRS---------DVTEREGCREHILEDEKPE 611
           VR+L+R L A+ RA AVKVAE Q K +L +         D  +G +
Sbjct: 595 VRNLERNLAALARAAAVKVAE-QVKILRLGKEIQPITTTLLDSRLADGGEVEMEVIPMEH 653

Query: 612 SISDTIDLALPPEMPILIDFHALKDILGPPMY-EMEVSQRLSQPGVAIGLAWTPLGGEIM 670
            IS+T +    P++ D L+ +LGPP + +  E + R++ PGV++GL WT +GGE+
Sbjct: 654 DISNTYE----NPSPMIVDEAMLEKVLGPPRFDDREAADRVASPGVSVGLMWTSVGGEVQ 709

Query: 671 FVEASRMDGEGQLTLTGQLGDVMKESAHLAISWLRSNAKKYQLINAFGSFDLLDNIDIHL 730
           FVEA+ M G+G L L+GQLGDV+KESA LA++W+R+  A    L+    +LL++ DIH+
Sbjct: 710 FVEATAMVGKGDLHLTGQLGDVIKESAQLALTWVRARAADLNLSPT-SDINLLESRDIHI 768

Query: 731 HFPAGAVTKDGPSAGVTIVTCLASLFSGRLVRSDVAMTGEITLRGLVLPVGGIKDKVLAA 790
           HFPAGAV KDGPSAGVT+VT L SLFS R VR+D AMTGE+T+RGLVLPVGG+KDKVLAA
Sbjct: 769 HFPAGAVPKDGPSAGVTLVTALVSLFSNRKVRADTAMTGEMTLRGLVLPVGGVKDKVLAA 828

Query: 791 HRAGLKQVIIPRRNEKDLEGIPGNVRQDLSFVTASCLDEVLNAAFDGGFTVKTRPGL 847
           HR G+K+VI+P RN KDL  +P  + D+     ++EVL+ AF+G    +++R L
Sbjct: 829 HRYGIKRVILPERNLKDLSEVPLPILSDMEILLVKRIEEVLDHAFEGRCPLRSRSKL 885  (SEQ ID NO:4)
```

FIGURE 2C

Hmmer search results (Pfam):
Scores for sequence family classification (score includes all domains):

| Model | Description | Score | E-value | N |
|---|---|---|---|---|
| PF00004 | ATPases associated with various cellular act | 121.1 | 4.3e-33 | 1 |
| PF01202 | Shikimate kinase | 27.1 | 1.4e-06 | 1 |
| PF00005 | ABC transporter | 7.6 | 0.49 | 1 |
| PF01695 | IstB-like ATP binding protein | 6.5 | 1.4 | 1 |
| PF00495 | Chaperonin clpA/B | 5.9 | 0.92 | 1 |

Parsed for domains:

| Model | Domain | seq-f | seq-t | hmm-f | hmm-t | score | E-value |
|---|---|---|---|---|---|---|---|
| PF01695 | 1/1 | 371 | 382 .. | 52 | 63 .. | 6.5 | 1.4 |
| PF00005 | 1/1 | 368 | 383 .. | 1 | 16 [. | 7.6 | 0.49 |
| PF00495 | 1/1 | 373 | 393 .. | 74 | 94 .. | 5.9 | 0.92 |
| PF01202 | 1/1 | 369 | 396 .. | 1 | 28 [. | 27.1 | 1.4e-06 |
| PF00004 | 1/1 | 370 | 565 .. | 1 | 220 [] | 121.1 | 4.3e-33 |

FIGURE 2D

```
   1 ATCATTAAAA AGTCAGGAAA CAACAGGTGC TGGAGAGGAT GTGGAGAAAT
  51 AGGAACACTT TTACACTGTT GGTGGGACTG TAAACTAGTT CAACCATTGT
 101 GGAAGACAGT GTGGCAATTC CTCAAGGATC TGGAACTAGA AATACCATTT
 151 GACCCAGCCA TCCCATTGCT GGGTATATAC CCAAAGGATT ATAAATCATG
 201 CTGCTATAAA GACACACACA CACGTATGCT TACTGCGGCA CTATTCGCAA
 251 TAGCAAAGAC TTGGAACCAA CCCAAATGTC CATCAATGAT AGACTGGATT
 301 AAGAAAATGT GGCACATATA CACCATGGAA TACTATGCAG CCATAAAAAA
 351 GGATGAGTTC ATGTCCTTTG TAGGGACATG GATGATGCTG GAAACCATCA
 401 TTCTGAGCAA ACTATCGCAA AGACCGAAAA CAAAACACTG CAAGTTCTCA
 451 CTCATAGGTG GCAACTGAAC AATGAGAACA CTTGGACACA GGGTGGGGAA
 501 CATCACACTC AGGGCCTGT CGTTGGGTGG TGGGGAGTGG GGGGAAGGG
 551 ATACCATTAG GAGATATACC TAATGTAAAT GACGAGTTAG TGAGTGCAGC
 601 AAACCAACAT GGCACATGTA TACATATGTA ACAAACCTGT ACGTTGTGCA
 651 CATGTACCCT AGAACTTAAA CTATAATAAA AAATAAAATT AAATTAAAAA
 701 CATGAAAAAA AATAAAAGTA TCAAGGTTGT AAAAAAAAAA AAAATTGGAC
 751 GGGCGCAGTG GCTCAGGCCT GTAATCCCAG CACTTTTGGG AGGCAAGGC
 801 GGGCAGATCA CTGAGGTCAG GAGATTGAGA CCATCCTGGC TAACATGGCG
 851 AAACCCCGTC TCTACTAAAA ATACAAAAAA TTAGCCGGGC AGTGGTTGCG
 901 GGTGCCTGTA GTCCCAGCT ACTCGGGAGG CTGAAGCAGG AGAATGGCAT
 951 GAACCCGGGA GGCGGAGCTT GCAGTGAGCC GAGATCTGC CACTACACTC
1001 CAGCCTGGGT GACAGAGCGA GACTCCGTCT CAAAAAAAAA AAAAAAAAA
1051 AAAAATTGAG GACTTGCCAC AGATTAGAGA ACACCTAGGA GATTTCATAA
1101 CAAAACACCT AGGAGATTTC ACAACAGGAT CCTGGATATT GGATCCTGGA
1151 CCAGATCCAA TGAAGGACAT TAGTGGGAAA ACTGGAAAA TTTGGGTAAG
1201 GCCTATAGGT TAAACGATAA TAATGTTAAT TTCCTGGTTT TGATCATTGA
1251 ACTATGATTA TGTAAGATGA TAACAGACGA AACTGGGTGA AAGGTATATA
1301 GGAACTCTGC TGTAGTTTTG TACATCTAAA ATCAATTCGG GCCGGGCACG
1351 TTGGCTCACG CCTGTAATCC CAGCACTTTG GGAGGCCGAG GTGGACGGAT
1401 CGCTTGAGGT CAGGAGTTAA AGACCAGCCT GGCCAACATG GTGAAATCCC
1451 CTCCCTACTA AAAATACAAC AATTAGCTGG GTGTGGTGGC GGGCATCTGT
1501 AATCCCAGCT ACTCGGGAGG CTGAGGCAGG AGAATCGCTT GAACCCGGGA
1551 GGCAGAGGCT GCAAGCCGTG GGTATCGCGC CATTGCACTC CAGCCTCGGC
1601 GACAGAGCGA GAATCTGTCT CAGAATAAAT AAATAAATAA ATAAATAAAT
1651 AATTAGTTCG AATCAAAAGT TAAAACACT TCAAGTATAT GTAAAAAATC
1701 GAAGAAAACG TTAAAAACAC TTCAAGTATA TACAATTCAA ATAAGATCAT
1751 CCTTCCAAAT ATACTCTGTA AGTGAGCGA AGGTCGCTGC ACGCTTGAGT
1801 GCACGTCTTT CGGCATAGGT AGGACGCTCA AGTCTTACCG GGAGGCTCTC
1851 CTAGAGAGCA GCGCGAAGCC ATGGCTTTTG GGCCCGGGA CGGACCGTAG
1901 CGCGTAGCCG GAAGCGGAGG CGTGGAGGCG GGTCTGAGGT TTGGTGACTG
1951 CGGGGCAGGC CGGGGGCAGC TGTCTGTCTG GCTCTTTTG ACAGCCCCCA
2001 GTGCGAAAGG CTGCCAGCAT GTCATCAGTG AGCCCCATCC AGATCCCAG
2051 TCGCCTCCCG CTGCTGCTCA CCCACGAGGG CGTCCTGCTG CCCGGCTCCA
2101 CCATGCGCAC CAGCGTGGAC TGGCCCGGCA ACCTGCAGCT GGTGCGGAGC
2151 CGCCTTCTGA AGGGCACGTC GCTGCAAAGC ACCATCCTGG GCGTCATCCC
2201 CAACACGCCT GACCCGGCCA GCGACGCGCA GGACCTGCCG CCGCTGCACA
2251 GGTAGGCCTG GCTGCCCCGG CGGGGCGGC GGCGGGCGCG GCCTCCTCGG
2301 GGGACCTGGG CCCAGGCCAC GGCTGCCTT GAGCGCGAGG CTCAGTTCGG
2351 GGCGGCCTTC GCGGCTCGGT TCCGCCTCTC TGGTGCTATC ACTTGCAAAA
2401 TGGGGATGTC AGATACCTGC CCCATGACCA TGAATGAGAT CGTTCATGAA
2451 GTAGTGCCTG ACACCTGGTG AAACTACGCA GTTCCCTACC GTTCTGGATA
2501 ATTTAATTTG AATCCTCTTC CCCCTCTCGG CAATTCCTGG CCCTCGGTCT
2551 TCAGCCTCCT AGGCCAGTGC TTTTAACTTT CCAGGCCCTT TCTTTCTCCC
2601 CGGTGATCTC TGCCTTCACT TGCCTTCGCT TTTCACCTTT CTCCCCACTG
2651 CCCTTTACTC CTATCCGCCT CCCCTTTTCT GTCACCCATC ATTTTGTCC
2701 GCTGAGGCAT TCTCTGCTCC GTGAGTTTTA ACTTTTCCTG TTTCATTCCT
2751 AAACTGCACT ATTTGTGGGT GCCTTCTTC TATACTCCCT GCCACCCTTC
2801 TCCTTCTCCC CCTAATCCTT CTGTTCCCT TTGTAAAGGG CCTTTACTGC
2851 TCACATTTTC GCTGGTCCCC CTTTCTGGAA CTTTCCTAGC TTCTCACCTC
2901 TGCTCCTTCA CTCATAACAT TTCTTAGGCC CCAGGTTAC TACTATATTG
2951 CCCAGTACCC TGCCCTATT GGTGTGACTT TGGGTGAGAG CTTTAACCTC
3001 TATTTCTTTT ATTCTGCAAT TTGGAAACTG ACAGCATCCA TCTCTTAGGC
3051 AAGTTATGAA GAATAAATTG AATAATGTGT ATATTCCACT TGCACCATG
3101 CATGATGGAT GACTTTGCTG TCCAGTACTG TGTAGTGCAT GTGGCTCGTC
3151 AAATTGAGAT GATAGAATTG CCAGTTGTCC TGGTTTGCTG CGATTGTCTG
```

FIGURE 3A-1

```
3201 TTTTAGCATT GAAAGTCCTA TGTTTTAGCC CCTCCGTCCC AGGGAAACCA
3251 GGAGGTTGGT CACCCTAAAT GTGCTGTAAG TGTACAATAC ACGCCAGATT
3301 TTGAAAAAAC TTTTTGATTA ATACATTTTA TATGGATTAA ATGTTGGAAA
3351 GGTAATATTT TGAGTACTTG GGGTTAATAA AATGTTAAGA TTTCTGCTGT
3401 TTTTACTTTA TAATGTGGCC ACTAAAATTT TATATGTGGT CCACATTATA
3451 TTTTTATTGG ACAATGCTGG TATATCGTAT GCTCTCAACA AGTATCTTCA
3501 AACTCACCTG CCAAGCACCC GCCTCCTATT CCTAACTCTA CTGGAGGTGT
3551 TGTGTTTTCA GTTAGAGCT TCTCCTTTCC TGGCAGTTAT CCCTTATTT
3601 TAAATTAGGG GTTCCTGACT CTGAATGGAT TTCCGGAGGG TTGGACATGT
3651 CTTATTTTC CTCAAAATCT TGTGACTATG TACATTTTT TAGGAGAATC
3701 CTTTGCTTTC TTCAGATTCT CAAAGGAGAC TGGTACCTCC CCCCACCCCC
3751 GTTAAAAGAA AGCAAAACAA AGCAACAAAG ACCAACAAAC CTTCCACAGC
3801 AGCCCAGTAT TCATTTATAT TGTAAAAGCC TTGATTTTCT CAAGCATGGA
3851 AAATATTTTG GCTCCCATCT GACCTGCTTT GGTTATTGCC TGAGTGGAAT
3901 TGGTCACATT CCAAGTTTCA GTACTCTTTG ATAAATTGTA TTGGATTCTA
3951 GTTTCCCAAC ATACGACTCT GCTCCTTCTG CTTACTTTTC CCAAATTATT
4001 TTGCCTTCTG TGCCCAGGCA CACTTAGTTC CCTGTCTAGG CAAGAGTCGT
4051 CATTATTAGA CTTCATTTTC TTTCTACTGT GCATATGTAT TGATTAGCCA
4101 TGGGCACATT GTGAACTTGA AAAGTCGATT TAGTCACATT TTAAGTTTCA
4151 CTATTGTTG GTATTATTCT GGCAAGATTT TGGAAGGTTT TTATTATTA
4201 TTCATTTGTG TATTTTTTGA GACAGAGTCT CATTCTGTCT CCTCCGCTGA
4251 AGTGCAGTGG CGTGATCGTA GCCCACCGCA ACCTTGATTG AACTCCTGGG
4301 CTCAAGTGAT CGTCCTGCCT CAGCTTCTGG AGTGGCTGGG ACTATAGGCG
4351 TGCACCACTA CACCCAGCTA ATTTTTAAAT TTTTTGTAGA AATGGGGTCT
4401 CACTATGTTG CTTAGGCTGG TCTCAAACTC CTGGACTCAA GCTATCCCT
4451 GCTTTGGCCT CTGGAGTAGC TGGGACTATA GGCAAGCGCC ACCATACCCT
4501 TCAGGTTTTT AATTTATTTT ATGAAAATCC CTCCAAAGCA ACAATCCTCA
4551 ATTCTCCTGC TTGAAAGTAA TCACTAATAA TCAGGTACTG TGTGATCTGA
4601 TCCTTGATGT TCATATTATT GCCTTTAACT GAGTAGCAAT GTTAAAATTT
4651 AATCATTTAA ATTAGAAAAC ATATATTCAT AAGTCTTCAT AGAAGTCCGG
4701 CATTATAAGA ACTCATCAGA CCATCTAGTT ATCCTAGAAG TATTGTTTGC
4751 TACTTAAAAA GCCTATGTGG AAAGATTGTA CCATATTCCT TGGTAATAGT
4801 TTCCAATGTC TTTTTTCTC TAATAGGGCC TTTAAAACAC TCTACTTAAA
4851 AAAAAAAAAA AAAAAAGGCT TTAACAATAC CAATACTGAG TAATCCATAG
4901 CATTAGCCTG TTTCCACGCA CAAGTCTGTC CTTCCCCAGT TACCTGCTTT
4951 TCTGTATGGT AGCCCAGAGG CCAGAAGAGG GGCTCTGTTC CTTTCTCTTG
5001 TTTCCTTTGC GCTATCCAGG TGACGCTGGC ACAGCCTTCA AAGAGCAGCA
5051 GAAGTAATTT GCTCCCAGCG TTCTTTGCCA CATAGAGTGG CAGGGTTAAA
5101 TGATTAAAA TTTAATCATT TAAATTAGAA AACATAGATT GAAAAGTCTT
5151 CATAGAATTC CAGCATTAAA AGAACTCATC AGACCATCTA GTTATCCTAG
5201 AAGTATTGTT TGCTACTTCA AAAGCCTATG TGGAAAGATT GTACGATATT
5251 CCTTGGTAAT AGTTTCGAAT GTCTTTTTTT CTCTAATATG GCTTTTAAAG
5301 CACTCTACTT AAAAAAAAAA AAAGCTTTAA TAATACCAAT ACCAGTTAT
5351 CCACAGTATT AGTCTGTTTC CATGCACAAA TCTGTCCTTC CCCAGTTACC
5401 TGCTTTTCTG TATGGTAGCC CAGAGGTGAG ATGAGGGCT CTGTTCCTGT
5451 CTCTGTTTC CTTTACACCA TCCAGGTGAC ACTGGCTGCA GCCTTCAAGG
5501 AGCAGCAGAA GTAATTTGCT CCCAGCGTTC TTTGCCACAC AGAGTGGCAG
5551 GATTAGATGT TGACTTACCT CTGCCACTTC CTGGTGGTT TTGAGTAGTA
5601 CAGTCCCTTT CTGCACGTTA GTGTGCAGGC ATGTTGCCTG CAGGAGCCTT
5651 TTTAAAGGAG GAGCTTTGGA CTTGTCCTGC AGTATAGAAC TTGGCTGGCA
5701 TGCTGACCCA GGGCACCCTG CATTTTTCTG CTTAGTAGAA CTGCATTTTT
5751 AGTGCTTCCT GAGTGACCCA TGTTTTCTT AGTGAAAAGG GGTCATAATT
5801 TAGTACTACC TGTACAATAT CCTTTCAAGC ATTTCAAGAT GGTCATCCAG
5851 CTTTCTTCCA AATTTACACT TTTCAGGGTA CATGGCTTCA TTTCCTCATA
5901 GTGCCGACTT CTCAGTCTCC CTCACCAGCC TGGTGTCAAA CTTGTGAGCT
5951 CAAGTGATCC TCCTGCCTCT GCTCCCAAA GTGTTAGGAT TACAGGCGTG
6001 AGCCACCATG CCTGGCCTAT GTTATAATT CTGTAGGTA GAAGTATAC
6051 CTATTGTCCA TGTAATGAG AAAAAGTAA AATTTGTCTT AAAATATAAT
6101 TAAGGAACTC AATTTATTAA ATTAAATTT ATCCTTTAAA TTTTAAATTT
6151 AAATTTATTT CTTAAATTTA TTTCTATTAC ATTTTCTTGT AACCATGTAC
6201 ACCTAAGTTG TTCTACTTTA ATTTTTTGA GACAGGGTCT CACTCTGTCA
6251 CCCATGCTGG TGCAGTGGTG CCATCTCAGC TCACTGCAAC CTTTGCCTCC
6301 CAGGTTCAAG TGATCCTCTC ACCTCAGCCT CCTGAGTGTC TGGGATTACA
6351 GGCATGTGCC ACAATGCCTA GCTATTTTTT TTTTTTTTT TGGTGGAGA
```

FIGURE 3A-2

```
6401 CGGGTTTTG CCATGTTGCG CAAACTGGTT TGAACTCCT GAGCCCAAGT
6451 GATCCACTTG CCTCGGCCTC CCAAAGTGCT GGGATTATAG GTGTGAGCCA
6501 CCATGCCATG TTCTACCTTT TTGAATCTCA TTTACTCACT TGTAATAAGG
6551 AAATAATACT ACCTTCTTCA TGGGGTGAAG GGAGGTATAA AATGAAGTAT
6601 ACATATGAAA GCCTTTTGAA ACTGCAAAGC ATTCTAAACC TATATCCAAA
6651 TGGGTAGTTT TAAATGTAGA TTTTCACAAA AGGGGATTAA AGAGAGGAGT
6701 GGGGAGGCCC CATATTATTC CAACACGGGC TGAACTGAAC TAACATCATT
6751 GCAGGAAGGT CTTGGAAGAT TAAAGATTCC AAGAAAAATT AAGGGCTTTG
6801 AGTAAAAAAA TTTTTAAAA GTGGCTGGGC CTGGTGGCAC GTGCCTGTAC
6851 TCCCATCTAC TCATGATGCT GAGGCGGAGG ATTACTTGAG CCCAGGTGAT
6901 CGAAGCTGCA GTGAGCTATA ATGGTACCAC TGCACTCCAG CCTGGGTGAC
6951 AGAGCAAGAT TCTGTCTATA GGAAAAAAAA AAAAAAAAA AGCAAGTGCT
7001 GGGCATATAG GCTGGAATTA GATATTTACA TAATATCCTC ATCTTGGAAA
7051 ACTTTTTCCA GTAGTGCTGC TTTTAGATTT TCCCACTACT GCAGTTGATG
7101 GTTCTTAAAT ATGTTTGGAA CTCTTATATT ATTTAGGTCA GTTTCCAAAT
7151 TACACAAATT GTAACCATTG TAGTCAGACC TCACTTGAAT GAAAACAATA
7201 TTTTACAAAC TCTGAGGGTA GATTCGAGTT AGGATTTGGA TTAAAACATT
7251 ATCTAAAAC CTCTGAGGGT AGATTCGAGT TAGGAGTTTC AAACTTCTT
7301 TGAACAATAT CATAATTAGG ATGTAGATTT ACAGAGCTAC TAGCTAAAGG
7351 GAAGGACACC AGTCATTGGG ATGTATAAGT TTGGATCTGT TGCAAAATTA
7401 AAATGCTGCC TTTTGAGCAT GCCTAATAAT GCACATACAA TAGAAGAGCC
7451 AGAATTTTTA GAAAAATGAC TGACTTGATA TACAACCTTT TGTATATCAT
7501 AGAAGGAAAA TATTAGTTGA GTATTTTGTT TATTTACCTG TTTGTATATA
7551 TAAAACCTGG GGCCCAATAT ACAATAGATT CTTTTTCACT ATGCTTTCA
7601 CCCACAGTGT CTCACCAGGT ACTCTGTTTC TAGCCATCTA TAATTTCATA
7651 GATGTTTTTC TTTAAAAGGG ATGTATTCTA GGCTGGGCGA GGTGGGTCTT
7701 GCCTGTAATC CTAGCACTTT GGGAGGCCAA GATGGGAGGA TTGCTTGAGG
7751 CCAGTAGTTG GAGATCAGCC TGGTCAACAT CATGAGATCC CATCTCTGTT
7801 AAAAAAGAA AAAAAATTT TTTTAAAGGG ATAATTTCTA GTCAACTATA
7851 AGTGATTTTA AGTAAAAAGC AATTAAGGCA TGTATACATC TGTACCTTTT
7901 GTAGGCATAG TATAAATTCA GCTTAATCTC TTCAGTTTGG AACATCTTCC
7951 TTTTCACAGCA AAAATATTGT ATTTGCTTTA TAAGAAAACC CCTTTTGGCC
8001 AGGTGTGGTG GCTCACGCCC GTAATCCTAG CACTTTGGGA GGCTGAGGTG
8051 GGTGGATTAC CTTAGGTCAG GAGTTCGAGA CCAGCCTGGC CAACATAGTG
8101 AAACCCTGTC TCTACTAAAA ATACAAAAAT TAGCTGGGCG TGGTGGTGTG
8151 TGCCCTGTAA TCCCAGCTAG TTGGGAGGCT GAGGCACGAG AATCCCTTGA
8201 ACCCAGGAGG CAGAGTGCAA TAAGCCGAGA TCACGCCATT GTACGTCAGG
8251 CTGGGCGACA GGGTGAGACT CCCTCTAAAA AACAAACAAA AAACCACAG
8301 TGGCTCACAC CTGTAATCCC AGCACTTTGG GAGGCCAAGG TGGGCGAATC
8351 ATGAGGTCAA GAGATCGAGA TCATCCTGGC CAACATGGTG AAACCTCATC
8401 TCTACAAAAA ATACAAAAAA TTAGCTGGGC GTGGTGGTGT GTGCCTGTAG
8451 TCCCAGCTAC TTGGGAGGCT GAGGCAGGAG AATCACTTGA ATCGGGAGA
8501 CGGAGGTTGC AGTGAGCCAA GATTAGGCTA CTGCGCTCCA GCCTGGTGAC
8551 AAAGTGAGAC TCCGTCTCAA AAAAAAAAAA CAAAAACAA AAAACAACTC
8601 TTTAGCATCA CCTTTTAGCA ATGACATAGC CCAAATAATT AAATTTGTCT
8651 CCTGATCGGA GATTTGGATT TGTCTCATCT CTCTTTCTGG TTCCTCCTTG
8701 GTTTCTACTT TGTAAACCCT TTAGGCCGGG GATCCAGTTT CTTGTCTGTG
8751 GATGTTTTAT ATACAAACAG GACTGTGAGC TCTTTCAGCA TTGTACAAAC
8801 AGTGATGAAT ATCATCTGCA ATTAATTATG TTAAGTTAT TCTCTAATCA
8851 GTTTAGAGGT GGCTCACTTC CTCAGGCAAT CTGAGTGGGC TTTCAGGAAG
8901 TGGGAAATAT TATCTACTAT TGATTGAAGA AAAGCAGCCA CAACACAAAT
8951 AAGTCAAAAT AATAGCTAAT TGCTAAATAA TTTCAAGTTT TTATGTATG
9001 TGATTTTTTT CCCTCACCAA TTTATCTTCT CAGTTGTTTG GCTTATTATT
9051 TAAATCAGTT TTTATTGTAA ACATGGTAAT GACTGAAAGG TAAGAAAAGG
9101 ATAGACGTAG TTCAGAATAA ACTGAGTGGC AGAAGAAGC CAAGGCTAT
9151 GTGTAATCTA CGGAATGAGT AATTTATAAG GAAGTAATCA AGAATTCACT
9201 GTGTATAGAA GTAAGCAAGT TCACTCACAT AGTCACATAC TGTATTACAT
9251 GATTTATTAT CTTTGAGATG GGCAGGTGTG GTGTTCTTCT ATTACCGCTT
9301 TCCTAGGGTG TTGAGAGTTC TAGTCCTTCT ATTTTCTTTT CTGGAATTAC
9351 CACTTTTCCT ATGGCTGAAG GGAGAAAATA TTATTTATTT TGGGATCTGG
9401 AATTGTCTTC TCAATGTTGA TTTTTGTATT TTATATAACT GACTTAGTTT
9451 GGATGAGGCT TCCTTTCTGT GAATTAAATT TATATGTGAC TTGATCAGAG
9501 TTGTATTTGC TGATGAGGAG CTGAGACTTG AAGCCTTTTC ACCTATTGTT
9551 AGGTAAAATG ATTACCACTT AGAACTAGGT TGAGACCTTT TGAGATGTGG
```

FIGURE 3A-3

```
 9601 GTCTTTCTTT AGCTCTCCTC AGTCTATGGC AGTGTGTGGA CTGTAATATT
 9651 TAGCCCTCAC ACTTAGAAAT TCAGTGTTAA GGGCATATAT ATAAGTTCCC
 9701 AGTATGTGAT GGCAGCTTGT GATAAGGTGG GTATGTGGAA GTTTCATAGA
 9751 CTGATTATGT AAGAAAACTG ACTTGATGTT AGTAGCACAA CTGGTGTTGG
 9801 AACGGAGATT TCTTAGATTG GTTTATGCTA TTTATATTTA AATGTATTTA
 9851 AATTGATAAT ATTTATCCTG GTATAAGATT GCCTTATTCT TAGTTGACAA
 9901 TGTTAATTTA AGATATGTAA TTCTCAGCTG CTTTTCTCTT ACATTTTTAC
 9951 GCTTGAATAA TCCAAGTGTT TACAAATTCC TACCTAATTT TTTAAAAGAG
10001 GTGCAGATTA TAGTGAGATG GTCTGCTTTG CCATATAGCT GAGGGTAGTG
10051 GCAGAAGAGG CCACATACTG GATGCTAAGT TAAATAGAGA AAAAATTTAT
10101 TTACACTTCA GATGTCTTTT GCTTAATGAA TGTATCAGAA AAGCCAACAC
10151 TTTCTGAAGT GAGTTTCTGT TCTACCGTAT TGAATGTTTG TAATACCGAT
10201 GTTTTGTGTG TTTTTCAGGA TTGGCACAGC TGCACTGGCC GTCAGGTTG
10251 TGGGCAGTAA CTGGCCCAAG CCCCACTACA CTCTGTTGAT TACAGGCCTA
10301 TGCCGTTTCC AGATTGTACA GGTCTTAAAA GAGAAGCCAT ATCCCATTGC
10351 TGAAGTGGAG CAGTTGGACC GACTTGAGGA GTTTCCCAAC ACCTGTAAAA
10401 TGAGGGAGGA GCTAGGAGAA CTATCAGAGC AGTTTTACAA ATATGCAGTA
10451 CAAGTAAGTT GCTTTTATTT TTTCTTAAAA CCCATTTTTC TTTGGTTCTT
10501 TTGCTTTCCT AAGATATGGT GAATCTGTTG GATAGTGAAG TTTTAGGACA
10551 GTATACATTT AAATGAGTTA GTAACATTAT ATATTAATTC TGATTTACTC
10601 TTATCTGGGG TTGTACCTAA ATCATTCCAG GACATATGG CCTACCCTTT
10651 CTAAAGTTTT CCAAATGTTA TTTCTACAGC TTTCCTTCTA ACTTCTACTG
10701 TCTCTAAACT AGATAATTAT TAAACCTAAA TATTTAAAGC TAAAAAACGA
10751 AATACTGCAC AGAAGCTGTC TGTCACTAAA ATATCTAGCC ACCATTTATA
10801 TAAATTACAA TATATTACTT CAAAAGTCAA GATCACATTG TCTAGCAGTA
10851 ACTATGGTAG ATCAAGCCTG TGGTGGGCTG ATTTCAAGTA TGGTTAAAAC
10901 CTTGATTAAC TAGAATGCTG GGAAGGAAGC ACATTTTAGA TATGCATTAA
10951 ATATTTGACT CTTTAATTCT AGTTCTTTTT GGTTAACTCT AGATAGAACA
11001 GAAAGCTCCT ATTCCCACCC CATTTTGTTT CAAACCTTAA TGAAACATAA
11051 AATTATAAAG TATAGTCTTC TACTTTTCTA TTAGTTTAAT CCAGTTGACTA
11101 TAACTAGATC TATGAGGATC AGATAATGTT TAAAAGTCAC AATTATAAAT
11151 ACTACTGATC ATTGAAATAT GTGTGGGGCA AGTGTTCATA GCCAGTGGTA
11201 TTTGTATCTG ATGTGGCATT TGAAGAGCCA TACTTACAGT GTAATGAACA
11251 ATAACAGAAA AATAGTAAAT TTGAGGGCCA GGTGCGCTGG TGCACACCTG
11301 TAATCCCAGC ACTTTGGGAG GCTGAGGTGG GTGGATTGCT TGAGCCCAGT
11351 AGTTCGAGAT CAGCCTAGGC AGCATGGTGA GATCCCGTCT CTACAAAATG
11401 TACAAAAATT AGCCGAGTGT GATGGTGCGT GCCTGTAGTC CCAGCTACTG
11451 GGGAGGCTGA GGTGGGAGGA TTACTTGAAC CTAGTAGGTG GAAGTTGCAG
11501 TGAGCCAAGA TTGCATCACT GCATTCCAGC CTGGGCAACA GAGCGAGACC
11551 CTGACTCAAA AAAAAAAAAA GAAAAATAGA AAATTTGAAT CTGTAATTTC
11601 TATATGGGCT GAAAGAAAGC ACTTTGAGGA AAGAAATTTC AGTTTGAAAA
11651 CTGGAATAAG TGAATATACT GCTTAGGAAT AAAGGAGATT GAGAGAAATA
11701 GAATTTCTTT TTCTTTTCAG CAGTGATGTT CCCTGGGTCT TTGTGCCTCT
11751 ATTGGACATA GATAGCTTCA TAGCCCTCTTT TGCTTTGCTT TTACTTCTTT
11801 GTACTTTGAA TCTAGAGGAA CTTTTTAAAC TTGTAAAGAT TTGCAGTGA
11851 CATTAAAGGA ATTTTTAGAA ATAAATAGAT CACCACACAT CTTACTGTCA
11901 TCATGCATCA AATTTAATTT TTGTTGTCT TCTGGGCTCA GTTCATATTC
11951 AATTATATGT TTTGTTTTTG TATCCATGTC TGAATGTTCAT ATTAAGTACT
12001 TTTGTTAATT TCATTGAGTT AATGTATACT AATTTTATPA TTTCTCTTTT
12051 TAGACATTAA AGTTATTTCC AATTATTCTC TTTCATCCCC TTCTGCATCT
12101 ACTTCTACTT CTGCATCTCT TCAATGAACT TCTTCAATAG CATCCTGTCT
12151 CCTAGTTCTT CTGTCTTGAA CCTTTTCTCT TCACTGAGCC TTTCTAAAAG
12201 AAGTCTGGGG CATCCCATTC CCTTGAGTAA AAGACTTTAA TGGCTATAGG
12251 ATGGACACCA AATTTCTTAG TATAACATTA AGACCGTTTG CAACTTGTCT
12301 TGGCCTATC TGTCTTGCGT CAACTCTAGT TATCACCTCA CTGACACCCT
12351 AGTTCTAGCT CTACTGAATG TAAAACAGCT TCACATTGAG TTATTTTATG
12401 TCTCTATGAT TCTGCCTTCA GTTCTCTGCT GGGAGTGCTC TTCCATCCTC
12451 GATTTTTTTT TTTTTTTTTG AAATGGAGTC TTGCCCTGTT GCCCAGGCTG
12501 GAGTGCAGTG GTGCAATTTC GGCTCACTGC AGCCTCCGCC TCCCGGGTTC
12551 AAGCGATTCT CCTGCTTCAG CCTCCCAAGT AGCTGGGATT ACAGGCATGC
12601 GCCACCACGC CCGGCTAACT TTTTGTGTCT TTAGTAGAGA TGAGGTTTCA
12651 CCATGTTGGC CAGGCTGGTC TCGAACTCCT GACCTCATGA TCCAACCGCC
12701 ACCACGCCCG GCCTCCATCT CTGAATTTTA AAATTGAATC TATGCTTTCC
12751 CAACAGCTGT AGGCTGTTAG CGCTCATCTC TGTGTGCCTT CACAGTCTGT
```

FIGURE 3A-4

```
12801 CATACATGTC ATTTAACATA ATGCTTATCA CATTGTATTG AAATGTATCT
12851 TATAGGTATT TTTCTCTAC CAAACTTGAA TTCACTTTTC TCCTTTAGCC
12901 ATCCTGTACT GAGCAGTGTT TTGGGTCTGG CAAATAGTTT GTACTCAGTA
12951 AATGTTTGGA AAATGAGTTT TAACTGTTTT ATTTTCGTGG GGTGAATTCC
13001 TAGTAGCAAG GGTATTCAAA TTTTATTATC TACTTCTTCC ACCTGAACAG
13051 CTTCATCGTA ATTATACTTT AATTCCCTTC ATTCTAGGCA GGTAATGGAT
13101 AAGTTCCAAA ATTACGATGT TGTTGGAGAG GTTTGAATAT TACTAGCACA
13151 TGAAATCTGA TTTGAACTGA CTAAATGAAG GTTTAGTACA TCATTATGAA
13201 TTAGTGTGAA CTAAGTTTTG CTATGTTAAC TTCTCTGAAA TCTCAGTCGC
13251 ATAATGTGAG TGTCTTTCTG GCTCATGCTT CATGCCTGAG ACTAGTGGGG
13301 GTTGTGTCTG CCTATTAAAG TCACTCGGAC CCAGGTGGAT TGGAGATTCA
13351 TCTAAAGACA TGCTTCCCTT ATCTCTAAGG CAGGAAAAGG AAATGGGCCG
13401 CATCTCTCAT TGGCTTGTAA TGCTTCTGCC CAGAAGGAGC TGTCACTTCC
13451 ACTACGTTTC ATGGATCAAT TTAAGACTCA TAGACACACC TATTAGTATA
13501 TTCGAAGGAA GTTAGAAAGA GCAGTGCCCA GAAGAAAAGG GGAGTTTGTC
13551 AGTAGCCCTA ATGACTATCA CAGTTACTGA AAGTGTGCCT TGGGCATAAT
13601 CTATCTTAAC TCCCAGATAT ACGCTGACAG TTGTTTTTCT AAAAGTCATT
13651 CACAGTGCTC AGATTCTAGT TAGTCCAAAT TGATATGGTT TGGCTGTGTC
13701 CCCACCCAAA TATCACCTTG AGTTGTAATA ATTCCCATGT GTCAGGGGC
13751 GGTGCCAGGT GTAGATAATT GAATTATGGG GGCGGTTCCC CCATACTGTT
13801 CTCTTGGTGG TGAATAAGTC TCACAAGATC AGATGGTTAT ATAAATGATA
13851 GTTCCCCTGC ACACGCTGTC TTGCCTGCTA CCATGTAAGA CAGGCCTTTG
13901 CTTCTCCTTT GCCTTCCTCC ATGATTGTGA GGCCTCCCCA GCCATGTGGA
13951 ACTGTGAGTC CATTAAACCT CTGTCTTTTA TAAATTACCC AGTCTCTGGT
14001 ATGTCTTTAT TAGCAGTGTG AGAACAGACT AATACAAAAT GTTATACTAA
14051 ATATTAATAT TTCATCCTCT GATTGGCCGT GATAATAGCA TCAACTATGC
14101 TAAATTTCTA ATAATACACA TATTCTAAT AATATGCATC TAATAGGGTT
14151 TATATTGTGA TTATGTAAGA GAATATTCTT GTTCTTAAGA ACAAGGGTCC
14201 TTAATCTGTC ACAGGATTAG AGATTTAAAG AATAAGGATC TCGATTCTGC
14251 AGCTTATCCT CAAATGTTCA TTAATTATGT GTGAGTGTGG AGAGAGAGAA
14301 AGCAAACATG GCAAAATGCC ACTTTTCAGT TGGTGAATTC AATGGTGAA
14351 TCTCGAAGAA GGATGTACAG GAGTTATTGT ATGATTCTTG CAACTTTTTT
14401 GTACATTTGA ATTTTTTTCA ATAGAAAGTT AAAAATAATC ATGGCACAGG
14451 TTTACAAAAC CCTTGTAAAC ATTAGTGTTA ACTACTTTTA AGCCATTATT
14501 GCTTTTCATT CTGATTGATG TTTTGAAAGT ACTTTTCTTT TCCTCTGAGG
14551 CCTGTAAAAT ACGTGGACTA TATTAATCAG TGATCTTTCA AAAACAAAGA
14601 CTGAGGCCCA AACATTAAAC CTAGATGGAA ATCTGATTTT TAAAAATTCA
14651 CAAATAATGC CAGATTTCAT TTAAAAGACT TTTTTTCCCC CTTCTAGTTG
14701 GTTGAAATGT TGGATATGTC TGTCCCTGCA GTTGCTAAAT TGAGACGTCT
14751 TTTAGATAGT CTTCCAAGGG AAGCTTTACC AGACATCTTG ACATCAATTA
14801 TCCGAACAAG CAACAAAGAG AAACTCCAGG TACAGTGTTC CCTTTTGAAC
14851 GCCAGGTTGC TTTGTCACTT TTTATTGAGA ACTAGATAGT GAGTAGTTAA
14901 GTTTTGACCT TCAAGAAAAA GATATTGGAG ACCCAAAGTA ATTGAAATGC
14951 TTTTACATTT AAACTGACTT TCAAATGTGA TTGTTTTATA TTTTGTTGA
15001 CACAAGCAGC TCTTTTATTT TATATTTTTG TTGACACAAG CAGCTCTTTT
15051 ATTTGCATAA TCAGTAATGG TAGTCAATTT ACAGAAAAG TTAAAGCAAA
15101 GAATCATAAA AAGGTAAATA TTTGACTGGG TGCTCACGCC TGTAGTCCCA
15151 GCACTTTGGG AGGCTGAGAT GGGTGGATCG CTTGAGATCA GGAGTTCGAG
15201 ACCAGCCTGG CCAACATGGT AAAACCCCAT CTCTACTAAA AATACAAAAT
15251 TAGCTGGGCG TGGTGGTGCG CGCCTATAAT CCCAGCTACT CGAGAGGCTG
15301 AGGCAGGAGA ATCGCTTGAA CCTGGGAGGC AGAGGCTGCA GTGAGCCAAG
15351 ATTGCACCAC TGCACTCCAG CCTGGGCAAC AGAGACTCTG CCTCTAAATA
15401 AATAAATAAA TAAATATTTA ATTTAACTTA AATATGTAGA CATTCTTTGA
15451 TTCACTATTT TTAAACGTGG AGCCATGGCC CTTCCCTTAT GTGTGGACCT
15501 GCTTTCTTAG AATCTTCATC ATGTTTCTTA TATAAATCAC ACCTATGATG
15551 CATTACTTAT AATTTTAAAT TTATATTTAT TTAAGTGAA ATGAATTTTA
15601 AAGACACTTG AAAAGTAATC CAAGTATAGA ATCCTACATT TACATGACTT
15651 AATCCCCAAA CTGTAAATACT TTAAGTTTTC TTGCACACTT ATTTTTAAGA
15701 TATTTTTAAA GCAGTATTTT TAATGAATCA TCCTAGAATA TTTGTTTGTT
15751 TTCAGTGAAA CAGCTCTTTC ATATGTTATC AGTTTATTTA ATACTTAAAT
15801 CCAACTGTTA TAATAGCAAA TACAACTAAC ACAAACAGGT TGGTTATACA
15851 CAGGAATTCA ATTAATCCAG TGGGAGTAGA AGAGTTACAG GACTGCCAGA
15901 GAGCCCCCTG GCTGTGGGCG GCAGCAGTGT GTTTACTGC GGGAACAGAG
15951 AGCGGCCTGT GCTCCGACAA ATCACTAGTG AGAGTTGGTT GAGTGCTTCT
```

FIGURE 3A-5

```
16001 GTTCTCTTGT GTATGTAAAC ATTTAATATT TTGAACCTAT AATTTGTTTA
16051 GATCTAATAT GAAAACACAT TCTGGGCTTC AAGAGAGTAA TTCCCAGAAA
16101 GAGTTGACGT CAACTGTGTG TCTGGTTTTT TCATCTTAAA AACACACAGC
16151 TTCGGCCGGG CGCAGTGGCC CACGCCTGTA ATCCCAACAC TTGGGAGGC
16201 CGAGGTGGGA AGATCACGAG GTCAGGAGAT CGAGACCATC CTGGCTAACA
16251 GAGTGAAACC CTGTCTCTAC TAAAAATACA AAAAATTAGC CGGGCATGGT
16301 GTCGGGTGCC TGTAGTCCCA GTTACTCTGG AGGCTGAGGC AGGAGAATGA
16351 CGTGAACCCA GGAGGGGGAG CTTGCACTGA GCCAAGATCT CGCCACTGCA
16401 CTCCAACCTG GGACAGAGCC AAGATTCCGT CTCAAAAAAA AAAGAAAAA
16451 AAAAAACCAC ACAGCTTCAT TTTAAAGTGA AAACCAAGA TCCTGTTTTT
16501 TCTTTCTTTT TTAAGGATTC TGATATTCAT CTCAAACAAC CTTGCTGATT
16551 AATATAGTTC ATTTGGTTGT CTTAGCCATA GTGTAGCTTT GAATACTGTT
16601 AATAATTTTT TTTTAACTTG GCAATTTAAA CCATGGCTCT GACTGTCTGT
16651 TTTTGGATTG TGTGTTTCTG AGAGAGATCC TATTGATTGA CTCACATTTC
16701 CTTAGATTTT AGATGCTGTG AGCCTAGAGG AGCGGTTCAA GATGACTATA
16751 CCACTGCTTG TCAGACAAAT TGAAGGCCTG AAATTGCTTC AAAAAACCAG
16801 AAAACCCAAG CAAGATGATG ATAAGAGGGT AAATATTTAT TTTAACCCAT
16851 TTCAGTTTTG AAAAAAAAAT AAGGAGAATA AAGAGAGGAA CAAAGAAGAA
16901 AAGTTTATTG TCTCCTACCA CTGGCACTAC TGATAAAATT TAGGTGTTTC
16951 CCTCTCATCC TTTTCTTTGC CTGGATTTTT TTTTAAAGCA TGTAAGCATT
17001 TTTCTCACTT TGTTTTGGTT ATCATCCAAA AGGATAATTT ACTGAGCCAT
17051 TTCCCCTTTT GTGTTGTTTC CAATGTTTTG TGTATTGTAA ACACTAACAA
17101 ATAACTATGA TGGGTGTCTT TGAGTATAAC ATTTTTTTAC TGCATGTAAT
17151 ACTAAGAAAC TAATACAAAA CTCTTTCTTA AAAGGACTAT ATGTTGTGTC
17201 AAAATTTGGC TGTTTTCAAC TTATAATAAG TTTCCATTTT TATTTAGTCA
17251 AACTCTTGAT CTTTTTTTGT TTCTAAGCT TAAGTCCTCT AACCTTCAGT
17301 GGCTTGATAA ATATTCACTT TCCTTTCAGT TTAATTTAG TTGATTTTTT
17351 AAAAAGTATT TAATTCTTTA ACCCATATAT TATTTTGAAG ACAGCAGTTG
17401 TATTTTTCCC TCAAATAGCT TTTTGTTTGA CTCAACACCA CTAATTAAAT
17451 AATCCTTCCC ATCCCCATTA TCATCTATTA CATTTATATG TATGATGGGA
17501 TCTGTTTGAA GTCTACCTTG ATCTGCTGAT TTTACTATTT TTATGTCTGG
17551 ACAGAGTTTA TATTAGGAAG ATATATTTGA TGTGGACAGG ATGTGAAAAT
17601 GGCATTTCTC TGAAGGTGTT GAGATGCAGC GCTCTGACTT AAGTTGAGGC
17651 GTTGAGAATT ATGTTAGCAA TTTGACGTTC ATCAGCGCAG AAGTCTTGTC
17701 ATCAAAGAGA ATACATTGTA GAGAAAGCCG AGCAGAAGGG AAGAACTCCT
17751 CCCCGGTGGG ACTAGAGAAG GGGCAGTCAA GTAGGCTGAG GAGAGAGATA
17801 GGAACAGTGA TGATCATGCT GGCGATTAGT ACTCCAGGAC ACCATGCTGT
17851 TTAAAACATG CAGAAAGCTG GATTATTCT GGCTTGAGAT CAGGTCAGGG
17901 ACTCAATTAC TCATTTTGTA TAGAGAGACA AATCCACTGG GAGTTGCAGA
17951 AAACTGCAAC TTACTCTCAG TAAAGTTTGC CATCACTTAA AATGAAAGTT
18001 TTTCAAAAGT GCTCCAGAAA ATAAGCAAGA GACAGTTATT TAAAAAGTAG
18051 GAATTAGGAT AATATTTGGA GTTAACCTAA AACTCTCTCC TTTTTGTTCC
18101 CCTAAGAGTT GAAAAGCACT GTTTTAGCAG TCAGGAAGGA AAAATGCATT
18151 AAAAAGTGCT TTTGTCTTAA CAATGAAATC ACTGATATGC TTATAAAAAT
18201 CTCACTTTTA AAAATATAT AATATGTTCA GTTTTTATT TATAATATTT
18251 TATCTGCTGA TGACTTATGT AAGAATAAAA GCATATATTT AGTACTTGTG
18301 TTTTTATAAA ATTAAATTTT TATTTACTGC TTTATGTTTT AAACATTTTT
18351 ATATTTGAAT GTATTAAATA GATAAATTTT CCAGGTTAAA AAATAAGTTC
18401 TGGGCTGAAT GCAGTGGCTC ATGCCTGTAA TCCCAGCTACT TTGGAGGCC
18451 AAGGAAGGAG AATTGCTTGA GGCCAGGAGT TCAAGACCAG GCTGGGCAAC
18501 ATAGTGAGAC CTCATCTTTA CAAAAAAAAT TTAAAAAATT AGCCAGCATG
18551 CTGGTGTGTG TCTGTAGTCC CAGCTATTTA GGAAGCTGAG GTGGAAGGAT
18601 TACTTGAGCC AGGGAGGTTG AGGCTGCAGT AAGCAGTGTT CATGCCCATTG
18651 CACTTCAGCC TGGATTACAA AGCTTGACCT TGTCTCAAAA AATAAAATGT
18701 TCTGGGGGCT TTTAAATTAA ATGCTAGTAT ATAATTTTGC TCCAGTAGTG
18751 GTTGTTTATT CATGAATTTC AAGGAGCATA TAAGGTAGTT TTAACATATG
18801 ATAGAGAGAT CATAGAGAAT ACAAAGGCCA TTTGACTTTG CACAGAATAT
18851 GTTTTTTAGA TTTGAAAGAA CAATTTTGGC AGGATGGGAA CAGATGCCGA
18901 AGGCTCACTG AAGTAATTGA TGAGGTAGGG GATCTGGTGG TTATAGCCAC
18951 TTGCTGGAGA AGCAGAACTT CACAAGAAAG GAAGTAAATA GTGCGATAGT
19001 TAACTAGAAG AAACTAGAGG TAAGAAAAAA ATATTTTGAA AGCAGGAAAG
19051 CTTTGAAGAC AAAATGAGCC CAGTGGTGGA AAGGTTGAAG ATGCTAGGAA
19101 GAAATTTGT AATGTAGGAG ATAAAATGGA ATTTTTTTCA GTCACCAAAT
19151 GGTAAGAAGT AATGTATTTC AAGAAAATAG TGGCTGCAAT AGTAGCTCAA
```

FIGURE 3A-6

```
19201 AGAAAGGTAA TTCCTAGATG GTTTAATTAT TTCTAGTATC CAGTTCCTTG
19251 AAATTTGTTT TCTCATGCAA GTATTATTGT AAGCATATAC CAAAGAATCA
19301 TGTCTACCTT ACGTTGGTCT ACTTCTGCAA TTCTGCTGCC TCTCTGTATA
19351 CAACTGCCTT TTGATTATCA TTCTGAACTT CACTTCCTAA AGATAGAGAC
19401 TGTAGTCATA AAAATATTTA TTCAGCACCA GTCATAATCT TATGTGTACC
19451 TGGGTACTTC GTTTCCAATT TATTTTGACA TACGGTTTTA CTTTTCTGCT
19501 TTCTATGTTA GGTTATAGCA ATACGCCCTA TTAGGAGAAT TACACATATC
19551 TCAGGTACTT TAGAAGATGA AGATGAAGAT GAAGATAATG ATGACATTGT
19601 CATGCTAGAG AAAAAAATAC GAACATCTAG TATGCCAGAG CAGGCCCATA
19651 AAGTCTGTGT CAAAGAGATA AAGAGGTAAA TTATAAAAGG CATTTGTTCA
19701 TTATTGTTTT CATTCTTGGT ACTCCTGATT AACACCACTT TCACTACTCT
19751 TTTCTCCAAT ACTGAGGATA CATAATACAA ATCTTCCACC TGCAGTGTGC
19801 TGTCAGGCAA TATAACTCTT GCAGCTGCCT TTTTGTTGTC TGAAAGAACA
19851 GACCATGCTT CTTTGTTTAT ACGTAATGTT TGTTCAGTTA GCATCATATT
19901 CTTCACATGT GACTTTTCTT CTCTAGATTA TAAACTCTCA AGGGCAAGGA
19951 CTGTCCATTT CTCTTTGTAC AAGACAAAGT ACAGGGAAAC CTTGATAACA
20001 GAATAGGATA TATGGGTTGA TTACATTTTC TGGATATCCC CAGTGTTAAA
20051 CTGAAAGCCA TTTTTCCTTT GCATACTTTT AACTTTATAA CTCTTATTAC
20101 ATTTTCTTTT ATTAGTCAAT TGTAGTGAGC CTGCTTGAAT GCTTAGTGTAG
20151 TTAATATTTG ACTTTCTGAG GCTTACAGTT AAGAACATTA GTAATTGTAG
20201 TTGATGGGTA TTTTATATTG CCTCTGACAT TAGTTAATAT ATGTAGAACA
20251 TTTATTATGT GCAGAACACT TTGCTAAGCA TTGCATATAT TATGGAAGTA
20301 GCATTTGTTA TTAAATATAT GATATTAGCT TGCTTTTATG AGCAGACCTC
20351 ACTCATCTCT GATACAAAAA AAAATGTATT GTATTATGCA TAGTTAGGCA
20401 CTTACATCTT ATTGTGATAA GTAAACCAAT GGATATAGTT CACTTGACTA
20451 TCCCTGTGAG CTTAAAAGGG ACACACACTA GTAAGGCCAT ATTTCCAGGT
20501 TAGAATTAGA TATAAATGTTT TCTCCTGCAG TTTGCAGGTA TCTGCCTTAT
20551 TTTGTTTTGT AAGTACCTTA AGTACTTAGA AAATATGAGA ATACTTTGTA
20601 GAGAAAGCAG AGCAGAAGGG AAGAACCCCT CCCTGGTGGG ACTCCAGAAG
20651 GGGCAGTTAA GTAGGCTGGG GAGAGAGATA GGAGTGGTGA TCATTACATT
20701 ACAAAACAAA ATAAACGTTT TATTATCTGG ATACTTTAAA ACTTTTTCAG
20751 ATTTGTTTAA ACATGCATGA TATATCTAAC CAAGAAAGAG AGCTGTGTT
20801 GATTTTTCTG TTATGGAATT TTTCTGTGTT CTTGAACATG TTTGCTGTGT
20851 ATTCTTTCTC CACAGACTCA AAAAAATGCC TCAGTCAATG CCAGAATATG
20901 CTCTGACTAG AAATTATTTG GAACTTATGG TAGAACTTCC TTGGAACAAA
20951 AGTACAACTG GTAAGCCAAA AAATAACACC TGTTTTGCAG TCTAATTGTC
21001 ACTCAGAAAG CTCATGCAAT TTTTCATTTC AAATTTACTC CACTGATTGT
21051 CGTACTGTTA AATTATTTTT GTTTTCAATT TTTTTGAAAC CATTTTATTG
21101 AAGTGTGATT GTCGTACAAA AAGCTGTATA TAATTAATGA ATACATCTCA
21151 GTGAGTTTCA GAATAAGTAT ACACCCATGA AACCATCACA ATCTTCATAG
21201 CCATAAACAT ATCCGTCACC TCCAAAGTTT CCTCCTACCT CTTTTGTGAT
21251 TATTATTATC ATCATTATTA TTGGCTTTTT TCTTTTGGTG CTGGTGGTAA
21301 GAACATTGAA CATAAGGTCT AAATGTTAAAT TAACAATATT GTTAGCCATA
21351 GGCACTTTTC TTTATAGTAG ATCTCTAGAA CTTATTTATC TTGCATAAGT
21401 GAAACTTTGT TCCTTTAAC CATCACCTCC CATTTCCTTC TCCTCTCATC
21451 CTGTGGCAAC TACTAGTCTA CTCTCCATTT CTATGAGTTT CACTATTTTA
21501 GATTCCACAT GCATTAAATA GGTGAAATCA TACAGTACTT GTCTTTCTGT
21551 GTCTGGCTTA TTTCACTTAG CATGATGCCC TCTAACCTAG AGGTCCATCC
21601 ATGTTGTCAC AGATGGCAAG ATTCCTTCT TTTTTAAGGT GCATAATATT
21651 CCATTGTGTG TCTATACCAC ATTTTCTTTA TTCACTTATG TGTCAGTAGA
21701 CATTTCAGTT ATTCCGTAT CTTGGCTATT GTAAGTAATA CTGCAGTGAA
21751 TACGGAAGTG CAGATAACTC TTTGAGATCC TGATTTCAGT TCCTTTGGCT
21801 GTTTACCCAG AGGTGGCATT GCTGGATCAT ATGTAAGTTG TATTTGAACT
21851 TTTTTAGTAA CTTCCATACT GTTTTCATAA TGGCTGTTAT CGGGGGACCT
21901 GCCCCAATAA TCATGTAGGT TCTTTTCTAT TTTCCTAAGC ATTGGCTGGC
21951 TTGAGAAATA AAGACACAGA GTACAAAAGA GAGAAATTTT AAAGCTGGGT
22001 GTCTGGGGGA GACATCACAC GTTGGTAGGA TCCGTGATGC CCCACAAGCC
22051 ACAAAAACCA GCAAGTTTTT ATTAGGGATT TTCAAAAGGG GAGGGAGTGT
22101 GCGAATAGGT GTGGGTGACA GACATCAAGT ACTTAACAGG GTAATAGAAT
22151 ATCACAAGGC AAATGGAGGC AGGGCAGAT CACAGGACCA CAGCTCCGAG
22201 GCGAAATTAA AATTGCTAAT GAAGTTTCGG GCACCATTGT CACTGATAAC
22251 ATCTTATCAG GAGACGGGGT TTTGAGATAA CGGATCTGAC CAAAATTTAT
22301 TAGATGGGAA TTTCCTCTTC CTAATAAGCC TGGGAGCGCT ATGGGAGACT
22351 GGAGTCTATC TCACCCTCTGC AATCTCGACC ATAAGAGACA GGTACGCCCC
```

```
22401 GGGGGGGCCA GTTCAGAGAC CTACCCCTAG GTGCGCATTC TGTTTCTCAG
22451 GGACATTCCA TGCTGAGAAA AAAGAATTCA GCGATATTTC TTCCATTTGC
22501 TTTTGAAAGA AGAGAAATAT GGCTCIGTTC TGCCCGGCTC ACCAGCGGTC
22551 AGAGTTTAAG GTTATCTCTC TTATTCCCTG AACAATTGCT GTTATCCTGT
22601 TCTTTTTCCA CGGTGCTCAG ATTTCATATT GCACAAACAC ACATGCTGTA
22651 CAATTTGTGC AGTTAACGCA ATTATCACAT AGTCCTGAGG CCACATACAT
22701 CCTCCTTGGC TGACAGGATT AAGAGATTAA AGTAAAGACA GGCATAGGAA
22751 ATCACAAGAG TATTGATTGA GGAAGTGATA AGTGTCCATG AAATCTTTAC
22801 GATTTATGTT TAGAGATTGC AGTAAAGACA GGCATAAGAA ATTACAAAAG
22851 TATTAATTTG GGGAACTAAT AAATGTCCAT AAAATCTTCA CAATCCACGT
22901 TCTTCTGCCA TGGCTTCAGC CGGTCCCTCC GTTGGGGTC CCTGACTTCC
22951 CGCAACACGC TGTACCAATT TACATTCCGA ACAACAGTGT ACAAGGGTGC
23001 CCTTTTCTCC ATATCCTCAC CTTCACTGAT GATGGTTTTT TTGTTTGTTT
23051 GTTTGTTTTT TTAAATAATG GCCATCCTAA CAGGCATAAA GTGCTTTCTC
23101 ATTGTGGTTT TGATTTGCAT TTCCCTGATG ATTAGTCATG ATAAGCACCT
23151 ATTTGATTTT TTGCCGTTAA GTTTCATGAG TTCCTTGTGT ATTTTGGATA
23201 TTAACCCCTT ATCAGAAATA TGGTTTGCAC ATATTTCTG CTGTTACATA
23251 GGTTGCCTTC TCATTTTGCT GAACTTTTTT TATTCTGTAC AGAAGCTTT
23301 CAGTTTGATA TAATTTCACT TGTTCATTTT TGCTTTTGTT GCCTTGACTT
23351 TGGTGTCAAT ATCCAAAAAT ACCATGCCCA GACCAATGTC AAGGAGCTTT
23401 TAAAATATAT TTTGTTCTAG GAGTTTTACA GTTTCAGGCC TTACATTTAA
23451 GTCTTTAATC CATTTGAAT TAATGTTTGT ACATGGTGTC ATATAAGGGT
23501 TCAAGTGCAT TCTTCTGCCT GTGGGTATCT GGTTTTCCCA CAACATTTTC
23551 TTGAAGAGAC TGCCCTTTCC CTATTGTATA TTCTTGGTGC CCTTGTTGAA
23601 AATTGGTTGA CCTTCTAGGT AACTTTATAG GTTTATTTCT GGGCCCTCTA
23651 TTCTATTCCA TTGGTCCGTG TGTCTGTTTT TGTGCCAGAA TCATACTCTC
23701 TGATTACTGT AGCTTCGTAA TATAACTTGA AGTCAGAAAG TCTGGTGCCT
23751 CCACGTTTGT TCTTGCTCAA GATTGGTTTG GCTATTCAGG GTCTTTTGTA
23801 ATTTCTTATT AATTTTAGGA TTTTTAAATC TATTTTTGTG AAAAATGTCA
23851 TTGGAATTTT AATAGGGATT ACATTGAACT TGTAAATTGC TTGAGTGGT
23901 ATAGACATTT TAACAACATT CTTCTAGTCT ACGAACATGT AATATCTTTC
23951 CATTTATTTG TGTCTGACTT ATTTCATCAG TGTTTTATAA TTTTTAGTGT
24001 ACAGACATTT TACCTCCTTG GTTAAGTTTG TACTTAAGTA TTTCATTCTT
24051 TCTGAAACTA TGTAAATGA GATTGTTTCC TTAATTTCTA TTTATTTATT
24101 TATTTTTTTG ACAGGAGTTT CACTCTTGTC GCCCAGGCTG GAGTGCAGTG
24151 GCATGATCTT GGCTCACTGC AACCTCTGCC TCCCAAGTTC AAGCGATTCT
24201 CCTGCCTCAG CCTCACGAGT AGCCTAAAT ACAGGCACCT GCCATGACAC
24251 CCGGCTAATT TTTTGTATTT TTAGCAGAGA CGGGGTTTCA CCATGTTGGA
24301 CAGGCTAGTC TCGAACTCTT GACCTCAAGT GATCCACCTG CCTCGGCCTC
24351 CCAAAGTGCT GGGATTACAA ACGTGAGCCA CTGGCTCTGG CCCTTAATTT
24401 CTCTTTGGAG AAAGGTTTTT TTTTTTTTTG AGCTTTATTG AAGTGTAATT
24451 GACGTACAGT AAACTTCACA AATGTAGTAT GTACATTTTG ATGAGTTTTG
24501 ACTTACATAT ACATCTGTAA TACCATCACC ATAATTAAGA TAATGAGCAT
24551 AACCCTCACC TCCAAAAGTT TCTTCCATGCT CTTTGATAAT CCCTTCCTTC
24601 TTCCCCGCCC CTTTCCTCCT TGCCTCCTAA TCCCCAAGCA ACCACTAAAG
24651 ATTAATCTGT ATTTTCTAAA ATTTCATATA AATGGAATCA TAGAGTAATGA
24701 GCCCTTTTT CTGGCTTCTT TAATTCAGCA TGATTATTTT GAGGTTCATC
24751 CATGTTGCTG TATATAACAG TAATTTGTTT CTTTTTATTG CTGGAGTTGT
24801 ATTCTGTTGT ATGGATATAC CATCATTTGT TTATCAATTC ATCTGTTGAT
24851 AGACATTTGG GTTGTTTTCA GTTTTTTGGC TATTAAAAAT AAAGCTGTCT
24901 CGGCACAGTG GCTCATACCT GTAATCCTAG CACTTTGACA GACCAAAGTG
24951 GACAGATCAT TTGAGCCCAG GAGTTTGAGA CCAGCATGAG TAACACAGGA
25001 AGACCCCAAC TCTATTTAAA AAAATAAAAT AATAAATGAA ATAAAAATAT
25051 TTAATAAAAT ATCAAAAAAT AAAGCTACTG TGAACTGTGG TAGTAAATTT
25101 ATTTTTAAAT TTATGTAATG TTTGCATGTG GTGACAAAAT ACTGCCTTTT
25151 AGTTGAAAGG AAACATTTCT TGGTACTCTG AGATGCCATG TGTGTCAGCA
25201 CTAGAGATGT GTAGCAGCCA TGTATCCATC ATGAAAATAA TTCCATTGTT
25251 TAGCATTGCA CATAGCACAA AGAACTGAAG ATGAATAAAT TATGGTATAA
25301 AAGGAGTCAT GTTAAGCTCC TAAACCATTA CTACACAGGA TTATGTCTAG
25351 ATAATTGTCA GTGTGGTTAT AAAACCATGA AAATGCCCATT CATATATATA
25401 TTTTTGAGAT GGAGTCTGGC TCTGTCACCC AGTCTGGAGT GCAGTGGTGT
25451 GATCTTGACT CACTGCAGCC TCCGCCTCCT GGGTTCAAGC AATTCTCCTG
25501 CCTCAGCCTC TCAAGTAGCT GGGATTACAG GCGCTTGCAA CCACACCCAA
25551 CTCATTTTTG TATTTTTAGT AGAGACAGGG TTTCACTACA TTGGCCAGGC
```

FIGURE 3A-8

```
25601 TGGTCTGGAA CTTCTGGGCT CAAGTGATCT GGCTGCTTTG TCCTCCAAAA
25651 GTGCTGGGAT TACAGACCTG AGCCACTGTG TCCAGCCTAA ATATCTTTGT
25701 TTGTTTGTTT GTTCGTTTTT TGAGATGGTG TCTTGCCCTG TCGGCCAGGC
25751 TGTAGTGCAG TGGTGTGATC TCAGCTCACT GCAACCCCTG CCTCCTGTGT
25801 TCAAGTGACT CTCCTGCCCT AGTCTACTGA GTAGCAGGGA TTACAGGCGC
25851 CTGCCACCAT GCCCAGCTAA TTTTTGTGTT TTTAGTAGAG ATGGGGTTTC
25901 ACCATGTTGG CCAGGCTGGT CTCGAACTCC TGACCTCAAG TGATCCTCCC
25951 ACCTCGGCCT CCCAAAGTGT TGGGATTACA GGTGTGAGCC ACCGAGCCTG
26001 GCCCCCCATT CATAATTTCT GAAAGAGAAG TTTACCTACC AAGTAGAGAT
26051 CTCAGATAGT AACCGAAAAC AAAAAGGAAA GCAGAGAGGA AAGAGTTGTA
26101 GGAAATATGT TTGCAGATTT TCCAGCTTA GAGGAGTCAG TAGATACCAT
26151 TTCAATCTTC TAATTATAAA TAAGGAAATT TATATTGAAA TTTGAAAAAT
26201 TTTTTACATG TAATCACATG TTATTCAAAA CAGGAAGCAT GCTTTCTGAA
26251 TCATTAACAG GAATAATTAG AAAAATATAT CCTGTATAGA AAAGATAGAA
26301 AATAATTTAT ACAGCATGGA AATCACCTTT ACTTAAAGA TTGAAAGAAC
26351 TTTTAAAATT GTCTTTACTT GGCATATTTC TTGCAAGAAA TTTCTTCACA
26401 GTGTTTTCAG TCTTTTCTAA ATTATCTTGA CTTTTATTCT TACCTTACTG
26451 AATGTGTTAA TCATGAATGG ATAACGCATT ATAACAAGTA CCTTTTTAGG
26501 TACAAGATGA TATTTGATG GAAACTTACT CTTCTTGAAC ATGATGACAT
26551 TGATGACCTA ACACTGAACC ATGTTTGCAT AACTAAAATA AATCCCACTG
26601 GGACTTAGTA TATTATTCTT TATAGATTTG ATTTACTAGC ATTTTAATAT
26651 TTACAGCTAT ATAAAAAGAT TTGTCTGAGG TTTTCTTTTA TGTTTACTGT
26701 GGTAGGTTTT AGTGTCAGGG CTAGCACTGT GAAACAATTG AGAAACTCTC
26751 TATCTTTCAC TTCTTCATAT ATTCATTGGT TGGGTTCTGG AGCCAGGAAA
26801 GGGGAAGAA ATTTTAGTTG TTCTTCTCCT ACTTCACTCA CCTAGGACTC
26851 TGACTAAAAT CAATAGTACT ATAATTAAAT TATATAGTTT ACTGCTTAGC
26901 TAGGTTTTT GGGGACTAG CTTGGGAACC AAATTACCAT CTCAGCCAT
26951 TTTTTTCCTT TATGAAATAT CCTTAGCAAA TTCTAAATAA TTAATTAAAA
27001 GATATGTATT AATTAATTAA AAGATTTCTG TGTATTTCTC TCTCCCATCT
27051 TCTTCTTTCA CTGCCAGCAT GATCAGGTGG CTGTGTATTA TACCCTGGCA
27101 GCCACCCAGC TAGTGAATTC ATTTTGGCTT CTGTTACCTG GTGTTTAATC
27151 TGAGTATTTT AAATGCTAAA TCTTATTAGT AAACCTGTTG AAAGCTTGCC
27201 TCTAGAAACA AAGCCTAACT CATACACTTC TGGTGAGACT TTGATACAAC
27251 TTTCTGTGTG GCAATTAGGC AATTCTTTAC ATCATCTGTT TTTTTTTTT
27301 TTTTTGACCC AGCACTTCTG TTCATAGAAG ATAAGCTGAA AGAAATCATT
27351 GCAGATATAT GGGAAGATTT AGTTCCAGTG ATGCACAGTT GAAGCATCTT
27401 TTATAAATGT AAAGATGTGT AAACAACTTG AATGCTCAGC AGTAGGGAAT
27451 TAGTTAAATG AATATAGATA ATTTAGTAAT GGAACATTAA GTAACCATAG
27501 AATGTTACTG ATAAATATAT GTGTGACAGT GAAAGTTGTC TGTCATATAT
27551 TAAGTGAAAA AAACATTTTA CAAAACTTAA AGCCCCCATA AAATCCCATT
27601 TTGAAAAATA GGTTTGTAAA TGCACGCACA CAGCCTGGAA TTACACATAC
27651 TGAAGTAAG GTAGTGGTGA TCTCTTGGGG GCATGAGATT ATGGGTAACT
27701 GTTTTCTTCT TTTCTGTTAG TGTTATCAGG TTTTCTGGAA TGAACATATG
27751 TTACTACTGA AATAAGGAAA AAAATCACCC TTTTTTTAA AAAACAAATG
27801 CCAGCACACA TACAATATGT AGAAATTAAG AAGTAATGCA TAACTAGAAA
27851 ATCATTCCAA ATAAAATGAT ATGAACATTG AGTTTTTAAT TGTGTAGTGC
27901 CTACTATCTC TGGGGACACT AAGTCTTAAG CAGAGAAACC AAACAAAATG
27951 CAGATCTCCT AGAATCCTCA TCTAGAAAGA TCCAAGTCTG TTCTTATCAC
28001 ATCTATTTTC AAAAAAAATA TTTTGCCCTC GTCATGCTTG AAAGGAGTTC
28051 TTTAACTTAA AAATTTTATG TGTTCTAATT ATTCTGTTG GGTTATTTGA
28101 CAGACCGCCT GGACATTAGG GCAGCCCGGA TTCTTCTGGA TAATGACCAT
28151 TACGCCATGG AAAAATTGAA GAAAGAGTA CTGGAATACT TGGCTGTCAG
28201 ACAGCTCAAA AATAACCTGA AGGGCCCAAT CCTATGCTTT GTTGGCCCTC
28251 CTGGAGTTGG TAAAACAAGT GTGGGAAGAT CAGTGGCCAA GACTCTAGGT
28301 CGAGAGTTCC ACAGGATTGC ACTTGGAGGA GTATGTGATC AGTCTGACAT
28351 TCGAGGACAC AGGTAGAACA CTTCTCTCAG TTTAATCTCT GATTCCTCTT
28401 TCTTTTTAAT TGACTAGAGC TCCCTAAAAG CTTAGGCATA GCATACATCT
28451 ATTTTCCTTA AAGGGCTATG TGTGGTACCT TGAATGAAAA GGACATTTAC
28501 AAGAAGTATC AGCTAGCCTA GAGCCTCTAA GCGTAATGAT AAACCCAAAC
28551 TAACCTTGAT TTGTATGACA GTGGATACTA CTCTGTGCCT CAACTTTCCT
28601 GGAATCTCTCA TTGAATGTAA TTATAAGTTA TTTATGATTG GATATTATTA
28651 TGTCTTTACA CTCTTTTCAA CCCAGTAGCA TGCCATAAAT AATGATCCCT
28701 AACTCTCAGA GTTAAAAAAA GTAACTGCAA TAGGGAGGGC CAATGGGAGG
28751 AGGTGAGAAG TCTTTGATAA CAAACTTGTT CTGATTGCAG TCTAAACTTC
```

FIGURE 3A-9

```
28801 CTCTTATGAA GGTTGGTTTG TATTATGAAT ATGAGTAATA AGGATAAATG
28851 TTAGCATAAT TATTAAGGCT TATTCTTGCA TTTTGGACTC ACTTTCTATA
28901 AAAAAACAAT AAACTGTAAG AACTGTCCCT CTAGGCTGGG CACAGTGGCT
28951 CATGCCTGTA ATCCTAACAC TTTGGGAGGC TGAGGTGGGT GGATTGTTTG
29001 AGCCTAACAG TTTGAGACCA GCCGGGGCAA CATAGGGAAA CACTTTTGTC
29051 TCTACAAAAT TTATATTTAA ATTTTTTAAT TTAAATTTT AATTTTTGTC
29101 TCCACAAAAA TTAAAAAATT ATGCAGGCAC AGTGGCATGC ACCTGTGGTC
29151 CCAGCTACTC AGGAGGCTGA GATGGGAGAA TCATTTAGGC CNNNNNNNNN
29201 NNNNNNNNNN NNNNNNNNNN NNNNNNNNNN NNNNNNNNNN NAACCAAGCG
29251 GCAAATAAGG AAACTTTGTC TTACACAAGT AAATTTACTT CTTCATTTAC
29301 ATTAAATTTG GTTCCACAAA AATATAAAAT TAAGCTAGGC ACAATGGCAG
29351 GCCTTGTGTT CCCAGCTCTT AGAAGGTCTA AATGGAGTAT CATTACGTCT
29401 TGAAAGTTCC AGTTTGCAGT AACCCATATT GTCCCCTGGC ACGCCAGCCT
29451 GGAGACAGAG ACATTATCTC AAACAAACAA ACAAACAAAC AACAACAAAA
29501 CTGTTTCTGA TTAATCTGAC ATTATTAGAA TCAGATTTGC ATGTTGCATT
29551 CATTGTTCTC ACTGGTCTCT TTGTTGATCT GATGGAAATT GCCTTGGGAA
29601 AGCATGAATT TACATTTCGT GGTTAAGGG ATTCATAGCA ATTGTAAGTT
29651 GTGAGAAAAC ATACCTATAG TGTATGTGTT AAAGAACATG TTTAAATGTA
29701 GGAACCATGA ACTGCTTATA AAAGAATATG ATCCTTTTTT AATATCTTGT
29751 TTTCTATTTG CCTTATTCAA AGGGATCCCT ATCCATAGAC AGGGATGGGA
29801 AACTGTTTCA GAAACTTTTC TATAAGAAAT GGTTATTTTT ATTCTCTTTT
29851 ATTTGCTCAC TTAAAATTCT TACGCATTTA AAAAGTATCA TTACTGGCCT
29901 TGTGTAGTAG CTCATGCCTG TAATCCCAGC ACTTTGGGAG GCCAAGGCAG
29951 GCAGTTGCTT GAGCTCAGGA GTTCAAGAAC AGCCTGGGCA ACTTGGTGAC
30001 ACCCCATCTC TAAAAAAATA ATAATAATAA ATTTTAAAAA AGACTCATCA
30051 CAAGATTTTA GTAAATAAAC AATGAGGCGT GCAGATCAGA GTAGAGAATT
30101 GATTTGGGTG ATTTCTTCTG GCAATTTCAA AAGATATTTT TGTTGCCTAG
30151 ACTTCTTATT CTTGCATGTA CCACTAGAGG CTATAGTTTG CTTTCGTAAA
30201 GGAATTGGCA TTTCTCTTGG ACCAAACTCA AAGAAGCTGC GTCTAGGGCC
30251 TAAATCTTCT AATTTTAGCT ACAGAGTAAG TATTGATGG CATTTAGAGA
30301 GTGAGTTCGT GGAATTAATG CTATGTGAAA TTGACATCAT AAGCACGTGA
30351 CATGTAGGTA ATTTGTTCTT ATTTCTTTTC ACATTGGTAT TGATTATTTG
30401 ATAAGGCTTG GAAAGCACTT ATTCAATACC TGACACACAG TGAGCATTCA
30451 CTAAAAATTA GCTTTAACCA TTATTTAAAT TCTATTAATA AATTCTCAGG
30501 AGGACAAATT TAGATTTACA AGCTTCAGTA TGAGTTTTTA TAAATTTCAA
30551 TCTGATTTTT TAATTGCCTT CTAAAATATT TATCCTATTC TCAGCATTAT
30601 TACTTAATTT ATACGGCAGA ATTATGGGAA AATGCATTTT TCTGTTGCCT
30651 ACTAATGGAC AGTGTATAGT GTCATGGTTC TCACCACTTA CAAACATCAC
30701 TGGATTAAAA TAAATCTCTA TTTTAAATCC TTACTGACAT ATAAAATTTG
30751 TTCTTTTTTT CAAGTGAATA TGCTTTTGTG TATGTGACTG TATTAAGAAA
30801 ATTGAGTCTG AAGAAAATAA GAATTGACTT TATGGGTCTT TTGTAAAAGG
30851 AGGTTGTGTT ACAATCACCA TTGCCTAAAA TATTTGTAAA TATAACCTTT
30901 TTAGAAAACGT ATATATGGAG GCTGTGATTG TTGCCCGAGTA AAAAGTATAA
30951 GGATTTGTTT TGTGAATCAT TCTATTCAGC CTGATTTTAG ATACACCTTG
31001 CTGGTAAGTG TTACTTAGCC ATCAGTGTAC CAGATGTTTG ATTAACTACT
31051 ATAGCAACCT GCCCTTGTC TGTTGGGGAC ATATTACCCA TCTACCCCGT
31101 GAATTATTAA AGCCTGGTCA AAAATTTTAT TTCAAACCCT GTTTGGAAGC
31151 ACGTGGAGAG TAGTGGGGTT CAGTTGTTGA GGAAAGGGTG AGGGCAGAGC
31201 ATGCACTTAG GTCAGTTATG AATTGAAGGT GAATAGGAGG AGGAGAGAAA
31251 GAACAACCGA CAATTCCAGC ACAACCATGG GTGTGCCTGG GGAACATGT
31301 GGTTCCATGT GACAGTTGAG GCATTTGGGA GACAACCCAG GTCTTGACGT
31351 TTGAGTACCG GTCACATGCT CACAGTTAGA GTTCATGAAA AGTTTTGTTT
31401 TTCCTCAGCC TTTGAGTAGG CACCACTGTT CCGCAGCCTT AGAATAGCCA
31451 AGGAAAAAGA AAGCCAGGGA AAAAGAAAGC TGCTTTGTTA TTGTCCTTGC
31501 TTATCCTCTC GATTTGCCA CTCACTCTCC CTGTTTTCCC ATGTGTGGAA
31551 CACTTTCCTT TTGCTAAAAG TACCTGCGTA TGAAGAAG GATGCCGATA
31601 AGTTGGGGAT TGATTTTAAA AACAAGCAAA GATATGTTTT TTATGGTTAA
31651 ATGATAATGA GGTGGGAGAT GGGAAGCAA AAGAGGCT TGCCTTAATA
31701 TTTAATCTTA AACTTGGAAA ATAATAGTCA TCTGACTAAA CATTGCCTCA
31751 TTTTTGTCTG TATTGTTTG AGTAGCTTAA AGGAAGAATA ATGTTTATGC
31801 TACGTATTAA CTCATTCAGT TTTTCAGTCT TTTCGATATT TCTCATTTGG
31851 ATTTATCTCC ATTGTGATTT TTCTGTCCAC TTTGTAAGCC ACAAAATACT
31901 CATTCCCTTC TATCAGTTTT AACAACTTAA ATTTTTATAT TTAAGTATTA
31951 CATTTAAATA ATTTAAGTCA ATTCACACAA ATATAAGGTA ACTAACTTCT
```

FIGURE 3A-10

```
32001 TTTAAGATGA AGTTTTATGA AATAATGTTT GCATAATTGT TTTTCATTTG
32051 TTCTTTGGTA AAAAGAAATA ATATATTATT GTTATGATAT ATCTTAAATC
32101 ACTGTGGATA TTAACTCCTA GAAATACTTT ACCAGCTGTT TACTTAGATA
32151 ATAAAATTAT ATTATTGCAA GAAATCCTTG TCTCAACTTT CAAACAAGAT
32201 GAGAAGAAAA ATGAACTTGT GATTCCACA TTGATACATT TTCATATGCA
32251 ACCTGAAATG GTAAGTTAT AAATAAACTA TTTCATTATT AGTTTCTACA
32301 AGGGAAAAAT AACTGAAGCA GCAAGCTTCT AATGTATTTT TTTAGCATAG
32351 TGTACCAGAT ATATTATGGT TTGCCCACTA TCCTTTCAAC TTACATTTGC
32401 ATGTAGCTCT TCTTTGCCTC TCCAAAACTT AGGTTTATTT TAAGCCCTCA
32451 ACCCAAGGCT TCTCCATTA ATGTAAGTGC AGTCAGTTAT GATTCACTC
32501 TTCTCTAAAC TGACCACCTA TTGTGCTCCT TTATCGAATA CGGGCCTCTG
32551 GCATTTCTAC CATACAACTG TGGAGATGAA ACATAAATAC GTTTATAAAA
32601 AGTACAAGCT TTCTCAGGCA GGGGATTTAT CGTCTATCTC CTTTATGTAC
32651 CCCATGATGC TTATTTAACA TGGTGCTAAA TGTGGTGAGC GCTCTCTGGG
32701 TGTTTGTGA ATTCATGTAA GATTAAAACA TAATATTTTG GAAGTTATGC
32751 AACCCTTTAG ACGAGTACAC CCATACAAAT TAGTCTATAA AAAGATTTAG
32801 GAATGACTAC CAGAAGAATA ATTGCATTTG TTTAGACATG CTATTATACA
32851 TTAAAATCCC AGTTTCTTAA AGACTGTTTT TCTTTTGAG ATCATTAGGA
32901 TCTTTTTTAA ACTGATTCCT TTTTCCAGTT TGAGATACAC ACACACACCC
32951 ACACACCCAC CCACACCCAC ACCCACACAT CCACACACCC TTGGTAGAAA
33001 ATGTGAAAAA TAAGGGGAAA AAATCCTCAT GTTTTTCTAC CGTACAAAGA
33051 TAATCACTGT TAACATTTGT TTGTTCTGC CAGACTTATC ATTGGATTTT
33101 AAGTAACAGA ATTGTAATCC TGTCATTTTC ACTTAACATT GTAACACTTA
33151 AACTCTTTTC TATTCCAAAT TCTTTGTAAA TTTTATTTTA ACAGTTTGCA
33201 TTATAGCCTG CGGGAGCCGA GCCCTTTAAT TGAATAGGTA GGAAGAGTGG
33251 ATGGTGAAAT GCCTATATTT TTCTCTCTTG TCTGCTATAA AAGACATTTG
33301 CAAAAGTTGC TTCCATGAGG CAGAAATTGA AATGGGACTC AAATTCAGGT
33351 GTACTGAATT CTGCTCTTGT GCTTTTTCCA GGAAACCAGA AGTAAACTTT
33401 AAGTAGCTGT TGCTAATAAT GATGAGCATC ACTGGAAAGC TCACTGTGTG
33451 CCAGGGACCG TGCTGTGTGC TTTGCCTGTG TTCTCTCATG ATCCTTATAT
33501 TAATATAACC CACCAGGTTG ACACTATTTT CCCATCTTA TAGGTGAGGA
33551 AACTGAGGCT TAGGTCAAGT AATTTGCCCA AAATAGTATT CAGAGGCTTG
33601 TACTGTGTTA CCTTTAGAGT GCTGATGGAA AGATGCTTTG AGTGCTGGCA
33651 CGGTGGATCT GGTGGGGAAC AATCTTACAG CTCTATATCT AGCCTCTACT
33701 CTGTGGTAAG ACCCCGTCTC TGTCATAAAA GTGCTCACTG GCTCTATAGA
33751 GGAGGTTATT ATACCCATGA ATAAAAACTA GGTTGTAAGT AACCATCAGA
33801 TGAGTTATGG GGCCAGTAAG TGCTGTAGAC ATTGCATTAT TAGAGCGATC
33851 CCTTTGTGAG AGGTAGTCAG AAAAGTTTC TTAGAATTGT TGGGATTTAC
33901 GTAGCAGGAA GAGGAGTATT AAGGGCAGGA AGGCACCATA TTTTTAAGAA
33951 AGGTAAAAAT TTTTAAGGGG CGTAATAGTA TCTTGATTGT GGTTGAAGCA
34001 AGAAAGTAAT GGCAGCAAGT TGGGAAGATG AATGGGAGCT GGATTGTGAA
34051 AAGCCTCGAA CTCCAGACAA AGGAATTTGA ACCTTATTCT GTAGGCTCTG
34101 GGAAGCAATG GAAAGTGTAA GAGGAATTGC TTATATACAG TGTGAGTAGA
34151 ATCTAGGATT CCAATTTTTT TAGAAAGGGT GCCTACCTAG AATATTATTT
34201 TCTCTCTGTG ACTTCAGGTG TAGAATGTC AGTACTTGTT TTTGAAGTTT
34251 ACTCATCAAA AAAGGAAAGG CAAATAAATA ACTGCAGCAA AAAATGACCC
34301 ATTAGAGCCT TTGAGATTCT TTAAAAAAAT TCCCTTCCCT ACCACTCTTA
34351 AAAATCAGAG TAATGGCAAA TCTGTAAGTT CTCTAGAAAA ATAATTGGAA
34401 AGAATTTATA AATTCTGAGT CTGGTCTTTC CTGTATCTGA TTCTGAAATC
34451 TTGAATGTGC TAATTCCTTA TATTAACAGG ACAATGTTTA TTGCCTTTGC
34501 TTCCCTGTGC CTTAGTCACC TTTCCCGGAT GAAAGGCATT CCCATGATAT
34551 TTTTAAGGCT TGCTTGCCTT TTCAAAGTTC ACTCTGTTTA TTCTGTCCTA
34601 CTTTATACCA GTCATGTGGC AGAAATCAGG CCTGCTCTGT GAATCGGCTT
34651 TGTGCAGATC ATGAGGTAAC TGTGGCTGTT CCACTTGTCA TTGATCATTT
34701 TCTTCTCGGC AGTCAGGCTT TTATGCCTTT TCAGAGACAG CATTTGCTTT
34751 GCACAACATA GACAGCAGGG TTATAATTAA AATTAGTAAA TTGCTGCTTT
34801 AAGTTTTGCT GGCTTTGTAA AAAGACACC TTTTTTGGTT TGATAAACTT
34851 ATGTGTTTTT ATTTCATGCC ACACTCTACA TCTGTCATAA TTATGTGGGT
34901 GATTCTTGTC CAAATACAAT AAAGCAGGCT CTCACATTTT AAGCGTTCAAC
34951 AAAATACCTG GCTGCTGAA CGTGGTTATT GCCAATTAGT GCATATGGA
35001 TGAATACAGT TTTGTTCAAA AGGACAGAAT AATGGAATTC TGATATAAAT
35051 ACTGTTGACC CCAGATCCTT ATACTATAAT TAATAGATTA TTTCCTCTGA
35101 AAATAAAAGA GATTGGAGTT TTTCTTTTTT GTTGTTGTTT TTGGTCTGCA
35151 TTCTGAGTGG CTGTTTGAAC TGATTTTAAT TTCCTTCATG AAGATGATGA
```

FIGURE 3A-11

```
35201 TGTTTTAGCT GGCCCAGGGG CAGCCATTTC AGTGTGCATA AAGGTGGTTG
35251 CGTTGGGTAG GGGGATGCTC AGAAAAATCA TGGAAAGCAT GGGAATTCAT
35301 AGGGTACTTT GGACATTTTG GAATCTTGAA GAGTAAGAAC CGTAACTGGT
35351 GACTTAAGTG TGTGTTTCT TCATTTCACC AAATGGCAAA ATGTGATACA
35401 GTTCTTCCAA TATCATGGGC AACTTGTAGC CAGAATTAAG TAGAAGATAA
35451 GATTAGAATT GAATATAATA ACTTTTGATT TATCATAGTG CCTTTTAAAT
35501 ACATAGTACC TCTTTGCTAT ATTATAGTGA TAGCTAAATG ATCTTTTCAC
35551 ATTCCTAAGT TTTGATTTCT GAATGGCGTC GCTCCTGCCT CCTGACATCT
35601 CACACTGTGA ATGTGCTACT TGCTTTCTCT AGGCGCACCT ATGTTGGCAG
35651 CATGCCTGGT CGCATCATCA ACGGCTTGAA GACTGTGGGA GTGAACAACC
35701 CAGTGTTCCT ATTAGATGAG GTTGACAAAC TGGAAAAAG TCTACAGGGT
35751 GATCCAGCAG CAGCTCTGCT TGAGGTAAGA TTTGGAAAAT TCCCTGTCTG
35801 TCTTCATACT GGAAGAGTAT GGAGGAGGGT TGATAATCAT ATTCAAGTGA
35851 TATACACAGT GGTGTAGCTT TAGTTATGGG AAAAACAGTT TGATACCGGC
35901 TGAGGTCTGA GCAATTGGC ACTAAATTA AAATGTTTT GAGATTTCTT
35951 TCACTAAGTC CCCTTTTTT TTATTTTCCT TTTGTATTTT AATCAGATAG
36001 TTTAACAAAG TTTTGTGCAC ACTTATTATC TAGAGGCCAA CAATCTACA
36051 CAGTTATGGC AAAAAAAACA GCAAGCAAGT CTCCTTCTCC CTGGGGTCCC
36101 CCATGCCTTC TTCTGCACTT TGACCTCTTC AGCTTTTAGT TGATTAACCC
36151 TATTTTCAAA ATAGCATGGC TATCTTGCAC TTCCTGATTT TTTTTTTT
36201 TAGTTTTTGT CATTTCTAT AGATGCCCC CAACAGGAGG TGAAGATTTT
36251 ACCTTTTTTC TTCCGTTGTC CCCACTGTAT CATTTTTATA CCTTAGATCT
36301 CGCAATAAGA ATTTTTTTCT TGTTTTTTG TGTTTTTT CTTGTGAATA
36351 CTAATACATC CATATTAGTA TTTACATTAT TATGATTATG TAAATGCTTT
36401 TCACAGCAGG AGCCACATGG TAAACTGTGA TCACTTTTCC TGTTCCTATT
36451 TTTGTTTTTC TCTACTTTTT AAGAATATTT TCAGAGTTAG CTGTCTTGTT
36501 TCTTTTGTTT ACTTTTTCAC CAATCGTCTA ATTCTGTCAA GACCTTCAGA
36551 CACTTTAGGT GTCTATCCA TTTTATCTTC TTAAGCGTCC GGTCTGAACT
36601 GGTTGTTTTT GACATCCGGT TTTATGGCTT CCTTCCTAGG TTCTCCCTTC
36651 ACCTCTCACC ATGTTGGATT TCCTGTCTCC TGTATTCCAT TTCTTGCTCT
36701 TTCTTGGTCC ATTCCCTCAT TTTGTGGTG TTAACTCCCT GATAGTTTCC
36751 TGAGAAAGCT TGCATGAGTG GTAAATGTTT TAGACTTTGC ATATCTGAAA
36801 ATGTCTTTAT GTTCCCTCA TACTTGATTA GTAATTTGAG TAAAGAATTC
36851 TGGTTGGAAA TAATTTTCT ATAGAATTGT ACTTTGCCCTC CATTTTACTT
36901 CACTTTCCCA TTTCCAGTGT TGCTGTTGGT AAAACTGATT CCATTCAGTT
36951 CCTATCCTTG CAGACCTGCT TTACCCTGAA AACTTTCAGG TTCTTCCCTT
37001 TATCCTGGGA TTCTGAAATT TCCTAATAAT CTGCCTTGGC ATGGGTTTCT
37051 TTTCATGCAT TTTTGCTCAT TCTTTCTTTG AATTCTTCCT GTTCTTTGGT
37101 TCTAAAATTT TTCTTAAATT CTTTTATTGA TGACTTTTCC CCTTTATTTT
37151 TTGGAACTCC CATGACTTGG ATATTATGTT TCAGACTTAT CTTTTCTCTC
37201 CTATTAGTCT CCACTTTTAT GTTTTGCTCT ACTTTCTGTG CAGACTTTCT
37251 CAGATTTATC TTTTAAAAAC CCTCTGAATT TATTATTCA AAAACTTTCT
37301 CTGCCATGTTC TTTTATAGTA TCCTGTTCTT GTTACATAGT TGTAATATAT
37351 CTTATCTCCA TGAGAAAGAT ACTTATAGAT ATATTTTAAA ATTTACTTC
37401 TCTGACCACT TGGTATATTA AAAAGAAAAA GAAAAAAATT ACTTCTCTTT
37451 AAGCTGCTTT TATCTGTTTA TTATATATT CTTTTAGTCT CTTTTATATT
37501 AGAGTCTTTC ATTAGATATC TGGACATTTT TGTTTGTGTG TTTATATTTA
37551 ATAGTAAGGG ACAAAAAGGC TGATTGGAGG CTATGAGCAT AGGAGTGGGG
37601 CTTATCAACA GTGAGTTCCA CAATAGAGTC AGCTGGCTGT GCTGTTTGGT
37651 TGAGGAATCT TCTACTCAAT AGCTTTAAGT CTTCCTTCTT AGGATGGTCA
37701 GATTCCTCAG AGAAGACTTC CTGTCTCTG CCTTGAGAAT GAAGGCCTGG
37751 CTGCCATCAT TCTGGGAACC AAGCAGGGGA AGAATGATTG GGTCGGGGG
37801 TATCACTGCA TTCAGCATCC GTGTATATGC ATTCACCTGA GCTCTTGTTT
37851 TCAGCATAGT ATATGTTCTT ATCAGCTGTG CCCAGGGTCC CCTGTGCAGA
37901 GAACCACTGT TTTATGTTCT TAAGAAAATA AACTTCCAGT GTTTGCTGG
37951 GGTGGGGGAG GGGATCTGGG ATCTGACTGC TTCCTAAATT TATTTCAGCC
38001 AGTCCTCCTT ATTTTAGCAC ATCAGCCCCT CCTCCCTTTT ACCCTTGCTT
38051 AAAATATTAT TAATGCAAAT TGATTTGTAA AATTGAGGAA AACTTACTTT
38101 GTGAAAGTTT TTATTTTTTT CTTGTTTATT TCGTGCTTT GAGCTGCCTC
38151 GTGCTTCCTG TTTTTTTTCT GTTTTGTGA TCTTAGAACA GGATGGCCTG
38201 GGACATGTGT CTTATTAAGC AGGAGACCAT ACATTCTGGT TTGCTTGGCA
38251 CATTCCCAGT TTATGCCTAA TATTAATTGC ACTCTTTTTT AGTCTCAGAA
38301 GTGGGTTTTG TTTGGACGAT AAAAAGTAC AGTTACCTTA CTAAAAGCC
38351 CTGGTATTTG GAGGTAAGGG TTTGATTTGG TTCAGTTTTG CTACTTTTTA
```

FIGURE 3A-12

```
38401 TTGTAAGATC ATTACCTTCT GGCTCCATAA CTGGTTCTTT TTACTATGAA
38451 GAGTAAAATA GTGAACATTA TTTAAGATTT TAGTAGTTTC TTATATAATA
38501 TCTTTAGACT TTCAGTTTAA TTTATATTGG GACATTTTTT CAGGTTATCT
38551 GACAGATTCT CCCATTAGAC ACTTACAGTT ATCCTGTTGA AAATAATTTT
38601 AGAGTATTCC CCTGACACTT AAATTTTTTC AACAACTGTT TTGAAGCAAG
38651 TTCACCAAAG ACAGCTTTAC AAGTAGTAGT AGATGATTAA GTCCCCTGTT
38701 TATTTGTTCA GTTGATAAAC AATATGTTTT AGGTCTTCAC CTATATATAC
38751 TTTGTAATGA TTCAATAATA TTTGTTAAAT TGATCTTTGA TAACAAGCAG
38801 CTAGCATAAT GATATTTTCT TGTCTGATGT AGACCTTGGT ACTCACTTTT
38851 TTGGCAGTCG ATTTATTAGC ATTCAAAAAA AAGGTATGAA AACCTCAAAT
38901 GATATCTCAG AGTAAATGCC CCCTGGGCCC ACGTACTAAT CACTGTAGTT
38951 TAGTTATGAA TAGCATTGGT TCCTTACAGA CTGTAAATGC TATAAAATGA
39001 AGCAAGACAT ACATATGGAG GAACTGAGTA TCTTGGTAGC TGACAGCCTC
39051 TTCCTCCCTG CTTGCCCAAG TCCTGGGTAA AAACCTCAGA CCTCACAGAT
39101 TGTTGAAACA ATTAAATAAC AGTACATATT AAAGCACTCT ATAAATGGTA
39151 AAGTACTGTA CAGATGTTAA TTTAATATCC ACTGATATTT CTTCTGTGTC
39201 CATTTTGAAA GCCACTTGCT GCTTCCATTG CCAGTAGGTT CACTTAAATT
39251 TAAAAAAAGA ACAAACTCAA TTACACAACA CGTTACATTT AAAGTGAATA
39301 TTCCTGAGAG TTTGGAGACC CAAGTATAGT TTTATTATCT TTCTACATAG
39351 AAAACCTGCT TTTAAAAAAT GATATCTAGA TATTATTTGT AAAATGTATA
39401 AGATTATTTT ATGTTTAAGC TAATTATATT ATTAAGGTAA TATAGCCCAG
39451 ATGTGAAGAA TGTAATAGTA GATGTAAATA TACACTAGAG TGCTTACTCT
39501 GAATAAAGAA TAAACTTTTT CTGCTGTGTA TTCTTCTTTT TATTTATGTA
39551 GGATATGCCC GTTTCCTTGA CCTACCATGT AATTGTTGCT TATGTAAAAC
39601 AGAATGTATT TCAAGTTATT ACTTAATATT GTCCAAAAAA GGAGAATTCA
39651 AAATTTAGAT GATCTCTTTT GAAAATTTAT TGGAAGACTA TAAAAATAGG
39701 TCCAACTACT TAATTAATAA ATGGTGGTAG GCAGTAGAAT TTGGGCAAGT
39751 CTATAACTGA GTAGCACTAA AATATTAGAT ATAAGGAAAG TAAGGGCTTG
39801 TATGTAATTA ATAGACTTGA AAGAAAATTA CAGAATTATT TTCTTACCAG
39851 ATATATGTTA TATTTATAAC TGGCACATGT CCAGACTTTA TTGTTAAATA
39901 TGAATGCATA TCTCAAATAC ATTTTTGTGT GAGTGGGCAA ATAAAATGCA
39951 TGGATACAAT AATTAATTGT CTTTATAGGC AATAATATTT ACAGTTCGAA
40001 AAACATATAT TCCCCAAAAT AGAGAAGTCA CTAGTCTAGA TATAGTAAAC
40051 TTCCTTTAAA ACTGAAGTTC TTACTTAATT CGAATTAGAT CCAGTTAGTA
40101 ATTAGACCAA TAGTATATTT ACTACTTAGA TACAGTAGAC ATGATCTTTT
40151 GATTTGAGCT ATACAATTAT TGTCAAAGAA TGTCAGAAGA GAGGGACTTA
40201 GACATCATCT AATCCAGCTT CATGCTCTTA AGGATAAAAA GCTTAAGGCC
40251 TAAGATATTA TTTTAATTTC TTATTTCACT ACATGCTATA TTAATGATAT
40301 AATTTCCAAA TATCGAATGG AGTTAAAAAA TGCCTTAAAT AAGGCATACC
40351 TTGTTTTATT GTGTTGTGCT TCATGTGACT TCACAGACTG TGTTTTTTTA
40401 ACAAATTAAA TGTTTATGGN NNNNNNNNNN NNNNNNNNNN NNNNNNNNNN
40451 NNNNNNNNNN NNNNNNNNNN NNNNNNNNNN NNNNGGGCAC CCGTGTATCC
40501 CCAGCCCCTC GGAAGCTTGA GCCAATAACA ATACCTTGAC CCGGGGAGGC
40551 AGAGTTTGCG GTCACCGAG GGGGGGGGGG GGCGTCGCAA CCTGGGTTAC
40601 AAACCAATAC TCTTTCTCCC GTCCCCGACA AAAAAAAGAA AGAAAGTGTT
40651 TATGGCAACC CCGTGTCAAG CAAGTCTGTT GACACCATT TTCCAACATC
40701 TTACTTCATG TCTGTATGTC ACATTTTGGT AGTTATTGCA ATATTTTTAA
40751 CTTTTTCATT ATTATATCCT ATTATGATGA TCTGTTATCA GTGATCTTTG
40801 GTATTGCTAT TGTGATTGTT TTGGGGCACC ACAAACTGCA CCCATATAAG
40851 ACAGCAAACT TAATCAATAA ATGTTGAGTA TGTACTAACT GCTCAACTGG
40901 CCAGGCATTC CCCTTTCTCT CTCCCTCTCC TCTGGCTCCT ATTCCCTGAG
40951 ACACAGCAAT ATTGAAATTA GCCAAGTAA TAACCCTGCA GTGGCTTCTA
41001 AGTGTTGAAG TGAAGGAAG AGTCACACAT CTCATTGTAA ATCGAAAGCT
41051 AAAAATAATT AAGCTTAGTG AGGAAGGCAT GTTGAAAGCT AGGCTCTTG
41101 TGCCAGATAG CCAAGTTGTG AGTTCAGAGG AAAAATTCTC AAAGGAAATT
41151 AGAAATGCTA TTCCAGTGAA CACACCAATG ATAAGAAAGT GAAATGGCCT
41201 TATTGCTGAT ATGAAGAAAG TTTTAGTGGT CTGGATAAAA GATTAAGCCA
41251 ACTACAACAT TCCCTAAAGC CGAAACCTAG TCCAGAGCAA GGCCCTAAGG
41301 CTCTTCAGTT CTATGAAAGC TGAGAGAGGT GAGAAAGCTG CAGAAGAAA
41351 ATTTGAAGCT AACAGAAGTT GGTTCATGAG ATTTAAGGCA AGAAGCCATT
41401 TCTACAACAT AAAGTGCAAA GGGAAGCAGC AAGTACTGAT GTATTGTAGA
41451 AGCTGCATCA TGTTATCTAT CCAGAACATC TAGCTAACAT CATTGATAAA
41501 GGTGGCTACA CTAAAAAACA GATTTTCTAT GTAGATGAAA CAGCCTTATT
41551 TTGTATTGGA AGAAGTGTCA TTTAGGACTT TCATGGCTAG AGAAGTCAGT
```

FIGURE 3A-13

```
41601 ACCTGGCTTC AAAGCTTCAA AGGGCAGGCT AACTCTTGTT AGGGGCTAAT
41651 GCAGCTGGTG ACTTTAAGAT GAAGCCAGTG CTCATTGACC ATTCTGAAAA
41701 CCCTAAGGCC CTTAAGAATG ATGCAAAATC TACTCTGCCT TTGTTCTGTA
41751 AATGGAACAA CAAAGCCTAG GTGACAATGC ATCTGTTTAT AGCATGGTTT
41801 TACTAAGTAC TTTAAGCCCA CTGTTGAAAC TTACCGTTCA AAAAAAATAG
41851 ATTCTTTTGA AAATATTACT GCTCGTTGTC AATGCTTCTG GTCACCCAAG
41901 AGCTGTGATG GAGATGTACA AGGAGATTAA TACTGTTTTC ATTCCTTATA
41951 AAACAACATC CATTCTGCAG CCCATGGATC AAGGAGTTAT TTTAACTTTC
42001 AAGTCTTATT ATTTAAGAAA CACATTTTTT AAGGCTATTG CTCCCATAGA
42051 TTATGATTCG TCCCATGCAT CAGGGCGAAG TACATTGAAA ACCCCTAGAA
42101 AAGATTCACC ATTCTAGATG CCATTAAGAA CATTCATGAT TCACGGGAGG
42151 AGGTCAAAAT ATCAACATGA ACAGGAGTTC AGGAAGAGTT GATTCCAGCC
42201 CTCATGGATG ACTTTGAGGG GTTCAGACTT CAGTGGAGGA AGTTACCGCA
42251 GTTGTGGTAG AAATAGCAAG AGAACTAGAA TTAGAACCCA AAGATGTGAC
42301 TGAAATACTG CAATCTCATG GTAAAACTTG AACAGATGAG GAGTTGCTTC
42351 TTACAGATGA GCAAAGAAAG CGGGTTTCTT GAAATGGAAT CTAGTCCTGG
42401 TGAGGATGCT ATGAACCTTG TTGAAATGAC AACCTTGATG TTGTGAACCT
42451 TGTTGAAATT CTAAACAAGA TTTAGAATAT TACATAAACA TAGTTGATAA
42501 AGCCAGCAAC AGGGTTTGAA AGGATTGACT TCAATTTTGA AAGAAATTCT
42551 ACGGTGGGCA AAATGCTATC GAATAGCAAT GCAGGCTATA AGAAATTGTT
42601 TCATGAAAGG AAGAGTCAAT AGATGAAGCA AATTTTACTG TTGCCTTATT
42651 TTAAGAAATC GCCACAGCCA CCCTAACTTT CAGCAGCCAC CACCTGATCA
42701 GTCATCAACC ATTAATATTG AGACAAGACA CTCCACCAGC AAAATGACAA
42751 CAACTAACAC TGAAGACTCA GGTGATTAGC ATTTTATAGC AAGAAAGTAT
42801 TTGTTAATTA AGGCATGTAC ATTGTTTTTT AGACATAATG CTATTGCACA
42851 CTTAATAGAC TATAGTATAT TGTGTAAACA TAACTTTTAT ATGCACTGGG
42901 AAACAAAAAA AAACATACAT GTGACTCACT CTGTTGCAAA ATTTGCTTTA
42951 TTGCAGTGGT CTGGAACTGA ACCCACAGTG TCTCTGAGGT ATACCTGTAT
43001 TGAGGAGGGG TTGCAAATTT TAGCACATAG GCAAATTTGC AAATATGGAA
43051 TAATAAGGAT CAACTGTAAT TACTGCTTTA TGCCATTATC TTTTAAATCA
43101 GATAAGAAAA AGTTACGTCA ACAATATATT TACACTGCCT TTTATGTTTG
43151 CAATGTAATC ACTTCTGCCA GTGCGCTCTA TTTCTTTGTG TGGATACTGT
43201 CTAGTGTCCT TAAACTTCAG TCTTTCATAT TTCTTGTCTC ATCTCCTGGT
43251 GACATATTCT CAGTTTTTGT TTTTCTGGGA ATGTCTTAAT TTCTCCTTCA
43301 TTTTTGAAGT AATTTTGTTG GTATAGAATT TGGGTTGACA ATTGTTTGCT
43351 TTCAGCCCTT TCGCATGTCC TCTCACCACT TTCTGGTCTC TGTGGTTTCT
43401 GCTGTGAAGC CAGCTGTTAA GCTTGTGGCG GATCTCTTAT GCCTAATGAG
43451 GGCAGCATTT TTCTCTCATA GTTTTCAGTA TTCTCTCTTT GTCTTTCATT
43501 TCTGACAGAT TGACTGTGTT TATGTGTGAT CCTCTGAGTT TACTTAGTTC
43551 TTTTTGAGCT TCTTGGATGT GTAGGTAAAT GTTTTTCATC AAATTTGAGA
43601 AGTATGTGGC CAGTATTTCT TCAAATATTC TTTATGCCCC TTTCTTTTTC
43651 CTCTCCTTCT GAAACTCGTA TTATGGTGTG TTGGTAATCT TTGTGGAGTC
43701 CCGTAGGTCT CTAAAGTGCT GTTCACTTTT TTTAAAGCCT TTTTTCTTTC
43751 TATTCTTCAG ACAGGATCAT CTCAGTTGAC CTGTCTTCAA GTTCATTGAT
43801 TCTTTCTTCT GCCAGCTGAA ATTGTCATTC AGCCCCTCTA GTGAATTTTT
43851 CATTCAAATT ACTGTAGTTT TCAACTCCAA AATTTCTATT TTAAAATTTT
43901 TATTATTTAT CTTTGTTTAT ATTCTCTATT TGTCAAGACA TCATTCTCAT
43951 ACTTTCCTGT AATTGTTTAG ACATGATTTC CTTTAGTTTT TTTAAATGTT
44001 AGTAAATATA ACAGAAAAAG TCCCATTTTT ACCACTTTTA TGTGTACAGT
44051 TCAGTAATGT TAAGCACATT CGCATTGTTG TGCAGCCAAT CTCCAGAACT
44101 TTTTCATCTT GTTAAAGTGA AGGTGTATAC TCATTACACA GCAATTCCCT
44151 GTTTCTTTCT CCCTCCCTCA GTCCCTGGCA GCTACCATTC TCTTTTCTGT
44201 TTCTATGAGT GACTACTCTA TATACCTCAT ATAAGTGCAT CATACGGTAC
44251 TTATCTTTTT ATAATTGACT GACTTCACTT AGTTCCCTCA AAGTTCATCA
44301 ATGTTGGGGC ATTAGTTTTT TAAGCATATT TATAGTAGCT GATTTGTAAT
44351 CTTTTTTTTT TTTTTTTGA GACGGAGTCT CACCATGTTG CCCAGGCTGG
44401 AGTGCAGTGG CGGGATCTTG GCTCACTGCA AGCTCCGCCT CCCAGGTTCA
44451 CACCATTCTC CCGCCTCAGC CTCCCAAGTA GCTGGGACTA CAGGTGCCTG
44501 CCACCAGGTC TGGCTAATTT TTGTATTTT TAGTAGAGAT GGGGTTTCAC
44551 CATGTTAGCC AGGATGGTCT CGATCTCCTG ACCTTGTGAT CTGCCCGCCT
44601 TGGCCTCCCA AAGTGCTGAG ATTACAGTCG TGAGCCACCG TGCCTGGCCG
44651 CTGATTTGTA ATCTTTATCT AATAAATCCA ACATGTCTTC CTTAGGGATG
44701 GTTTCCATTG ACTTCTCTTT TTCTTTTTG AGACAGGGTC TCGCTCTGTC
44751 ACCCAGACTG GAGTGCAGTG GCGCACTCAT GGCTCATGGC AGCCTTGACC
```

FIGURE 3A-14

```
44801 TTACCCAGGC TCAAGTGACC CACCCACCTC AGCCTCCCGA GTAGCTGGGA
44851 CTACAGGCAC ACACCAGCAT GCCTGGCCAA TTTTTTGTAG AGACAGGGTT
44901 TCGCCATGTT GGCCAGGCTG GTCTCGAACT CCTGAGCTCA AGCAATTTGC
44951 TCACCTTGGC CTCCCAGAGT ACTGGGATTA CAGGCATGAG CCACTGAACC
45001 CAGCTGACTT CTCTTTTTTT TTTTACTCT TTAGGGCCGT ACTTTTGTAT
45051 TTCTTTGTGT GTGTCTCATA ATTTTTTTG TTGAAACTGA ATATTTAGAG
45101 TGTTATATTT ATATTAAATA CAGTCAGATA TATAATTGAA TAATATAACC
45151 TTAAGGGTTT TTTGTTTGTG CTGTTGTTGT TGCTGTTTGT TTAGTGACTT
45201 TCTGGTTTCA TTCTGTAAAG TCTGTTTTAT TCATTAATGT GTGACCACTG
45251 AAGTTGCTCA GTTTGTTTAG TGGTCAGCTA GTGACCCGAC AGAGATTTCC
45301 TTAAGTACCT GGACAGTAGC TCTCCCACTC CTTGCCCAAG GGGCTCTTAT
45351 GTGTGTATTG AAGTGGGCCT TTCACACTTT GGCAGATGGT TTACAACTCT
45401 GCCTTAGCCT TCACTTCCTG CTTTTGCAGA GCCTCAGTGT CTGCCAAAGA
45451 TGAGCTTATA GGGCCTTCTC AGGTCTTTCC TGGATATACT TAGAGCCTGC
45501 ACATTCACAT GAAATTTGG ATTCTCAGGC ATATGTCAAG GCTTTTCAAA
45551 GTCCCCATGA ATATCTCATT TCCAGTTTT TCCATTTAAG TTTTTTGGTC
45601 AGCCTCTTGT TAGTCCCAAC TAGTTTCATT GCCTCAGGCA GCTGCAGGTG
45651 TAAAACAGTT GCCACTGGTT GTTTTTGGCA AATGTCCTAA GGATAAAACT
45701 GTTCTCACAG AGTGTTCTCT GAGTTAAGTC AAATAAGGAT ATGGAGCTCT
45751 TCTAAGGAAC TGCCAGAGTC AAACAGGGAC AGTTCTCTGG GGATGGGGCT
45801 TTTGAAGGAT TGTAATCCTT TTCTACCCCC TAACAGGATT GCTAGGCTAC
45851 TGGTTTTCAC AGCTACTGGG GTTATGAGGC TGTTGATTTT GCTACCATGA
45901 ACTTGAGAGA AAGGGATGAG TGTAAAGCAA GTTAAAATAT CACAAAGCTC
45951 GTTCTGTTTA TTGAGATTCA GCTGTTTTTC TTGAATAAGC ACTCCTCAAA
46001 TTGTTGCAAG TTAGTATGTA GCATTCTGAA AAAGTTGATT TTGACAATTT
46051 TTGCTAGTGC TCTCATTGCT TTTCTGGAGG AGCAGATTTT CAGAGTTTCT
46101 TACTCTACCA TTATATAATA GAAGTGCTTC CTCCCCCATT TCATTTTGAT
46151 TCTGTGCTTG AATGATTTCA CTGCATGCTT CTGATACTTG TATTTTGGTT
46201 TATCACTTGT TCAGATGAAA TATATCTTCA GGTTACTTCA TTCAAAGATT
46251 TGTGTGTGAG TTGTATTTTG AATCTCTTCT ATATTTGAGA AGGCTTCTTT
46301 GTTGTCTGCA CCAGTAGTAA TATATATGTA AATAAAATAA GAATGTATTA
46351 GTCTTCTTCT TTTTTTTTT TTTTTTTTT GAGACGGAGT CTTGCCCTGT
46401 CACCCAGGCT GGAGTGCAAT AGTGCAATCT TGGCTCACTG CAACCCTCGC
46451 CTCCCAGGTT CAAGCGATTC TCCTGCCTCA GTCTCCTGAG TAGCTGAGAT
46501 TACAGGCACG TGCCACCACG CCTGACTAAT TTTTGTATC TTTAGTAGAG
46551 ATGGGCTTTC ACCATGTTGG TTAGGCTGGT CTCGAACTCC TGACCTCGTG
46601 ATCCATCCGC CTCGGCCTCC CAAAGTGCTG GTATTACAGG CATGAGCCAC
46651 CGCGCCCAGT CAGAATGTAT TAGAATGTAT TTCTTAAGAC TGCCATAACA
46701 AAATACCACA GACTGGGTAG CTTTGAAGAC CAAACAGAAA TTTATTTCCT
46751 TATGGTTTTG GAGGCTAGAA TTCCAAGACC AAGGTGTTTA TAGGTTTGAT
46801 TTCTCCTAAG GCCTCTCTCC TTGGCTTACA GACAACCGAC TTGTGGCTGT
46851 GTCCTGGGA GACCTGTGTG CATGCATCCC TGGGGTCTCC TCTTTCCTCT
46901 TATAAGGGTA CCAATTGTAT TAGACTAGGG GCCCACTCTT ACCTTCATTT
46951 AACCTTAATT ACCTTCTTAA ACACCCTGTC TCCAAATACA GTCTTCACCC
47001 TGACTGCCCT TGAGACAGAG CGGAGGGGT TAGGGATTCT GTCAATTTG
47051 AGGGGGCACA ATTCAGTCCA TAACAAAGGA CATATATAAT AGATACATAA
47101 TATATATGTA CCAGTGTGCC CATATCATGT ACTTTATGTA AAACGAAATC
47151 AGTTTTAAAA GGTAATTATA TTTTCAATGA AAGCACTGTG TTCTAATTAG
47201 ATAATTGTTT TTACTTCATA ATATGTCTAT CCTAGCTTAT TATATAAATA
47251 AAAGTGTCAA CTCTGTTATT TTCTTGTGGT TCATACCTTT GCCTATACCC
47301 TTTTTAATGA TACTTGCAG GAATCTTTTT AAACCACTCA ACCCATTGT
47351 AATATTAGGC TCTGTGAACC CGGAAAATTT GAGACAGGTC TCAGTTAATT
47401 TAGGAAGTAT ATTTGGCCAA GGTTGAGGAC GCGCGCCCAT GACACAGCCT
47451 CAGGAGGTCC TGACGACACG TGCCCAAGGT GGTCAGAGCA CAGCTTGATT
47501 TTATACATTT TAGGGAAGCA TGAACGGTCA ATCAGCATAT GTAAGGTGAA
47551 CATTGGTTTG GTCTGGAAAG GCAGGACAGC TCTCTGGAGA GGGCTTCCAG
47601 GTCACAGGTA GATAAGAGAC AAACCCTTGT GTTCTTTTGA GTTTCTGATT
47651 AGCCTTTCCA AAGGGGGCAA TCAGGTTTAC CTCAGTGAGC AGAGGGGTGA
47701 CTTTGAATAG AATGGGAGGC AGGTTTGCCC TAAGCGTTCC CAGCTTGATT
47751 TTTCCCTCTA GTCTGGGTGAT TTTGGGGGCC AAATATATTT TCTTTTCACA
47801 GCACACATGG ACAGCAATGT GCTGTAATTA TAGTTAAGCC AGATAAGTGA
47851 GGACACCACA GGCAGCCTTC GACCTTATGG AACTTCTTCT AAGTGAAGAC
47901 ATCAATTCCA TTTTGGATAT TAAATATTTA CAAGCTATTT TTTTCTGGTA
47951 TTTATAAATA AAAAAGATAA ATACAAATAC TAATATTTTC TACTTGCACT
```

FIGURE 3A-15

```
48001 TTGGTGGGTC ATTTTCCACT TTTGTGACCA CTGGTCTAAA TAGATAAACA
48051 AATGTCTTCA CAAATGGGTA GTAGGTTCAC AGGTGTTCAT TTTGTTATTA
48101 TGCATCATAT CTTATATATA TTACATATAT TTGATGTATT CAAGATTGTA
48151 AAATATTTTA AACTAGTGAT AATTTTGCTT GAAAATTCTG TAGGTGTTAT
48201 TCTAATGACA TTCTCATTTT TATTGCACAG GAGGAGGAAT CTAAATCTTT
48251 TCAATCTATA GTGTCAAGGT CTTCTAGAAT ATTTTCGTTT CTTTAATCCC
48301 TATTTTAATT TACTGAGACC TCTTCTTTAG TTATATTAAC CAGTTATGAA
48351 TTGTATCTCT TAATTTTTCC CGTATTTATC CCCTACATGT CTCTAAAGCC
48401 CTTTTTCTTC TATGTCCTGA ACACTTTTCT CAAGTTTGTC TTTATCACAG
48451 ATTTAATTTC CATAGTTGAG GATATAGAGG AAAAGTAAAC TCAGTTTCTC
48501 CTACTGCACT CTCACAACAC AGAACACCTC TGACCAAATG CACGGGTTTT
48551 TTCTCCATAT GCCAAGCAAG CAGTTCTTCA GCAACCGACC ACAGCTGGGT
48601 GTCCTCTAAT TCAATTCTGA CAAAGTGTAT CAGATCCTAC GGGTTGAGCA
48651 CTGAGTCCCA CAAGACTGCC TCCCCCTTCA GATGCCAGTC GTGAGTTGAC
48701 TTCCAGAACG TGTGACCAAC CAGTTATAAA TTGGAGTACC CACAAGCCCC
48751 CCTCCTCAGG TTTGCTTAAT TTGCTAGAGT AGCTCACAGA ACTCAGGGAA
48801 ACAATTTACT TGCATTTACT GGTTTATTAA AAGAATATTT TAAAGAATAC
48851 AAACAAACAG CACAGGAGCT TCCATCCCAG TGAAGTCAGG GTCCACCAGT
48901 CTTCTTGCAC CTGGGTGTGC TCAAATTCAC CTTCCTGGAA GCTTCCTGAC
48951 CTCAGTCCTT TGGGGTTTTT AATGGAGGCC TTGTCACATA GGCTCGATTG
49001 ATTAAATCAC TGGCCATTGG TGATCAACTC AACTCTTAGC TCTTCTCCCC
49051 TCCCAAGAGA TTGGGCTGGG GAACTGACAA GTCCTCAGCC CTCTAATCAT
49101 GCCTTGGTCT TTCCTGTGAC CAGCCCACAT CCTGAAGCTG TGGAGGGACT
49151 GCCAGCCACC AGTCAATCAC TAACATACAA AATGATACTT ATCACTTTGG
49201 TGATTCCAAG GATTTTAGGA GTTGCATGTC AGGAAACAAA GAGATGAAGG
49251 CCAAATATAT ATTTTACAGT ATCATAATAG TATTAATTGT GTGTGGCTTT
49301 CAGAGCTGAT TTTAGTTATG TTATTTTATC TTTATTTTCT GTTGTGAAA
49351 ATTTCAACCA TAGCAAAAGC AGAGAAGATA GTATAATGAA TTCTGTGGAC
49401 TCATCACCCA GCTTTAATAT CTTGTTTCAT CTATTGCTTC CCATTCTCCC
49451 CTACCCAACC TCTGATTATT TTGAAGCAGA TTCCAGACAT CATCTTTTCA
49501 TAAATGTTTC AGTAGCTATC GACAAAAGAT ATACACTTTT AAAAAGCATA
49551 ATCATACTAT ATCACACCTA AAGATGACAG TTACCTAGTC TTGTGTAATG
49601 AACTCTATGT AATCTATTCC TGGATTGCCT ACAGACATCT ATAGTTCTTC
49651 TCTTGTCAGA AATTATTATT GAAGAATAAT TCTCAGTGTA CATTCCTCCC
49701 ACGGTTCATC CCATTGTGAC TTCACATTCC TAGGAATAAT GGGTCATATC
49751 ACAGCTATTT CCATTCCCAG TCATACTTTG TAGGTAGGAA TTATAGTCCT
49801 AGGATTGATA CAGAAAATCT TTTAGTTGGG GAGAATAAAG GAGAAACAGC
49851 CCTAATTATT TTTGAAAGTG GCCCTGGATG TGGGCAGTAG AATCCCTGCT
49901 CTGAAGTTAG GGTAAGAAGA TGAGGTTTGA TAGCTACAAA GCTCTTAATT
49951 GTAATTTTCG TCCTTCCATG GACTCACCAG TTTGCCTCGG AGCTTCATCT
50001 GAGTAGTGAT TACCAGAAAT TATTTTCTGC CAGAATATTG ATCAGTATTT
50051 CTGATGCTGT TTAAATTCTA TATGTCTTTT TATGCTTTTG AAAACCAGAA
50101 AGTATCTGAG ACAGGTCTCA ACCAGTTTAG AAGTTTATTT TGGCAACGTT
50151 CTCCAGAGAT GATTGTGAGG GCTTCAGTAT TTAAAGGGGA ATGGGCAGAT
50201 ATTGGGGAAA GAGGAAGAAA TTTTAAAAGG TATGAGTAGA CAAGAGACAA
50251 ACGGTTGCAT TCTTTTGAGT CTTTGATCAG CCATTCACCT GTGAGAGGGG
50301 AGCAGAGGAA TAGTCACTGA CGCATTCATC TAGCTTAGTG AATCTGCATT
50351 TCTACATAAG ATAAAATAAA TATAGCGTAC AGGAAGCCAT CAGATATGCA
50401 TTTGTCTCAG GTGAGCAGAG GGATGACTTT GAGTTCTGTC CTTTGTCCTG
50451 TATGTGTAAA GAATAAGCTA TCAATTTACA TGGTTGGGGT GAAATTCAAC
50501 AGAACTGTTA CAGGTTAAAG ATCTTGGGGC CTACAAGGAA TTTCTCAGTG
50551 GGGGATTGT GAGGGAGATA TGTAGCTTTT TTGTCTTTG TAGCTATCTT
50601 ATTTGGAAAC AAAATGGGAG GCAGGTTTGT GTGACGCAGT TCCAGCTTG
50651 TCTCTTCCCT TTGCTTAGT GATTTGGGGG TCCTGAGATT TACTTTCCTT
50701 TCACACTCTT CCTGAGTAAA AGAGGAAGGC AGGCAAATTG GGCACAAATT
50751 TAGCCTAAGT CTGCCTCCTT ACATATTAAT ATTTTAAGTT TGGCCTAAAG
50801 GTTTCCCCTT ACAAAGTAAA CTGCAGCCTA ACTAGCTGTG TAAACACACT
50851 ATTCTTAACA CCAATCACAG ATTTTCAGCA AGTCACAGGA AGTCAGCTGT
50901 TAACAAACTT TAAATAAAGC AAACACCAAG CTGTAAGCAA TCCCGCTGTT
50951 TCTGTACACT CTTTGTTTTC TGCATGTCGC TTTCCTTTTT CTGTCCATAA
51001 ATATTATCAA ACCATATGCC AGAGTTTCTC TGAACCTATT CTGTTTCTGG
51051 GAGCTGCCCA ATTTGAGACT TGTTCTTTGC TCAATTAAAC TGTTAATTTA
51101 TCTAGAGTTT TTCTTTTAAC AAGCATCACT AATTTTTTCT CCTTATAATC
51151 TAGGTATTCT GTCACACTGT TTTAAAAACC TCCTTCATAA TTCAGAAACA
```

FIGURE 3A-16

```
51201 TTGCTTTATT AATTTTCCTA CTTTTTAAAA ACGCTAGTGT CTTAAAATTT
51251 TAAGAGAAAA AAATTACTTG TTCAAGTCTG ACAGCCATTT CTAAAACATA
51301 TCCAGCATAT ATGAATTACA TATGCTTAGA GCCATTAAAG AATAGAATTT
51351 TTTCCGGCCA GGCATGGTGG CTCATGCCTG TAATCCCAGC ACTTTGGGAG
51401 GCCGAGGTGG GCAGATCACG AGGTCAGGAG ATCGAGACCA TCCTGGCTAA
51451 CATGGTGAAA CCCCATCTCT ACTAAAAATA CAAAAAAGTA GCCGTGCATG
51501 GTGGCGGGCG CCTGTAGTCC CAGCTACTCG GGAGGCTGAG GCAGGAGAAT
51551 GGCGTGAGCC CGGGAGGCGG AGCTTGCAGT GAGCCGAGAT CGCGCCACTG
51601 CACTCTAGCC TGGGCGAAAG AACGAGACTG TCTCAAAAAA AAAAAGAAT
51651 AGATTTTTTT CCTTAGCTAG TGTTAAAAAA TTACTCATGA CGCTTATTAA
51701 AGGTGGTAAG GATTACTTTA TTCAAGGTGG GAGACTACGT ATAAGAAACA
51751 CTGCAATGGG GTTTTGCAGT GACAGGAGGA GAGTGAATGG GGAATCAGTA
51801 GAGGGAAACA TTCTAAGAGG AAGAATTGGG GTTACGGGGG ATTCTCACTA
51851 GAAGGACACA ACAGAACTCT TGCTGAAGGG AGGCCAGGGT GAAAGATAC
51901 TGGGTTAGAA GTGAGAACAG ATACGTATGG GTATGGGTCA TTTTTGCTAA
51951 CCTGACTTAG CAGGATTCTT GCTCAAATTG GATTTTACAA AGACAGAGGG
52001 AAGGCTGACA TTGGCTAGT TGAGCAGAGG ACTCAGAGGA GCCTGACTCA
52051 AGTTTGCGTC AAAAGAAGAG CGTTTTTGTC ACTAGATGAT GGTTTTAACT
52101 ATTTTCCATA CATAAACATT TTCCGTACCT AAACAGTTTG TTTGTTCATT
52151 TGTTTGTTAG TTTGTGTTGG ATTTTCACTC TGTCGCCCAC GCTGGGAGTGC
52201 AGTGGCGTGA TCTCAGCCCA CGGCAACTTC TGCCTCCAAA GTTCAAGCAA
52251 TTCTCATGCC TCAGCCTCCC GAGTAGCTGG AGCTACAGGC ATGTGCCACC
52301 ATACCAGGCT AATTTTTGTA TTTTTTTTA GTAGAGACAG AGTTTCACCA
52351 TGTTGGCTAG GCTGGTCTCA AACACCTGAC CTCAACTGAT CTGCCTGCTT
52401 CGGCCTCCCA AAGTACTTGG ATTACAGGTG TGAGCCACCG TGCCCGGCCT
52451 GTGAACAGTT TTTAGATGAT TAGTAGAATAG TAAGACCACT CTTAACCAAT
52501 TCAATACTGA ACATAATTAG TTTTCCTTGA TTACTTGAAA GTACTTGTTT
52551 TTTAATGATA TTAAACATTA TTAAGTCTTG TGAAAATGTG AAATTAGAGC
52601 TTTCTGGGAA TTCTAGATAG AGTTTCCAGT AATAATTAAT GTTAACAAA
52651 ATTCAGAATT ATGTATGAGG CCTAGAATTA AGACTAGCTT GGGGCTGGGC
52701 GTGGGTAGGGC ACGTCTGTAA TCCCTGCACT TTGGGAGGCC AAGGCAGGTG
52751 GATTGCTTGA GGCCAGGAGT TGAGACCAA TCTGGCCAAC ATGGTGAAAC
52801 CCCATCTCTA CTAAAATTGC AAAAATTAGC CAGGTGGGGG TGGTACGCAC
52851 CTGTAATCCC AGCTACTCAG GAGGCAAAGA TGTAGTGAG CTGGAGACCA
52901 TGCCACTGCA CCTCAACCTT GGTGACAAAA TGAGACTCTG TCTCAAACAA
52951 AACAAAACAA AACAAAACAA AAAACTAACT TTGGATAGTT TTGAAAATAA
53001 GTAAAACTTC AGAAAGAATC AGAAGGTAGG AAAAACTGCT TATATAGTTA
53051 AATTGTGTT GGTGAGTATA TTAGTCATTT TATTGCCTTT TTGAATATGT
53101 ATGGCAACCC TATTTATAGT AATTGGGCGT AAGTGAGAGT GTTAATATGT
53151 TTAAGGTTTG GAACATGTAG AAGCTGTTGG TGCCTTATGA AAGTTCTGCA
53201 CCAGCCCCTT AGCAACAAGT GCCTGTGACT TGAAGCTCTT TAATGTACAG
53251 TTGCACATTT TAAGAATCCA AGTTGACTGA TAAATTATCT AATGTATCTA
53301 ATTCAAATAT TTTTAAGAGC TATTGTAATC CCAGTACTTT GGGAGACTGA
53351 GGCAGGCGGA TCACTTGAGG TCAAGAATTT GAGACCAGCC TGGCCAACAT
53401 GGTGAAACCC CATCTCTACT AAAAATACAA AAGTTAGCCA GGCATGGTGG
53451 CGCACACCTG TAGTCCCAGC TACTCAGGAG GCTGAGGCAG GAGAATGCT
53501 GGAACCCGGG AGGCGGAGGT TGCAGTGAGC TGAGATTGTG CCACTGCACT
53551 CCAACCTGGG CAACAGAGTA AGACTCTGTC TCAAGAAAAA AAGAGTTATT
53601 GATGTTTTGC TTATTATAAG CAGCAATGTT TTGTAGTAAG CCATTTTTAA
53651 ATAGTGAATT TTTGCTGTA TCAGAATATA GTAGCATAGT AATTTTTACT
53701 CTTATTTAAC TCATAGCAAA GGTTACTCTT ATTTGGAATT CTCCTTTCAG
53751 TTAAATAATT TATACCAGAC TTTCTGAAAA TGTTTGAGGA GGATTATATG
53801 GGTTCTTATT TACTGGTTCT TTGAGAATTT CAAAATACTT TACACATTTG
53851 CTTTATATTC CCATAGCAGT TTAGATAGGG TGTGTTACCA AGATGGAAAC
53901 TGGTTCTGCA GGACTGGTAA CTTATGATGG CCAAACAATG AGTCATTAAT
53951 AAATAGATTT TTGAACAAAG CTTGAAACTG TAATTTCTGC TGCTTTGTGC
54001 TATTACATTT TCAGAAATTT TGACACTGAA CGTATTTTAT TTTTTAAAA
54051 GTATGTAGAA TGTAGAGAAT GCAAATAATA ATGCTCAGAT GTTAGTTTTG
54101 TCTGTTTCTT AAATTCTTCT GAGCAGAAAT ACCAACCTTG CCAGTACATC
54151 ATGTGTGTTT TCACTTATAT ACAGCCTTCT GTTGGCACTA CTAAAGTTTT
54201 TAAAATGTTT TTGTTCTCC CCTAGGTGTT GGATCCTGAA CAAAACCATA
54251 ACTTCACAGA TCATTATCTA AATGTGGCCT TTGACCTTTC TCAAGTTCTT
54301 TTTATAGCTA CTGCCAACAC CACTGCTACC ATTCCAGCTG CCTTGTTGGA
54351 CAGAATGGAG ATCATTCAGG TTCCAGGTAC CTGACTCTTA AATCATTATG
```

FIGURE 3A-17

```
54401 ATACATCTTG CCTTTCTGAC CATAACTTTA AAATTAGTTA TGCTATGGAG
54451 TTTTGACTAA AAGAAGTTCA TTTGCCAACA TACAATCTTC AGAAGTTCTG
54501 AGGAATGTAT ATAAATCAGT TTCTATGTAG CTTCAAAGTC TGGAAGAGCA
54551 AAACAGCAAA CGTTGACAAC AACAATTTCA GATTTAATTA GCATGAAAGA
54601 ATGATAATTT TATGACAAAT AAGACATTCT TCTTTAGTAT AATTTCTAAA
54651 ATGGCAGGCT GTGTGTGGTG GCTCACACCT GTCATCCCAG CACTTTTGGG
54701 AGGCTGAGGC AGGTGGATCA CTTGAGGTCA GGAATTCGAG ACCAGCCTGG
54751 CCAACGTGGT GAAACACCAT CTCAATAAAA ATACAAAAAT TAGCCTGGCA
54801 TGGTGGCGGG CGCCTGTAGT CCCACCTACT CGGGAGGCTG AGGCGGGAGA
54851 ATTCCCTTGA ACCTGGGGAA GGGGAGGTTG CAGTGAGCCT CACGCCACTG
54901 CACTCCAGCC TGGGTGACAG AGTGAAACTC CATTTCAAAA AAAAAAAAA
54951 AAAAAGAGTA ACTGAACTTT CTCATAAAAT CTGGCCTCAC TTTTATATTA
55001 AAGTGCATGC CGCTTTTAAA TTCCTCTTGA ATCGTGTCAAA TAGTTAAATT
55051 TTTTAAATGT CTTCCCTGTC ACTGGAGCGT GCAAAATGTA TTCCTTCAGT
55101 TACTAACACT AGATAAGTTA TAGCATTTTC ACCTTATTTT AATTGCTCAG
55151 AATTGTTTTT CCCTGGAAGA GATCAAATAT CACTGAGTTT TTTTTTAATG
55201 TAGAGTAGAA TCTAAATGTC TTTATTTATT TAATTATTTA GAGACAGAGT
55251 CTAGCTTGTT GCCCAGGCTG GAGTGCAGTG GCACGATCTC GGCTCACTGC
55301 AGCCTCCGCC TCCGAAGTTC AAGTGAGTCT CGTGTGTCAG CCTCCCAAGT
55351 AGCTGAGATT ACAGGCACTC GTGACCACGC CCAGGTAATT TTTGTATTTT
55401 TAGTAGAGAC CATGTTGGCC AGTCTGGCCT CGAACTCCTG GCCTCAAGTG
55451 ATCTGCCTGC CTTGGCCTCC AAAAGTATAA GGATTACAGA CGTGAGCCAC
55501 CATGTCCAGC CTAAATGTCT TTTACTTATT TTTTCTTTTT TTGAGATGGA
55551 GTCTCACTCT GTCACCCAGG CTGGAATGCA GTGGCACAAT CTTGGCTCAC
55601 TGCAACCTCT GCCTCCTGGT TCAAGCGATT CTTGTGCCTC AGCCTCCTGA
55651 GTAGCTGGGA CTACAGGTGT GCACCATCAC ACCTGGCTAA TTTTTGCATT
55701 GTTAGTAGGG ACAGGGTTTC GCCATATTGG CCAGGCTGGT CTTGAACTCC
55751 TGACCTTAGG TGATTCACCC GCCTCAGCCT CCAAAGTGCT GGGATTACAG
55801 GCGTGAACCG CCACACTCGG CCCTAAATGT CTTTAGATTC TAAATGTAAT
55851 CTAAATGTAT TTTTCATATT AATCTGAAAT ATATTTTTAC TACTAAGTGA
55901 ATTATAATTG GATTTCTGTT TGTTTTTTTT TTGAGATGGA GTCTCACTCT
55951 GTCACCAGGC TGGAGTGCAG TGGCACGATC TCAGCTCACT GCAACTCTCTA
56001 TGTCCCAGGT TCAAACAATT CTCTTGCCTC AGCCTCACAA GTAGCTGGGA
56051 CTACAGCCGT GCACCACCAC GCCCAGCTAA TTTTTGTATT TTTAGTAGAG
56101 ATGGGATTTC ACCATGTTGG CCAGGAAGGT CTCAATGTCT TGACCTCATG
56151 ATCCACCCAC CTTGGCCTCC CAATATAACT GGATTCTTA ATTATCTGTG
56201 AGCATTGCAG GTTCCTGTAT TTAGTTTTAA AATATGGTAG AGTAAAAAGT
56251 TAATTGTGTG TATTTAAAGT CTAAAGTAAA TAAGTAATGA ATTCCCTGGA
56301 AACTCCAAGT TATGGCAGAA AATTCATTAG ATACACTAAA GTAAAGTGAA
56351 AGAATCAGGA CAGCTGCTGC AGAGGGGAGC ATATGATGCC ACCTTCTTCC
56401 TTTGGCAGAT TTAGCTGTCC GATCTTCTAG CTTCCTGGT GTTTACTAAC
56451 CTCTTTCCAT TCAAAGGTG CCTTATCAAT TCATATTTTT AATTTTTGCT
56501 TGTTAAATGG AAAGGGACAT TAGTTGGAAT TTGTCTTAC GGGATTTAGA
56551 GACAAAGGAA ATCTATATTT ATTCAGGCTA TTAAATAACA ACATTATGTG
56601 TTCTAAATAT ACTATATATA GAAAAAATAC ATATATACAT ACATAAATAT
56651 ATATGCACAC ATATATAAAT ACATACACAC ACACACACAC ATATATATAT
56701 ATACCATCAT GTGGAGGAAA AAACCTTTTA TATGGACATC TTAGGTTTTC
56751 TTTTGCTGCT ACAATTTATT TTATAGTCAT AGTTCTGGAA ACAGTATCTT
56801 TAGAGCCCTT CCCTTGGAAC CCACTGCTTA TTTAATTGAG GTGTGTGTGT
56851 GTGTGTGTGT GTGTGTGTGT GTGTGTGTGT GTGTGTGTTT CAAGTATAGA
56901 TCAAATTAGG CTAAAAAGAT GCATTTATTC TTCTATTTGA AATTTCAGAG
56951 GATTTGAGGA TAAGAGATA ATTGTCTCTA AGATTTGAGG TGTTTTCCTC
57001 TTTGGGAAAT ATATCATTTA ATCAGAAAAC TTTCAAGCAC TGTGCTTAGT
57051 AAATGCTTGT TTTGTTTGTG AAAACGTTGG AAATTTTAAC AATTATTGAC
57101 TTAGATCAAA TTTCTTTTTC TTTTTTTTTT TGGAGGCAGT CTCTGTTGCC
57151 CAGGCTGGAG TGCAGTGGTG CAATCTCAAC TCATTGCAAC CTCCACCTCC
57201 CCAGCTGAAG CAATTCTCGT GCCTCAGCCT CCAGAGTAAC CAGGACTACA
57251 GACATGCGCA ACCATGCTCA GCTAATTTTT TGTGTTTTTA GTAGAGACAG
57301 GGTTTCGCCA TGTTGCCCAG GCTGGTCTCA AACTCTTAAG TTCAAGTGAT
57351 CCGCCCGCCT CAGCCTCCCA AAGTGCTAGG ATTACAGGTG TGAGCTAACG
57401 TGCCTGGCCA GAATAAATTT CTTCATTGTA ATTATAGTCT CATTTGAAAT
57451 AATACTTAAA TTTGTTCTAA ATCTAAGATC CATTTAATGC TACATTTGAT
57501 TCATTAAAAA AGCATGGCAC TGGCTGGGAG CAGTGACTCA TGCCTATAAT
57551 CCTCAGCACT TTGGGAGGCT GAGGNNNNNN NNNNNNNNNN NNNNNNNNN
```

FIGURE 3A-18

```
57601 NNNNNNNNNN NNNNNNNNNN NNNNCTATAA TCTCAGCACT TGGGAGGCT
57651 GAGGCTGGTG GATCACTTGA GGCCAGGAGT TTGAGACCAG CCTGGCCAAC
57701 TTGGCAAAGC CCTGTCTACT GAAAATACAA AAATCAGCCA GCGTGGTTGT
57751 GCATGCCTGT AATCCCAGCT GCTCGGGAGG GTGAGGCAGG AGAATCACTT
57801 GAACCTGAGA GGTGGAGGTT GTAGTGAGCA GAGATCACGC CACTGCACTG
57851 CAGCCTGGGC GACAGAGCAA GACTCTGTCT CTAAAAAAAA AAACAAAAAA
57901 CAAAGCATGG CATTATGGGA GCCATGTAAA TAATTACAAA ACAAGATCTC
57951 TTCTTTTCCA GGTTATACAC AGGAGGAGAA GATAGAGATT GCCCATAGGC
58001 ACTTGATCCC CAAGCAGCTG GAACAACATG GGCTGACTCC ACAGCAGATT
58051 CAGATACCCC AGGTCACCAC TCTTGACATC ATCACCAGGT TAGTTAGCCA
58101 TCCTGAGGCT TCATTAACTC CAGGCAACTT TTGAGTATTT ACTGAGTTAC
58151 CAAACAGGAC ATAGAGTATC AATATTTGAG TTTTTCATCT TTTGAGATAA
58201 GCCACAGTCT CCTGAAAAGG AGATTAGTTT ATTGGCATCC CATAGCATCC
58251 ATTTCTCTTT CTTCAACAAC TTCCAGCAAG TGTTATCATA ACTATTGATT
58301 TACACCGTTC TCTACACTAG GCAGAAGTTT ACAGAGAAAC CATTTGGAAT
58351 ATTGTTATAG CTAAAGCTGA AATTTATGCT TTGCCACAAT AGCAATATAA
58401 GGGGTTAATT TGATCATTTA AAAACCAAAT ACATGGCAAA TATAGAGACA
58451 CTTTTTATGC CCAGGATCTT GAAAGTTGTT GAATTCTCTT AAGAGGTGAT
58501 ATGCTACTTT CAGATAATCT GATTTAAGTT ACTCACTTTT CTTTTCTTCT
58551 CTTTGGCTGA GAGATTTTTA AAATCCTTAG AATTTTGATC TTCAGAATTA
58601 ACACTGGAAC AATAGAGAAG GTGCCTTCCC AAGTTTACTA CCAAATGCTT
58651 AAGCCTGTAG CAAGCAGTGT GTAAATTATC TGAATAGAGT ATTGCTTAGT
58701 CTAATTTACA GATTCCCTGT TTGAATGGAA AATATACTCT GTTGAGAATT
58751 TATATCCACC ACAGCCTCTT ACAGTTTTCC TAGCTCAGTA TTACAGATCC
58801 ATTGCATCAT CCAGCAAGTC ATGTCAGGCT GCCAAGCTCT CCTCTTGCGG
58851 CCCTTTTCTA GTAACTACTG TTTTTAAGAG ATTTGAAGTA TCTCTCTATT
58901 TTGAACTTTG ACTTAGAGTT TGGCCAGACT GTCTTTTGAT CTATGCCTTC
58951 TTATGGATCT ATTTAGATTT ATATACAAAG CAGTAAGACT AAGTCTTACC
59001 TGGGGGTTCC TTTTCTTAAT TTGTCTTGTG ATTTATGGTG TAGATAATGC
59051 CAGGAGAAAT AAATTAAGTG ACTTATATGT CTGAGTCTTC CAACAATATC
59101 ATTATTCCAG ATAACACCCA TGATGCCTTT GGGTAACTTT CAATAAGTCA
59151 TTTAACATTT TTGATAGCTT CCCCATCTGT AAAATATGAG GGATGGAGAA
59201 AAATCCAGAG TTTATCTGAA TAATAATGAT TCTGAAGAGT GATCATTATT
59251 TATATTTCCC AGTTGTTACC TAGAGAACTG TTTCTTTTTT TATGTATACT
59301 TGTTAACTCA AAATATCAGA TCTTAAAAGC TGTGGACATA AGGAAATATC
59351 TGGAGCAGTT TTGTTAGTTT TGATATTGTT TTTAAAAACA GCACAAGTAT
59401 GTACTATTCC AGGCACAGTT TTTGGATATT TAGTGAGTTA CCAAACTTAG
59451 GACATAGAGT ATCAATATTT GAGTTTTTCA TCTTTTGTGA TAAGTCACAG
59501 TCATAGACCC TAAATGTTCTA GTCTTTCTTA TCTCCAAGTA TAACTCACCT
59551 GCTTGAATAC TTCCAGTCCC AGTATGCTTA ATTCTAGCGA ATAACTACCT
59601 TTTCATGGGT AATTCTAACT GTAACAAAGA TATTCTTTTT ATTTATTTAT
59651 TTATTTTTTA AGACAGGTTT TCATGCTGTT ACTCAGGCTG GAGTGCAGTG
59701 GCATGATCTT GGGTCACTGG AGCCTCTGCC TCCTAGGCTC AAGCCATCTT
59751 GCCATCTCAG CTCCCAAGTA GCTGGGACCA CAGGTGCATG CCGGGCGTGG
59801 TGGTGTGTGC CTGTAATCCC AGCTACTCGG GAGGCTGAGG CAGGGAATT
59851 GCTTGAACCA GGGAGGTGGA GGTTGCGGTG AGTTGAGATC GTGCCACTGC
59901 ACTCCAGCCT GGGCAACAGA GTGAGACTCC GTCTCAAAAA AAAAAAAATA
59951 GAGATGGGGT TCTCACCATC TTGGCCAGGC TGGCCTGGAA CTCCTGAGCT
60001 CAAGTGATAA TTGTTACAAA GATACTCTTT CTATTCACTT TTCTATAATT
60051 TTCTTCTTCT GCCTTATAGG AGCACCTGGA ATCTAAGTGT AATTCCTCCT
60101 TGTACAGCCC TTCTGACATT AAGATAAAAT ACTATCAGGT GCTGCACACT
60151 AAGTGTTCTC TTCTTCAAGC TAACCATTCC TCTCCTCTGT ACCATTCCTC
60201 TTGATGTAGT TTCAAGACTT CTCACCCTCC TGATTAGTCT TCTTCTGAAA
60251 GAATCCTGTA TATCAATGTG TCTTTTAAAA TTAAACACCC AGAATTGAAC
60301 ACAGTGTTTC AGATAGAGTC TAAACAGTTC ATGGTATAGG AAGCCCATGC
60351 TTTTCTTATT CTGACTATAT TATTTTATGA CTGTATCTCT AGATTCTTAG
60401 CTTTTTAAAG ATTATTCTCT TCCCTTTTTC AGTGAATTTC GCTAAGCTTG
60451 GCATATCCCA TTTGTATTT ATAAAGCTGA ATTTTTTAAA GCCCAAATGT
60501 AGAAGTTGTT AAGATGCCTC CCTGTTTTCT CCCTTATTGA AATTATACGT
60551 AGTTGCATAA TATAGGCTTT ATATCCTTCT ATACCTTTGA CTGAGAACTG
60601 TATTAGAGTG TTTAGCTAAG AGCTTTTTAT CTGTCTTTTC TCAGAACTTT
60651 TAAAATCTGC TTTCCTAAAG TCTACAGTGT ATGTCTGACT TAATCAAATG
60701 TATGGCTTTG TCAAATCCAA TTCTTCAGAT AAAACTGCAT TCTCCACCTG
60751 ATCCTGTCCA TTCAGGTCCA TCCAAAGCTG AGTGGCCAAA AGTGGTTTCA
```

FIGURE 3A-19

```
60801 CTATATAATG GTCTGTGGAA TGACTTAACG GAGTTTGATT CTAATGTACA
60851 TGTGTTTAAA GCAGCTCTGC TTAAACCACA CATAGCATCT TTTTCACAAA
60901 GTCCTCAAAG TCAGTGCTGT CATCACTTAG CATACCTTCT TCCTTTAGAA
60951 ATCTTCACAA TGAAAATACA CTGAAGAAAG GTGGTTAGCA AAGTGCCTAG
61001 TGAAAACCAG ATTTCTGTCT CAGATTTGTT TTTGTTTTAG TTCCACAAAG
61051 AGCACAATTT CTCTTATTCT TTCAGTAGTA TTTCAAATAC AATGAATTTA
61101 TCTAGAATTT TCCTAAATTG ACAAATTTTG TTTAAGAAAA CTCTTCAACA
61151 AATTACCGAG GAGTAAATGG TTTTTTATAT GCTGCCAAGT TTACTTTGGC
61201 AATGTAAATT GAACTAGAAC TAGGGTTCAT TTTTAAGTGT AGGATTATAA
61251 TTCAAGATAA TCTGTATAAA GGAAATTGTT GTAGCTGAAA ATAGATCAAA
61301 GTATTGAAGA AATAACAATA ATGAGGAGTT TTAAGTGTGG AAAAGTTAGT
61351 ACTCAAGAAA GGGTAATGAA CTTTTAAATG TACACTGTTT TACCAAAAAT
61401 GTTAATCACA TTACCTCTCT ATTTTTTTAA GTGGTATATA GTCAAAAATA
61451 AAATATTTTT GTTTGATGAC AGGTATACCA GAGAGGCAGG GGTTCGTTCT
61501 CTGGATAGAA AACTTGGGGC CATTTGCCGA GCTGTGGCCG TGAAGGTGGC
61551 AGAAGGACAG CATAAGGAAG CCAAGTTGGA CCGTTCTGAT GTGACTGAGA
61601 GAGAAGGTTG GTGACCTTGT TCTGGCATTC TCAGGCCTGG TGGCTAGGAG
61651 TGAGTGACAG AAGAAGGTTG GGTATGGAGG GGAAGGTGTT GGGTAGTCCT
61701 TGGAGCAGTG GCACACATGA CTCCACTGTT AAATGCATCC AGTAAGTAAT
61751 ACCTTAATGT TTCAACATAT TTCATCCAGA GGATTGTCTT TTACAAATAG
61801 CACAGTTTTA ACTGGAATAA TAATATGAAT GCTTTGAGGA TATAGGAACT
61851 GTATTAGGGT TCACTAGAGG GACAAGACTA ATAGGATAGA TGTGTATATG
61901 AAGAGAGTT TAAGGAGTAT TAACTCACAC AATCACATGG TGAAGTCCCA
61951 CAATAGGCCA TCTGCAGGCC GAGGAGCAAG GAAGCCAGTC CAAGTTCCAA
62001 AATCTCAAAA GTAGGGAAGC CGACAGTACA GCCTTCAGTC TGTGGCCGAA
62051 GCCCCAAGAG CCCCCAGCAA ACCACTGGCG TACGTTCAAG AGTCCAAAAG
62101 TTGAAGAACT TCGAGTCCAA TATTCGAGGG CAAGAAGCAT CCAGCACGGG
62151 AGAAAGCTGA AGGCCAGAAG ATTCAGCAAG TCTGATCCTT CCAGCTTCTT
62201 TTCTCTGCTT TATTCTAGCC ATGCTGGAAG CTGATTAGAT GGTGCCCACT
62251 CAGATTGAGG GTGGGTCTGC CTCTCCTAGT CCGCTGACTC AAATGTTAAT
62301 CTCCTTTGAC TATATCCTCA CAGACACACT GGAACAATAC TTTGCATCCT
62351 TCAATCCAAA GTTGAAACTC ACTATTAACC ATCACAGTAA CTTTCTCCAG
62401 ATGTATAATG ATGGTGTACG TTATGTATGG GTTCTGGTGT TATCTTATTT
62451 CTTTCTGACC CAGACAGTTA AGTCTTTAAA TAATTTATAA CATAAAAAGT
62501 TTTTACAACA TAAGACAATC CATGCTGTTC AGGTACTGCA AGGACAGACC
62551 TTTGTACTCT GGAATAGCTC CATGTGTAAT AATTTTTCAC ACATTTTCTT
62601 TTATGGATAA ACAACTAAAT GTAATTTAAA TTATTCTTTA AAAAATTATT
62651 GTGAAGGTGT TCTATTACTG GAATTAATCA AATGTGGATG TTCCTTTGGT
62701 ATCTACTTAA AATGTTTTAA CTGGCCAGGC ACAGTGGCTC ATGCCTTTGA
62751 TCCCAGCACT TTGGAAGGTT GAGGCAGGCA GATGACTTGA GGTCAGGAGT
62801 TTGAGACCAG CCTAGCCAAC ACGGTGAAAC CCCGTCTCTA CTAAAAATAC
62851 AAAAATTAGC CAGGCGTGGT GTTGGGCGCC TGTAGTCCCC GCTACTCTGG
62901 AGGTTGAGGC AGGAGAATCG CTTGAGCCCA AAAGTCAGAG GTTGCAGTGA
62951 GCAAAGGTCA TGCCCACTGC ACTCCATCTG GCAACGGAG CGAGACTCCA
63001 TCTCAAAAAA ATAAATAAGT AAATAAAATA AAATGTTTTA ATTTCTTGCC
63051 CCAAAACTGT AAGGGGTCTC AGTTCATCAT ATCATGCTGT TATGCAGTTT
63101 GCCAAAACTT GCTTTAACAA ACATGAGTTG TAGGGAATTG ACAATTTCTT
63151 TCATAGTAAA GAGATTTATT AGATTTTTCT ATCATTTCCA TAGCTGTTTC
63201 CAGAAAGGAG TTGGATGACT GTGATTAAAG AACCATAATT TATGGTGGAC
63251 CCAGTTGAAC AGACACAGCC AAATGTCTTT CTTGTTTTTC CATCAGTGGC
63301 TGAACACAGT GCATTTTACA GCAGTAGCAT CAGAGTCAGC TTTCACAGAA
63351 TCCTTCTGTG GCCAGTACAG TGCTTCACCC CTGCCTCCCC ACGCCTGGAA
63401 CCTCACTGGT TCATTTTCTC CAGAGAGCGA AGCTCCTATC TTCTGTTGGA
63451 TTGGAGGGAG GCAGTGCCTT CATTATGTGG AGTAGGAGTA GAGGTAGTGA
63501 GTTCTAATTG TATTTTATCC AGACTTTAAA ACTTGTGCTT TATTTTTATT
63551 ATTTTTATTT TATTTTACTT TTTGAGATGG AGTCTCGCTC TGTCGTCCAG
63601 GCTGGACTGC GGTGGCACAA TCTTGGCTCA CTGCAACCTC CGTCTCCGAG
63651 GTTCAAGTGA TTCTCCTGCC TCAGCCTCCC CAGTAGCTGG TACTGTAGAC
63701 GGATGCCACC ACGCCCGGCT AATTTTTGTA TTTTTAGTAG AGACAGGGTT
63751 TCACCATGTT GGCCAGGCTG GTCTTCAACT GCTAACCTCA GGTGATCTGC
63801 CCACCTTAGC CTGCCCAAGT GCTGGGATTA CAGGTGTGAG CCACTGCGCC
63851 TGGCTTTATT TTTATTTTTT ATTTTTACTC TGCCTGGGA GAATCTAGAA
63901 AACTTTGCC TTTTGTCCCA CTCTTCATCC ATGCTTTCAG GGCTACCTTG
63951 AATTCTTTAG CTTTTGTAGA CTTTTAGGAC CCACATCAAC TTGTTGTTCT
```

```
64001 CTATCTCTAG CCCCACAAAT GTTGAGGTTT CTGCTTTCTC TAGCCTGTTA
64051 AGTGTTGGTT ACTTTTTGTC CATGTACTTT TTGTTTCCCA AAATTTTGTC
64101 AGCATCTCTT GTCAGCTGAT GTCCTCTTG TCATTATTTT TGTTCTTGTG
64151 GGTTTATATA TTTTTTATTT CTTAATTGTC ATTTTAATAC TATTCAGACA
64201 GGAAGTAAAA ACGCATGCTC AGACTACCAT TTATAGAAAT TTGAATTTAA
64251 AAAAAATGTC CTAGGTGAGG GAGTACCTAT CAAGGGTGGA AATCACTTGT
64301 GTAGATGACA GTGACAGTGG AGAACTGAAG TCTATAAAAG TTAAGACCTA
64351 GATCTAGATG CTCCTGAATT TCCCCTTTTT ATTCTTAACA ACACTTCCTT
64401 TGTGCTGTGA TCTCAAGCAA CTGAGCCTAG GTCTTTTTAT TCTTGTCTGA
64451 TATAACAGAA GGTAGAGGAT GAAATAAATG AGTTTATTAG GTAACACATT
64501 TTGAAAATTG TGTTTAAGAT TTAGATGATA TATTTTAGAA CTTCTAATAA
64551 ATTCAGAGGA ATTCAATGTC AAAGGAAACT TTGTATAGT TATACATTGC
64601 TTAATGTTTA TACATACATC CATGTAGCAT ACTTCTAATA ATATCTTTAA
64651 TTATACTAGT TATTTTAAAA TAACCCACAA ATACTCAAGG AATTGTTCAG
64701 TTTGTGAACT GTGTGAGAAC TACAGTTTTT CATGGTAACA TTTATTTGTG
64751 TGGTTTTTAA AAGTGATCAC AGGACATCTC CTAAAGATA ATATAGTTAA
64801 GCAGATTTGC TTAGTTAAGA TATTACCAAG AGCATCTAGA TGAATAATTA
64851 GAATAAATAC TTGTCTCTTG GAGACGATTT TGGGTGTAGT CTTTACTAGA
64901 GGCATAGGTA TGGACTCCAA GTTGGCTCTA ATATTATGAG ATACCCTIGA
64951 GTAAATAACA GCCATTCTCT AGACCTTAGT AGAATGATTA TTAGGTGTCC
65001 TGAATTGTTT ATGACCTCAA CCAAACCAAA AGAATAATTT CTACAAAAGA
65051 GTCTATGTTA GGTTTCATA GCACCAAGTT CAAATGGAGC TTAGTAATGA
65101 AAATTTTCTC ATTAAGAAAT GAATTAATTA AAATTAAGAG CATAAAATAA
65151 GACAGTTGTT TTAGAAACTT CAAGTAATAC AGTGTGGGAG TTATTTTAA
65201 TGTTAAAAAT AAAGCTTTCC TAATTCAAGC ACGAGAGACA GAAAAAAAAT
65251 AATAAGGCTG AACTTGGAGT TACTGCCAGG AAGAAAAGTA ATTTTAGGCC
65301 ACAAGCTTCA AAACAGGCAG AAACCTCCAG TGTATCAAAC AAACTTTCTG
65351 GAATAGGCCC AGAAGCACTG ATCTGTGAAC AGTTGTCTTT GTATTTGTGG
65401 GGTCTTAACT GGCAGTTAAA GAGACTAAAT AATAGCAGG AGTTTAAAAA
65451 GCAGGTGAGA TTTAGAATTG ATCGATCTGT GTTAGCGGAG GAACATTTAT
65501 GGTTTCAGTC ACTTACCTAT AAAGTATGAG AATTGTTCT TTAAAAGAAT
65551 GCTGCCTCTG TTTTTCTGCA TGTTGTTAGT ATTTTCTGAA TTGCCGTTTT
65601 CCTTTCTAGG GTATTTGTTG GGTTGAGAGA TTAGTTGGAT TACATGACTA
65651 CAGTTTTATT CTGCTTTTTG CCTGCCTTTT GCCAAGAAAG ACACAAATGT
65701 CCCATGTATT TAATTTTGCA CACTTCAGTG TTTCTAAACA GGGTAAATAT
65751 TCATTTGTTT AAGTACCCAT GTATCATATA TTCAATTTAT ATCTAGCAAG
65801 ATTTTTCCTC AAAAATTATC CTAAGCAAAG AAGGATTTAT ATTATAATCA
65851 GTCCTTATAA AGTTTCTCAT AATACACTGC ATTCTCAATT ACTTTATTTT
65901 TGAAGAACAT AGTATTGAG GAAGTTACAT TAAACAGAAA GAACCTGGGT
65951 AGATACTAGT TTCTGATTAT TTTCATAGAA GTCACCTGAA AAATTGGTTA
66001 GAAAAAAAG ACAAAATTAA TACAAATTTA ACAGTTATTT GTGAAATATG
66051 TAAATGTTGT GTTATTCCAT TTGCTGTGC TACAAAGGAA TACTTGAGGC
66101 TGGGTAATTT ATAAAGAAAA GAGATTTGTT TGGGTCAGAG TTCTGCAGGC
66151 TCTATAACAG GCACAGTGCT AGCTTATAAG GTGAGACCTT AGGTAGCTTA
66201 TAATCATGAT GGAGGACAAT GGGAGAGCAG GCATGTCACA TGGTGAGAGA
66251 GGGAGCAAGG AAAGAGCCAG GGACCTTTTA ACAACCAGCT GTCATGTGAA
66301 CTCATTACCA TGGGAAGGC ACCAAGCCAT TTATCAGGGA TCTGCCCCTG
66351 TGACCCAAAC ATCTCCCAGT AGGTCCTCC TCCAACATTG GAAACAAAG
66401 CTATAGTAAC CAAAACAGCA TGGTACTGGT ATAAAAATAG ACACATAGAT
66451 CAATGAACA GAATGCAGAA ACTAGAAATA AAGCCACAAA TCTACAGCCA
66501 ACTGATCTTT GGCAAAGTAG ACAAAAACGT ACACTGGGAA AGGACAACCT
66551 ATTCAGTAAA TGGTGCTGAG AAAATTGGAT AGCCATCTGC AGAAAGAATG
66601 AAACTGAACC ACTCTCTCTC TTATTTTATA TAAAAATCAA CTCGAGGTTA
66651 GGCTAGGTGG CTCACACCTG TAATCTCAGC ACTTTGGGAG GCTGAGGTGG
66701 GTGGATCACT TGAGGTCAGG AGTCTGAGAC CAACCTGGCC AAAATGGTGA
66751 AACCCCGTCT CTACTAAAAA TACAAAAATT AGCTGGGCGT GCTGGTGCAT
66801 GCCTATAGTC CCAGCTACTC GGGAGGCTGA GACAGGAGAA TCACTTGAAC
66851 CCAGGAGGCG GATGGTGCAG TGAGCCCGAG ATCGCGCCAT TGCACTCCAG
66901 TGTAGGGGTA TCGCAGCGAG ACTCTGTCTC AAAAAAAAAA AAAAAAAAGT
66951 CAACTCAAGA TAGATTAAAG ACTTTAAATG TAAAATCCAA AACTAAAACA
67001 TACTAGAACA AAATCTAGAA AAAATTCTTC TAGACGTTGC CATAAACAAA
67051 GAGTTCATGA CTAAGACCTC AGAAGCAAAA GCAACAAAAC CAAAGTAGA
67101 CAGATGAGAC TTAATTAAAC TAAAAGCTT TTTATACAGC AAAAGAAACA
67151 ACAGAGTAAA CAGACAGCTT GCAGAATAAG CAAAAATATT TGCAAAATAC
```

FIGURE 3A-21

```
67201 ATATGCAAAA GACCAATACC CAGAATCTAC AAGGTAACTC AAGCAACTCA
67251 ACAACAACAA AAGAACCCCA AATAACCCCA TTAAAAAGTA GGCAAAGGAG
67301 ATGAAAGACA TTTTTCAAAA GAAGACATAC AAGTGGCCAG GAAGCATTTG
67351 AAAAAATGCT CAATATCACT AATCATCAGA GAAATGAAAA ATCTATGAGA
67401 TACCATCTTA TACCAGTCAA AATGGCTATT TTTAGAAAGT CAAAAGTAAC
67451 AGATGTTGGT GAGGATGTGG AGAAAAGGGA GTGCTTATAT AGTGCTGGGA
67501 GAAATGTAAA TTAGTACCAC CTCTATGGAA AACATATGGA GAGTTCTCAA
67551 AGAACAAAAA ATAGAACCGT CATTTGATCC AGCAATCCCA CTACTGGGTA
67601 TATACCCAGA GGAAAAGAAT TCATTATGTC AAAAAGATAC CTGCACACAT
67651 ATGTTCGTTT TATCTGATAT AAAAAGTCTG TTTTATCTGG TATAAAAAGA
67701 ATGGAATCAT GCCTTTTGCA GCAATATGGA TGAAACTGAA GGCTGTGACA
67751 ATAACTCAGA AATTCAAATA CTGAATATTC TCATTTATAA GTGGAAGCCA
67801 AATAATGTGG ACATATGAAC ATAGAGTGTG GAATAATAGA CACAAGCATG
67851 AGCTATCATG CCCAGCCTCA AAAAATTTAA TTTCCCTCTT AATTTTGTCA
67901 TTGACCCAAA GGTTGTCCAG GAGCATGTTG TTTAATTTAC ATGTGTTTGT
67951 ATATTTTTGA GAGTTTCTCT TCAGATTGAT TTTAGTTTT ATTCCATTGT
68001 GTGAAGATAC TTGATATGAT TTTGATTTTT TTTTAAATTT ATTGAGACTT
68051 GTTTTGTGGC CTGACGTTTG GTCTGTCTTG GAGAATGTCC CATGTGCTAA
68101 TGAGAAAAAT GTATCTTTTG TGGTTGTTGG GTAGAAATGTT CTGTAAATGT
68151 CGTTAGGTC CATTGGTTT TAAGTTCAGT GTTTCTTTGT TGACTTTGTC
68201 TGTCTCAGTG TTGAAGTCCC ACATTTTGTA TTGCTATCTG TCTCTTTTCT
68251 TAGGCCTAGT AGTATTGTT TTATTAATCT GGTACTCCAG TTTGGGAGT
68301 ATATACTTAG GATTGTTATA TCTTCTTGTT GAATTGATCC CTATGTCATT
68351 ATATACTGGC CTTTAAAAAA AAAAAAACTA TGTTGATTT AAAGTCTGTT
68401 TTATCTAATA TAAGTATAGT TACTCTTGCT TGCTTTTGGT TTCCTTTGC
68451 ATGGAACATT TTTCCACCCC TTTACCTTCA GTCTGTGTGT CTTTAACAGT
68501 AAGGCAAATT TCTTGTAAGC AGCATGTAGT TGTTGTTTTT TAATCCATTG
68551 CACCAATTTA TATCTTGAA GTGGTGCATT CAAGGTTAAT ACTGATGCAT
68601 GAGGTTTTGT TCCAGTCATA ATGTTAATTG CTATCTAGTT GCTTTGTAGA
68651 TTTTTTTTTT TCTTTTAAGC AAGAGTCTTG AGTCTTGCTC TGTCACCCAG
68701 TCTGGAGTGC AATGGCGCGA TCTTGGCTCA CTACAACCTC CACCTCCCA
68751 GTTCAAGCGA TTCCCTTGCT TCAGCCTCCC AAGTAGCTGG AATTACAGGT
68801 GCATGCCACC ATGCCTGGCT AATTTTTGTA TTTTTAGTAC AGACGGGATT
68851 TTGTCACGTT GGCCAGGCTG GTCTCGAACT CCTGACCTCA GGTGATCCTC
68901 CCGGCCTTGGC CTCCCAAAGT GCTGGGATTA CAGGCGTGAA CCACCGCAAC
68951 CAGCCAGCTT TGTAGATTCT TGTTTGTTT TTGTTCCCG CTTTGTGGTC
69001 TTCTGGAGTT CTGTCATGTT GCCCTTTTAT TTCTTTCTTT TCCTTATTTG
69051 TATAATTGTT TCATAAAACT TGTGAGTTTC ATGTGTTTTT ATGATAGAGT
69101 ATCACCTTTT GTTCCCATGT TTAGAACTTC TTTAAATATT TCTCATAGGA
69151 CCAATCAAGT GGTGATGAAT TCCCTCATTT GCTTATCTGG GAAACACTTT
69201 ATTTCTCCTT CATTTGTGAA GCTTACACTA GCAGGATACA AAATTCGAGT
69251 TTGACCATTT TCTTTAAGCA CTTTGAAAAT AGAATCCCCG TCTCTTCTGG
69301 CTTCTGAAGT TTCTGCTGAG AAGTCCACTG TTAGTTTGAT GAAGTTTCCT
69351 GTATAAGTGA CTAGACACTT TTACTGTATT TAGGGATTTT CCCTTCACAT
69401 TGACCTTAGA CAGCCTGATG ACTAGATGCC ATGGTGAGAT CCTTCTCGCA
69451 ATGTATTTGG CTGGAGTTTG TTGAGGTCT TGTATCTGGA TGTCTAGATC
69501 CTTTGCTAGA CTAGGGAAGG TTTTCTCAAT TATTTCTCA AATAGGTTTT
69551 CTGAAATTTT TGCTTTTTCT TCTCCTCTAG GAATACCTAT GATTCATAGG
69601 TTCCAATGTC TTATGTAATC CCTTACTTTT CAGAGGCTCT ACTCATTTTT
69651 TAAAATTCTT TTTTCTTTTT TTTTTTGTC TGACTGGATT AATTGAAAAA
69701 ACCTATCTTA AAGTTCTGAG GTTCTTCTT CTGCTTGGTC TAGTCTGTTG
69751 TTGAAGCTTT CAAATGTATT TTATAATTCC TTCAATGAAT TTTTTATTTC
69801 CAGGAGTTCT GTTTGGTTTT CTTTTTAAAA TACCTATCTC TTTGGTAAAT
69851 TTCTCATTCA TTTCCTGAAC TGATTTTCTG ACTTCTTTGT ATTAGTTTTC
69901 AGATTTCTCT TGTATCTTGT TGAGCTACTT TTTTTCTTTT AATTTAATTT
69951 TATTTTGAAA CAGGGTCTCG CTCTGTTGCC TTGTCTGGAG TGCAGTGATG
70001 CAGTCATAGC TCATTGTAAG CCCAAGCAGT CCTCTGCCCT ACTGTCCTAA
70051 GTAGCTACAA ATTCAGGCAC ATACCACCAC ACCTAGCTTA TTTTTTTATT
70101 TTTTGTAGAG ATGGAGGGTT ATACTGTGTT GCCCAGGCTA GTCTTGAACT
70151 CCTGGCCTTA AGTGATCCTC CTTCCTCTTG CCTGGCCTTC CTAAACTATT
70201 GGGATTGCAG GCATGAGTCA CTGTGCCCTG CCCCTGACAG CTTCTTCTTT
70251 TTTTTTTTT CTGAGACAGA GTTTCACCCT GTCACCCAGG CTAGAGTGCA
70301 GTGGCACGAT CTCGGCTCAC TGCAGCCTCC ACCTCCTGGG TTCAAGTGAT
70351 TCTTGTGCCT CAGCCTCCTG AGTAGCTGGG ATTACAAGCG TGCGTTACCA
```

FIGURE 3A-22

```
70401 TGCCTGGCTA ATTTTTGTAT TTTTTTAGTA GAGATGCGGT TTCACCTTGT
70451 TGGCCAGGCA GGTCTTGAAC TCCTGGCCTC AAGTGATCCA TCCACCTTGG
70501 CTTCCTAAAG TGCTAGGATT ACAGGTGTGA GCCACTGTAT CCAGCCCCTG
70551 ATAGCTTCTC TAAATCAGTG TTTTGAATTC TTTATCTGGC ATTTTGAAGA
70601 TTTGTTTTTT AGTTAGGATC CATTGCTAGA GAATTACTGT GTTTCTCTGG
70651 GGGTGTCATA GCACCTTTTT TTTTTCATAT TTCCAATATT ACTGTGCTGA
70701 TTCATTTGTA TCTGGGATAA CAGTTGCTTC TTATTATTTT TTAGTTTACT
70751 TTTGTTGGGG CAGGACTTTC TTTCCCTTGA GGATGTATCT ATTATGTATG
70801 TTGAGTAGGG TCATTTGGCT TTGCTTCAGG GTGCATTCAG TGACATAGAC
70851 ACTGTATGAT AGCCTTGGTT ATAAAGTAGT CTTAGTATGG TGGCTTTCTC
70901 AAATGCCAGT GACAGTAGTA ATGTACGGGG TGGGTGATTG GGCTCAAGGC
70951 CTCCTGCCTA GCTGGGGTGG ATGATGGTGG CAGCAGAGGT CGTGCAAAAC
71001 TTGCTTTCTT CCAAGGCACT ATGCAGTTGT ATCAATAGAT GTGTAATGG
71051 GTGGTGCAGG TTGACTTCCC AGCTAGGAGG TGGTGCCTGC AGATGAGCGT
71101 CAGCTGCAAT AGTGGCAGTA GGGTGATTAA CCTTTGTAAT TCAAGAATTA
71151 TTCAGGTATC TCAGGTACCG AGCTGGGCCG TGAAACTCTC AGGGGTCCTG
71201 GTCTTGTGCT GTGCTTCCAG GGTAGATTGT GGGGTGAAGC CAGGCAGGCT
71251 GGACCAGCCA AGCTCATGTT TGAGCCCCCT GAATGGGTAC TTAGGGCCTG
71301 GGATAAAATT TCCAGAGGCT GCCTCATACA TTGTTTCAAG AATTACTTTA
71351 TCTTAGATAA TCTTGGTATC TGGTAGTGTA AGTCTTCCAG CTTTGTTCTT
71401 CTTCAGAATT GGGTTGGCTA TTGTAGGTCC TTCAAATATC CATGTAAATT
71451 TTAAAGTCAG TTTGTCATTT TCTACCAACA AGTAAATAAA TAAAAACTCC
71501 TGGGGCATTT TTATTATGAT TCCGTTGAAT CTGTAAATCT AGTTGGGGAG
71551 AATTGACAAT TGTATTATC AAGTCTTCTA ATTCATGACC AGCTTCATTT
71601 ATTTAAGTCT TCTTACATAA GTTTTTTTTC TTCAGCTTTT AAGTTCCAGG
71651 GTACATGTGC AGGATGTACA AGTTTATTAT GTAGGTAAAC ATGTGCCATG
71701 GTGGTTTGCT GCACAGATAA TCCATCACCC AGGTATTAAG CCCAGCATCC
71751 ATTAGCTATT CTTCCTGATG CTCTCCCTCC CCTCACTCCC ACCCACAACA
71801 GGCCCCAGTG TGTATTTTTC CCTGCCATGT GTCCATGTGT TGTCATTGTT
71851 CAGCTCCCAC TTATAAGTGA GAACATGCAG TGTTTGGTTT TCTGATCCTG
71901 CATTAGTTTG TTGAGGATAA TGGCTTCTAG TTTCATCCAT GTCCCTGCAG
71951 AGGACATGCT CTCGTTCCTT TTTATGGCTG CATAGTATTT CATGGTGTAC
72001 ATGTACCACA TTTTCTTTAT CCAGTCTGTC ATTGATGCGC ATTTGGGTTG
72051 ATTCCATGTC TTTGCTATTG TGAATAGTGC TGCAATGAAT ATATATAAAT
72101 CATTCTGTTT CTTTGGCTAT ATACCCAGTA GTGGGATTGC TGGATCAAAT
72151 GGTATTTCTG CTTCTAGATC TTTGAGGAAT CACCACACTG TCTTCCACAA
72201 TGGTTGAACT AATTAAACTC CCACCAACAG TGTAAAAGCA TTCCTTATTC
72251 TTCACAACCT CGCCAGCATC TGTTGTTTCT TGACTTTTTA ATAATTGTCA
72301 TTCTGACTGG CGTGAGATGG TATCTCATTG TAGTTTTTAT TTGCATTTCT
72351 CTAATGATCA GTGATGTTGA GCTCTTTGTC CTATGTTTGT TGGCAACATA
72401 ATGTCTTCTT TTGAGAAGTG TCTGTTCATG TCCCTTGCCC ACTTTTTAAT
72451 GGGGTTGTTT TTTTTTTTCC TGTGTAAATTT GTGTTCCTGG TAGACTCTAG
72501 ATACTAGACT TTTGTCGGGT GGATAGATTG AAAAATTCTT TTCCCATTCT
72551 GTAGGTTGTC TGTTCACTCT GATGATACTT TCTTTTGCTG TGCAGAAGCT
72601 CTTTAGTTTA ATTAGATCCC ATTTGTCAAT TTTTGCTTTT GTTGCTATTG
72651 CTTTTGTCAT TTTCTTCATG AAATCTTTGC CGTGCCTAT GTCCTGAATG
72701 GTATTGCCTA GATTTTTTTC TAAGGTTTTT ATAGTTTTGG GTTTTACATT
72751 TAAGTCTTTA ATCCATCTTG AGTTATTAAA TAATTTTGT ATAAGGTGTA
72801 AGGAAGGGGT CCAGTTTCTG TTTTCTGCAT ATGGCTAGCC AGTTTTCCCA
72851 GCACCATTTA TTAAATAGAG AATCCTTTCT TCATTGGTTA CTAGTACAAA
72901 AACAGACACA TAGACCAATA GAATAGAATG GAGAACTCAG AAATAAGACC
72951 ACACATCTAC AACCATCTGA TCTTCTTAAA TAAGTTTTTT AAGAGTTTTG
73001 ATCATTTTCT GTGGCACACT TTTACATAAT TTTTCTTTAG ATATCTTCCT
73051 AGGTATTTGA TCTTTATGTG TATATTATTG TAAATAACGT TCTTAAAATT
73101 TTGTTTTCTA ATTTTTTGTT GGTAGTGTAT GACAATGCAA TATTGGCCTC
73151 CTGTTCAACA AACTTGCCAC ATTCACTTAT TAATCATAAT TGTTTGTGGA
73201 ATCTTTTGGA TTTTCTGCAT CTACCATCCT GTAATCACAA ATGCAGATGT
73251 CAGTTTTTAC TTCTTCCTTT CCAACGTTAT ACCTTTTATT TAATTTCTTC
73301 CCTAATATGT TGGCTAGGAC CTCCTGGGAA ATGCTGAATA GAAATAATGA
73351 TAATAGACAA AGTAAGCAGG ATAAAAGCCT ATGAAGAAAT TACCAACTGA
73401 CATAGGCTTT GCTTTGTAGC TTTAGGTCAC CCCTCATCAC CTAATATTAT
73451 AAAATGACAA TTCGGTAGGA TTCTCAGAAA CTGTCCAGTT TGACCCTGAT
73501 TTAATTCTCA ACATTCTCCA GTAAACACTA TGCCTTGCCT GTTTGACTTT
73551 GTTAACAGAC ATGTCAGACA ATCATGTGGT GAAGTGTGAT TTTACTTGTT
```

FIGURE 3A-23

```
73601 TATTCAACCT GAGATTTGCT GACAGTTCGT TCTGTGTTGC TGTAACAGAA
73651 TACCACAGAC TGGGTAATTT TAAATGAGCA GAAATGTATT GGTTCACAGT
73701 TCTGGAGGCT GAAGAGTCCA ATGTCAAGGT GCCAGCTTCT GACAGGAACC
73751 TTCTTGCTGC ATCTTCACAT GGCAGAAGGG CAAAGAAAGA GAAGGGGCC
73801 TGAACTCACT CTTTTATAAG GATATCAGTC TCACCCATAA GGGCAGAATC
73851 TTCAGGAACC TAAGAGCAAC TTGTTACTTC ATGGCCTACT GACCTCTTAA
73901 AAGTCTCACT ACTTAATATT GTTACAATGG CAGTTAAATT TCAACATGAA
73951 TTTTGAAGGG GACAAACATT TAAACCATAG CACTGACTTT CTTGAATTTG
74001 TATACTCTTT TATTGGTTTT GGAAAGATTT TGGCCATTAT CTTTTCAAAT
74051 ATTCTTCCCA TTTTTTTACT CTTCCTTCTG GGATTCTGAG AAGAGAGCCC
74101 TTCACTGTCT CTTATCCTCC TTTCTATTTT TTTTTTGTTT GTTAATTTTT
74151 CTCTCTCATT CAGTTTAGAT ATTTTCTGTT GCCCTGTATT CCAGTTTGTT
74201 ATTGCTTTCT TCTATTTTTT TGTGGTCTGC TATTAAGCCT ATGAAGTTCT
74251 TAATTACCAT ATTGTAATTT TTTTTTTTTT TTTTTTTAC TTTTAGAATG
74301 GCCACTGGAT ATTTTTTTTT TCTTTCTTTA AGACAGAGTC TCACTCTGTC
74351 ACCCAGGCTA AAGTGCAGTG GCACGATTTT GGCTTACTGC AACCTTGCC
74401 TCCTGGATTC AAGCGATTCT GATGTCTCAG CCTCCTGAGT AGCTGGGATT
74451 ACAGGCGTGT ACCACCATAC CCAGCTAATT TTGTATTTTT AGTAGAGACG
74501 GGGTTTCACC GTGTTGGCCA GGCTGGTCTC GAACTCCTTA CCTTAGGTGA
74551 TCTGCCCTCC TCTGCCTGCC AAAGTGCAAA GTGCTGGGAT TACAGGCATG
74601 AGCCACCGCG CCCAGCCCAT TGGATTCTTT TTTTTTTTTT TTTTTTTTGA
74651 GACGGAGTCT CGCCCTGTTG CTCAGGCTGG CATGCAGTGG CGTGACCTTG
74701 GCTAACTGCA ACCTTCACCT CCCAGGTTCA AGTGATTCTC TTGCTTCAGC
74751 CTCCCGAGTA GCTGGGATTA CAGGCGCCCG CCACCACACC CGACCAATTT
74801 TTGTATTTTT AGTAGAGACG GGGTTTCACC ATGTTGGCCA GGCTGGTCTT
74851 GAACTCCTGA CCTCAAGTGA TCCACCCACC TTGGCCTCCC AAAGTGCTGG
74901 GATTACAGGC ATGGGCCACC ACACCCGGCC AGGATTCTT GTATATATAT
74951 GGACTCCAAT AGATTCTCCA TTGATATTTT CTATCTTTTT ATCTATTTAA
75001 TCCCTCCTTT TCCCTATTTT CTTGGACATG CTAGTCATTA TTTTGAAAAT
75051 CTCTACCTTA ACACTCCATT ATCTGATTCA GTTATGTTTG GTGTTTGTTT
75101 TGTTTGTATT ACCTTTTTTT CCCCCTTGAT TTCTAGTTTT TTGTTCTGTT
75151 TTTTAGCATT TCTTGTATTT TTTTACTGGA TGCCAGACAT TGGATGAAAA
75201 ATACAAGGGC TGTAACTATT ATCCTCTGAA AAGTGTTACA TTTTCTTCTG
75251 ATTGGTAACT ACAGTACCAA CCTGTCACTC TGTCCTGTCA AGGCTGAGTT
75301 TTAGGCTTTG TCAGGACTCG TCAATTTCAG TTTGGGTCTT ATTACTGGGA
75351 TACAGTCTTT ATTTTTATTA TGTGGTACTC CCAGGATGTA GTTCTTATTC
75401 CTTCGTGGGT GACCCTTACT TCTAGAGCAT GATCTTTCTG AGTTCTCACA
75451 TGAAAATCCA ATCAGGTCTT TAGCATCCTG GCTTCTCCTT TCTCCTGGGT
75501 TTCTAAAAGA CTCACCCTGA ATACATTCAA CTTAGGAGTT AGTCAACAGC
75551 TTGAGGGGGA TTTAAGTGCA GATTTTTGAG ATCCTTCTTT TTGGTTTCTT
75601 CCTTTATTGG GATTTTGCCA ATGAAGTCCC AGTTGCTTTG ACAACCTCTA
75651 ATTTTCAGAA TTACTTTTGA CTAAATGTTT TATGATTCTA AACATACCAT
75701 CTACTCTGTC AATTCTGAAT TATGGTGATA CTCAATTCTA CCTCAAATCC
75751 CAAAGAAAAG AGGGGGAAAA AACAACAAAA CTAAGAAGAA ACATTGCTTT
75801 TGTTTTGTAG CTTTAGGCTT CTAACCTATAT AATTGACTAT TATAAAATCT
75851 CATTTGAGTA GGATCTTTAG TAGCCACCTA CTTTGACTGT GATTTGATTT
75901 ATAAATCCCT TCACAACATT CCTCAGTAAA CACCATGCTT TGCCTGTTTG
75951 ACTGGTTAA CAGACATGTC TTTATAAACT TGGCTATCCA TTTTCCAGTC
76001 TGTAGGAAAA GAGAAGCTGT AAGTTGGAGA AAAGGCTAGT GGTTGGGTGG
76051 TGAGTCATAA GCAATAAGAT TTGATGTCAG TGATGACAGG CCTGTCCTCT
76101 TATGATAGAT TCCTTGAGCC CCCTGCTGAC CACAAAGCTT TGGCTGGCTA
76151 GACCACAAGT CTGTCTCCCT CAATGACAAT TTTTGTAGCT CAATATGGAT
76201 CCTATTTTGT GTGAGTTGCA TTTGGAGATT TATTGTTTAT CTGCTGTATT
76251 TGCCTTAGGT GGGACAGTGA AATCAACCTA ATGTAGTGGA AGGAAGTAGG
76301 TATTACATCC TTAATTCCTT GATATACATC CTTTTATTAT GTGGTACTCC
76351 CGGGATGTGG TTTTTCAGAT TTGGAGAAGA ATAGTTAAAA AAAAAAATG
76401 CAGAAAGGAT CAAAAGCACT TGATTCTCTC GCAGGGACAG CTTCCTGTTT
76451 TGGTTGAGGA AGGAGCTGCA CTTAAAATAA CTAGCATAAA GCATGCTTAG
76501 GGCTTGCTTT CCAGACAACC TCAATTTAAA ATGCATCAAA AGCCAGGTGT
76551 GGTGGCTAAC ATCTGTAATC CCAGGCACTT GGAGGCTGA AGAGGGCAGA
76601 TCACTTGAGG TCAGGAGTTT GAGACCAGCC TGGCCAACAT GGTGAAACCC
76651 CATCTCTTCT AAAAATACAA AAAATTAGCTG GCCGTGGTGG CACACACCTG
76701 TAGTCCCAGC TACTTGGGAG GCTGAGATGG GAGGATCATT TGAACCTGGG
76751 AGGCGGGGAT TGCAGTGAGC CGAGATCACA CCACAGCACT CTAGCCTGGG
```

FIGURE 3A-24

```
76801 CAACAGAGCA AGACTCTGCC TCAAAAAAG AAAGAAAATA AAATTCATCA
76851 AAATAAAATA TTTGAATTTT ACAGCACTAG TTCTTTTCAT TCATTGACTT
76901 TCATTCTCCC ACTTTACCAC ACCTTTAACT ATTGGCAAGA ATGTGGTGAG
76951 TGGGAGAAAG CGTATCCTGC CACGTAAGCA AGTATACCTA GAGCCAAGGG
77001 GTCAGAGTGT CACAGAGGAG AGCCACATGC TGATGGGCTT GTGTTCGTTC
77051 CCACTCACTG ACTATGCAAG CGCCTCTTCT CTTAGCCTTT CTCAGGATGC
77101 AGTTCTCCAG GGAGGAATCA GCCTTCTGTT GGGCTGCTTT CAGAGCTCTT
77151 TGTTGTGGCT TCCTGCCATT GACTTTGCAA GCCCTAAGCA TGCTTTATGC
77201 TAGTTATTTT AAGTGCAGCT CCTTCCTCAA CCAAAACAGG AAGCTGGCTC
77251 TGCAAGAGAA TCAAGTGCTT TTGATCCTTT CAGCTTTTTT TTTTTTTGAC
77301 TATTCTTCTC CAAATCTGAA ACATATCCAT TCTGTCTAC GGCCATGAGT
77351 GCATTTATGT TAACAGAAAA TGCTAAATTT AATGTTTAGA AAGTAACCTC
77401 TGTGGCCAGA CATGGTGACT AATGCCTGTA ATCCTGGCAC TTGGGAGGC
77451 CGAGGCAGGC AGATCACTTG AGGCCAGGAG TTCGAGACCA GCCTGGCCAA
77501 CACAGTGAAA CCCTGTCTCT ACTAAAAATA GAAAAAATTA GTTGGGCATG
77551 GTGGTGGGTG CCTGTAATCT CAGCTACTTG GGAGGGTGAG GCAGGAGAAT
77601 CACTTGAGCC CAAGAGGTGG AGGTGCAGT GAGCCAAAAA TCAAGCCACT
77651 GCACTCTAGC CTGGATGACA GAGCAAGACT CTCTCAAAAA AAATAAAAG
77701 TAACCTCTGT GCTTTGTGTA ACTTTTTGCT AAATTCCTGT CTTTGTCTTC
77751 TTGGAACAGT CTTCTACTTG TTACAGGATC TTCCTATCTT TGGATTTTA
77801 TATTAGTTTT AATATAAAAT TAATATAGTT TTATATTATA TAGCCCACTG
77851 ACATGGCTGT TAGCTGACCT CAGTTCCTTG CTGACTTGGC CAGAGCCTTC
77901 AGTTTCTTAT CTCTGGTAAG AGGTAATGTG TCTCTCCCTA GGGCAAGGCT
77951 GTGACAGCTG GCTTCTCCCA GAGGGAATGA TGTGTGAGAG AAGCAGGGAG
78001 AGTAAGAATC AAGACAAAAC TGCAGTCTTT TATACCCATC ACTATTGCCA
78051 TATTCTCTTG GTCACACAGC CCAACCCTGG TATGATATGG GAGGCACTAA
78101 CTCCATGGGG ATGGGATATC TGGGCACCAT CTTGAAGGCT AGCTGACACA
78151 GATTATTTT TGTGCGTGTG CCTGTAAGAA TTTTTTGGCC AGGCGTGGTG
78201 GCTCACGCCT TTAATCCCAG CACTTTGGGA GGGCGAGGTG GGTGGGTCAC
78251 GAGGTCAGGA GTTCAAGACC AGCCTGGCCA AGATGGTGAA ACCCCATCTC
78301 TACTGAAATA CAAAAATTAG CCAGGCATGG TGGCAGGGGC CTGTAATCTC
78351 AACTACTCGG GAGGCTGAGG CAGGAGAATC GCTTGAACTT GGGGGCGGA
78401 GGTTGCAGTG AGCCGAGATC ACGCCACTGC ACTCTAGCCT GGGCAGCAGA
78451 GTAAGACTCT GTCTCAAAAA AAAAAAAAA AAAAGAATT TTTCTAAGCC
78501 CGCATTGAAG TTTATACTGT AGAATATCCA TCAAACTTGA GCTGATTTCT
78551 TATCAAAGAC CCAGGTTGCA CAGATAGGGG TTAGAAGTTT GGATTCGGTT
78601 TTGCATTTTC AGTATTTAAA GTCTTGTTTC ATCTTGTTCA TTCTTACCTT
78651 TCCTTTGATT GTATTAGTAG CTCAGGACAA ATAAGAATTT ATAATTTCC
78701 AAGGAACTAA GGTTGCTGTT GAGGAATATG GGTTTCAGAG ACAAGAGTTT
78751 AGGCACTGGC TCATTGGTAC TAAGCTTCAG GGGTTGTAG TGTTGTTAGA
78801 GCTAATTGGA TTTTACAAAT AAGCCAAGAT TATTAAAAA AAAAAATAGA
78851 TCTAGAGAGT AACACTTTCT GTGCTAAATC CATTGCATTT GATGGGATAC
78901 TAGGCAGTAT GCTATGTCCA AACTTCTAAA ATCAGGCGGT GGTCTAACGT
78951 TGAGGTGAAA ATATCATGTT GGGTATATAC TGCCAATATC ATGAAGATAT
79001 ACTAAATATT ATTTTCTGAG TCTGACATTT ACACTGATTT ACTGATTTAT
79051 CCCTCATCAA TATTGCCCTG GTTTAAGAGA GACTTGTTTG CCTGTAACGA
79101 CCGGGAGGAA GCTTCAATGA AGGCAAAAAT CTAACTATAA TAGGAGCCAA
79151 ACATTTGTTA TTTGAATTCC AATTGGGGAC AGGAAAATAA AATATTATCA
79201 AATAATTATA AAGTCATCAT TCTGTTAAAT GAATCATATA GGAAAATGCA
79251 TTGACCTTAA AACAGAGTCT GGCTCTGTTA CCCGGACTGG AGTGGAGTGG
79301 CCTGGTTTCA ACTTGCTGCA ACCTCCACCT CACGGGCTTA AGCTGTCCTC
79351 CCACCTCAGT CCCTAGAGTA GCTGGGACCA CAGGTTTGC CATGTTGCTC
79401 AGGCTGTTCT CAAACTCCTG AGCTCAAGAA ATCACCTGT CTCAGCCTCC
79451 TGAAGTGCTG GGATTACAGG CGTGAGCCAC CGCGCCCGGC CTGCAGTGAC
79501 CTTTGGTTGT CATTGTTATA CATTATCAAA ACAACTCAA GTTACAAGAG
79551 TATTAAAGCA ATACTTAATG GTTTAAAAA AAATATTACA AAAGGTCTCT
79601 GCATTTTAAC TACTCATCTA AATAATTGTC TAGGAATATT TTCTGAATCT
79651 CTAATACAGG AAATGAGATT TATTAATACA TAAAACCCAC TGAAACAGG
79701 GGTGCAAACT TTCTTGTCTG GTACTAAAGA TGGATTCCTA TGTTTTGGGC
79751 CCTTGTTTAT ACCAGTTTAT TCAATCAGTG AGTCAGCTAG CATTTACTGA
79801 ATAGTCATAT GGGTTGCTTA ATGATGGGGA TAATGTTCTG AGAAGTGCAT
79851 CCCTGGGAAA TTTTGTCATT GTGGAAACAT CATAGAGTGT ACTTACACAA
79901 ACCTAGATGG TATAGCTTTC TACACACCTA GGCTATATGG TATAGCCTGT
79951 TAATCCTAGG CTATAAACTT CTACAGCATG TGACTATACT GAATACTGTA
```

```
80001 GGCAATTATA ACAGAGTGGT ATTTGTATAT CTAAACAACA GATGAACAAT
80051 AAAGAAAAAA TAAACAACAA ATAAAAGCTG GTACTTCTGT ATAAAGGCAC
80101 TTACCATGAA TGGAGTTGCA GGACTGGAAG TAGCTCTGCG TGAGTCAGCA
80151 AGTGAGTGGG AGTGAATGTG AAAGCCTAGG ACATTACTGT GTATATACTA
80201 CTATAGACTT ATTAACACTG TACACTTAGC CTGTATTTTT TAATTTTTTT
80251 CTTTTTTTTT TTTTACTTCT TTTTCTTTTT TTGAGACAGG CTGTGTTGCT
80301 CAGGCTGGTC TTGAACTCTT GGGCTCAAGT GATCCTTCTA CCTCATCCTC
80351 CTAAGTAGCT GGGATTACAG GTGTGTGCCA CCACACCCAG CTTTTTAAAA
80401 CTTTTCAAAT CTTTTATAAT AACACTCAGC TTAAAACACA AATACACTGT
80451 ATAGCTATAC AAAAAATATT TTTACCCCAT TTATGCCTAG TGCTCCATTA
80501 TTGGAACACT AAGCTTGTGG GAGTTATTTA TATCCTACTG CTCAAGGTCA
80551 TTGCCAAGGT CTGATTTTTC ACAAAAAAAA ATTCACAACT TCTGGCATAA
80601 ATGGGTTAAT ATCCTTACTG TATATAAGCT TTTTTAAAAA TTGTTTTACT
80651 TTTTAAACTT CTTTGTTAAA AGCAAAGACA CAGACACACA TTAGCCCAGT
80701 CCTGAACTAG GTCAGGATCT TCAGTTTCAC TGTCTTCCAC TTCCACATCT
80751 TGGCCCACTG GAAGGTCTTC AGAGGCAGTA ACATGCATGG ATAACAGTGC
80801 CTTCTACCTT CTGAAGGACC TGCCTGAGGC TGTTTTACAG TTAACTTCTT
80851 TTTTACAGAA GGGAGTACAC TCTAAAATAA TGATGAAAAG CATAGTATAG
80901 TCCAGGCACG ATAGTGTGTG CCTGTAGTCC CAGCTACTCA GGAGGCTGAG
80951 GCAGGAAGAT TGCTTGAACC CATGAGTTCA AGACCAGTCT GGGCAACATA
81001 GCGAGACTCC ACCTCTAAAA ATATATATAA GAATAAAAAA TTTTTTTTAA
81051 ATGAAGCATA GTAAGTACAT AAACCAATAA CATAGTCACT CACTATGACT
81101 ATGAAGTATT ATGTACTGTA TGTAATTGTA CGTGCTGTGC ATTTATACAG
81151 CTGGCAGCAC AATAGGTTTG TGTACACCAA GCATCACCAC AAAGATTTGG
81201 GTAATGCATT CCATTGCCCT AACGGGGCTA CAACATCACT AGGCAATAGG
81251 AATCTTTCAG GTCCGTTGTT GTCTTCTGGG ACTTCTGTCA TATATGTGGT
81301 CTGCCTTTGA CCAAAATGTT GTTATGCAGT GGGTGACTAT ACCCACTATA
81351 TGTTCAAGTT CTAAATTGGA TTCTGGGAAG CTGATTAAAG AGAAAATAAT
81401 GTGTAGTCTA TTGGAAGAGG TAGATAAACA ATTTTTAAGT GAAATAATTG
81451 GTGTAGTTTTA ACCTCTGTGG AGGCACTGAA CTGATCATTG AAAGCTCTAT
81501 TTTACTTACT AAAGATATGG TAGCTTATAA AAATTACTTA TAGTAAATGG
81551 ACATGAAAAG GTCATTTGCT TACATCTCTA AATTCATTTT GATGGAAAAA
81601 TAGTGGAAAA ATGTTTGCAG ATACCCTTTT GTTTGTTTGT TTTTTTCATA
81651 ATAGATAATT GCCACTAAAA TTGAAGAATG GCCAGGTCCG TTGGCTCATG
81701 CCTGTAATCC CAGCACTTTG GGAGGCCAAG GCGGGTGGAT TACTTAAGCT
81751 CAGGAGTTCA AGATTAACCT GGCCAACATG GCAAAACCCC GTCTCTACTA
81801 AAAATACAAA AAATTAGCCA GGTGTGGTGG TGCACACGCC TGTGTCCCA
81851 GCTACTTGGG TGACTGAGGC ATGAGAATCA CATGAGCCTG GGAGGCGGAG
81901 GTTGCAGTGA GCTGAGATTG TGCCACTGCA CTCCAGCCTG GCAACAGGT
81951 GAGACTCTGT CTCCAAAAAA AAAAAAAAC AACTAAAATT GAAAAATACC
82001 TCACAGTCAT AACTTCCATC TGTATCTCAG TGGTTATTAT GTAGAAATGT
82051 TCAGTAGGTA AACTTGAAAG AAAAATGTATT TGGTAATCGT AAGGTTGTGT
82101 TGCCACCCCC AAAATAATGA AGAAAATACC AACAGAAAGA AAAAGGATTT
82151 ATTGCTGGCC TGAAGGTTCT TCTGGGCATT TGATCTACAG ATTTCTCCAT
82201 TATAGCTAGT TCCTTTAAAA AAATAAAAAA CATTGAAAAT ATGCAGACCC
82251 AAATGCCTTG GCAGCCCTGG TCAGTAACTT GAATCTCAGT TGCACTTAGC
82301 ACAATTCCTC TGGCTGGGAA GATGTTGTTT TGGAAAGAT TAACCTGAAA
82351 TGCAGCACG AATTATACAG TTGGAAATAC TCAGGTTTTT CTGATTTTTT
82401 TCAAAAGATA CTTTGCTTTT CCTTTTCTGC CTTACCATGG GAAGGTCCTT
82451 AGATGCATCA TATCCTTGTC AGTTTAGCCT TGTGACACAT ATTTCTGCAA
82501 TTTTGTGCAA TAAGAAAGCC ACTCGAAATC TCAGCATTTC ATGTCACTTT
82551 TAAAGTAGGC TCAGTTAAAA CAAAACCACT TGATTGTTTG TATAACCACA
82601 ACCATATGTG TCTTTCTCTC CATGCTTAAA CAAGGTCTGA AATCGTGTGT
82651 CAAACAGTTG AGATGTAAAC ATCTCCTCCT CACACATAAC CCCTCTGCCA
82701 TGTTGTTATT TATATCCCCA GTAACACACT TCTTGTCCCT GACACAAGTA
82751 CAGCCGTCTC CACATTCCAT TTTGCTCCTA CTCCATCAGC TTGCAAGAAA
82801 AATTTTAATC ATTCAAAAAT AATTGTTACA TAATTACTTT TCACTGATTA
82851 AAAATATTTG TTTACTTGAC AAAATTAGCA TTAAAAACAG TAATTCTTTG
82901 GCAGATTAAT AAGTATTTTG ATGATTTGTC ATTTTTCACA GATGTTGATA
82951 AAATTTAAGA ATTACATAGC CGAAATTTGG TCTAATTCAA CAAACCACAA
83001 TTGACTCTTT TGGTAAGGCC CTATGACGAA TGGTATGGGA GAGTGGAGTT
83051 TATCCAATCT GACTTTCATT TTATTGATAC GGAAACTGGG GCCCCATTTG
83101 TTCTTTTTTT TAATGCTAC ATAATATACA TATTTATGGG GTATAGTGTG
83151 ATGTTTCAGT ACATGTATAC ATTGTGTAAA AATCAAATCA GGCTGTTTAG
```

```
83201 CATATCTGTC ACCTCATATA TTTATCATTT CTTTGTGGTA AGTATATTTA
83251 AAATTCTCTA TTCTAGCTAT TTTGAAATAT ACAATACTGT TAACCATAGT
83301 CACTGTGCAA TAGAACAGTG GTCCCCAACC TTTTTGGCAC CAGGGACCAA
83351 TTTCATGGGA GACAGTTTTT CCACGGACCT GTGGGTGGT GGTTTCAGGA
83401 TAAAACTCTT CCACCTCGGA TCATCAGCAT TAGATTCTCA TAAGGAGCAC
83451 CCACCCTACA TCCCTCACAT GCACAGTTCA TAATTCACAA TAGAGTTTGA
83501 GCTCCTATGA GAATCTAATG CCGCTGCTGA TCTGACCGGA GGCGGTGCTC
83551 AGGCCGTAAT GCTTGCCCAC CCGCTGCTCA CCTCCTCCTG ACAGGCCATG
83601 GACTGGTACT GACCAGTCCA CAGCCTAGGG TTTGGGACC CCTGCAGTAG
83651 AACACCAGAA CTTATTCCTC CTATTTATCT GCAATTTTGT ACCCATTGAC
83701 CAATCTCTCC CCATCCCCAC TATCTCTCCC CTTGCCAGTC TCTTGTAACC
83751 ACTGTTCTAC TCTCTGTTTC TGTAAGATCA ACTTCTTTAG ATTCCACATA
83801 TAAGTGAGAT CATGCAGTAT TTGTCTTTTG GTGCCTGGCT AATTTCACTT
83851 AATATAATGT CCTCCAGGTT CAACCATGTT GCCACATGTG ACAGGATTTT
83901 ATTCTTTTTG TGGCTGAATA ATATTCCATT GTTTATATAT GTCACATTTT
83951 CTTTATCCAT TCATCCGTTG ATGGATGCTT ACGTTGATTC CATATATTTG
84001 CTATTGTGAA TAGTGCTGCA ACAAACATGG AAGTGCAGAT ACCCCTTTGA
84051 CATATTCATT TCCTTTGGAT AAATGCCCAT TGTGGGATT GCTGGATCAT
84101 ATGATAGTTC AACTTTTAGA TTTTGAGAAA CCTCCATACT GTTTTCCATA
84151 ATGGCTGTAC TAATTTACAT TCCAGCCACC AGTGTGTAAG AGTTCTCCTT
84201 TCTCCACATC CACACCAACT ACAGGTGGCT TTTCTAGACT GGACTTTAGG
84251 TTGGGACAAA AAGTGTCTTT GAGAGTCAGT AGTCCTAAATA CTGTACTGTG
84301 AATGCTGTGG ACTTAGGCAG TTTGTTTAAG CTTGTTTAAA CTGGGTCTCT
84351 CTTTCCTTAG ATATAAATGG AGGGTTAGAC TGGATCTTTA AGCTTCTGCC
84401 CAGCATTTAA TGTTCTGTTT ATTGTGGTTC TAGCCTGTGC TTCTTGAATT
84451 CCTGATTCTT CCTGAATTCT GCTAAGCATC AGAATGCAGT CTATACATTC
84501 TCAACAGCTT CCCAAAGACA TGATATTAGT ATAACAGAAA CAGTAGTAGT
84551 CCTTTCTTGG AAAATTATCC CCATTTCTGG ACCCTATTT ATTGCTGGCT
84601 GCAATTAACA GGTTCTTGTA TGTCCCATCC TTCCCTCCTC CTCCCTAACC
84651 CACAGGCATT AAAAACCTGC TGTTTGTGAA AATGAACACT TCTTTGATAA
84701 TCTGGAAGAA GGGGTTCCTG TTACCAGAAA ATTTAGCTCT TGAACTCCTG
84751 GGACTGGGCT TGAAAGCATA GTACTATTAT GCTTCAGATT AAGCAGGGTA
84801 TAGAGAATAA GGAGTGATCA CAAAAATTCT GTCTTGAATA AAGATGATGA
84851 TAGATATCCC AGGGCCCTCT GTGGTTAGAT AGTCTCCATT TCTACCACAT
84901 TCTGAGGAAT TGTGGGTGTT GCGCTTTTTA TGTTTCTGGC CTCCCTGCTA
84951 CTTGCCATTG GTTGGATCAC TGGCCAAGAG CTACCGAGAA CTACCATTTT
85001 GCTTCAAGAT TTTTTCAAAC AGCAAGGAAC TTTTTTATTT TTTAACAGAG
85051 AGCTACTGAA GTTTCCTGAG TTATTACAAC CCCCTTATCC TTCCTCCTTA
85101 CTTCCCCTTT CAATAATTCC CTTTCCTCCC TCTTCCCACA GCAGTTCTTT
85151 GGCTATTGGG CCTGTTTTCA TTGAAATCAT CTTCCGTGTG CAGAGGGAAA
85201 ATGAATAGAG AAGAACAGTT GACTGTGTCC AAGTGATAGC TGCTTGCTTA
85251 GGAAAAGCCT GGTCCTTCCC CAGAGGAGTC TGTCCCTATA GGACTTCCCT
85301 CCATAATAGC TGTGCTTCCA TCAGCTCTAG AGGATGGCTT AGCCCCCTTC
85351 GGGGGTACAC CGCATTTCAC TCTCACTTGG CTCACAGCA TCACCACAGT
85401 CCATGCTGTG AGTGCATTGC TGGTTCTGCC CCCGTGCTGT GTGCATCTCT
85451 GCTGCTTTAA TGCTGGGAAA CTCCGTGGTT ATGCCCCAAC TATCTTGGCA
85501 ATGTTCTGAA TCAGACATAG ATAATACCTA TTAAAGGTAT TAATAGGCCA
85551 ATAATACCTA GTAAAGAAGA GCTGGATAT ACCTCTGCAT AGATTAAAATC
85601 AACTAGAAAA CACTAGCCCC CTCCCATTTT CAGACCGATT TTATTTCTTT
85651 TAAGTGGGAA AATAGTCGAA GTGGGATGAA GCAGAGCTAG CTTATTCTAC
85701 TCATTTTATA TTTCTGTGGC CTTTTCAACC TCTGTTTAAC AGCACTTTAT
85751 TACTTAGTTT TTTTGTTTTG TTTTGTTTTT TTGGGATGGA ATCTCACGTT
85801 GTCGCCCAGG TTGGAGTGCA GTGGCATGAT CTCGGCTCAC TGCAACCTCC
85851 ACTTCCCGGG TTCAAGCGAT TCTCATGTGT TAGCCTCTCA AGTAGCTGGG
85901 ATTACAGGCA CCTGCCACCA GGTCCGGCTA ATTTTGTGT TTTCATTAGA
85951 GATGGGGTTT CACCATGTTG GCCAGGCTGG TCTCGAACTC CTCACCTCAG
86001 GTGATCTGCC CGCCTCAGCC TCCAAAGTG CTGGGATTAT AGGTGTGAAC
86051 CACCACGCCC AGCCTCACTT TATTACTTTT AAGAATATGC TTCAAAATAG
86101 TTTGTAAAGA AGATTTTAAT AGGAGCACT TATATGAAAT ATAATAGTGA
86151 TATATAGTAT AGCATAGAGC AGAGTCTTCA GTCTTTGTAT CTTTTTCTTT
86201 TTTTCTTATG CATATTTAAT GTATGTGATT CCCAACCGTT GTGTGATTGT
86251 GGTCAGAGCC CTGTCTGTGG GATGCTGGGT AGAATGACAT TGTAGAGAGC
86301 ACTTTGTTTT CTTGTAATTG AAGGGTTTGG GGTGAGAATA TGTGAGTCAT
86351 AGAAATCTGT ATAGTAAATA TTACTCTAAA AAGGGAGCCA TCAGGATCTG
```

```
86401 GGAGAATTTG CTAAAGGAAA ACTAAGAATG AAAAAAAGGC CAGGTACAGT
86451 GGCTCACTCC TGTAATCCCA ACACTTTGAG AGGCCAAGGC AGGAGGACCT
86501 GAGGCCAGGA GTTCAAGACC AACCTGGCCA ACATAGTGAA ACCCCGTCTC
86551 TACTAAAAAT ACAAAAATTG GGCCGGCGCC GGTGGTTCAC ACCTGTAATC
86601 CCAGCACTTT GAGAGGCTGT GGCGGGTGAA TCACGATATC AGGAGTTCGA
86651 GACTAGCCTG ACCAACATGG TGAAACCCCG TCTCTACTAA AAATACAAAA
86701 ATTGGGCGGG GCGCAGTGGC TCACACCTGT AATCCCAGCA CTTTGAGAGG
86751 CCGTGGCGGG TGGATCACGA TATCAGGAGT TCGAGACTAG CCTGACCAAC
86801 ATGGTGAAAC CCCGTCTCTA CTAAAAATAC AAAAATTAGC CAGGCATGGT
86851 GACGTGTGCC TGTAATCTCA GCTTCTCAGG AGGCTGAGGC AGGAGAATCA
86901 CTTGAACCCA GGAGGTGGAA GTTGCAGTGA GCCGAGATCA CACCATTGCC
86951 CTCTAGCCTG GGTGACACGG GGACTCCGTC TCAAAAAAAA AAAAAAAAA
87001 AATTGGCCAG GTGTGGTGGT ACACACCTGT AATCCCAGCT ACTTGGGAGG
87051 CTGAGGCATG AGAATCGCAT GAACACAGAC GGCAGAGGTT GCAGTGAGCT
87101 GAGATCACAC CACTACGCTC CAGCCTCTGT CTCAAAAAAA AAAGGGGGGG
87151 AGGGGCGGTG GGGGAGCGG GAGCCAGTAT ATAATTCAGT ATCTCTCATC
87201 TATACATATT AAGGCTTTTG ACCATTACCA AATTCTCCCA GCAGCTCTCT
87251 GAGAGTACTG TAATTCTGGT TTTGCTGATT AGAAAACCAG ATACAAAGAG
87301 GTAAAGTCAC CTTGTTCTAG GCCACTAGGT GGTAATCTGA GTCAGGACTG
87351 GAGACAATGA TTTATTTTTA ATATCTCATG TAATGTTAAT CTCATAACTC
87401 AGGGCATAAC TCTTTTACCA TTTTGGACTA TATCATTTCA TTCATATGAT
87451 AAAGACACTG TAGCTTCCCC CTCACCTGCA GCTTCACTTT CTGCAGTTTT
87501 AGTTACCTGT GGTCAACCAT CGTCCAAAAA TATTAACTGG AAAATTCTAG
87551 AAAATAATCCA CTCGTAAGTT TTAAATTGTG CACTATTCTG GGCAGTGTGA
87601 TGAAATGTCG AGCCATCCTG CTCTGTGTGA CCCTGGACAG GAAGCCTCTC
87651 TTTGTCCAGC ATATCCATGC TGTATGACTC CCGCCCCTTT AGCCACTCAG
87701 CAGCCATCTC ACTTACCAGA TCAACTGTCT TGGTTTCAGG GTGTTTGTGT
87751 TCAAGTAACC CTTCCTTTAC TTAATAATGG ACCCAAAGCC AAGAGCAGTG
87801 ATGCTGGCAT TCTGGGTTTA TTTTATTAGT ATTGTTGTAA ATCTCTTACT
87851 TTGCTTAATT TATAAATTAA ACATGATCAT AAGTACATAT CTATAGGGAA
87901 AAAATGGTAT ATATAGGGTT CTGAACCATC CTGCATTTCA GGTATCCACC
87951 GTGGGGTCTGG AAATGTATCG CCTGTGGAGA AGGGGTGACT ACTGTGTAG
88001 TAAAAATCAC CCTGTGTGAA ATGTTATATC CTCCCCTTTC CTCAGTTTAA
88051 CGTTGTTTTG AAAGAATTTT CTCACATTAC TTGAAAACAC TTAGGAAACC
88101 ATTTTTAGTG ACTGTAGTAT TTTACCAGTT AGATATGCCA TGGTTTACTT
88151 AACCATGTTC CTAATGTTGG GTACTTATAT TGGATCTAAG TTTTGCTGTT
88201 ATTTGTAGTG CTGCGATGGG TGACTGTGCA CAAACCCTTG CCTGTACTTT
88251 TGTGTATTTC CCTAAGGATA GATTGCTGCA AAAAGAACC ACTGAGTGTG
88301 AGACTGTAAA TATTTGGAAG GCTTTCAGTC TATTTCCATA TTGCTTTCT
88351 GAAAGATTGA ACCAGTTTAT ACTTCTGTAA GCAACAGTGT TTGAGAAGAT
88401 CTCTTTACTT TTTTTAACAT TGACCTTTGT CATTTCTTAA ACTTTACTAG
88451 TTATTTTGGT AACCGGCTTG TTTTTATAAT TTGAATTTCT TTGCTTCTCA
88501 GTGAAATAAT AGTTTCTTTT ATAGGAGTAT TAACCATTTG TTAAGAACCA
88551 CTATTTTAGT CCAAAAGAAA GGTATATAAG AAGAAACTG CACAATTCCA
88601 GTGGGAAGGA CTTGGGGTCA GGGTCCCTGA TATGTTGGAA GGTTGAACTT
88651 TTTGTTGTTG GTTTTTCCCC TTGCCTTAAA AAGTCCATAT TGCTTGAATG
88701 TTGCAATCTT GGGCAAGGCC AGCAATTAAT CCAAGGGATG ATGCCACTGT
88751 CTTCTCCGG TGCTGGTCCT TTCTGACAGA GAACATGGTA CTAGGCCTGA
88801 GTGCTTGAAT GCTTGCACAT AGGACCCAGA AGGTGCACAT ATAACCGGGG
88851 GTTCGTTCCT TGAGTGATAT CTTGTGAGA TGACATTTG CTTGTTGGTT
88901 GTTTGTTTTA TAATGAGGAA TCAAAGTGGG TATTCTAGGA AGATCCAGTG
88951 TTTCCCTACT CACACTTTGC ATTACACACA GTCCAGGGGG TGACTCAGAA
89001 TCCAGTGCTG TCCTGCCTCT CCCAGTTGGC TGACACCATT TTCTTGACTG
89051 GAGCCTTAGT TTTCTAGGCA TATATTCTAA TGATGGAACA TTTTGAAATG
89101 CAGATTATTT TTGAGGTTAC TGAATTTTTT AATAACACAG CTGCTGTCCC
89151 TAAATTGCCA TCTTTTATAA GGTCTAGTTG CATTAGAAAT AGCTCTCCCA
89201 ACCCCACTCC CCCAGTGCTC AGAACGCTGA ACCCCGTACT ACACTTGGAA
89251 AAGGATTGGA TGTCCTAAAG CATTGGTTAT GTAATTGTGG GTTGGCTTTC
89301 ACCCACTGAG CTTTACTTCC TCCTGTGATC GTGAAATACA AGCTGGCAAC
89351 AGTAATTAGA TCTCAGAAAA GCTTGTCACA AAGCACCACA GACTAGAGAA
89401 ACTTGTAAGC TCTTTTTGCA CTGGCTGAAG TTTTTGAGTA CCACTACCTT
89451 CCATCTATAG TGTAGTAACC TTAGACAGGT AGTGCTTTTC TTCTCGTGCAT
89501 TAATTTTAAT TAAGCAATGA CACCTACTTT CTTTTCCACT CTGAGATCTG
89551 CATGTAGCTA AACTTATCAG GTGAGTGCTT TCCCATCTTT GATCATTGAT
```

```
89601 ACTGCTTGGA ATATACGGA AAAAGAGCAG CAAGCAGAAA ATCTCCCATT
89651 TCCACAAGCT GCTGACTAAC TCAGAATTGC TAGATTTTGT GAAGCAAATG
89701 AATGCTATAA AAGAAGTCAG AAAGATCAGG GAAGCTGTCC CTAGGACTTG
89751 GTCAGGCCAA ACCTTGAAAT ATCAAGTGAT GTTACAGAGG TACAATTATG
89801 AGAATATATA TAACTCAAGA CTTACATATG TGATAAATAG TGCATTGCTC
89851 TTTGCCGTCT CCAAAGGATT TTCTTTTTTT TTTTTTTTTG AGACGGAGTC
89901 TCACTGTGTC GCCCAGGCTG GAGTGCAGTG GCGCGATCTC GGCTCACTGC
89951 AAGCTCTGCC TCCCGGGTTC ACGGCATTCT CCTGCCTCAG CCTCCCGAGT
90001 AGCTGGGACT ACAGGCACCC ACCACCACGC CCAGCTAATT TTTTGTATTT
90051 TTAGTAGAGA CGGGGTTTCA CTGTGTTAGC CAGGATGGTC TGATCTCCT
90101 GACCTCGTGA TCCACGCGCC TCGGCCTCCC AAAGTGCTGG GATTACAGGC
90151 GTGAGCCACC ACGCCTGGCC AGGATTTTAT TTTTAATTCT CACAGCAATT
90201 CTGCAGAGAG AGGTAGTGAG AGGTTTAATG CTTTGTTCAA CATAATTTGC
90251 TGTTAAATAG CCATTCATTG GCAGAAAATC TGAACTGTTG TGTTTTCCTT
90301 CCTGTGTCAT TCATGGTTTC AGTCCTGAAG AGGAGCCCAC TAGAGCCCAA
90351 CAGGAGAGGA GAGTGGGAGA ATCCCTCACC CAGAAGTTCA CAGTGGTATC
90401 ATTTAGTGAC ACTCAGGATG TCTCCAGTTA TTGTTAGAAT TTAAAGTTAG
90451 GTTCATCCCT GTGAGGTCCA AGAAAATATA AAAATAAAAT AAGGGTCTAC
90501 TAGTATTAAA CATACTCTGT AATCACTTTT GAAAGGAAAG GAGTTAGTGG
90551 AAAAAAATGA AGAACCATAG CGAAACTAAA ATAAATATAT GTAGATATAT
90601 TGCTGGACGT GGTGGCTCAC ACCTGTAATC CCAACACTAT GGGAAGCTGA
90651 GGCAGCCAGA TCACTTGAGG TCAGGAGTTC AAGACCAGCC TGGTCAACAT
90701 GGTGAAACCC CGTCTCTACT AAAAATACAA ACATTAGCC AGGCTCAGTG
90751 GCTCACACCT GTAATCCCAG CAGTTTGGA GGCTGAGGTG GGCGGATCAC
90801 CTGAGGTCAG GAGTTCGAGA CCAGCCTGGC CAACATGCTG AAACCCCATC
90851 TCTACTAAAA ATGCAAAATT TAGCTGGGCA TGGTGGCACA TGCCTGTAGT
90901 CCCAGCTACA GGGAGGTTGA GCCAGGAGAA TCGCTTGAAC CCAGGAGGTG
90951 GAGGTTGCAG TGAGCCATGA TTGTGGCACT ACACGCCCGC CTGGGTGACA
91001 CAGCGAGACT CCATCTCAAA AAAAAAAAAA TTACATATAT ATACACATAC
91051 ACACACACAC AAACATTAGC CGGGCATGGT GTTGTGCACC AGTAATCCCA
91101 GCTACTCTGG AGGCTGAGGC AGGAGAATTG CTTGAACCCA GGAGGCAGG
91151 GTTGCAGTGA GCCGAGATTG CACCACTGCA CTGCAGCTTG GGTGACAGAG
91201 CGAGACTCTG TCTCAAAAAA TATAGATAGA TAGACAATGT TAGATAACTG
91251 CATAATTATT ATATGTGTGT ATTAATATAC GAAGCAATCA CTTTCAGAAG
91301 GAATAGTGTG TTAAAAAAG GTAATGAAAG ATTTAAAAC AAAACACTTC
91351 ATGAGACAAG AAGTTAGAAC AATTACGGCA AACTAAAAGA AAAAGCTAGG
91401 AATGAGATCG AATACAGCCA AGTATTTCCT GCAGTTTTAA AACCCTCTACT
91451 CCCCATTTTG GGTTTCTGCC CACAGATTAC GTAATATTTT TGTTACTTG
91501 AACTGGAATT ACAAAGATTG ATACAGAAGA TGGTCCGATA AGTCAATTGG
91551 GTCCTGCTCC TTGTATGTCT AGGTCCAAAC CAAAATGAGT CAATATTTGG
91601 ACAAGATATC AGCCATCCAG GGCTTATAGG CAGGTAAAGG AGATGGCCCA
91651 TTATTACAGG GATTTCAAAC CAGGCTTTGT ATTCTCTTAC CCTGGCACTG
91701 CCAATTATAT TTATTTATTG GAAATGATA ACCTTAGAGT TAAGCTATAT
91751 GCTTATAAAA GAGGCACTGC TTATATGGGT TCTATCATGT CCAGGTTTAC
91801 ATTGCCCGTT AGAAAACAGG ACACCTGCGT GGGTGCAGCA ACTCATGCCT
91851 GTAATCCCGA CACTTTGGGA GGCCAAGCGA GTGAGGATCG CTTGAGCCCA
91901 GGAGGTCAAG GCAGCAGTGA GCTGTGTTCA CACCAGTGCA CTAGACACCA
91951 TCTCAAAAAA AAAAAAAAGT GTTGGGGGGA GAGAGAGAAA GAGAGAGAGA
92001 GAGAGAAGAG GAGGGGAGGG GAGGGGATAC CTGATCAGAC TCCTCTGAAG
92051 AGGGAATTGA AAAGTTTGTC ACAAGCCCTG AGTTATGCTG ATATAACAGA
92101 GAATTGTTAG ATCAGAGAAT CCAAAGTAAC CTACTGCGCT TAGCCCTTCA
92151 GTCTTTGTCC TAGCTATAGG CCATAAAGTT GAATAGTGCC GGGAATTGTT
92201 CTTGACTTAA GAATATAATG GTCAAAAAGG ACAGGCAAAG TTGTTTCCCT
92251 TCTGGAACTT ACACTTTAAT GGGGAGATA GACAATAAGC AAGTAAAAGT
92301 AATGAACAA GGCAATTGCA AATACCACCC TGGGTGAGCT CTTGAAACAC
92351 AAATTATTTC ACCTGCATTC CACAGATACA CAGGTGAATG TTTGCCTTGA
92401 TAAATGCATA AAAGTGACTG AACTTTTGAG GTCCACTGGG CTTTTGTTTG
92451 ATATTTACTG CTAGTGAATT TTCCAGCCTG CAAATCTCTT AGAACTTCTA
92501 AATACATTTT TTTTTCTTTT AGGTTGCAGA GAACACATCT TAGAAGATGA
92551 AAAACCTGAA TCTATCAGTG CACTACTGAA CTTGGCTCTA CCACCTGAAA
92601 TGCCGATTTT GATTGATTTC CATGCTCTGA AAGACATCCT TGGGCCCCGG
92651 ATGTATGAAA TGGAGGTCAT TCATTCTTTT TATTTCTTTT TGCTCCAGTC
92701 AATGAAAGGA ACACTTTATT GAGGCCCCAG GGCCGTAGGG CCTGGGCAGG
92751 AGGCTGCCCT TTGGGGAAGG AATAGCCTTA TTCGACCTTC TTTTTGGGAC
```

FIGURE 3A-29

```
92801 GCAGGTTGTT GGTGTGGCCG CACTTCTTGC AGCAGTTGAC TGCATGGGGG
92851 CGCAGGCGAG CACAGCTCTT GTGGCACATC ATCTTCTTGC AGTTGTATTT
92901 CTGGGCAAGG TGGCAGAGGG AAGGCTCCGT AATGCCACCT CACAGGCACA
92951 GCATCAGGCG CAGGGTGGAC TCTTTCTGGA TGTTGTAGTC TAAGAGTGTG
93001 TGGCCATCCT TCAGCTGTTT GCCCTCAAAT ATCAGACACT GCTGGTCAGG
93051 TAAGATGCCC TACCTGTCTT GAATTTGGCC TTGACATTC TCAGTGGCAT
93101 CACTGGGCTC GACCTCAAGG GTGATGGTCT GGCCTGTGAG GGTCTTCACA
93151 AAGATCCACA TCTCAGCGTC TGCAGCTTGG CCAGTCTCAC TCCATTCTCA
93201 TTTTTTGTT GGTACTCACT GGTGTACTCA GGTGGTTGCT TAACAGAGAA
93251 GTAAAATTGG ATGTTTCCAG AGGCTGAATT TTGCCCTTAAG ATGGAAACTT
93301 TATTTCTATA TGGTATTGTG TTTTAGTGCT TATTGTGATA ATATGACTTG
93351 CCAGGAGCCA GAGATCCCAG CCATATCCTC TTTTAGAACC CCAGTCTCAT
93401 TTTATTCTCT ACCATTCAGT TCCATTTTAA GGACAATGCC TCTGACTCTT
93451 CTTCTTAGAA AAATTACATA TTCTTATGTG TACTTTAAGG AGGGATTCT
93501 TGTGCTATC AAGGGCTTGG GGAAGAGGC GGGAATCAA CCTGATACAG
93551 GTCTGAAAAC ATGAGCATAG CTTAGCTTCA GACTGTGCTA GTGCAGACCC
93601 AGATGACATC TTTCAGGAAC CTATTGTTCC ATTGTTAATA GTTCCTTTAG
93651 GGTTAAACCC ACATGCAGGT CTAGCCCTAT TTCATCTTT CTCTCCTAAC
93701 TGTACCTCAC AGCAGAAGGC CTGGGTGCCA AGACCGAGTT GAAGCAGCTG
93751 ATGGAAATAG ATGTTAGACT ATAACTGCTA AGGGCATTGT GAAATAATTT
93801 ATAGGTGCTT AGATGAGCTT TCATAGGTTG GTTACTATAA AAATGTTTGT
93851 ATTATACTAC TGAATTTAGC TTTATCATCA CCTCCTTATC AGTTTAAGGA
93901 AAAAATATTT TCAGAAAATA AATCTGATAA ACTATGTAGA AGATAATCTC
93951 TCCATCTAAC ATTTGAAATC ATTACCAGTA GATATGGTTT TCCTCAAGTT
94001 CTTACAACTG AGCAGATGAG AAATAGCCCC CAAGCCTGTC TTGTTTATCC
94051 ATTTAAACTC TAAACTGGTC ATTAAAGCTA ATGAGCCTCT CTACAGAGCT
94101 CTCAGTTACA AGAATAGAAC TTGTTTACTC TTGACAGTAA ATCTGGACTT
94151 GAACAATAGA ATCAGAAGCA TTGTTTTGAT TATTTGAATT CTTAAGATAT
94201 CATGGATTG AATTTTGAAG TGTTGAAAGA ACTGAGCAA AACATTGTTG
94251 ATTGAGAAAG TGAACAAAAC CTGCTTTCTC GTTCTGGGAG GATCCAGTGA
94301 CATTGTGAGT GAAGACGCAA ACAGGTTTTG ACTCCTGCAT GGCGATGAC
94351 CTTTTTCTGT AGGCTTACCA GAAAGTACA TTCCAACAGT TCTTTGAGGA
94401 TTTAAACTAG AGCAGCAAAT AAAGACAAAA GATTAATGCA TGTCTCTGTT
94451 GCATATACCC CTCTCTCCCA GCCATTTCTG CTGATGTTAA GTTGGAAGC
94501 ATTGCTGACA TTCCTGGAGC ATTAGCAAAG AAAGAGCCAA GAGAACAGAA
94551 ATGAGAAATT TTATAAACAC TGCTTACCAG TTATCCTTGT TAGCATGGGA
94601 GAACCTTATT TTCCTTGTAG CATGTGAGCT TTAACATAGT AACACTTTTA
94651 CCAACATGAG TCTGCAGAAA GACTCCAGTA GCCATTTGT CTTTTATAGA
94701 TAGCATCTTA GAATGGAAGA TGTGGTGTGT CACATGCGTG CGTGCGGAGA
94751 GACCACCAAA CAGGCTTTGT GTGAGCAACA AGGCTGTTAT TTCACCTGGG
94801 TACAGGTGAG CTGAGTCCGA AAAGAGAGTC AGCAAAGGGA GATAGGGGTG
94851 GGCCCGTTTC ATAGGATTTG GGTGGGTAGT GGAAAATTAC AGTCAAAGGG
94901 GGTTGTTCTC TTGCTGGCAG GGGCGGGGGT CACAAGGTGC TCAGTTGGGG
94951 AGCTTCTGAG CCAGGAGAAG GAATTTCACT AGGTTAATCG CTCAGTTAAG
95001 GTGGGACAGA AACAAATCAC AATGGTGGAA TGTCATCAGT TAAGGCAGGA
95051 ACCAACCATT TTCACTTCTT TTGTGATTCT TCACTTGCTT CAGGCCATCT
95101 GGATGTATAC ATGCAGGTCA CAGGGATAT GATGGCTTAG CTTGGGCTCA
95151 GAGGCCTGAC ATGGTGTTTT GAGTGTTGGG AACATTGTGT TCATTTTTTT
95201 CATACTTGAA AGTGAGAACT CACCCTGTAG CCGGGTGTCT CTACCTGTAG
95251 TGGTCTGATG ACCACCAGCC CCAAATTACT TAACCACA GTCTACCTCT
95301 GCTTTTGCAT CTATAAAATT AAGATTTATG GAACATTTCT TTCTTGTCCG
95351 TGAGGGCTGT CACTGTGCTA GGAGTGTAAT TCCATTTTAC ATACAAGGGA
95401 AAAAGTTTGA AGAGATTAAA TGAATTGTAC AAATTCACGT AAGTGGCAGT
95451 TGGTAGAGTT AGGATTCAGA CTCAGATCAG CTTATTCCAA GTCCATTATT
95501 CTTTCTACCT TTCTACAGTA CCCTGTCAGG CCAAAATAAT TCCTGCCCTT
95551 GTCTGCTAGA AGAGAGTGGC AGTGATGTAT GAGAGTTTTT TAAAAAGGCA
95601 TCTGCTCTAC ATCAGATTCT CATTCATATT CTTACCAACT CTGTTGCTCT
95651 GTTTGGAAT GGGAGAGGCT GGGCTCAACT TGTTGACCAC TCCCATTTTT
95701 GTATCTCTTG GCTATCAGGC ACTGTGTAAG GCCCTCCACA GTGATCATTT
95751 AATCCTCAGT CATGGTTGTC TTCCAATAA CAGTTGAGGA AACAGGCTTA
95801 GAGTATTTAA ATAACTTGAG AGAAGACACA ACTTATGCCA GAAATGAGAT
95851 TTGGTTCTAG ACCTGACCAA CTCCAAACCT AGTGCTGTTT ATTACTCTAG
95901 AAAAACATCA CAGGCAACCT GAGCAGGGCC TCTGTTCATT GCAGAGAGCT
95951 CACAGGTGGA CCTGAGCAGG GCGTCTGTTC TTTGCACCTC ACAAGTGGCC
```

```
96001 AGTCTTATTT CTCTACTTCT TTGTGCTTTC CTAGGCAAAG AATCTGAAGA
96051 GAGAGGTTAT ACTAGGAATA CTGGAATACA TGTTGAGGTG TTCCCAAGAT
96101 GTTATAAGAT ACCTTTCATT TGTTTGTTTT TACTTTTTGA GATGAGGTCT
96151 CACTCTGTCA CCTAGGCTGG ATTGCAGTGG CATGATCATA GCTCACTGCA
96201 ACCTCCACCT CCTGGGCTCC CACTTCAGCC TCCTGAGTAG CTGGGACCAC
96251 AGGCGTGTGC TACCATACCC AGCTAATTTT CTCTGTATTT TTTGTAGAG
96301 ATGGGGTTTC ACCATGTTGT CCCAGACTGG TCTCAAACTT CCTGAGCTCA
96351 AGCCATCCAC CTGCCTCAGC CTTCCCAAAG TGCTGGAATT ATAGGCATGA
96401 GCCACCAAAC CCAGCCGATA CCTTTTTTTT GTCTAAATGC CTGTATTCTC
96451 CCTTAGGGTA AATTACAGTC TAGGGTCTGT GGTTTCTTCT AGAAAGAGTT
96501 TGATTCATTT AATAAATACC TATTAAGGAC CTAACATGTG CTTCTGGCAA
96551 CACAGTAGTA AACAAGCAAG GTATGATGTC TGCCTTCATG GATCCCACTT
96601 TAATGCAGGA AAACAATAGA CAAGTAAACA AATAATCACA AATTGAAGTT
96651 GATGCTATAG AGAAAACAAA CAGGGTGGTA CTGAGATAGA CAGTAACTAC
96701 TCTAGCTATA TCTGAGGTCT GTTTTAGAGG TAGAAGTAGA CATGCTGATG
96751 GGAAACATTT GGGGAATGAA GGAAACAGTT ATCAAAAGGG ACTTACATG
96801 TTCTCGCCAG AGTGACAGGG CATGTGTAGT AGTGCTGTTT ACTGAGATGG
96851 GGAAGACTTG GGGAGGGAGA TGAGGAGAGA GTGTTGCAAA GAAAACTGAG
96901 AGCTCTTTTG AACACATTAC AGTTGAAATA TCCAGGCTGG GCGCGGTGGC
96951 TCATGCCTGT AATCCCAGCA CTTTGGGAGG CTGAGGCAGG TGGATTGCTT
97001 GAGTCTGGGA GTTCAAGACC AGCCTGGGCG ACACGGCAAA ATCCCTTCTC
97051 TACAAAAAAT ACAAAAATTA GCTGGGTGTG GTGGCTTATG CCTGTAGTCA
97101 CAACTACTTG GGAGGCTGAG GTGGGAGGAT CACTTGAGCC TGGGAGACGG
97151 AGGTTGCAAT GAGCCAAGAT CACGCCACTG CATTCCAGCC TGGGTGACAG
97201 AACAAGACCC TGTCTCAAAA AAATAAAATA AAGTTAGAA ATATCTGTGA
97251 GGCATAGAAG TAGAGACATT TGGACATTCA GATCTATGC TCAGAGGAAA
97301 TACCCAAGAT GGAGATTTTA GAATTATTAG AAAATAGAGG ATATTTAGAG
97351 CCCCAGATAT TGAGGCTTTC ACATCACCTA AGAAAAAAGG ATACATTTTT
97401 AAAAAGCAGG TAGTCTAGAA GCAAGCCCTG AAGAACAGCA TTATTTAGGG
97451 ATCATATAGA GAGAAGAGGA GCCAACAAAG AAGTCGGGAA AAACAGAAAG
97501 GGACTGGGAA GGAACAAGCC TTCAGGGAAG AGGAAAACCA GGATGTTGTG
97551 CTGCCATAGA GACAGAAGAG GAGAGTATTT CAAGAAAGAG GGGACATCAA
97601 AATGTGTTTA CTGTTTGAGA GATCAAAAGA AGATCAAGGT CAGAACAAAT
97651 GTGTATTGGA TTTGATGGCA TGAAGGTTGT TGGTGACCTT GAAAGAGATT
97701 TCACAAGGAA GGAGTGGTGG GGATGGTAGA AATTGGAGTA TGTTGAAGAG
97751 AGAATGGGAG GCGAGGAAGT AGAATTAGTG TGTAGGCAGC TCTTTAGAAG
97801 TTTGGCTGTA AACAATTGCA GAGAAATGAG GCAGCTAGAA GAGAATATGG
97851 ATGTCAAAGG GAGAATGTTT TCAAAATAGT AGCTGCTGCT GAGAGTAAATC
97901 CAGTAGAGAG CACAGACTGA TGTTGCAGGA CAGAGCCAGTG GTACGATAGA
97951 AACAAAGTCT CCAGGAAAGT GAGAGGGGT GGGACCCAAA GCACCAGTGA
98001 GGAAATGGCT TTTGTTGGGA GAAGGGATAC CTTTTGCAGG ATATTTATGTA
98051 GAAAGGGACA AGAATATTGA GTTATTTATA AGGAAAGAT TATAATGATG
98101 GGGCTAACGT GTGTGAGCTG CACAAGAGAG GAGTGAAGTT AGGGCAGAGC
98151 TGCTGTATGA TGGGAATGTG CTGGAGTTCA TGGCTTGAGT ACAGGCGAGC
98201 TAGAAGGATA AGAAATGATG GTCAGGGGTT TCAGAGGTAG CATGGTTTCT
98251 GTTGGTGATA AGTACCTGGA AGAGGGTGGC TGAGTTCAGG AGGCATTTAA
98301 AGAACTGAGA AGCCAGGTTC TGGAAGAGCA TCATGCCTTC ACTGAAGACA
98351 CCCAGGGTGA TAGCAGGGGC TGGGCAGAA AGGAAGGAGC AGAGTTTAGA
98401 ATCTTCCTGA ATGTCAGAGA CAGTGAAGAG AGAGTCAGGA TGGTAAAGCC
98451 AGCTGCCATA AGCAGGGGCT CAGAAGGGTA GAAGAATAAG GCCTGAAAGT
98501 TGCAAGGCAG CCTCTTACTG ACTAAATTTT AAACTTAGTC TCTTTGAGCT
98551 TGATGTCTTC CTCTGATAAA TGGTGGTAAG CATGTGCACG TTATCACAGA
98601 GTTCAAATTT GGTGAGTCAG TGTACCCACT GCATTGCCCA GTAATACTAA
98651 AAAAGAAAAA ACAAATACTA ATTTCTGCAA CTACCATACT CCCTAAAAAC
98701 AGAGACCTAC CCCCAATCAC CAAAAAATCC CCATTGTTTT TCTAATCCAA
98751 ATTTTGTACA TATTTAATAA CCTTATACCA CCACTTACTA TTTTTTTACT
98801 TTCATCGAAG ATGAATCTAC AAAAATATAT TAATGTCAAA AAATATTACT
98851 GACCTAGCAA ACTGGCAGTT GGGAAGTAAG GTAAGAAGGC ACACTTTTAT
98901 TAATTAATAA TATCTTTTGT ATTCCCTAAA CAGATTGAAA AATGATGGAT
98951 TAGTTCATTC TTGCATTCCT ATAAAGAAAT ACCTGAAACC AGGCACAGTG
99001 GCTCACGCCT GTAAATCCCA GCGCTTTGGG AGGCCAAGGT GGGCGGATCG
99051 CTTGAGTTCG AGACCAACCT GGGCAGCAAA GTGAGACCTG GTCTCTACAA
99101 AAAATACAAA ATATTACCCG GAAGGCTGAG GTGGGATCCA CCTGAGCCCA
99151 GAAGGTTGAG GCTGCAGTGA GCTGTGATCA CACCATTGCA CTCTAGCCTA
```

FIGURE 3A-31

```
99201 AGTGACAGAG TGAAAACTCT GTCTCAAAAA AAACAAAGAA CCACCTGAGA
99251 CTGGGTAATT TATAAAGAAA AGAGGTTTAA TTGGCTCACG GTTCTGAAGG
99301 TTCTAAAGGA AGCATAGCTC CAGCATTAGG CCAGGTGCAT TGGCTCACAC
99351 CTGTAATCCC AGCACTTTGG GAGGCCAAGG GCAGGCGGAT CATGAGGTCA
99401 GGATTTCGAG ACCAGCCTGG CCAATATGGT GAAACCCTGT CTCTACTAAA
99451 AATACAAAAT TAGCTGGGCG TGGTGGCGCA CACCTGTAGT CTCAGCTACT
99501 CGAGAGGCCG AGGCAGAAGA ATCACTTGAA CCCAGGAGGC GGAGGTTGCA
99551 ATGAGCTGAG ATCGTGCCAC TGCACTCCAG CTTGGGACAC AGAGTGAGAC
99601 TCCATCTCAA AAATAAATAA ATAAATAAAT AAATAAATAG CTCCAGCATC
99651 AGCTTCTGGG GAGGCCTCAG GAAACTTACA GCCTTGGCAG AAAGTGAAGG
99701 GGGAGCCGGC ATGTCATGTG GCCAGAGCAG GAGCAAGAGT GCAGGAGGGG
99751 AGGTGGCCAC ATGCTTTTAA ACAACCCACC TCCACAAGA ACTCACTCAC
99801 TATTGCGAGG ACGACAGTAC CAAGGGGATG GGCTAAACC ATTCATGAGA
99851 AATTTCCCTC CGTGATCCAG TCACCTCCCA CCAGGCCCCA CCTCCAGCAC
99901 TGAGGATTAT AGTTCAACAT GAGATTTGGT GGAGACACAG ATCCAAACCA
99951 TATCAAATGG GTTCTAGGAA CTTAGCCTAG ATTTCAGATT TAGGAACAGT
100001 ATCATAGGTC ACCTTTTCAA AATACATAAA GTTTCCTACA GAAACAATAT
100051 CAATTAAGTG CATGTTTTAA AAATAAAAAT AAAGGTTACT ACAAAAAAAG
100101 TGGGGAGGAG CAGGAGTGGG TGCAGGTGTC CCCAGGAAGC CTAGGCATAG
100151 CTCACACTGC ATGTGCTATC ACGGCGAGAC TCAGAACTGC CCCGAATCCG
100201 AGGAGGGGCC ATGCGAGTAG GTGGGCCTAG GCACCTCCTC AGTCACTGGC
100251 TGTGCCCTTT CACTCTGTCA CTGGGAGACA GAATCCTGAG TTTTCTGCTT
100301 CAGGGAGCCT GCATGGAAAG AGTAGGTCAC TGCCGGAAAT CAGGCTAGTT
100351 TTAGCAAAAG GAACGGACAT TAGGCACCTC CAAAGGGACA AAGGACCAAT
100401 ATACCTGGTT GGGGACAGGA TTCTGTCATT TGATTATTCC TGACTCATGT
100451 TTTCATGAGG TAGTCCCCCA CCTCATATAA AAGCCTCAGT GTTGGCTTCT
100501 GACCATGGTG TATGAAAAGC CCTTGTCTAA AGGTTACTGC CCTGAGAAAA
100551 TAATAAAGGA AGAAGAGGAT AGACATGAAG ACACTTTAAA GCCTCCTGAA
100601 TAGAATGCAT CCAGAAGCGA ATTCCAGGAG ATTCTGTCAT CATGCTTGCC
100651 TTTCAAGCAA ACAAAATTAG CTGCTAGAAC TGAGAAAGAG TGTAAACACC
100701 AACTAAATGC CTCAAAGAAT CATGGTAGTA AATTACTTCT CCATGTTGCT
100751 CCATATAAAC CTGCTGTGCC ACCTGTTGAA GGCAGCACTG ATGCTGCATG
100801 TTCAGTCTGG TCCAAGGCCC CAACAGGAAT CCGTTGTGCC AAGAAAAGGC
100851 CCTACTGGAA GGATTGGAGA GCAGCTGGTT CTCAGCAATG CAAGCATCAG
100901 GCCAGGCTGG GGCTGCTTAA TGCTGCTTAA GAGATGACAG TGGTGGACCC
100951 CAACACCTCT CCAAGGGATG TAGAATCTGC TTTTCCCATT TCTGAATGCT
101001 ACTGAAACAA ATCTACAACT AGAAAAATCA AATATTCATG AATTCAAGAC
101051 TTGGGATCTC AGTACTAAGA CTTTAAAGAA GTTGCCAGAT GGATCGCTTC
101101 TGTGGTGACA GCCCTGGCAG GAGCCATTCA GTGCTCTATG AGCTACAAAA
101151 GAAACCAGTT GATGGTGTGA ACACCACTAC AGAGCAACCT GCACACCACA
101201 GCAATTTGAC AGCTCAGGTT CTGTGTCTCA TGTGGCACCG TGCTTGTCCT
101251 TGGAAAGAAG GCCTACAAAA TTCTTCATAT CTCCATTCCT TGACATCTGC
101301 TGGCAAACTC CCACTCATAT TTTAAGACTC AGCCTCTCCT GTGACACCTG
101351 TGTCTTCTCT CCAAACAGGG AGGGACGCTT GCCTCTTCAG AGCTCCCCAC
101401 ACTGGAGTAT AACTGCTCCT GTGTCTGATG CCCTTAGTCT CAGTGCCAGG
101451 AGGTATTCAT GCTTATGTCC CCATGGCCTG TAACAGAGCC TGCATCAGGA
101501 TGCTTGGGTAA AGGACTGTTG AATGAATGTC AAATATGGGT CCCTCTGATG
101551 GGTCTATACG TGTTGATCTA GGATTGGAAG GGTCACAAAG AGTTGTGCAT
101601 GCTTACAATT TCAATCAAAT ATCACTATTT TTAGTTAAGA GGGAAGAGTA
101651 GTGTGAAATT GGCAATAATT AGATACTCCA AATGTTCTTT AAAAACTAAT
101701 AGCATTGATG TATTAAGAAT GCAATCAGCC GGGCACAGCA GCTCACACCT
101751 GTAATCCCAG CACTTTGGGA GGCTGAGGCA GGTGGATCAT GAGGTCAGGA
101801 GTTCGAGACC AGCCTGGCCA AGATTGTGAA ACCCCGTCT CTACTAAAAA
101851 TACAAAAATT AGCCGGGCAT GGTGACGCAC ACCTGTAGTC CCAGCTACTT
101901 GGGAGGCTGA GGCAGGAGAA TTGCTTGAAC CCAGGAGGTG GAGGTTGCAG
101951 TGAGCCCAGA TCGTGCCATT GCACTCCAGC CTGGGTGACG AGCGAAACTC
102001 AGTCTAAAAA AAAAAAGAAT GCAATCATAC ATTAGAAGAC ACATTCTGTT
102051 TTAGATTTTT ACTTAAATAT TTTAAATACT TCCTTAATCT GCAATATTTAC
102101 CTTATTGATA GATTTCAGAA GAAATTGATC ATTTCATTGA ACAAGATTTA
102151 TTAGACACAT AAGGAAAGTG AATCATAACA ACTGTACAGG TGGGAAATTG
102201 AACAACAAAA ATGACCCTGA GATACCCACA TTCTACTTTG GCATATAGTG
102251 GGAAAACAT TCTAGACTTC AAGTCTAGGC CTATCTTGGC TAAATGTAACC
102301 GATGACTTCA CAAACCATTT ATGGGACTAG AAGCTGAAAG GAAAGTACTG
102351 GTGGATAAAC ATCATATTGA AATTATGTTG AGTCACTTAT TTGCTATAAA
```

FIGURE 3A-32

```
102401 ACACAAATTG TTTTGTGTAA AGGGGTTAAG ATGGCTGGAA AACTGTCTCC
102451 ACTCAAGAGC AAGAAAGCAG CATGTGTCTT ACCCTGTACC TTCATTTTTA
102501 CTTGTACTTC ATAATTTCTG AGGGAGAAAT ACGTGGAAAC CAGATGCTTG
102551 ATATAGTTTC AGAACACGTC CTTAAAGAAT ATGACTCCAA GTCTAAGAAT
102601 TGTAGGTCCT TTGCTTCTTA GATAACTACT GTTAGCCTTG ATCACAGAGA
102651 TTCCAGGTTT AATAACTTCA GTTCTCCCCA CTGTGTATAT AGATGTTAAG
102701 TTACACAGAT TTGGCATTAT TCCCATTTTC AGGTTAATAT CAGAACACTT
102751 GTTATCAAGT CAGGATAGTA ATTGTGAGCC TAGATGCTCT AGGTTTGGCC
102801 ATACGTGGTT ATCTACACCA CCAACTGTTC CAATTAACAA TTTACCAGTT
102851 GCTTCTACCC AAAGTACCAA GACTCCAGCA AATGGGGAAT ATTGGAAACT
102901 GGCTTGGCTT CTTGAAGCAA CATGGTAATC AATAAGAATC TTGGCTGGGC
102951 ATGGTGGCTC ATGCCTGCAG TCCAGCACT TTAGGAGGCC AAGATGGAAA
103001 GATGGGAAGA TGGCTCAAGC CCAGGAGTTC AAGACCAGCC TGGGCGACAT
103051 CGTGAAACCC CATCTCTACA AAAAAATACA AAAATTAGCT GGGTATGGTC
103101 GTGGGTGCCT GTAGTCCCAG CTGCTGGGA GCTGAGGTGG GAGATCACCT
103151 GAGCCCAGGA GGCAGTTGCA GTGAGCCAAG ATTGCACCAC TGCACTCCAG
103201 CCTGGGTGAC AGAGTGAGAC TCTGTCTCAA AACAAACAAA ACAACAATCT
103251 GGCTGGGCGC GGTGGCTAAT GTCTGTAATC CCAACACTTT GGGAGGCTGA
103301 GGAGGCAGAT CACTTGAGGT CAGGAATTCG AGACCAGCCT GGCCAACATG
103351 GTGAAACCCG TCTCTATTAA AAATACAAAA ATTAGCCGGG CATGGTGGCA
103401 CACACCTGTA ATCCCAGCTA CTTGGGAGGC TGAGGCAAGA GAATTGCTTG
103451 AACCAGGAGG CAGAGGTTGC AGTGAGCTGA GATCATGCCT CTGCACTCCA
103501 GCCTGAGCTA CAGAGCGAGA CTCTGTCTCA AAAAAACAAA AAACAAAAAC
103551 AAGAAGAATC TTACTACTGC TTCTTGGGG ATACTTTTGG TATTATTTTG
103601 ACAAATGAAT TGTGAGGATT CAAATATAAG AAAGGGATTA TTCTTGGTAG
103651 AGTTAACAAA ATTGTACCAA ATGACTTTTT GTGTTAAACA CGATTCATTC
103701 ACCCAACCCT AGAAAGGAGC CTGAATGAAG TCTAATTTGG GTGACAGATT
103751 CCCACACAAA TTAGATGTAT GTCATTCAGG TATAGAGAAT TGATTTTATA
103801 TTAGAAAAAA CAAACCTTGT AAACAGTTTT ATAAATAACT GTTTCATGAT
103851 TTTCCTTAAG TAGTACTGAT CTCTTACATA TAGATGTTT GTGTCTTTCG
103901 CCTCAAGTTA GTATAGAACA GGGCAAGTGG CAAAGCTCGA GGAAAGTGTG
103951 ACCTGAGGTA CATGCTGTCA GCTTGATGCT GGAGTTTGGC CTCTCAAATC
104001 TCTAACCTGT TAAATGAAGT TAATTAGGAT TAATTTTTTT TAATGTATGT
104051 TTACTACTGA AAATAAGTGC TGGCCCAGAC GCAGAGGCTC ACGCCTGTAA
104101 TCCCAGCACT TTGGGAGGCC GAGGCTGGCA GATCACCTGA AGTCAGGGAG
104151 TTTGAGACCA GCCTGGCCAA CATGGGGAAA CACTGTCTCT ATTAAAAATA
104201 CAAAAATTAG CTGGGTGTGG TGATACATGC CTGTAATCCC AGCTACTCGG
104251 AGCCTGAGGC AGGAGAACTG CTTGAACCCA GGAGGCGGAG GTTGCATTGA
104301 GCCAAGATTG TGCCATTGCA CTCCAGCCCA GGGACAGAG TGAGACTCAT
104351 GTCTCAAAAA AAAAAAAAAA AAAAGAGGA AAAGAAGTGC CCAATAGCTT
104401 CAATGGATGC CACATAATTT TGGAATAATT TTTACAATCA GGAATTTCAT
104451 TGTCCAAGCC CCTTAGAAAA AGAAGCAACC CAGCCCCATA CCCAGAAAGT
104501 CAAGCTGTAT AGTGCTGTTC CTTAGTGAGG ACGGTCAACT CTCAGTAGAA
104551 AAATCTCCTG TTTGGATTAG TGCTTAGTTG ACCTATTGTG TTCAGTTCCT
104601 CTAACATGAG TAACTTCTAT TGGATAGGAA ATTTTGAAGC TCAAAGGGTG
104651 TAATGAGAGT TAACATTACT GATTTTCCAC TGTTACTTTT TAGTGTTTTC
104701 ATAACTTGGA TGTGTTAACC TATGCCCAT CAACTATGCT CCTAGTCTCA
104751 GGTGACAACA TGTTCAATTT AAGATGGCAG GCAGTACAGT GGACCTCTCT
104801 CATCCCATGG GAAGGAACC AGGATGTTTA TTATGTAGTA TTGTATAGTC
104851 TCTGCAGCGA TAATAGAGAA AGTTAAAGGT AAGCGGTGGA GAAGTAAAAT
104901 CTAGAGTTTC TAATATAACC CTTCTCACTT TTCTTTTCAA AAAAAATAAG
104951 AGGGTCTCAC CATGTTGCCC ACACTGGTCT CTATCGAACT CCTGGGCTCA
105001 AGCGATCCTG TCGTCTCAGC CTCCCAAAGT GCTAGGATTA CAGGCATGAG
105051 CCACTCTGCA TGGCCAAGCT CACTCTTCTT AAAGGTCTGC TAGTAAGAGG
105101 GTTTCTACTT TTTGAAACAA ATTCATGATT ACCTAAAATG AAGCTAGGTT
105151 ATGAAGTATA TATAAATATG CAGCCCAATA GGCTGGGTGT GGTGGCTCAC
105201 ACCTGTAATC CCAGCACTTT GGGAGGCTGA GGCAGGCAGA TCACTTGAGG
105251 TCAGGAGTTT GAGACCAGTC TGGCCAACAT GGTGAGACCA CATCTCTACA
105301 AAAAATACAA AAATTAGCGG GTGTGGTGGC CTGTGTGCGC CCATAGTACC
105351 AGCCACTTGG GAGGCAGAGG CAGGAGAATC ACTTGAAGCC AGGAGGCAGA
105401 GTTTTCAGTG AGCTGAAATT GTGTCACTGT ACTTCAAGCC TGGGCAATGG
105451 AGTGAGACTG TCTCAAAATA TATATATATT TGCAGCCCAA TAAAGATACT
105501 TAGATAAAAC TATTGGGTTT ATTCCTTGAA AACTAGGGCA TGTGTAGCTA
105551 GATCTGGCTC ATAAAAAGCA AAGTTATTTA CATATAATTTT AAGGTAAAAT
```

FIGURE 3A-33

```
105601 TGCCTCTGAT AAATGTCAAA GAGGAAGTTT AGGTCTTTCT TCTGGCAGAA
105651 AGCCAGAGAG TAAGTGCTGA ATGTGACGCA GAATCATGTT AGGTAACAAG
105701 GACTTTGAGG TAAGTGGCTG AAGTCTTCTG TGGAGTCAGC CGACTCTTGC
105751 AGGATTGTGT GGTATCAGTC ACCTTTAGCA TTTGCCAACC CAACTCTGAT
105801 CATTCTTCTT CTTTCAAGGT ATCTCAGCGT TTGAGTCAGC CAGGAGTAGC
105851 AATAGGTTTG GCTTGGACTC CCTTAGGTGG AGAAATCATG TTCGTGGAGG
105901 CGAGTCGAAT GGATGGCGAG GGCCAGTTAA CTCTGACGGG CCAGCTCGGG
105951 GACGTGATGA AGGAGTCCGC CCACCTCGCT ATCAGCTGGC TCCGCAGCAA
106001 CGCAAAGAAG TACCAGCTGA CCAATGGTAG GAGCCTGCAC CCGGCCAGGC
106051 AGGCGTGACC CAGGAGGCGG TACCTTCCAT GGGGAGACT GGCATGAGCT
106101 CGAGACTGCC AGTTACACAT CTAGCAAAGT ACACACCGTT TTGAACCCCT
106151 GTGGAAATCC TAGTTCCCAT TTCAGGACTA TTTGACTAGT GCCTGAACTA
106201 GAAACTAATT CAAAAGGTTT ATTTTGTTTT AATACGACTT AGAGTAGAAT
106251 GGAACTGTTC TTCCACACCC TCACCCAAAT TGTACTGTCC ACCAATATTT
106301 TGAAGAATTC ATTACCCAA AACATTCATT TTGTTTGTG ACTTTTTTTT
106351 TAGGAGAAAA AGAAAACAGG TTTAATTTTT CTACATTAAA GTCCCTTTTT
106401 CCTTTTTAAA GCTTTTGGAA GTTTTGATCT TCTTGACAAC ACAGACATCC
106451 ATCTGCACTT CCCAGCTGGA GCTGTCACAA AAGATGGACC ATCTGCTGGA
106501 GTTACCATAG TAACCTGTCT CGCCTCACTT TTTAGTGGGC GGCTGGTACG
106551 TTCAGATGTA GCCATGACTG GAGAAATTAC ACTGAGAGGT CTTGTTCTTC
106601 CAGTAAGTAT GAAAAAACAA TTTATATGGT TATTTTTTAT TTAATTTTTG
106651 AAAATTAATA TTATTTTTAA ATACGGGTTT GCCTTCTTTC TATGAAAACC
106701 TTGGTTTTAA GTATATATTA TATTTTTATG CCTGTACTA ATTCATATTT
106751 TAAAATTTTG ATCAAATAAA AGAAAACTG ACAATTTTTC ACATTTTCCT
106801 TTTTTTTTT TTTTTTTTT TGAAATAGAC AGGTCTCACT CTGTTGCCCA
106851 GGCTGGAGTG CAGTGGTGTG ACTGTAGCTC ACTATAGCCA CCAAGTCCTG
106901 GGCTCAAGCG ATCCTCCTGT CTGTCTCCCG AATAGCTGGG ACTATAGGAG
106951 CACGCCACCA TGCTCAGCTA ATTTATTTTA TTTTGCGTAG AGACAGGGTC
107001 TCTCTGTGTT GTCCAGGCTT GTCTCAAACT CCAGGTCTCA TGCAGTCCTC
107051 TCATCTCCAC CTCCCAAAGT GCTGGGATTA CAGGCGTGAG CCACCACATT
107101 CAGCCCACGT TTCCCATTCT AAGATTTGCT AAGGGAAAAA AATATTAGTG
107151 TGGTCATCAG AAATATTGGC AGTTACATGA AAATTTGAGG CCTTGTTCTA
107201 CTTGACAAAT TGTTAAAGAT ATAGCACATG TGCAAAATGG GATAGTAGTT
107251 GTTTTTAAGC TTTAAGCCCA TTTCTTAAAT TTGAAGTTTC TTTGAGACCT
107301 CCTGTCCCCC TGCAGAAAAC TTTGCTAGTA TAGAATGGAA ACTCTAATAA
107351 AGATTAACCA TATCTAATGA CTACATTTTG AAAAGGTTCT ATACATGTGG
107401 GGTCTTGAGG CTCCAGATCC TAAACTGCTT ATAAAAATAG TGTGATAAAA
107451 TGTACAGAAC TTGAGAGTAT TTAAAGTTGT TAGTTGAGTA TTAGTCTACA
107501 ACAGACTAGA CTACAATTTT AGTCCACAAC AAGATTTTGG CAGGTTCATA
107551 GCAAGATGAG GAAAAAAAAA AAGAAATAGT CTTTTTTTCT TTTTTCTATC
107601 GAGATGGAGT CCGGCTCTCT TACCCAGGTT GGAGTACAGT GGCACAATCT
107651 TGGCTCACTG CAACCTCTGC CTCCCAAGTT GAAGTGATTC TCCTGCCTCA
107701 GTCTCTCAAC TAGCTGGGAT TACAAGCATG CGCCACCACG CCCGGATAAT
107751 TTTTTCTATT TTTAGAACCT CCATAGAACA AATGGGTTTT CTACTTGGTC
107801 CCCTCTCAGA GCAAATCGTA GCCCAAGTAA AGGCTTCTGC AGCCTCAGGA
107851 GAGACAGCCA CAGCGGCCTG GGGTACACCT TCAGCTCCAG ACCATTACAA
107901 GAGGCAGGAT GGAAAGCAGC AGCACTTGAA AGAAAGGCCT GTGAAAGCTG
107951 GAGAAAACCT CCTTTGAGAA CAGAGGACAA GACGGGGCTT TGGGATTTGA
108001 AAGTGGTCAA AGAATTATTC AGGAAAAAAC TATAGTGAAA AACAATTTGT
108051 TGTTAGAACT CCAACATCTA AAAGGAGTTC TAACAAACAG GAAAATGGAA
108101 TGGAACAAAT TATCCAAGAA ATAACTGAAC ATTTCCTAGA AGTTAAGGCA
108151 TCTTGAGATC GAAAGGACCA TTACTAACCA GGAAAAACAT TTCATCCCCT
108201 TGACTTTTCA GATTACTGAG GATAAAGCGG CCTCAGCACT GACACTGGAT
108251 GTGCAGTACC TTCAAAACTA TGAGGGAAAA TGGCCCAGGC GTGGCAGCTG
108301 ACGTCTGTAA TCCCAGCACT TTGGGAGGCT AAACAGGAGG ATAGCTCAAG
108351 TCCAGGAGTT CAAGACCAGC CTGGGAAATA TATCTCTACA AAATTGTTT
108401 TAAAAATAGT AAGGAGGCTG GGTGTGGTGG CTCACGCCTG TAACTCCAAC
108451 ACTTTGGGAG GCCAAGGTGG GCGTATCACT TGAGGTTAGG AGTTTGAGAC
108501 CAGCCTGGCC AACATGGTGA AACCCTGCT CTACTAAAAA TACAAAAAAA
108551 TTATCCGGAT GTGGTGGCGC ATGCCTGTAA TCCCAGCTAC TCAGGAGGCT
108601 GAGGCAGGAG AATCGCTTGA ACCTGGGAGG CAGAAAGTTG CAGTGAGCCA
108651 AGATTGTGCC ACTGCAACTC TAGCTTGGGT GACAGAGTAA GACTGTCTCA
108701 AAAAAAAAA AAATAGTAAT GAAAGCTGTG AGGGAAAATG TTTTACATCT
108751 AGTCTTGTAT ACATGGCCTT AGTATCAATC AAGTGTGAAA GTAAAATATT
```

FIGURE 3A-34

```
108801 TTCAAACATG CAAGGAATCA GTTCATCTTA CACTCTTTTG AAGAAGGTAC
108851 TTTGAAGGAG TACTTCAGCA GCATGAACAA AACCTTGAAA GAAGATGCCA
108901 GTGGGCGGG AAGGCCTGGA GCAGCCAGCC AGTCTTAATT GGAGCAGATG
108951 CAACACATTA CCCCAAAGCA AGAATACTCC ATACTCTTCA AGTTCCTGTG
109001 GCCCAGGAAT TCAGAGAGG CTGAGCTGG TTCTGTGGC CCAGGGTCTC
109051 TGGCCTTACA GTCTAGGTTC CAGCCAGGCT GCAGTCACAT GAAGGCTGAC
109101 AGGCTGGAGA AACTGCTTCC ATGGTGGTTG ACTCATGTGA CTGGCAAATT
109151 GGTCCCATCT AGTGGCAGGA GGCCCCAGTT CCTCACCTGA TGGACTTGCC
109201 CATAGGCTGC TTGAGTGACC TCAGACATTA TGACTGGCCA CCTCCAGGGC
109251 AGGTGATCAA GAGAGATTCA GGCAGCAGCT CTGGTTTTTT GTGACTCAGC
109301 CGTGGAGATC ATACAGCATC ACTCCCACCA CACTCTGTTT CTTACCGAGT
109351 CACAAAGCCT GGCCCACATT CAAGCAGGG GACCATTGTA GACATGTTTG
109401 AAAGCCACCA TAGGAGCCTA GTTAGGGAT ACATTTTCTT CATTAACCAG
109451 CATGGAGGTT CTGGCTTTAA ACCTGTAGAG AGGGAAGTAA CCCCAGCACA
109501 CAGCTAAGCT CTGCAGGAGC GGGCTCATG GTCAGAATCA CGTGCTGCTT
109551 TTTCAGATCA ACCTAAAGAC TAGACGGTTG TGATTACACC TGAATGCCAA
109601 TTTACTTTGA CAGCATTTAT AAAAACAATC ATTGACAGAA GAGGAACTCA
109651 TACCTATCAA CAATTTAGAA TCCCCTCAT CAGAGTCTTT AATATAACAC
109701 CAATTGAAAC ATTAAAAAAA GGTTACTACT TATCCTTTTT CCTGGCTTTC
109751 CTAGCTCATG CTATAACAAA ACGGAAGATG ATTTGGATGT TTTAAAATAG
109801 TAGTGGTTAA ATTCAGTGAA AGAAAGCTGG GTCAGGGTTT CTTTCAGCTT
109851 GAGGGTGATC ATTAACCCTA AAAACTTTTT TCTCTCCTTA CAGGTGGGTG
109901 GAATTAAAGA CAAGTGCTG GCGGCACACA GAGCGGGACT GAAGCAAGTC
109951 ATTATTCCTC GGAGAAATGA AAAAGACCTT GAGGGAATCC CAGGCAACGT
110001 ACGACAGGAT TTAAGTTTTG TCACAGCAAG CTGCCTGGAT GAGGTTCTTA
110051 ATGCAGCTTT TGATGGTGGC TTTACTGTCA AGACCAGACC TGGTCTGTTA
110101 AATAGCAAAC TGTAGGTCCA AATCTCAATT TTTAGAATT TTAAGTTATG
110151 AAGTGCTCAA AGGTACTGAC ACAGTTGATT TTATTCACAC CATTAGGGGT
110201 ATGCAAGATG TCCCTGTTTT ATAAACATAA TCACAACAGT AATAAACCTC
110251 AAGTAGTGGC TAGTGTTTAG TATAGAAATA TAACAATGTTG ATTTAGTAAA
110301 CTGATAAAAA TCGAATTCTT GTCTTTTAG TGGGATCCTT ACTGTCCCTG
110351 GAAAGATATA GCATAGTGGT TCTCAGCACA GTCTCCAGAA CAGAAGCATC
110401 TGTAGTACCT GGTAACTTGT TAGAAATGTA CATTCTCAGG CTCCACAGCA
110451 GGCCGCCTGA ATCAAATCCT GGGAGGTGGG GACAGAAATC TGTGTTTTAA
110501 GAAGCCTTCC AGGTAATTCT GCTGCACACT CAAGTTCAGG AACCACCGGT
110551 ATAGACCATT ACCTTAGTGG ATTTACCTGT AGAGTTTATT GGATCCTGAA
110601 ACCAATCAAT TACTTAGAAC TAGGCAAAGA TGAAAGTATA GCCAACTATT
110651 CTTGGCTATA TATATATATT CAAGTGGGCC GGGGTGATG GCTCACACCT
110701 GTAATTCCAG CACTTTGGGA GGTCGAGGTA GGCAGATCAC CGAGCCCAAG
110751 AGTTCAAGAC AATCCTGGCC AACGGCGAAA CTCTGTCTCT ACAAAAAATA
110801 TACAGGCGTG TTAGCATGTG CCTGTAATCC CAGCTTCTTG GGAGGCTGAG
110851 GCACAAGAAT TGCCTGAACC CAGGAGGTGG AGGTTGCAGT GAGCTGGGAT
110901 CGCGCCATTG CACTCCAGCC TGGCTGACAG AGCGAGACTG TCTCTAAAAA
110951 AAAAAGACTC AAGTGGACCC TACAATGAAG CCTACACATC CCAATAGAAC
111001 CCCCTTCTTA TGCTGAGGA AGCAGCCCTC AGAACATGAT AGCTTGTATC
111051 CAGCAGAGTG GCACGTGCTG GCACACCTCA CAGAAGCACC CTGGCCCTGG
111101 ATGCCTGCAA CCTCAGAAGA GTGCAGCTCC CAGCGGGAGG CAGCCATCCA
111151 TCTGGGATGG TCCTAAGCAT GGAATCCTAA CTCCTGATTC CGTCTCCTAT
111201 TTCTTGCTTG GCTACGCCAG TTCCCAAATC TGGTAGATGT CCATGCCCAT
111251 GTGCTCCTGC TGGACTCAA TTCAGGCTAT GTATGACTAT GAAGTCAGGC
111301 TCATCTGCTT ACTGGCTGTG TGAACTTTTT GTATCTTGT TTCTTCATC
111351 CATGAAATCC AAGTAATACT ACCTAATTGT TACTGTGGAG ATTAAGTTCA
111401 AATGCAATGT ATAGTAATAT TAAGCAATTT CTAGTTATTA TTCTAGCCAG
111451 TAATGGACTT CAGAATCTTT TATTACACAA TATAACAATA TGTATGTAAA
111501 GACATTTTGG AATTTCCTGG ATGAGAAGGA AGTCTGGGCT GGGCATGGTG
111551 GCTCACGCCT GTAACCCTAG CACTTTAGGA AATCGAGGCG AGTGGATCAC
111601 TTAAGCTCAG GAGTTCAAGG CCAGCCTGGG CAACATGGCA AAACCCCATT
111651 TCTACAAAAA ATACAAAAAT TAGCTGGGCA TGGTGGCACC CGCTGTAGT
111701 CCAGCTACTT GAGGCTGAGA TGGAGGATG AGGGAGGTCG GGGCTGCAGT
111751 GAGCCAAGAT CACGCCACTG CACTCCAGCA CCCTGGGCGA CAGAGTGAGA
111801 CCCTGTCTCA AAAAAAAAAA AAAAAAAAG ATTGGGCCAA AATACTGTGA
111851 TAAAATAGCA GGCCTGCTGA TAAAAGTTTA TCTGAATGCA TTGAGAGGAA
111901 AAGTCCAGAC CTAGGACTAG TTATGGCAGT TGGAGAGAAA GAACATCGGG
111951 ATGTTTGAAA ATATGCCATT GACTATCTTA ACTACTGTAA TTTTATCATT
```

FIGURE 3A-35

112001 TCCAACGTCA TCTAACTGGG GACTAGAACA AACTGTGAAT TCACTTTCAG
112051 CAACCAGAGG GCGCTAATCC ACACCCACAT CGCTCTGCCC TGTTCCACCC
112101 AGCAGGGCA ACAAGGATAT AACTTGGGGT TC (SEQ ID NO:3)

FEATURES:
Start:      2019
Exon:       2019-2251
Intron:     2252-10218
Exon:       10219-10453
Intron:     10454-14697
Exon:       14698-14829
Intron:     14830-16705
Exon:       16706-16828
Intron:     16829-19511
Exon:       19512-19675
Intron:     19676-20865
Exon:       20866-20960
Intron:     20961-28103
Exon:       28104-28362
Intron:     28363-35632
Exon:       35633-35774
Intron:     35775-54225
Exon:       54226-54376
Intron:     54377-57961
Exon:       57962-58088
Intron:     58089-61472
Exon:       61473-61606
Intron:     61607-92522
Exon:       92523-92665
Intron:     92666-105818
Exon:       105819-106026
Intron:     106027-106411
Exon:       106412-106602
Intron:     106603-109893
Exon:       109894-110112
Stop:       110113

SNPs:

| DNA Position | Major | Minor | Domain | Protein Position | Major | Minor |
|---|---|---|---|---|---|---|
| 12469 | T | - | Intron | | | |

Context:

DNA
Position

12469    AACCTTTTCTCTTCACTGAGCCTTTCTAAAAGAAGTCTGGGGCATCCCATTCCCTTGAGT
         AAAAGACTTTAATGGCTATAGGATGGACACCAAATTTCTTAGTATAACATTAAGACCGTT
         TGCAACTTGTCTTGGGCTATCTGTCTTGCGTCAACTCTAGTTATCACCTCACTGACACC
         CTAGTTCTAGCTCTACTGAATGTAAAACAGCTTCACATTGAGTTATTTTATGTCTCTATG
         ATTCTGCCTTCAGTTCTCTGCTGGGAGTGCTCTTCCATCTCTGATTTTTTTTTTTTTTTT
         [T,-]
         GAAATGGAGTCTTGCCCTGTTGCCCAGGCTGGAGTGCAGTGGTGCAATTTCGGCTCACTG
         CAGCCTCCGCCTCCCGGGTTCAAGCGATTCTCCTGCTTCAGCCTCCCAAGTAGCTGGCAT
         TACAGGCATGCGCCACCACGCCCGGCTAACTTTTTGTGTCTTTAGTAGAGATGAGGTTTC
         ACCATGTTGGCCAGGCTGGTCTCGAACTCCTGACCTCATGATCCAACGGCCACCACGCCC
         GGCCTCCATCTCTGAATTTTAAAATTGAATCTATGCTTTCCCAACAGCTGTAGGCTGTTA

Chromosome map:
Chromosome 16

FIGURE 3A-36

ISOLATED HUMAN PROTEASE PROTEINS, NUCLEIC ACID MOLECULES ENCODING HUMAN PROTEASE PROTEINS, AND USES THEREOF

RELATED APPLICATIONS

The present application is a divisional of U.S. application Ser. No. 09/741,150, filed on Dec. 21, 2000 and issued on Aug. 20, 2002 as U.S. Pat. No. 6,436,689, which claims priority to U.S. Provisional Application No. 60/252,410, filed on Nov. 22, 2000.

FIELD OF THE INVENTION

The present invention is in the field of protease proteins that are related to the ATP-dependent protease subfamily (a type of mitochondrial Ion protease homolog 1 precursor), recombinant DNA molecules, and protein production. The present invention specifically provides novel peptides and proteins that effect protein cleavage/processing/turnover and nucleic acid molecules encoding such peptide and protein molecules, all of which are useful in the development of human therapeutics and diagnostic compositions and methods.

BACKGROUND OF THE INVENTION

The proteases may be categorized into families by the different amino acid sequences (generally between 2 and 10 residues) located on either side of the cleavage site of the protease.

The proper functioning of the cell requires careful control of the levels of important structural proteins, enzymes, and regulatory proteins. One of the ways that cells can reduce the steady state level of a particular protein is by proteolytic degradation. Further, one of the ways cells produce functioning proteins is to produce pre or pro-protein precursors that are processed by proteolytic degradation to produce an active moiety. Thus, complex and highly-regulated mechanisms have been evolved to accomplish this degradation.

Proteases regulate many different cell proliferation, differentiation, and signaling processes by regulating protein turnover and processing. Uncontrolled protease activity (either increased or decreased) has been implicated in a variety of disease conditions including inflammation, cancer, arteriosclerosis, and degenerative disorders.

An additional role of intracellular proteolysis is in the stress-response. Cells that are subject to stress such as starvation, heat-shock, chemical insult or mutation respond by increasing the rates of proteolysis. One function of this enhanced proteolysis is to salvage amino acids from nonessential proteins. These amino acids can then be re-utilized in the synthesis of essential proteins or metabolized directly to provide energy. Another function is in the repair of damage caused by the stress. For example, oxidative stress has been shown to damage a variety of proteins and cause them to be rapidly degraded.

The International Union of Biochemistry and Molecular Biology (IUBMB) has recommended to use the term peptidase for the subset of peptide bond hydrolases (Subclass E.C 3.4.). The widely used term protease is synonymous with peptidase. Peptidases comprise two groups of enzymes: the endopeptidases and the exopeptidases, which cleave peptide bonds at points within the protein and remove amino acids sequentially from either N or C-terminus respectively. The term proteinase is also used as a synonym word for endopeptidase and four mechanistic classes of proteinases are recognized by the IUBMB: two of these are described below (also see: *Handbook of Proteolytic Enzymes* by Barrett, Rawlings, and Woessner A P Press, NY 1998). Also, for a review of the various uses of proteases as drug targets, see: Weber M, Emerging treatments for hypertension: potential role for vasopeptidase inhibition; Am J Hypertens 1999 November;12(11 Pt 2):139S–147S; Kentsch M, Otter W, Novel neurohormonal modulators in cardiovascular disorders. The therapeutic potential of endopeptidase inhibitors, Drugs R D 1999 April;1(4):331–8; Scarborough R M, Coagulation factor Xa: the prothrombinase complex as an emerging therapeutic target for small molecule inhibitors, J Enzym Inhib 1998;14(1):15–25; Skotnicki J S, et al., Design and synthetic considerations of matrix metalloproteinase inhibitors, Ann NY Acad Sci 1999 June 30;878:61–72; McKerrow J H, Engel J C, Caffrey C R, Cysteine protease inhibitors as chemotherapy for parasitic infections, Bioorg Med Chem 1999April;7(4):639–44; Rice K D, Tanaka R D, Katz B A, Numerof R P, Moore W R, Inhibitors of tryptase for the treatment of mast cell-mediated diseases, Curr Pharm Des 1998 October;4(5):381–96; Materson B J, Will angiotensin converting enzyme genotype, receptor mutation identification, and other miracles of molecular biology permit reduction of NNT Am J Hypertens 1998 August;11(8 Pt 2):138S–142S

Serine Proteases

The serine proteases (SP) are a large family of proteolytic enzymes that include the digestive enzymes, trypsin and chymotrypsin, components of the complement cascade and of the blood-clotting cascade, and enzymes that control the degradation and turnover of macromolecules of the extracellular matrix. SP are so named because of the presence of a serine residue in the active catalytic site for protein cleavage. SP have a wide range of substrate specificities and can be subdivided into subfamilies on the basis of these specificities. The main sub-families are trypases (cleavage after arginine or lysine), aspases (cleavage after aspartate), chymases (cleavage after phenylalanine or leucine), metases (cleavage after methionine), and serases (cleavage after serine).

A series of six SP have been identified in murine cytotoxic T-lymphocytes (CTL) and natural killer (NK) cells. These SP are involved with CTL and NK cells in the destruction of virally transformed cells and tumor cells and in organ and tissue transplant rejection (Zunino, S. J. et al. (1990) J. Immunol. 144:2001–9; Sayers, T. J. et al. (1994) J. Immunol. 152:2289–97). Human homologs of most of these enzymes have been identified (Trapani, J. A. et al. (1988) Proc. Natl. Acad. Sci. 85:6924–28; Caputo, A. et al. (1990) J. Immunol. 145:737–44). Like all SP, the CTL-SP share three distinguishing features: 1) the presence of a catalytic triad of histidine, serine, and aspartate residues which comprise the active site; 2) the sequence GDSGGP which contains the active site serine; and 3) an N-terminal IIGG sequence which characterizes the mature SP.

The SP are secretory proteins which contain N-terminal signal peptides that serve to export the immature protein across the endoplasmic reticulum and are then cleaved (von Heijne (1986) Nuc. Acid. Res. 14:5683–90). Differences in these signal sequences provide one means of distinguishing individual SP. Some SP, particularly the digestive enzymes, exist as inactive precursors or preproenzymes, and contain a leader or activation peptide sequence 3' of the signal peptide. This activation peptide may be 2–12 amino acids in length, and it extends from the cleavage site of the signal peptide to the N-terminal IIGG sequence of the active, mature protein.

Cleavage of this sequence activates the enzyme. This sequence varies in different SP according to the biochemical pathway and/or its substrate (Zunino et al, supra; Sayers et al, supra). Other features that distinguish various SP are the presence or absence of N-linked glycosylation sites that provide membrane anchors, the number and distribution of cysteine residues that determine the secondary structure of the SP, and the sequence of a substrate binding sites such as S'. The S' substrate binding region is defined by residues extending from approximately +17 to +29 relative to the N-terminal I(+1). Differences in this region of the molecule are believed to determine SP substrate specificities (Zunino et al, supra).

Trysinogens

The trypsinogens are serine proteases secreted by exocrine cells of the pancreas (Travis J and Roberts R. Biochemistry 1969; 8: 2884–9; Mallory P and Travis J, Biochemistry 1973; 12: 2847–51). Two major types of trypsinogen isoenzymes have been characterized, trypsinogen-1, also called cationic trypsinogen, and trypsinogen-2 or anionic trypsinogen. The trypsinogen proenzymes are activated to trypsins in the intestine by enterokinase, which removes an activation peptide from the N-terminus of the trypsinogens. The trypsinogens show a high degree of sequence homology, but they can be separated on the basis of charge differences by using electrophoresis or ion exchange chromatography. The major form of trypsinogen in the pancreas and pancreatic juice is trypsinogen-1 (Guy CO et al., Biochem Biophys Res Commun 1984; 125: 516–23). In serum of healthy subjects, trypsinogen-1 is also the major form, whereas in patients with pancreatitis, trypsinogen-2 is more strongly elevated (Itkonen et al., J Lab Clin Med 1990; 115:712–8). Trypsinogens also occur in certain ovarian tumors, in which trypsinogen-2 is the major form (Koivunen et al., Cancer Res 1990; 50: 2375–8). Trypsin-1 in complex with alpha-1-antitrypsin, also called alpha-1-antiprotease, has been found to occur in serum of patients with pancreatitis (Borgstrom A and Ohlsson K, Scand J Clin Lab Invest 1984; 44: 381–6) but determination of this complex has not been found useful for differentiation between pancreatic and other gastrointestinal diseases (Borgstrom et al., Scand J Clin Lab Invest 1989; 49:757–62).

Trypsinogen-1 and -2 are closely related immunologically (Kimland et al., Clin Chim Acta 1989; 184: 31–46; Itkonen et al., 1990), but by using monoclonal antibodies (Itkonen et al., 1990) or by absorbing polyclonal antisera (Kimland et al., 1989) it is possible to obtain reagents enabling specific measurement of each form of trypsinogen.

When active trypsin reaches the blood stream, it is inactivated by the major trypsin inhibitors alpha-2-macroglobulin and alpha-l-antitrypsin (AAT). AAT is a 58 kilodalton serine protease inhibitor synthesized in the liver and is one of the main protease inhibitors in blood. Whereas complexes between trypsin-1 and AAT are detectable in serum (Borgstrom and Ohlsson, 1984) the complexes with alpha-2-macroglobulin are not measurable with antibody-based assays (Ohlsson K, Acta Gastroenterol Belg 1988; 51: 3–12).

Inflammation of the pancreas or pancreatitis may be classified as either acute or chronic by clinical criteria. With treatment, acute pancreatitis can often be cured and normal function restored. Chronic pancreatitis often results in permanent damage. The precise mechanisms which trigger acute inflammation are not understood. However, some causes in the order of their importance are alcohol ingestion, biliary tract disease, post-operative trauma, and hereditary pancreatitis. One theory provides that autodigestion, the premature activation of proteolytic enzymes in the pancreas rather than in the duodenum, causes acute pancreatitis. Any number of other factors including endotoxins, exotoxins, viral infections, ischemia, anoxia, and direct trauma may activate the proenzymes. In addition, any internal or external blockage of pancreatic ducts can also cause an accumulation of pancreatic juices in the pancreas resulting cellular damage.

Anatomy, physiology, and diseases of the pancreas are reviewed, inter alia, in Guyton AC (1991) Textbook of Medical Physiology, W B Saunders Co, Philadelphia Pa.; Isselbacher K J et al (1994) Harrison's Principles of Internal Medicine, McGraw-Hill, New York City; Johnson K E (1991) Histology and Cell Biology, Harwal Publishing, Media Pa.; and The Merck Manual of Diagnosis and Therapy. (1992) Merck Research Laboratories, Rahway N.J.

Metalloprotease

The metalloproteases may be one of the older classes of proteinases and are found in bacteria, fungi as well as in higher organisms. They differ widely in their sequences and their structures but the great majority of enzymes contain a zinc atom which is catalytically active. In some cases, zinc may be replaced by another metal such as cobalt or nickel without loss of the activity. Bacterial thermolysin has been well characterized and its crystallographic structure indicates that zinc is bound by two histidines and one glutamic acid. Many enzymes contain the sequence HEXXH, which provides two histidine ligands for the zinc whereas the third ligand is either a glutamic acid (thermolysin, neprilysin, alanyl aminopeptidase) or a histidine (astacin). Other families exhibit a distinct mode of binding of the Zn atom. The catalytic mechanism leads to the formation of a non covalent tetrahedral intermediate after the attack of a zinc-bound water molecule on the carbonyl group of the scissile bond. This intermediate is further decomposed by transfer of the glutamic acid proton to the leaving group.

Metalloproteases contain a catalytic zinc metal center which participates in the hydrolysis of the peptide backbone (reviewed in Power and Harper, in Protease Inhibitors, A. J. Barrett and G. Salversen (eds.) Elsevier, Amsterdam, 1986, p. 219). The active zinc center differentiates some of these proteases from calpains and trypsins whose activities are dependent upon the presence of calcium. Examples of metalloproteases include carboxypeptidase A, carboxypeptidase B, and thermolysin.

Metalloproteases have been isolated from a number of procaryotic and eucaryotic sources, e.g. *Bacillus subtilis* (McConn et al., 1964, J. Biol. Chem. 239:3706); *Bacillus megaterium*; Serratia (Miyata et al., 1971, Agr. Biol. Chem. 35:460); *Clostridium bifermentans* (MacFarlane et al., 1992, App. Environ. Microbiol. 58:1195–1200), *Legionella pneumophila* (Moffat et al., 1994, Infection and Immunity 62:751–3). In particular, acidic metalloproteases have been isolated from broad-banded copperhead venoms (Johnson and Ownby, 1993, Int. J. Biochem. 25:267–278), rattlesnake venoms (Chlou et al., 1992, Biochem. Biophys. Res. Commun. 187:389–396) and articular cartilage (Treadwell et al., 1986, Arch. Biochem. Biophys. 251:715–723). Neutral metalloproteases, specifically those having optimal activity at neutral pH have, for example, been isolated from *Aspergillus sojae* (Sekine, 1973, Agric. Biol. Chem. 37:1945–1952). Neutral metalloproteases obtained from Aspergillus have been classified into two groups, npI and npII (Sekine, 1972, Agric. Biol. Chem. 36:207–216). So far, success in obtaining amino acid sequence information from these fungal neutral metalloproteases has been limited. An npII metalloprotease isolated from *Aspergillus oryzae* has been cloned based on amino acid sequence presented in the literature (Tatsumi et al., 1991, Mol. Gen. Genet. 228:97–103). However, to date, no npI fungal metalloprotease has been cloned or sequenced. Alkaline metalloproteases, for example, have been isolated from *Pseudomonas aeruginosa* (Baumann et al., 1993, EMBO J 12:3357–3364) and the insect pathogen *Xenorhabdus luminescens* (Schmidt et al., 1998, Appl. Environ. Microbiol. 54:2793–2797).

Metalloproteases have been divided into several distinct families based primarily on activity and structure: 1) water nucleophile; water bound by single zinc ion ligated to two His (within the motif HEXXH) and Glu, His or Asp; 2) water nucleophile; water bound by single zinc ion ligated to His, Glu (within the motif HXXE) and His; 3) water nucleophile; water bound by single zinc ion ligated to His, Asp and His; 4) Water nucleophile; water bound by single zinc ion ligated to two His (within the motif HXXEH) and Glu and 5) water nucleophile; water bound by two zinc ions ligated by Lys, Asp, Asp, Asp, Glu.

Examples of members of the metalloproteinase family include, but are not limited to, membrane alanyl aminopeptidase (*Homo sapiens*), germinal peptidyl-dipeptidase A (*Homo sapiens*), thimet oligopeptidase (*Rattus norvegicus*), oligopeptidase F (*Lactococcus lactis*), mycolysin (*Streptomyces cacaoi*), immune inhibitor A (*Bacillus thuringiensis*), snapalysin (*Streptomyces lividans*), leishmanolysin (*Leishmania major*), microbial collagenase (*Vibrio alginolyticus*), microbial collagenase, class I (*Clostridium perfringens*), collagenase 1 (*Homo sapiens*), serralysin (*Serratia marcescens*), fragilysin (*Bacteroides fragilis*), gametolysin (*Chlamydomonas reinhardtii*), astacin (*Astacus fluviatilis*), adamalysin (*Crotalus adamanteus*), ADAM 10 (*Bos taurus*), neprilysin (*Homo sapiens*), carboxypeptidase A (*Homo sapiens*), carboxypeptidase E (*Bos taurus*), gamma-D-glutamyl-(L)-meso-diaminopimelate peptidase I (*Bacillus sphaericus*), vanY D-Ala-D-Ala carboxypeptidase (*Enterococcus faecium*), endolysin (bacteriophage A118), pitrilysin (*Escherichia coli*), mitochondrial processing peptidase (*Saccharomyces cerevisiae*), leucyl aminopeptidase (*Bos taurus*), aminopeptidase I (*Saccharomyces cerevisiae*), membrane dipeptidase (*Homo sapiens*), glutamate carboxypeptidase (Pseudomonas sp.), Gly-X carboxypeptidase (*Saccharomyces cerevisiae*), O-sialoglycoprotein endopeptidase (*Pasteurella haemolytica*), beta-lytic metalloendopeptidase (*Achromobacter lyticus*), methionyl aminopeptidase I (*Escherichia coli*), X-Pro aminopeptidase (*Escherichia coli*), X-His dipeptidase (*Escherichia coli*), IgA1-specific metalloendopeptidase (*Streptococcus sanguis*), tentoxilysin (*Clostridium tetani*), leucyl aminopeptidase (*Vibrio proteolyticus*), aminopeptidase (*Streptomyces griseus*), IAP aminopeptidase (*Escherichia coli*), aminopeptidase T (*Thermus aquaticus*), hyicolysin (*Staphylococcus hyicus*), carboxypeptidase Taq (*Thermus aquaticus*), anthrax lethal factor (*Bacillus anthracis*), penicillolysin (*Penicillium citrinum*), fungalysin (*Aspergillus fumigatus*), lysostaphin (*Staphylococcus simulans*), beta-aspartyl dipeptidase (*Escherichia coli*), carboxypeptidase Ss1 (*Sulfolobus solfataricus*), FtsH endopeptidase (*Escherichia coli*), glutamyl aminopeptidase (*Lactococcus lactis*), cytophagalysin (Cytophaga sp.), metalloendopeptidase (vaccinia virus), VanX D-Ala-D-Ala dipeptidase (*Enterococcus faecium*), Ste24p endopeptidase (*Saccharomyces cerevisiae*), dipeptidyl-peptidase III (*Rattus norvegicus*), S2P protease (*Homo sapiens*), sporulation factor SpoIVFB (*Bacillus subtilis*), and HYBD endopeptidase (*Escherichia coli*).

Metalloproteases have been found to have a number of uses. For example, there is strong evidence that a metalloprotease is involved in the in vivo proteolytic processing of the vasoconstrictor, endothelin-1. Rat metalloprotease has been found to be involved in peptide hormone processing. One important subfamily of the metalloproteases are the matrix metalloproteases.

A number of diseases are thought to be mediated by excess or undesired metalloprotease activity or by an imbalance in the ratio of the various members of the protease family of proteins. These include: a) osteoarthritis (Woessner, et al., J. Biol. Chem. 259(6), 3633, 1984; Phadke, et al., J. Rheumatol. 10, 852, 1983), b) rheumatoid arthritis (Mullins, et al., Biochim. Biophys. Acta 695, 117, 1983; Woolley, et al., Arthritis Rheum. 20, 1231, 1977; Gravallese, et al., Arthritis Rheum. 34, 1076, 1991), c) septic arthritis (Williams, et al., Arthritis Rheum. 33, 533, 1990), d) tumor metastasis (Reich, et al., Cancer Res. 48, 3307, 1988, and Matrisian, et al., Proc. Nat'l. Acad. Sci., USA 83, 9413, 1986), e) periodontal diseases (Overall, et al., J. Periodontal Res. 22, 81, 1987), f) corneal ulceration (Burns, et al., Invest. Opthalmol. Vis. Sci. 30, 1569, 1989), g) proteinuria (Baricos, et al., Biochem. J. 254, 609, 1988), h) coronary thrombosis from atherosclerotic plaque rupture (Henney, et al., Proc. Nat'l. Acad. Sci., USA 88, 8154–8158, 1991), i) aneurysmal aortic disease (Vine, et al., Clin. Sci. 81, 233, 1991), j) birth control (Woessner, et al., Steroids 54, 491, 1989), k) dystrophobic epidermolysis bullosa (Kronberger, et al., J. Invest. Dermatol. 79, 208, 1982), and l) degenerative cartilage loss following traumatic joint injury, m) conditions leading to inflammatory responses, osteopenias mediated by MMP activity, n) tempero mandibular joint disease, o) demyelating diseases of the nervous system (Chantry, et al., J. Neurochem. 50, 688, 1988).

Aspartic Protease

Aspartic proteases have been divided into several distinct families based primarily on activity and structure. These include 1) water nucleophile; water bound by two Asp from monomer or dimer; all endopeptidases, from eukaryote organisms, viruses or virus-like organisms and 2) endopeptidases that are water nucleophile and are water bound by Asp and Asn.

Most of aspartic proteases belong to the pepsin family. The pepsin family includes digestive enzymes such as pepsin and chymosin as well as lysosomal cathepsins D and processing enzymes such as renin, and certain fungal proteases (penicillopepsin, rhizopuspepsin, endothiapepsin). A second family comprises viral proteases such as the protease from the AIDS virus (HIV) also called retropepsin. Crystallographic studies have shown that these enzymes are bilobed molecules with the active site located between two homologous lobes. Each lobe contributes one aspartate residue of the catalytically active diad of aspartates. These two aspartyl residues are in close geometric proximity in the active molecule and one aspartate is ionized whereas the second one is unionized at the optimum pH range of 2–3. Retropepsins, are monomeric, i.e carry only one catalytic aspartate and then dimerization is required to form an active enzyme.

In contrast to serine and cysteine proteases, catalysis by aspartic protease do not involve a covalent intermediate though a tetrahedral intermediate exists. The nucleophilic attack is achieved by two simultaneous proton transfer: one from a water molecule to the diad of the two carboxyl groups and a second one from the diad to the carbonyl oxygen of the substrate with the concurrent CO—NH bond cleavage. This general acid-base catalysis, which may be called a "push-pull" mechanism leads to the formation of a non covalent neutral tetrahedral intermediate.

Examples of the aspartic protease family of proteins include, but are not limited to, pepsin A (*Homo sapiens*), HIV1 retropepsin (human immunodeficiency virus type 1), endopeptidase (cauliflower mosaic virus), baciliform virus putative protease (rice tungro baciliform virus), aspergillopepsin II (*Aspergillus niger*), thermopsin (*Sulfolobus acidocaldarius*), nodavirus endopeptidase (flock house virus), pseudomonapepsin (Pseudomonas sp. 101), signal peptidase II (*Escherichia coli*), polyprotein peptidase (human spumaretrovirus), copia transposon (*Drosophila melanogaster*), SIRE-1 peptidase (*Glycine max*), retrotransposon bs1 endopeptidase (*Zea mays*), retrotransposon peptidase (*Drosophila buzzatii*), Tas retrotransposon peptidase (*Ascaris lumbricoides*), Pao retrotransposon peptidase (*Bombyx mori*), putative proteinase of Skippy retrotransposon (*Fusarium oxysporum*), tetravirus endopeptidase (*Nudaurelia capensis omega* virus), presenilin 1 (*Homo sapiens*).

Proteases and Cancer

Proteases are critical elements at several stages in the progression of metastatic cancer. In this process, the proteolytic degradation of structural protein in the basal membrane allows for expansion of a tumor in the primary site, evasion from this site as well as homing and invasion in distant, secondary sites. Also, tumor induced angiogenesis is required for tumor growth and is dependent on proteolytic tissue remodeling. Transfection experiments with various types of proteases have shown that the matrix metalloproteases play a dominant role in these processes in particular gelatinases A and B (MMP-2 and MMP-9; respectively). For an overview of this field see Mullins, et al., Biochim. Biophys. Acta 695, 177, 1983; Ray, et al., Eur. Respir. J. 7, 2062, 1994; Birkedal-Hansen, et al., Crit. Rev. Oral Biol. Med. 4, 197, 1993.

Furthermore, it was demonstrated that inhibition of degradation of extracellular matrix by the native matrix metalloprotease inhibitor TIMP-2 (a protein) arrests cancer growth (DeClerck, et al., Cancer Res. 52, 701, 1992) and that TIMP-2 inhibits tumor-induced angiogenesis in experimental systems (Moses, et al. Science 248, 1408, 1990). For a review, see DeClerck, et al., Ann. N. Y. Acad. Sci. 732, 222, 1994. It was further demonstrated that the synthetic matrix metalloprotease inhibitor batimastat when given intraperitoneally inhibits human colon tumor growth and spread in an orthotopic model in nude mice (Wang, et al. Cancer Res. 54, 4726, 1994) and prolongs the survival of mice bearing human ovarian carcinoma xenografts (Davies, et. al., Cancer Res. 53, 2087, 1993). The use of this and related compounds has been described in Brown, et al., WO-9321942 A2.

There are several patents and patent applications claiming the use of metalloproteinase inhibitors for the retardation of metastatic cancer, promoting tumor regression, inhibiting cancer cell proliferation, slowing or preventing cartilage loss associated with osteoarthritis or for treatment of other diseases as noted above (e.g. Levy, et al., WO-9519965 Al; Beckett, et al., WO-9519956 A1; Beckett, et al., WO-9519957 A1; Beckett, et al., WO-9519961 A1; Brown, et al., WO-9321942 A2; Crimmin, et al., WO-9421625 A1; Dickens, et al., U.S. Pat. No. 4,599,361; Hughes, et al., U.S. Pat. No. 5,190,937; Broadhurst, et al., EP 574758 A1; Broadhurst, et al., EP 276436; and Myers, et al., EP 520573 A1.

ATP-Dependent Proteases (Mitochondrial Lon Protease Homolog 1 Precursor)

The present invention provides a novel human ATP-dependent protease. ATP-dependent proteases, such as Lon proteases, require ATP hydrolysis for function and play critical roles in numerous important biological processes, such as organism development, gene transcription, intracellular proteolysis and protein biogenesis, prevention of non-specific or excessive proteolysis (Goldberg, *Semin Cell Biol* 1990 December;1(6):423–32), and intercellular signaling. Therefore, novel human ATP-dependent proteases are useful for modulating/regulating any of these important biological processes, particularly for diagnosing, preventing and/or treating defects in proteolysis, gene transcription, intercellular signalling, and numerous human developmental disorders.

Many ATP-dependent proteases are involved in modulation of proteolysis, insertion of proteins into membranes, and disassembly or oligomerization of protein complexes (Suzuki et al., *Trends Biochem Sci* 1997 April;22(4): 118–23). Proteolysis is critical for maintaining the stability of important metabolic enzymes and for effectively removing terminally damaged polypeptides (Porankiewicz et al., *Mol Microbiol* 1999 May;32(3):449–58). ATP-dependent proteases may be found in mitochondria and chloroplasts, as well as in the cytoplasm.

In *E. Coli*, Lon ATP-dependent proteases together with Clp ATP-dependent proteases, account for 70–80% of the energy-dependent degradation of proteins. Lon and Clp both interact directly with substrates to cause degradation (Maurizi et al., *Experientia* 1992 February15;48(2) :178–201). Proteolysis in *Escherichia coli*, such as by Lon proteases, eliminates abnormal and misfolded proteins from the cell and also reduces the time and amounts of availability of key regulatory proteins (Gottesman et al., *Annu Rev Genet* 1996;30:465–506).

Lon-type proteases catalyze the ATP-dependent degradation of mitochondrial matrix proteins. In yeast, mitochondrial Lon-type proteases has been found to be involved in a variety of critical mitochondrial functions, including mitochondrial protein turnover, assembly of mitochondrial enzyme complexes, and maintenance of mitochondrial DNA integrity. Furthermore, Lon-type proteases are essential for respiratory function (Barakat et al., *Plant Mol Biol* 1998 May;37(1):141–54).

The importance of Lon proteases in development is further illustrated in *Myxococcus xanthus*, in which disruption of a lon gene (specifically, the lonD gene), encoding a Lon protease, has been shown to block development at an early stage. The lonD-disrupted strains of *Myxococcus xanthus* could not form fruiting bodies nor myxospores (Tojo et al., *J Bacteriol* 1993 July;175(14):4545–9).

The bsgA gene of *Myxococcus xanthus* encodes another ATP-dependent protease that is critical for the regulation of early gene expression during fruiting body formation and sporulation in *Myxococcus xanthus*. *Myxococcus xanthus* strains with mutated bsgA genes are unable to initiate a required cell-cell interaction, thereby leading to an inability to transcribe normal levels of many developmentally induced genes (Gill et al., *J Bacteriol* 1993 July;175(14) :4538–44).

Novel Lon proteases may also be useful as markers during spermatogenesis, and during mitochondrial and germ cell development (Meinhardt et al., Hum Reprod Update 1999 March–April;5(2):108–19).

For a further review of ATP-dependent proteases, including Lon proteases, see Schmidt et al., Curr Opin Chem Biol 1999 October;3(5):584–91; Etlinger et al., Revis Biol Celular 1989;20:197–216; and Langer et al., Experientia 1996 December 15;52(12):1069–76. Barakat et al., Plant Mol Biol 1998 May;37(1):141–54, Suzuki et al., Science. 1994 April 8;264(5156):273–6, Teichmann et al., J Biol Chem. 1996 April 26;271(17):10137–42, van Dijl et al., Proc Natl Acad Sci USA. 1998 September 1;95(18):10584–9, Van Dyck et al., J Biol Chem. 1994 January 7;269(1):238–42, Rep et al., Science. 1996 October 4;274(5284):103–6, Campbell et al., Mol Biol Cell. 1994 August;5(8):899–905, Witte et al., EMBO J. 1988 May;7(5):1439–47, Wang et al., Proc Natl Acad Sci USA. 1993 December 1;90(23):11247–51, Leonhardt et al., Mol Cell Biol. 1993 October;13(10):6304–13, Fu et al., Biochemistry. 1998 February 17;37(7):1905–9.

Protease proteins, particularly members of the ATP-dependent protease subfamily, are a major target for drug action and development. Accordingly, it is valuable to the field of pharmaceutical development to identify and characterize previously unknown members of this subfamily of protease proteins. The present invention advances the state of the art by providing a previously unidentified human protease proteins that have homology to members of the ATP-dependent protease subfamily.

SUMMARY OF THE INVENTION

The present invention is based in part on the identification of amino acid sequences of human protease peptides and proteins that are related to the ATP-dependent protease subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate protease activity in cells and tissues that express the protease. Experimental data as provided in FIG. 1 indicates expression in humans in retinoblastomas (eye), melanotic melanomas (skin), endometrium adenocarcinomas (uterus), adenocarcinomas (ovary), schizophrenic brain, kidney and human heart.

DESCRIPTION OF THE FIGURE SHEETS

FIG. 1 provides the nucleotide sequence of a cDNA molecule sequence that encodes the protease protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in humans in retinoblastomas (eye), melanotic melanomas (skin), endometrium adenocarcinomas (uterus), adenocarcinomas (ovary), schizophrenic brain, kidney and human heart.

FIG. 2 provides the predicted amino acid sequence of the protease of the present invention. (SEQ ID NO:2) In addition structure and functional information such as protein family, function, and modification sites is provided where available, allowing one to readily determine specific uses of inventions based on this molecular sequence.

FIG. 3 provides genomic sequences that span the gene encoding the protease protein of the present invention. (SEQ ID NO:3) In addition structure and functional information, such as intron/exon structure, promoter location, etc., is provided where available, allowing one to readily determine specific uses of inventions based on this molecular sequence. As illustrated in FIG. 3, an insertion/deletion SNP variant ("indel") was identified at position 12469.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a protease protein or part of a protease protein and are related to the ATP-dependent protease subfamily. Utilizing these sequences, additional genomic sequences were assembled and transcript and/or cDNA sequences were isolated and characterized. Based on this analysis, the present invention provides amino acid sequences of human protease peptides and proteins that are related to the ATP-dependent protease subfamily, nucleic acid sequences in the form of transcript sequences, cDNA sequences and/or genomic sequences that encode these protease peptides and proteins, nucleic acid variation (allelic information), tissue distribution of expression, and information about the closest art known protein/peptide/domain that has structural or sequence homology to the protease of the present invention.

In addition to being previously unknown, the peptides that are provided in the present invention are selected based on their ability to be used for the development of commercially important products and services. Specifically, the present peptides are selected based on homology and/or structural relatedness to known protease proteins of the ATP-dependent protease subfamily and the expression pattern observed. Experimental data as provided in FIG. 1 indicates expression in humans in retinoblastomas (eye), melanotic melanomas (skin), endometrium adenocarcinomas (uterus), adenocarcinomas (ovary), schizophrenic brain, kidney and human heart. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known ATP-dependent protease family or subfamily of protease proteins.

Specific Embodiments

Peptide Molecules

The present invention provides nucleic acid sequences that encode protein molecules that have been identified as being members of the protease family of proteins and are related to the ATP-dependent protease subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the protease peptides of the present invention, protease peptides, or peptides/proteins of the present invention.

The present invention provides isolated peptide and protein molecules that consist of, consist essentially of, or comprise the amino acid sequences of the protease peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the protease peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated protease peptide can be purified from cells that naturally express it, purified from cells that have been altered to express it (recombinant), or synthesized using known protein synthesis methods. Experimental data as provided in FIG. 1 indicates expression in humans in retinoblastomas (eye), melanotic melanomas (skin), endometrium adenocarcinomas (uterus), adenocarcinomas (ovary), schizophrenic brain, kidney and human heart. For example, a nucleic acid molecule encoding the protease peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the protease peptides of the present invention are the naturally occurring mature proteins. A brief description of how various types of these proteins can be made/isolated is provided below.

The protease peptides of the present invention can be attached to heterologous sequences to form chimeric or fusion proteins. Such chimeric and fusion proteins comprise a protease peptide operatively linked to a heterologous protein having an amino acid sequence not substantially homologous to the protease peptide. "Operatively linked" indicates that the protease peptide and the heterologous protein are fused in-frame. The heterologous protein can be fused to the N-terminus or C-terminus of the protease peptide.

In some uses, the fusion protein does not affect the activity of the protease peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant protease peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A protease peptide-encoding nucleic acid can be cloned into such an expression vector such that the fusion moiety is linked in-frame to the protease peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the protease peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part* 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the protease peptides of the present invention as well as being encoded by the same genetic locus as the protease peptide provided herein. As indicated by the data presented in FIG. 3, the map position was determined to be on chromosome 16 by ePCR, and confirmed with radiation hybrid mapping.

Allelic variants of a protease peptide can readily be identified as being a human protein having a high degree (significant) of sequence homology/identity to at least a portion of the protease peptide as well as being encoded by the same genetic locus as the protease peptide provided herein. Genetic locus can readily be determined based on the genomic information provided in FIG. 3, such as the genomic sequence mapped to the reference human. As indicated by the data presented in FIG. 3, the map position was determined to be on chromosome 16 by ePCR, and confirmed with radiation hybrid mapping. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a protease peptide encoding nucleic acid molecule under stringent conditions as more fully described below.

FIG. 3 provides information on a SNP that has been found in the gene encoding the protease protein of the present invention. Specifically, a thymine indel at position 12469 was identified.

Paralogs of a protease peptide can readily be identified as having some degree of significant sequence homology/identity to at least a portion of the protease peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a protease peptide encoding nucleic acid molecule under moderate to stringent conditions as more fully described below.

Orthologs of a protease peptide can readily be identified as having some degree of significant sequence homology/identity to at least a portion of the protease peptide as well as being encoded by a gene from another organism. Preferred orthologs will be isolated from mammals, preferably primates, for the development of human therapeutic targets and agents. Such orthologs will be encoded by a nucleic acid sequence that will hybridize to a protease peptide encoding nucleic acid molecule under moderate to stringent conditions, as more fully described below, depending on the degree of relatedness of the two organisms yielding the proteins. As indicated by the data presented in FIG. 3, the map position was determined to be on chromosome 16 by ePCR, and confirmed with radiation hybrid mapping.

FIG. 3 provides information on a SNP that has been found in the gene encoding the protease protein of the present invention. Specifically, a thymine indel at position 12469 was identified. Non-naturally occurring variants of the protease peptides of the present invention can readily be generated using recombinant techniques. Such variants include, but are not limited to deletions, additions and substitutions in the amino acid sequence of the protease peptide. For example, one class of substitutions are conserved amino acid substitution. Such substitutions are those that substitute a given amino acid in a protease peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant protease peptides can be filly functional or can lack finction in one or more activities, e.g. ability to bind substrate, ability to cleave substrate, ability to participate in a signaling pathway, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in finction. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as protease activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol Biol.* 224:899–904 (1992); de Vos et al. *Science* 255:306–312 (1992)).

The present invention further provides fragments of the protease peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a protease peptide. Such fragments can be chosen based on the ability to retain one or more of the biological activities of the protease peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the protease peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in protease peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

Accordingly, the protease peptides of the present invention also encompass derivatives or analogs in which a substituted amino acid residue is not one encoded by the genetic code, in which a substituent group is included, in which the mature protease peptide is fused with another compound, such as a compound to increase the half-life of the protease peptide (for example, polyethylene glycol), or in which the additional amino acids are fused to the mature protease peptide, such as a leader or secretory sequence or a sequence for purification of the mature protease peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a protease-effector protein interaction or protease-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, proteases isolated from humans and their human/mammalian orthologs serve as targets for identifying agents for use in mammalian therapeutic applications, e.g. a human drug, particularly in modulating a biological or pathological response in a cell or tissue that expresses the protease. Experimental data as provided in FIG. 1 indicates that protease proteins of the present invention are expressed in humans in numerous cancers, including retinoblastomas (eye), melanotic melanomas (skin), endometrium adenocarcinomas (uterus), and adenocarcinomas (ovary). Furthermore, expression has also been observed in the schizophrenic brain and kidney. These expression patterns have been determined by a virtual northern blot analysis. In addition, PCR-based tissue screening panel indicates expression in human heart. A large percentage of pharmaceutical agents are being developed that modulate the activity of protease proteins, particularly members of the ATP-dependent protease subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in humans in retinoblastomas (eye), melanotic melanomas (skin), endometrium adenocarcinomas (uterus), adenocarcinomas (ovary), schizophrenic brain, kidney and human heart. Such uses can readily be determined using the information provided herein, that which is known in the art, and routine experimentation.

The proteins of the present invention (including variants and fragments that may have been disclosed prior to the present invention) are useful for biological assays related to proteases that are related to members of the ATP-dependent protease subfamily. Such assays involve any of the known protease functions or activities or properties useful for diagnosis and treatment of protease-related conditions that are specific for the subfamily of proteases that the one of the present invention belongs to, particularly in cells and tissues that express the protease. Experimental data as provided in FIG. 1 indicates that protease proteins of the present invention are expressed in humans in numerous cancers, including retinoblastomas (eye), melanotic melanomas (skin), endometrium adenocarcinomas (uterus), and adenocarcinomas (ovary). Furthermore, expression has also been observed in the schizophrenic brain and kidney. These expression patterns have been determined by a virtual northern blot analysis. In addition, PCR-based tissue screening panel indicates expression in human heart.

The proteins of the present invention are also useful in drug screening assays, in cell-based or cell-free systems. Cell-based systems can be native, i.e., cells that normally express the protease, as a biopsy or expanded in cell culture. Experimental data as provided in FIG. 1 indicates expression in humans in retinoblastomas (eye), melanotic melanomas (skin), endometrium adenocarcinomas (uterus), adenocarcinomas (ovary), schizophrenic brain, kidney and human heart. In an alternate embodiment, cell-based assays involve recombinant host cells expressing the protease protein.

The polypeptides can be used to identify compounds that modulate protease activity of the protein in its natural state or an altered form that causes a specific disease or pathology associated with the protease. Both the proteases of the present invention and appropriate variants and fragments can be used in high-throughput screens to assay candidate compounds for the ability to bind to the protease. These compounds can be further screened against a functional protease to determine the effect of the compound on the protease activity. Further, these compounds can be tested in animal or invertebrate systems to determine activity/effectiveness. Compounds can be identified that activate (agonist) or inactivate (antagonist) the protease to a desired degree.

Further, the proteins of the present invention can be used to screen a compound for the ability to stimulate or inhibit interaction between the protease protein and a molecule that normally interacts with the protease protein, e.g. a substrate or a component of the signal pathway that the protease protein normally interacts (for example, a protease). Such assays typically include the steps of combining the protease protein with a candidate compound under conditions that allow the protease protein, or fragment, to interact with the target molecule, and to detect the formation of a complex between the protein and the target or to detect the biochemical consequence of the interaction with the protease protein and the target, such as any of the associated effects of signal transduction such as protein cleavage, cAMP turnover, and adenylate cyclase activation, etc.

Candidate compounds include, for example, 1) peptides such as soluble peptides, including Ig-tailed fusion peptides and members of random peptide libraries (see, e.g., Lam et al., Nature 354:82–84 (1991); Houghten et al., Nature 354:84–86 (1991)) and combinatorial chemistry-derived molecular libraries made of D- and/or L- configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant proteases or appropriate fragments containing mutations that affect protease function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) protease activity. The assays typically involve an assay of events in the signal transduction pathway that indicate protease activity. Thus, the cleavage of a substrate, inactivation/activation of a protein, a change in the expression of genes that are up- or down-regulated in response to the protease protein dependent signal cascade can be assayed.

Any of the biological or biochemical functions mediated by the protease can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the protease can be assayed. Experimental data as provided in FIG. 1 indicates that protease proteins of the present invention are expressed in humans in numerous cancers, including retinoblastomas (eye), melanotic melanomas (skin), endometrium adenocarcinomas (uterus), and adenocarcinomas (ovary). Furthermore, expression has also been observed in the schizophrenic brain and kidney. These expression patterns have been determined by a virtual northern blot analysis. In addition, PCR-based tissue screening panel indicates expression in human heart. Binding and/or activating compounds can also be screened by using chimeric protease proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native protease. Accordingly, a different set of signal transduction components is available as an end-point assay for activation. This allows for assays to be performed in other than the specific host cell from which the protease is derived.

The proteins of the present invention are also useful in competition binding assays in methods designed to discover compounds that interact with the protease (e.g. binding partners and/or ligands). Thus, a compound is exposed to a protease polypeptide under conditions that allow the compound to bind or to otherwise interact with the polypeptide. Soluble protease polypeptide is also added to the mixture. If the test compound interacts with the soluble protease polypeptide, it decreases the amount of complex formed or activity from the protease target. This type of assay is particularly useful in cases in which compounds are sought that interact with specific regions of the protease. Thus, the soluble polypeptide that competes with the target protease region is designed to contain peptide sequences corresponding to the region of interest.

To perform cell free drug screening assays, it is sometimes desirable to immobilize either the protease protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of protease-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a protease-binding protein and a candidate compound are incubated in the protease protein-presenting wells and the amount of complex trapped in the well can be quantitated. Methods for detecting such complexes, in addition to those described above for the GST-immobilized complexes, include immunodetection of complexes using antibodies reactive with the protease protein target molecule, or which are reactive with protease protein and compete with the target molecule, as well as enzyme-linked assays which rely on detecting an enzymatic activity associated with the target molecule.

Agents that modulate one of the proteases of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of protease protein activity identified according to these drug screening assays can be used to treat a subject with a disorder mediated by the protease pathway, by treating cells or tissues that express the protease. Experimental data as provided in FIG. 1 indicates expression in humans in retinoblastomas (eye), melanotic melanomas (skin), endometrium adenocarcinomas (uterus), adenocarcinomas (ovary), schizophrenic brain, kidney and human heart. These methods of treatment include the steps of administering a modulator of protease activity in a pharmaceutical composition to a subject in need of such treatment, the modulator being identified as described herein.

In yet another aspect of the invention, the protease proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the protease and are involved in protease activity. Such protease-binding proteins are also likely to be involved in the propagation of signals by the protease proteins or protease targets as, for example, downstream elements of a protease-mediated signaling pathway. Alternatively, such protease-binding proteins are likely to be protease inhibitors.

The two-hybrid system is based on the modular nature of most transcription factors, which consist of separable DNA-binding and activation domains. Briefly, the assay utilizes two different DNA constructs. In one construct, the gene that codes for a protease protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a protease-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the protease protein.

This invention further pertains to novel agents identified by the above-described screening assays. Accordingly, it is within the scope of this invention to further use an agent identified as described herein in an appropriate animal model. For example, an agent identified as described herein (e.g., a protease-modulating agent, an antisense protease nucleic acid molecule, a protease-specific antibody, or a protease-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The protease proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in humans in retinoblastomas (eye), melanotic melanomas (skin), endometrium adenocarcinomas (uterus), adenocarcinomas (ovary), schizophrenic brain, kidney and human heart. The method involves contacting a biological sample with a compound capable of interacting with the protease protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered protease activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a-peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the protease protein in which one or more of the protease functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and protease activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in humans in retinoblastomas (eye), melanotic melanomas (skin), endometrium adenocarcinomas (uterus), adenocarcinomas (ovary), schizophrenic brain, kidney and human heart. Accordingly, methods for treatment include the use of the protease protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the protease proteins. Antibodies can be prepared from any region of the peptide as described herein. However, preferred regions will include those involved in function/activity and/or protease/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that protease proteins of the present invention are expressed in humans in numerous cancers, including retinoblastomas (eye), melanotic melanomas (skin), endometrium adenocarcinomas (uterus), and adenocarcinomas (ovary). Furthermore, expression has also been observed in the schizophrenic brain and kidney. These expression patterns have been determined by a virtual northern blot analysis. In addition, PCR-based tissue screening panel indicates expression in human heart. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in humans in retinoblastomas (eye), melanotic melanomas (skin), endometrium adenocarcinomas (uterus), adenocarcinomas (ovary), schizophrenic brain, kidney and human heart. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in humans in retinoblastomas (eye), melanotic melanomas (skin), endometrium adenocarcinomas (uterus), adenocarcinomas (ovary), schizophrenic brain, kidney and human heart. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in humans in retinoblastomas (eye), melanotic melanomas (skin), endometrium adenocarcinomas (uterus), adenocarcinomas (ovary), schizophrenic brain, kidney and human heart. Thus, where a specific protein has been correlated with expression in a specific tissue, antibodies that are specific for this protein can be used to identify a tissue type.

The antibodies are also useful for inhibiting protein function, for example, blocking the binding of the protease peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nucleic acid arrays and similar methods have been developed for antibody arrays.

Nucleic Acid Molecules

The present invention further provides isolated nucleic acid molecules that encode a protease peptide or protein of the present invention (cDNA, transcript and genomic sequence). Such nucleic acid molecules will consist of, consist essentially of, or comprise a nucleotide sequence that encodes one of the protease peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIGS. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIGS. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIGS. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the protease peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (antisense strand).

The invention further provides nucleic acid molecules that encode fragments of the peptides of the present invention as well as nucleic acid molecules that encode obvious variants of the protease proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene.

FIG. 3 provides information on a SNP that has been found in the gene encoding the protease protein of the present invention. Specifically, a thymine indel at position 12469 was identified.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6× sodium chloride/sodium citrate (SSC) at about 45 C, followed by one or more washes in 0.2×SSC, 0.1% SDS at 50–65 C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate fill-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, an insertion/deletion SNP variant ("indel") was identified at position 12469.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. As indicated by the data presented in FIG. 3, the map position was determined to be on chromosome 16 by ePCR, and confirmed with radiation hybrid mapping.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that protease proteins of the present invention are expressed in humans in numerous cancers, including retinoblastomas (eye), melanotic melanomas (skin), endometrium adenocarcinomas (uterus), and adenocarcinomas (ovary). Furthermore, expression has also been observed in the schizophrenic brain and kidney. These expression patterns have been determined by a virtual northern blot analysis. In addition, PCR-based tissue screening panel indicates expression in human heart. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in protease protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a protease protein, such as by measuring a level of a protease-encoding nucleic acid in a sample of cells from a subject e.g., mRNA or genomic DNA, or determining if a protease gene has been mutated. Experimental data as provided in FIG. 1 indicates that protease proteins of the present invention are expressed in humans in numerous cancers, including retinoblastomas (eye), melanotic melanomas (skin), endometrium adenocarcinomas (uterus), and adenocarcinomas (ovary). Furthermore, expression has also been observed in the schizophrenic brain and kidney. These expression patterns have been determined by a virtual northern blot analysis. In addition, PCR-based tissue screening panel indicates expression in human heart.

Nucleic acid expression assays are useful for drug screening to identify compounds that modulate protease nucleic acid expression.

The invention thus provides a method for identifying a compound that can be used to treat a disorder associated with nucleic acid expression of the protease gene, particularly biological and pathological processes that are mediated by the protease in cells and tissues that express it. Experimental data as provided in FIG. 1 indicates expression in humans in retinoblastomas (eye), melanotic melanomas (skin), endometrium adenocarcinomas (uterus), adenocarcinomas (ovary), schizophrenic brain, kidney and human heart. The method typically includes assaying the ability of the compound to modulate the expression of the protease nucleic acid and thus identifying a compound that can be used to treat a disorder characterized by undesired protease nucleic acid expression. The assays can be performed in cell-based and cell-free systems. Cell-based assays include cells naturally expressing the protease nucleic acid or recombinant cells genetically engineered to express specific nucleic acid sequences.

The assay for protease nucleic acid expression can involve direct assay of nucleic acid levels, such as mRNA levels, or on collateral compounds involved in the signal pathway. Further, the expression of genes that are up- or down-regulated in response to the protease protein signal pathway can also be assayed. In this embodiment the regulatory regions of these genes can be operably linked to a reporter gene such as luciferase.

Thus, modulators of protease gene expression can be identified in a method wherein a cell is contacted with a candidate compound and the expression of mRNA determined. The level of expression of protease mRNA in the presence of the candidate compound is compared to the level of expression of protease mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate protease nucleic acid expression in cells and tissues that express the protease. Experimental data as provided in FIG. 1 indicates that protease proteins of the present invention are expressed in humans in numerous cancers, including retinoblastomas (eye), melanotic melanomas (skin), endometrium adenocarcinomas (uterus), and adenocarcinomas (ovary). Furthermore, expression has also been observed in the schizophrenic brain and kidney. These expression patterns have been determined by a virtual northern blot analysis. In addition, PCR-based tissue screening panel indicates expression in human heart. Modulation includes both up-regulation (i.e. activation or agonization) or down-regulation (suppression or antagonization) or nucleic acid expression.

Alternatively, a modulator for protease nucleic acid expression can be a small molecule or drug identified using the screening assays described herein as long as the drug or small molecule inhibits the protease nucleic acid expression in the cells and tissues that express the protein. Experimental data as provided in FIG. 1 indicates expression in humans in retinoblastomas (eye), melanotic melanomas (skin), endometrium adenocarcinomas (uterus), adenocarcinomas (ovary), schizophrenic brain, kidney and human heart.

The nucleic acid molecules are also useful for monitoring the effectiveness of modulating compounds on the expression or activity of the protease gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in protease nucleic acid expression, and particularly in qualitative changes that lead to pathology. The nucleic acid molecules can be used to detect mutations in protease genes and gene expression products such as mRNA. The nucleic acid molecules can be used as hybridization probes to detect naturally occurring genetic mutations in the protease gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the protease gene associated with a dysfunction provides a diagnostic tool for an active disease or susceptibility to disease when the disease results from overexpression, underexpression, or altered expression of a protease protein.

Individuals carrying mutations in the protease gene can be detected at the nucleic acid level by a variety of techniques. FIG. 3 provides information on a SNP that has been found in the gene encoding the protease protein of the present invention. Specifically, a thymine indel at position 12469 was identified. As indicated by the data presented in FIG. 3, the map position was determined to be on chromosome 16 by ePCR, and confirmed with radiation hybrid mapping. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a protease gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant protease gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., Science 230:1242 (1985)); Cotton et al., *PNAS* 85:4397 (1988); Saleeba et al, *Meth. Enzymol.* 217:286–295 (1992)), electrophoretic mobility of mutant and wild type nucleic acid is compared (Orita et al., *PNAS* 86:2766 (1989); Cotton et al., Mutat. Res. 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the protease gene in an individual in order to select an appropriate compound or dosage regimen for treatment. FIG. 3 provides information on a SNP that has been found in the gene encoding the protease protein of the present invention. Specifically, a thymine indel at position 12469 was identified.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control protease gene expression in cells, tissues, and organisms. A DNA antisense nucleic acid molecule is designed to be complementary to a region of the gene involved in transcription, preventing transcription and hence production of protease protein. An antisense RNA or DNA nucleic acid molecule would hybridize to the mRNA and thus block translation of mRNA into protease protein. FIG. 3 provides information on a SNP that has been found in the gene encoding the protease protein of the present invention. Specifically, a thymine indel at position 12469 was identified.

Alternatively, a class of antisense molecules can be used to inactivate mRNA in order to decrease expression of protease nucleic acid. Accordingly, these molecules can treat a disorder characterized by abnormal or undesired protease nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the protease protein, such as substrate binding.

The nucleic acid molecules also provide vectors for gene therapy in patients containing cells that are aberrant in protease gene expression. Thus, recombinant cells, which include the patient's cells that have been engineered ex vivo and returned to the patient, are introduced into an individual where the cells produce the desired protease protein to treat the individual.

The invention also encompasses kits for detecting the presence of a protease nucleic acid in a biological sample. Experimental data as provided in FIG. 1 indicates that protease proteins of the present invention are expressed in humans in numerous cancers, including retinoblastomas (eye), melanotic melanomas (skin), endometrium adenocarcinomas (uterus), and adenocarcinomas (ovary). Furthermore, expression has also been observed in the schizophrenic brain and kidney. These expression patterns have been determined by a virtual northern blot analysis. In addition, PCR-based tissue screening panel indicates expression in human heart. For example, the kit can comprise reagents such as a labeled or labelable nucleic acid or agent capable of detecting protease nucleic acid in a biological sample; means for determining the amount of protease nucleic acid in the sample; and means for comparing the amount of protease nucleic acid in the sample with a standard. The compound or agent can be packaged in a suitable container. The kit can further comprise instructions for using the kit to detect protease protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the protease proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the protease gene of the present invention. FIG. 3 provides information on a SNP that has been found in the gene encoding the protease protein of the present invention. Specifically, a thymine indel at position 12469 was identified.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified protease gene of the present invention can be routinely identified using the sequence information disclosed herein can be readily incorporated into one of the established kit formats which are well known in the art, particularly expression arrays.

Vectors/Host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals.

The person of ordinary skill in the art would be aware of the numerous regulatory sequences that are useful in expression vectors. Such regulatory sequences are described, for example, in Sambrook et al., *Molecular Cloning: A Laboratory Manual.* 2nd. ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual.* 2nd. ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enteroprotease. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990) 119–128). Alternatively, the sequence of the nucleic acid molecule of interest can be altered to provide preferential codon usage for a specific host cell, for example *E. coli*. (Wada et al., *Nucleic Acids Res*. 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J*. 6:229–234 (1987)), pMFa (Kujan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf9 cells) include the pAc series (Smith et al., *Mol. Cell Biol*. 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufnan et al., *EMBO J*. 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual* 2nd, ed., *Cold Spring Harbor Laboratory*, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual*. 2nd, ed., *Cold Spring Harbor Laboratory*, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing finctions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as proteases, appropriate secretion signals are incorporated into the vector. The signal sequence can be endogenous to the peptides or heterologous to these peptides.

Where the peptide is not secreted into the medium, which is typically the case with proteases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a protease protein or peptide that can be further purified to produce desired amounts of protease protein or fragments. Thus, host cells containing expression vectors are useful for peptide production.

Host cells are also useful for conducting cell-based assays involving the protease protein or protease protein fragments, such as those described above as well as other formats known in the art. Thus, a recombinant host cell expressing a native protease protein is useful for assaying compounds that stimulate or inhibit protease protein function.

Host cells are also useful for identifying protease protein mutants in which these functions are affected. If the mutants naturally occur and give rise to a pathology, host cells containing the mutations are useful to assay compounds that have a desired effect on the mutant protease protein (for example, stimulating or inhibiting function) which may not be indicated by their effect on the native protease protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a protease protein and identifying and evaluating modulators of protease protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the protease protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence(s) can be operably linked to the transgene to direct expression of the protease protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, protease protein activity/activation, and signal transduction, may not be evident from in vitro cell-free or cell-based assays. Accordingly, it is useful to provide non-human transgenic animals to assay in vivo protease protein function, including substrate interaction, the effect of specific mutant protease proteins on protease protein function and substrate interaction, and the effect of chimeric protease proteins. It is also possible to assess the effect of null mutations, that is mutations that substantially or completely eliminate one or more protease protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated polypeptide having an amino acid sequence consisting of SEQ ID NO:2.

2. An isolated protease having an amino acid sequence consisting of SEQ ID NO:2.

3. A composition comprising the polypeptide of claim 1 and a carrier.

4. A composition comprising the protease of claim 2 and a carrier.

* * * * *

SEQUENCE LISTING

<160> NUMBER OF SEQ ID NOS: 4

<210> SEQ ID NO 1
<211> LENGTH: 2594
<212> TYPE: DNA
<213> ORGANISM: Homo sapien

<400> SEQUENCE: 1

```
gtgcgaaagg ctgccagcat gtcatcagtg agccccatcc agatcccag tcgcctccg      60 ctgctgctca cccacgaggg cgtcctgctg cccggctcca ccatgcgcac cagcgtggac     120
tcggcccaca acctgcagct ggtgcggagc cgccttctga agggcacgtc gctgcaaagc     180
accatcctgg gcgtcatccc caacacgcct gaccccgcca gcgacgcgca ggacctgccg     240
ccgctgcaca ggattggcac agctgcactg gccgttcagg ttgtgggcag taactggccc     300
aagccccact acactctgtt gattacaggc ctatgccgtt tccagattgt acaggtctta     360
aaagagaagc catatcccat tgctgaagtg gagcagttgg accgacttga ggagtttccc     420
aacacctgta aaatgaggga ggagctagga gaactatcag agcagtttta caaatatgca     480
gtacaattgg ttgaaatgtt ggatatgtct gtccctgcag ttgctaaatt gagacgtctt     540
ttagatagtc ttccaaggga agctttacca gacatcttga catcaattat ccgaacaagc     600
aacaaagaga aactccagat tttagatgct gtgagcctag aggagcggtt caagatgact     660
ataccactgc ttgtcagaca aattgaaggc ctgaaattgc ttcaaaaaac cagaaaaccc     720
aagcaagatg atgataagag ggttatagca atacgcccta ttaggagaat tacacatatc     780
tcaggtactt tagaagatga agatgaagat gaagataatg atgacattgt catgctagag     840
aaaaaaatac gaacatctag tatgccagag caggcccata aagtctgtgt caaagagata     900
aagagactca aaaaatgcc tcagtcaatg ccagaatatg ctctgactag aaattatttg     960
gaacttatgg tagaacttcc ttggaacaaa agtacaactg accgcctgga cattagggca    1020
gcccggattc ttctggataa tgaccattac gccatggaaa aattgaagaa aagagtactg    1080
```

```
gaatacttgg ctgtcagaca gctcaaaaat aacctgaagg gcccaatcct atgctttgtt    1140
ggccctcctg gagttggtaa aacaagtgtg ggaagatcag tggccaagac tctaggtcga    1200
gagttccaca ggattgcact tggaggagta tgtgatcagt ctgacattcg aggacacagg    1260
cgcacctatg ttggcagcat gcctggtcgc atcatcaacg gcttgaagac tgtgggagtg    1320
aacaacccag tgttcctatt agatgaggtt gacaaactgg gaaaaagtct acagggtgat    1380
ccagcagcag ctctgcttga ggtgttggat cctgaacaaa accataactt cacagatcat    1440
tatctaaatg tggcctttga cctttctcaa gttcttttta tagctactgc caacaccact    1500
gctaccattc cagctgcctt gttggacaga atggagatca ttcaggttcc aggttataca    1560
caggaggaga agatagagat tgcccatagg cacttgatcc ccaagcagct ggaacaacat    1620
gggctgactc cacagcagat tcagataccc caggtcacca ctcttgacat catcaccagg    1680
tataccagag aggcagggt tcgttctctg gatagaaaac ttggggccat ttgccgagct    1740
gtggccgtga agtggcagaa ggacagcat aaggaagcca gttggaccg ttctgatgtg    1800 actgagagag aaggttgcag agaacacatc ttagaagatg aaaaacctga atctatcagt    1860
gacactactg acttggctct accacctgaa atgccgattt tgattgattt ccatgctctg    1920
aaagacatcc ttgggccccc gatgtatgaa atggaggtat ctcagcgttt gagtcagcca    1980
ggagtagcaa taggtttggc ttggactccc ttaggtggag aaatcatgtt cgtggaggcg    2040
agtcgaatgg atggcgaggg ccagttaact ctgaccggcc agctcgggga cgtgatgaag    2100
gagtccgccc acctcgctat cagctggctc cgcagcaacg caaagaagta ccagctgacc    2160
aatgcttttg gaagttttga tcttcttgac aacacagaca tccatctgca cttcccagct    2220
ggagctgtca caaaagatgg accatctgct ggagttacca tagtaacctg tctcgcctca    2280 cttttttagtg ggcggctggt acgttcagat gtagccatga ctggagaaat tacactgaga    2340
ggtcttgttc ttccagtggg tggaattaaa gacaaagtgc tggcggcaca cagagcggga    2400
ctgaagcaag tcattattcc tcggagaaat gaaaaagacc ttgagggaat cccaggcaac    2460
gtacgacagg atttaagttt tgtcacagca agctgcctgg atgaggttct taatgcagct    2520
tttgatggtg gctttactgt caagaccaga cctggtctgt aaatagcaa actgtaggtc    2580 caaatctcaa tttt                                                      2594
```

<210> SEQ ID NO 2
<211> LENGTH: 852
<212> TYPE: PRT
<213> ORGANISM: Homo sapien

<400> SEQUENCE: 2

```
Met Ser Ser Val Ser Pro Ile Gln Ile Pro Ser Arg Leu Pro Leu Leu
  1               5                  10                  15

Leu Thr His Glu Gly Val Leu Leu Pro Gly Ser Thr Met Arg Thr Ser
                 20                  25                  30

Val Asp Ser Ala His Asn Leu Gln Leu Val Arg Ser Arg Leu Leu Lys
             35                  40                  45

Gly Thr Ser Leu Gln Ser Thr Ile Leu Gly Val Ile Pro Asn Thr Pro
         50                  55                  60

Asp Pro Ala Ser Asp Ala Gln Asp Leu Pro Pro Leu His Arg Ile Gly
 65                  70                  75                  80

Thr Ala Ala Leu Ala Val Gln Val Gly Ser Asn Trp Pro Lys Pro
                 85                  90                  95
```

-continued

```
His Tyr Thr Leu Leu Ile Thr Gly Leu Cys Arg Phe Gln Ile Val Gln
            100                 105                 110

Val Leu Lys Glu Lys Pro Tyr Pro Ile Ala Glu Val Glu Gln Leu Asp
        115                 120                 125

Arg Leu Glu Glu Phe Pro Asn Thr Cys Lys Met Arg Glu Glu Leu Gly
    130                 135                 140

Glu Leu Ser Glu Gln Phe Tyr Lys Tyr Ala Val Gln Leu Val Glu Met
145                 150                 155                 160

Leu Asp Met Ser Val Pro Ala Val Ala Lys Leu Arg Arg Leu Leu Asp
                165                 170                 175

Ser Leu Pro Arg Glu Ala Leu Pro Asp Ile Leu Thr Ser Ile Ile Arg
            180                 185                 190

Thr Ser Asn Lys Glu Lys Leu Gln Ile Leu Asp Ala Val Ser Leu Glu
        195                 200                 205

Glu Arg Phe Lys Met Thr Ile Pro Leu Leu Val Arg Gln Ile Glu Gly
    210                 215                 220

Leu Lys Leu Leu Gln Lys Thr Arg Lys Pro Lys Gln Asp Asp Asp Lys
225                 230                 235                 240

Arg Val Ile Ala Ile Arg Pro Ile Arg Arg Ile Thr His Ile Ser Gly
                245                 250                 255

Thr Leu Glu Asp Glu Asp Glu Asp Glu Asp Asn Asp Asp Ile Val Met
            260                 265                 270

Leu Glu Lys Lys Ile Arg Thr Ser Ser Met Pro Glu Gln Ala His Lys
        275                 280                 285

Val Cys Val Lys Glu Ile Lys Arg Leu Lys Lys Met Pro Gln Ser Met
    290                 295                 300

Pro Glu Tyr Ala Leu Thr Arg Asn Tyr Leu Glu Leu Met Val Glu Leu
305                 310                 315                 320

Pro Trp Asn Lys Ser Thr Thr Asp Arg Leu Asp Ile Arg Ala Ala Arg
                325                 330                 335

Ile Leu Leu Asp Asn Asp His Tyr Ala Met Glu Lys Leu Lys Lys Arg
            340                 345                 350

Val Leu Glu Tyr Leu Ala Val Arg Gln Leu Lys Asn Asn Leu Lys Gly
        355                 360                 365

Pro Ile Leu Cys Phe Val Gly Pro Pro Gly Val Gly Lys Thr Ser Val
    370                 375                 380

Gly Arg Ser Val Ala Lys Thr Leu Gly Arg Glu Phe His Arg Ile Ala
385                 390                 395                 400

Leu Gly Gly Val Cys Asp Gln Ser Asp Ile Arg Gly His Arg Arg Thr
                405                 410                 415

Tyr Val Gly Ser Met Pro Gly Arg Ile Ile Asn Gly Leu Lys Thr Val
            420                 425                 430

Gly Val Asn Asn Pro Val Phe Leu Leu Asp Glu Val Asp Lys Leu Gly
        435                 440                 445

Lys Ser Leu Gln Gly Asp Pro Ala Ala Ala Leu Leu Glu Val Leu Asp
    450                 455                 460

Pro Glu Gln Asn His Asn Phe Thr Asp His Tyr Leu Asn Val Ala Phe
465                 470                 475                 480

Asp Leu Ser Gln Val Leu Phe Ile Ala Thr Ala Asn Thr Thr Ala Thr
                485                 490                 495

Ile Pro Ala Ala Leu Leu Asp Arg Met Glu Ile Ile Gln Val Pro Gly
            500                 505                 510

Tyr Thr Gln Glu Glu Lys Ile Glu Ile Ala His Arg His Leu Ile Pro
```

515                 520                 525

Lys Gln Leu Glu Gln His Gly Leu Thr Pro Gln Gln Ile Gln Ile Pro
    530                 535                 540

Gln Val Thr Thr Leu Asp Ile Ile Thr Arg Tyr Thr Arg Glu Ala Gly
545                 550                 555                 560

Val Arg Ser Leu Asp Arg Lys Leu Gly Ala Ile Cys Arg Ala Val Ala
                565                 570                 575

Val Lys Val Ala Glu Gly Gln His Lys Glu Ala Lys Leu Asp Arg Ser
            580                 585                 590

Asp Val Thr Glu Arg Glu Gly Cys Arg Glu His Ile Leu Glu Asp Glu
        595                 600                 605

Lys Pro Glu Ser Ile Ser Asp Thr Thr Asp Leu Ala Leu Pro Pro Glu
610                 615                 620

Met Pro Ile Leu Ile Asp Phe His Ala Leu Lys Asp Ile Leu Gly Pro
625                 630                 635                 640

Pro Met Tyr Glu Met Glu Val Ser Gln Arg Leu Ser Gln Pro Gly Val
                645                 650                 655

Ala Ile Gly Leu Ala Trp Thr Pro Leu Gly Gly Glu Ile Met Phe Val
            660                 665                 670

Glu Ala Ser Arg Met Asp Gly Glu Gly Gln Leu Thr Leu Thr Gly Gln
        675                 680                 685

Leu Gly Asp Val Met Lys Glu Ser Ala His Leu Ala Ile Ser Trp Leu
690                 695                 700

Arg Ser Asn Ala Lys Lys Tyr Gln Leu Thr Asn Ala Phe Gly Ser Phe
705                 710                 715                 720

Asp Leu Leu Asp Asn Thr Asp Ile His Leu His Phe Pro Ala Gly Ala
                725                 730                 735

Val Thr Lys Asp Gly Pro Ser Ala Gly Val Thr Ile Val Thr Cys Leu
            740                 745                 750

Ala Ser Leu Phe Ser Gly Arg Leu Val Arg Ser Asp Val Ala Met Thr
        755                 760                 765

Gly Glu Ile Thr Leu Arg Gly Leu Val Leu Pro Val Gly Gly Ile Lys
770                 775                 780

Asp Lys Val Leu Ala Ala His Arg Ala Gly Leu Lys Gln Val Ile Ile
785                 790                 795                 800

Pro Arg Arg Asn Glu Lys Asp Leu Glu Gly Ile Pro Gly Asn Val Arg
                805                 810                 815

Gln Asp Leu Ser Phe Val Thr Ala Ser Cys Leu Asp Glu Val Leu Asn
            820                 825                 830

Ala Ala Phe Asp Gly Gly Phe Thr Val Lys Thr Arg Pro Gly Leu Leu
        835                 840                 845

Asn Ser Lys Leu
    850

<210> SEQ ID NO 3
<211> LENGTH: 112132
<212> TYPE: DNA
<213> ORGANISM: Homo sapien
<220> FEATURE:
<221> NAME/KEY: misc_feature
<222> LOCATION: (1)...(112132)
<223> OTHER INFORMATION: n = A,T,C or G

<400> SEQUENCE: 3
atcattaaaa agtcaggaaa caacaggtgc tggagaggat gtggagaaat aggaacactt      60

-continued

```
ttacactgtt ggtgggactg taaactagtt caaccattgt ggaagacagt gtggcaattc    120
ctcaaggatc tggaactaga ataccatttt gacccagcca tcccattgct gggtatatac    180
ccaaaggatt ataaatcatg ctgctataaa gacacacaca cacgtatgct tactgcggca    240
ctattcgcaa tagcaaagac ttggaaccaa cccaaatgtc catcaatgat agactggatt    300
aagaaaatgt ggcacatata caccatggaa tactatgcag ccataaaaaa ggatgagttc    360
atgtcctttg tagggacatg gatgatgctg gaaaccatca ttctgagcaa actatcgcaa    420
agaccgaaaa caaacactg caagttctca ctcataggtg caactgaac aatgagaaca     480 cttggacaca gggtggggaa catcacactc aggggcctgt cgttgggtgg tggggagtgg    540
gggggaaggg ataccattag gagatatacc taatgtaaat gacgagttag tgagtgcagc    600
aaaccaacat ggcacatgta tacatatgta acaaacctgt acgttgtgca catgtaccct    660
agaacttaaa ctataataaa aataaaaatt aaattaaaaa catgaaaaaa aataaaagta    720
tcaaggttgt aaaaaaaaa aaaattggac gggcgcagtg gctcaggcct gtaatcccag    780
cactttgggg aggccaaggc gggcagatca ctgaggtcag gagattgaga ccatcctggc    840
taacatggcg aaacccgtc tctactaaaa atacaaaaaa ttagccgggc agtggttgcg     900
ggtgcctgta gtcccagct actcgggagg ctgaagcagg agaatggcat gaacccggga    960
ggcggagctt gcagtgagcc gagatctcgc cactacactc cagcctgggt gacagagcga   1020
gactccgtct caaaaaaaaa aaaaaaaaa aaaattgag gacttgccac agattagaga     1080
acacctagga gatttcataa caaaacacct aggagatttc acaacaggat cctggatatt   1140
ggatcctgga ccagatccaa tgaaggacat tagtgggaaa actggcaaaa tttgggtaag   1200
gcctataggt taaacgataa taatgttaat ttcctggttt tgatcattga actatgatta   1260
tgtaagatga taacagacga aactgggtga aaggtatata ggaactctgc tgtagttttg   1320
tacatctaaa atcaattcgg gccgggcacg ttggctcacg cctgtaatcc cagcactttg   1380
ggaggccgag gtggacggat cgcttgaggt caggagttaa agaccagcct ggccaacatg   1440
gtgaaatccc ctccctacta aaatacaac aattagctgg gtgtggtggc gggcatctgt    1500
aatcccagct actcgggagg ctgaggcagg agaatcgctt gaacccggga ggcagaggct   1560
gcaagccgtg gtatcgcgc cattgcactc cagcctccgc gacagagcga gaatctgtct    1620
cagaataaat aaataaataa ataaataaat aattagttcg aatcaaaagt taaaaacact   1680
tcaagtatat gtaaaaaatc gaagaaaacg ttaaaaacac ttcaagtata tacaattcaa   1740
ataagatcat ccttccaaat atactctgta agtgaggcga aggtcgctgc acgcttgagt   1800
gcacgtcttt ccgcataggt aggacgctca agtcttaccg ggaggctctc ctagagagca   1860
gcgcgaagcc atggctttg ggcccgggga cggaccgtag cgcgtagccg gaagcggagg    1920
cgtggaggcg ggtctgaggt ttggtgactg cggggcaggc cggggcagc tgtctgtctg    1980 gctcttttg acagccccca gtgcgaaagg ctgccagcat gtcatcagtg agccccatcc    2040
agatccccag tcgcctcccg ctgctgctca cccacgaggg cgtcctgctg cccggctcca   2100
ccatgcgcac cagcgtggac tcggcccgca acctgcagct ggtgcggagc cgccttctga   2160
agggcacgtc gctgcaaagc accatcctgg gcgtcatccc caacgcgcct gaccccgcca   2220
gcgacgcgca ggacctgccg ccgctgcaca ggtaggcctg gctgccccg cggcggcggc    2280 gggcggcgcg gcctcctccg gggacctggg cccaggccac ggcctgcctt gagcgcgagg   2340
ctcagttcgg ggcggccttc gcggctcggt tccgcctctc tggtgctatc acttgcaaaa   2400
tggggatgtc agatacctgc cccatgacca tgaatgagat cgttcatgaa gtagtgcctg   2460
```

-continued

```
acacctggtg aaactacgca gttccctacc gttctggata atttaatttg aatcctcttc    2520
cccctctccg caattcctcg ccctcggtct tcagcctcct aggccagtgc ttttaacttt    2580
ccaggccctt tctttctccc cggtgatctc tgccttcact tgccttcgct tttcacctt    2640
ctccccactg cccttactc ctatccgcct ccccttttct gtcacccatc attttgtcc     2700
gctgaggcat tctctgctcc gtgagtttta acttttcctg tttcattcct aaactgcact    2760
atttgtgggt gcctttcttc tatactccct gccaccctc tccttctccc cctaatcctt    2820
ctgtttccct ttgtaaaggg cctttactgc tcacattttc gctggtcccc ctttctggaa    2880
ctttcctagc ttctcacctc tgctccttca ctcataacat ttcttaggcc ccaggcttac    2940
tactatattg cccagtaccc tcgccctatt ggtgtgactt gggtgagag ctttaacctc     3000
tatttctttt attctgcaat ttggaaactg acagcatcca tctcttaggc aagttatgaa    3060
gaataaattg aataatgtgt atattccact ttgcaccatg catgatggat gactttgctg    3120
tccagtactg tgtagtgcat gtggctcgtc aaattgagat gatagaattg ccagttgtcc    3180
tggtttgctg cgattgtctg ttttagcatt gaaagtccta tgttttagcc cctccgtccc    3240
agggaaacca ggaggttggt caccctaaat gtgctgtaag tgtacaatac acgccagatt    3300
ttgaaaaaac ttttttgatta atacatttta tatggattaa atgttggaaa ggtaatattt    3360
tgagtacttg gggttaataa aatgttaaga tttctgctgt ttttacttta taatgtggcc    3420
actaaaattt tatatgtggt ccacattata tttttattgg acaatgctgg tatatcgtat    3480
gctctcaaca agtatcttca aactcacctg ccaagcaccc gcctcctatt cctaactcta    3540
ctggaggtgt tgtgttttca gtttagagct tctcctttcc tggcagttat cccttatttt    3600
taaattaggg gttcctgact ctgaatggat ttccggaggg ttggacatgt cttatttttc    3660
ctcaaaatct tgtgactatg tacatttttt taggagaatc ctttgctttc ttcagattct    3720
caaggagac tggtacctcc ccccaccccc gttaaaagaa agcaaaacaa agcaacaaag     3780
accaacaaac cttccacagc agcccagtat tcatttatat tgtaaaagcc ttgattttct    3840
caagcatgga aaatattttg gctcccatct gacctgcttt ggttattgcc tgagtggaat    3900
tggtcacatt ccaagtttca gtactctttg ataaattgta ttggattcta gtttcccaac    3960
atacgactct gctccttctg cttacttttc ccaaattatt ttgccttctg tgcccaggca    4020
cacttagttc cctgtctagg caagagtggt cattattaga cttcattttc tttctactgt    4080
gcatatgtat tgattagcca tgggcacatt gtgaacttga aaagtcgatt tagtcacatt    4140
ttaagtttca ctatttgttg gtattattct ggcaagattt tggaaggttt ttattattta    4200
ttcatttgtg tatttttga  gacagagtct cattctgtct cctccgctga agtgcagtgg    4260
cgtgatcgta gcccaccgca accttgattg aactcctggg ctcaagtgat cgtcctgcct    4320
cagcttctgg agtggctggg actataggcg tgcaccacta cacccagcta atttttaaat    4380
tttttgtaga aatggggtct cactatgttg cttaggctgg tctcaaactc ctggactcaa    4440
gctatcccct gctttggcct ctggagtagc tgggactata ggcaagcgcc accataccct    4500
tcaggttttt aatttatttt atgaaaatcc ctccaaagca caatcctca attctcctgc     4560
ttgaaagtaa tcactaataa tcaggtactg tgtgatctga tccttgatgt tcatattatt    4620
gcctttaact gagtagcaat gttaaaattt aatcatttaa attagaaaac atatattgaa    4680
aagtcttcat agaagtccgg cattataaga actcatcaga ccatctagtt atcctagaag    4740
tattgtttgc tacttaaaaa gcctatgtgg aaagattgta ccatattcct tggtaatagt    4800
```

```
ttccaatgtc ttttttctc taatagggcc tttaaaacac tctacttaaa aaaaaaaaaa    4860
aaaaaaggct taacaatac caatactgag taatccatag cattagcctg tttccacgca    4920
caagtctgtc cttccccagt tacctgcttt tctgtatggt agcccagagg ccagaagagg    4980
ggctctgttc ctttctcttg tttcctttgc gctatccagg tgacgctggc acagccttca    5040
aagagcagca gaagtaattt gctcccagcg ttctttgcca catagagtgg cagggttaaa    5100
tgatttaaaa tttaatcatt taaattagaa aacatagatt gaaaagtctt catagaattc    5160
cagcattaaa agaactcatc agaccatcta gttatcctag aagtattgtt tgctacttca    5220
aaagcctatg tggaaagatt gtacgatatt ccttggtaat agtttcgaat gtcttttttt    5280
ctctaatatg gcttttaaag cactctactt aaaaaaaaaa aaagctttaa taataccaat    5340
accgagttat ccacagtatt agtctgtttc catgcacaaa tctgtccttc cccagttacc    5400
tgcttttctg tatggtagcc cagaggtgag atgaggggct ctgttcctgt ctcttgtttc    5460
ctttacacca tccaggtgac actggctgca gccttcaagg agcagcagaa gtaatttgct    5520
cccagcgttc tttgccacac agagtggcag gattagatgt tgacttacct ctgccacttc    5580
cttggtggtt ttgagtagta cagtcccttt ctgcacgtta gtgtgcaggc atgttgcctg    5640
caggagcctt tttaaaggag gagctttgga cttgtcctgc agtatagaac ttggctggca    5700
tgctgaccca gggcaccctg cattttctg cttagtagaa ctgcattttt agtgcttcct    5760
gagtgaccca ttgttttctt agtgaaaagg ggtcataatt tagtactacc tgtacaatat    5820
cctttcaagc atttcaagat ggtcatccag cttctccca aatttacact tttcagggta    5880
catggcttca tttcctcata gtgccgactt ctcagtctcc ctcaccaggc tggtgtcaaa    5940
cttgtgagct caagtgatcc tcctgcctct gtctcccaaa gtgttaggat tacaggcgtg    6000
agccaccatg cctggcctat gtttataatt cttgtaggta gaagtggtac ctattgtcca    6060
ttgtaatgag aaaaagtaa aatttgtctt aaaatataat taaggaactc aatttattaa    6120 attaaattt atccttaaa ttttaaattt aaatttattt cttaaattta tttctattac    6180
attttcttgt aaccatgtac acctaagttg ttctactta attttttga cagggtct    6240 cactctgtca cccatgctgg tgcagtggtg ccatctcagc tcactgcaac ctttgcctcc    6300
caggttcaag tgatcctctc acctcagcct cctgagtgtc tgggattaca ggcatgtgcc    6360
acaatgccta gctatttttt tttttttt ttggtggaga cggggttttg ccatgttgcg    6420
caaactggtt tcgaactcct gagcccaagt gatccacttg cctcggcctc ccaaagtgct    6480
gggattatag gtgtgagcca ccatgccatg ttctaccttt ttgaatctca tttactcact    6540
tgtaataagg aaataatact accttcttca tggggtgaag ggaggtataa aatgaagtat    6600
acatatgaaa gccttttgaa actgcaaagc attctaaacc tatatccaaa tgggtagttt    6660
taaatgtaga ttttcacaaa aggggattaa agagaggagt ggggaggccc catattattc    6720
caacacgggc tgaactgaac taacatcatt gcaggaaggt cttggaagat taaagattcc    6780
aagaaaaatt aagggctttg agtaaaaaaa ttttttaaaa gtggctgggc ctggtggcac    6840
gtgcctgtac tcccatctac tcatgatgct gaggcggagg attacttgag cccaggtgat    6900
cgaagctgca gtgagctata atcgtaccac tgcactccag cctgggtgac agagcaagat    6960
tctgtctata ggaaaaaaa aaaaaaaaa agcaagtgct gggcatatag ctggaatta    7020 gatatttaca taatatcctc atcttggaaa acttttccca gtagtgctgc ttttagattt    7080
tcccactact gcagttgatg gttcttaaat atgtttggaa ctcttatatt atttaggtca    7140
gtttccaaat tacacaaatt gtaaccattg tagtcagacc tcacttgaat gaaaacaata    7200
```

```
ttttacaaac tctgagggta gattcgagtt aggatttgga ttaaaacatt atcttaaaac   7260
ctctgagggt agattcgagt taggagtttc aaaacttctt tgaacaatat cataattagg   7320
atgtagattt acagagctac tagctaaagg aaggacacc agtcattggg atgtataagt    7380
ttggatctgt tgcaaaatta aaatgctgcc ttttgagcat gcctaataat gcacatacaa   7440
tagaagagcc agaattttta gaaaaatgac tgacttgata tacaaccttt tgtatatcat   7500
agaaggaaaa tattagttga gtattttgtt tatttacctg tttgtatata taaaacctgg   7560
ggcccaatat acaatagatt cttttcact atgcttttca cccacagtgt ctcaccaggt    7620
actctgtttc tagccatcta taatttcata gatgttttc tttaaagggg atgtattcta    7680
ggctgggcga ggtgggtctt gcctgtaatc ctagcacttt gggaggccaa gatgggagga   7740
ttgcttgagg ccagtagttg gagatcagcc tggtcaacat catgagatcc catctctgtt   7800
aaaaaagaa aaaaaattt ttttaaaggg ataatttcta gtcaactata agtgatttta     7860
agtaaaaagc aattaaggca tgtatacatc tgtaccttt gtaggcatag tataaattca    7920
gcttaatctc ttcagtttgg aacatcttcc tttcacagca aaaatattgt atttgcttta   7980
taagaaaacc ccttttggcc aggtgtggtg gctcacgccc gtaatcctag cactttggga   8040
ggctgaggtg ggtggattac cttaggtcag gagttcgaga ccagcctggc caacatagtg   8100
aaaccctgtc tctactaaaa atacaaaaat tagctgggcg tggtggtgtg tgcctgtaa    8160
tcccagctag ttgggaggct gaggcacgag aatcccttga acccaggagg cagagtgcaa   8220
taagccgaga tcacgccatt gtacgtcagg ctgggcgaca gggtgagact ccctctaaaa   8280
aacaaacaaa aaaccacag tggctcacac ctgtaatccc agcactttgg gaggccaagg    8340
tgggcgaatc atgaggtcaa gagatcgaga tcatcctggc caacatggtg aaacctcatc   8400
tctacaaaaa atacaaaaaa ttagctgggc gtggtggtgt gtgcctgtag tcccagctac   8460
ttgggaggct gaggcaggag aatcacttga atctgggaga cggaggttgc agtgagccaa   8520
gattaggcta ctgcgctcca gcctggtgac aaagtgagac tccgtctcaa aaaaaaaaa    8580
caaaaaacaa aaaacaactc tttagcatca ccttttagca atgacatagc ccaaataatt   8640
aaatttgtct cctgatcgga gatttggatt tgtctcatct ctctttctgg ttcctccttg   8700
gtttctactt tgtaaaccct ttaggccggg gatccagttt cttgtctgtg gatgttttat   8760
atacaaacag gactgtgagc tctttcagca ttgtacaaac agtgatgaat atcatctgca   8820
attaattatg tttaagttat tctctaatca gtttagaggt ggctcacttc ctcaggcaat   8880
ctgagtgggc tttcaggaag tgggaaatat tatctactat tgattgaaga aaagcagcca   8940
caacacaaat aagtcaaaat aatagctaat tgctaaataa tttcaagttt tttatgtatg   9000
tgatttttt ccctcaccaa tttatcttct cagttgtttg gcttattatt taaatcagtt    9060
tttattgtaa acatggtaat gactgaaagg taagaaaagg atagacgtag ttcagaataa   9120
actgagtggc agaaagaagc caaaggctat gtgtaatcta cggaatgagt aatttataag   9180
gaagtaatca agaattcact gtgtatagaa gtaagcaagt tcactcacat agtcacatac   9240
tgtattacat gatttattat ctttgagatg ggcaggtgtg gtgttcttct attaccgctt   9300
tcctagggtg ttgagagttc tagtccttct atttctttt ctggaattac cacttttcct    9360
atggctgaag ggagaaaata ttatttattt tgggatctgg aattgtcttc tcaatgttga   9420
tttttgtatt ttatataact gacttagttt ggatgaggct tcctttctgt gaattaaatt   9480
tatatgtgac ttgatcagag ttgtatttgc tgatgaggag ctgagacttg aagcctttc    9540
```

```
acctattgtt aggtaaaatg attaccactt agaactaggt tgagaccttt tgagatgtgg    9600
gtctttcttt agctctcctc agtctatggc agtgtgtgga ctgtaatatt tagccctcac   9660
acttagaaat tcagtgttaa gggcatatat ataagttccc agtatgtgat ggcagcttgt   9720
gataaggtgg gtatgtggaa gtttcataga ctgattatgt aagaaaactg acttgatgtt   9780
agtagcacaa ctggtgttgg aacggagatt tcttagattg gtttatgcta tttatattta   9840
aatgtattta aattgataat atttatcctg gtataagatt gccttattct tagttgacaa   9900
tgttaattta agatatgtaa ttctcagctg cttttctctt acattttac gcttgaataa    9960
tccaagtgtt tacaaattcc tacctaattt tttaaaagag gtgcagatta tagtgagatg  10020
gtctgctttg ccatatagct gagggtagtg gcagaagagg ccacatactg gatgctaagt  10080
taaatagaga aaaaatttat ttacacttca gatgtctttt gcttaatgaa tgtatcagaa  10140
aagccaacac tttctgaagt gagtttctgt tctaccgtat tgaatgtttg taataccgat  10200
gttttgtgtg ttttttcagga ttggcacagc tgcactggcc gttcaggttg tgggcagtaa  10260
ctggcccaag ccccactaca ctctgttgat tacaggccta tgccgtttcc agattgtaca  10320
ggtcttaaaa gagaagccat atcccattgc tgaagtggag cagttggacc gacttgagga  10380
gtttcccaac acctgtaaaa tgagggagga gctaggagaa ctatcagagc agttttacaa  10440
atatgcagta caagtaagtt gcttttattt tttcttaaaa cccattttc tttggttctt   10500
ttgctttcct aagatatggt gaatctgttg gatagtgaag ttttaggaca gtatacattt  10560
aaaatgagtta gtaacattat atattaattc tgatttactc ttatctgggg ttgtacctaa  10620
atcattccag gacatattgg cctaccctt ctaaagtttt ccaaatgtta tttctacagc   10680
tttccttcta acttctactg tctctaaact agataattat taaacctaaa tatttaaagc  10740
taaaaaacga atactgcac agaagctgtc tgtcactaaa atatctaggc accatttata   10800
taaattacaa tatattactt caaaagtcaa gatcacattg tctagcagta actatggtag  10860
atcaagcctg tggtgggctg atttcaagta tggttaaaac cttgattaac tagaatgctg  10920
ggaaggaagc acattttaga tatgcattaa atatttgact ctttaattct agttctttt   10980
ggttaactct agatagaaca gaaagctcct attcccaccc cattttgttt caaaccttaa  11040
tgaaacataa aattataaag tatagtcttc tactttttcta ttagtttaat ccagtgacta  11100
taactagatc tatgaggatc agataatgtt taaaagtcac aattataaat actactgatc  11160
attgaaatat gtgtggggca agtgttcata gccagtggta tttgtatctg atgtggcatt  11220
tgaagagcca tacttacagt gtaatgaaca ataacagaaa aatagtaaat ttgagggcca  11280
ggtgcgctgg tgcacacctg taatcccagc actttgggag gctgaggtgg gtggattgct  11340
tgagcccagt agttcgagat cagcctaggc agcatggtga gatcccgtct ctacaaaatg  11400
tacaaaaatt agccgagtgt gatggtgcgt gcctgtagtc ccagctactg gggaggctga  11460
ggtgggagga ttacttgaac ctagtaggtg gaagttgcag tgagccaaga ttgcatcact  11520
gcattccagc ctgggcaaca gagcgagacc ctgactcaaa aaaaaaaaa gaaaatagaa   11580
aaatttgaat ctgtaatttc tatatgggct gaaagaaagc actttgagga aagaaatttc  11640
agtttgaaaa ctgaataag tgaatatact gcttaggaat aaaggagatt gagagaaata   11700
gaatttcttt ttcttttcag cagtgatgtt ccctgggtct tgtgcctct attggacata   11760
gatagcttca tagcctcttt tgctttgctt ttacttcttt gtactttgaa tctagaggaa  11820
cttttttaaac ttgtaaagat tttgcagtga cattaaagga atttttagaa ataaatagat 11880
caccacacat cttactgtca tcatgcatca aatttaattt ttgttcgtct tctgggctca  11940
```

```
gttcatattc aattatatgt tttgttttg tatccatgtc tgatgttcat attaagtact    12000
tttgttaatt tcattgagtt aatgtatact aattttataa tttctctttt tagacattaa    12060
agttatttcc aattattctc tttcatcccc ttctgcatct acttctactt ctgcatctct    12120
tcaatgaact tcttcaatag catcctgtct cctagttctt ctgtcttgaa cctttctct     12180
tcactgagcc tttctaaaag aagtctgggg catcccattc ccttgagtaa aagactttaa    12240
tggctatagg atggacacca aatttcttag tataacatta agaccgtttg caacttgtct    12300
tgggcctatc tgtcttgcgt caactctagt tatcacctca ctgacaccct agttctagct    12360
ctactgaatg taaaacagct tcacattgag ttatttatg tctctatgat tctgccttca     12420
gttctctgct gggagtgctc ttccatctct gattttttt tttttttg aaatggagtc       12480
ttgccctgtt gcccaggctg gagtgcagtg gtgcaatttc ggctcactgc agcctccgcc    12540
tcccgggttc aagcgattct cctgcttcag cctcccaagt agctggcatt acaggcatgc    12600
gccaccacgc ccggctaact ttttgtgtct ttagtagaga tgaggtttca ccatgttggc    12660
caggctggtc tcgaactcct gacctcatga tccaaccgcc accacgcccg gcctccatct    12720
ctgaattta aaattgaatc tatgctttcc caacagctgt aggctgttag cgctcatctc     12780
tgtgtgcctt cacagtctgt catacatgtc atttaacata atgcttatca cattgtattg    12840
aaatgtatct tataggtatt ttttctctac caaacttgaa ttcacttttc tcctttagcc    12900
atcctgtact gagcagtgtt ttgggtctgg caaatagttt gtactcagta aatgtttgga    12960
aaatgagttt taactgtttt atttttcgtgg ggtgaattcc tagtagcaag ggtattcaaa   13020
ttttattatc tacttcttcc acctgaacag cttcatcgta attatacttt aattcccttc    13080
attctaggca ggtaatggat aagttccaaa attacgatgt tgttggagag gtttgaatat    13140
tactagcaca tgaaatctga tttgaactga ctaaatgaag gtttagtaca tcattatgaa    13200
ttagtgtgaa ctaagttttg ctatgttaac ttctctgaaa tctcagtcgc ataatgtgag    13260
tgtctttctg gctcatgctt catgcctgag actagtgggg gttgtgtctg cctattaaag    13320
tcactcggac ccaggtggat tggagattca tctaaagaca tgcttccctt atctctaagg    13380
caggaaaagg aaatggggcg catctctcat tggcttgtaa tgcttctgcc cagaaggagc    13440
tgtcacttcc actacgtttc atggatcaat ttaagactca tagacacacc tattagtata    13500
ttcgaaggaa gttagaaaga gcagtgccca gaagaaaagg ggagtttgtc agtagcccta    13560
atgactatca cagttactga aagtgtgcct tgggcataat ctatcttaac tcccagatat    13620
acgctgacag ttgttttct aaaagtcatt cacagtgctc agattctagt tagtccaaat     13680
tgatatggtt tggctgtgtc cccacccaaa tatcaccttg agttgtaata attcccatgt    13740
gtcaggggc ggtgccaggt gtagataatt gaattatggg ggcggttccc ccatactgtt     13800
ctcttggtgg tgaataagtc tcacaagatc agatggttat ataaatgata gttcccctgc    13860
acacgctgtc ttgcctgcta ccatgtaaga caggccttg cttctccttt gccttcctcc     13920
atgattgtga ggcctcccca gccatgtgga actgtgagtc cattaaacct ctgtctttta    13980
taaattaccc agtctctggt atgtctttat tagcagtgtg agaacagact aatacaaaat    14040
gttatactaa atattaatat ttcatcctct gattggccgt gataatagca tcaactatgc    14100
taaatttcta ataatacaca tatttctaat aatatgcatc taatagggtt tatattgtga    14160
ttatgtaaga gaatattctt gttcttaaga acaagggtcc ttaatctgtc acaggattag    14220
agatttaaag aataaggatc tcgattctgc agcttatcct caaatgttca ttaattatgt    14280
```

```
gtgagtgtgg agagagagaa agcaaacatg gcaaaatgcc acttttcagt tggtgaattc    14340
aattggtgaa tctggaagaa ggatgtacag gagttattgt atgattcttg caacttttttt  14400 gtacatttga attttttca atagaaagtt aaaaataatc atggcacagg tttacaaaac    14460
ccttgtaaac attagtgtta actactttta agccattatt gcttttcatt ctgattgatg    14520
ttttgaaagt acttttcttt tcctctgagg cctgtaaaat acgtggacta tattaatcag    14580
tgatctttca aaaacaaaga ctgaggccca acattaaaac ctagatggaa atctgatttt    14640
taaaaattca caaataatgc cagatttcat ttaaaagact tttttttcccc cttctagttg    14700 gttgaaatgt tggatatgtc tgtccctgca gttgctaaat tgagacgtct tttagatagt    14760
cttccaaggg aagctttacc agacatcttg acatcaatta tccgaacaag caacaaagag    14820
aaactccagg tacagtgttc ccttttgaac gccaggttgc tttgtcactt tttattgaga    14880
actagatagt gagtagttaa gttttgacct tcaagaaaaa gatattggag acccaaagta    14940
attgaaatgc ttttacattt aaactgactt tcaaatgtga ttgttttata tttttgttga    15000
cacaagcagc tcttttattt tatattttg ttgacacaag cagctctttt atttgcataa    15060
tcagtaatgg tagtcaattt acagaaaaag ttaaagcaaa gaatcataaa aaggtaaata    15120
tttgactggg tgctcacgcc tgtagtccca gcactttggg aggctgagat gggtggatcg    15180
cttgagatca ggagttcgag accagcctgg ccaacatggt gaaaccccat ctctactaaa    15240
aatacaaaat tagctgggcg tggtggtgcg cgcctataat cccagctact cgagaggctg    15300
aggcaggaga atcgcttgaa cctgggaggc agaggctgca gtgagccaag attgcaccac    15360
tgcactccag cctgggcaac agagactctg cctctaaata aataaataaa taaatattta    15420
atttaactta aatatgtaga cattctttga ttcactattt ttaaacgtgg agccatggcc    15480
cttcccttat gtgtggacct gctttcttag aatcttcatc atgtttctta tataaatcac    15540
acctatgatg cattacttat aattttaaat ttatatttat ttaaagtgaa atgaattta    15600 aagcacttg aaaagtaatc caagtataga atcctacatt tacatgactt aatccccaaa    15660
ctgtaatact ttaagttttc ttgcacactt attttttaaga tattttaaa gcagtatttt    15720 taatgaatca tcctagaata tttgtttgtt ttcagtgaaa cagctcttc atatgttatc     15780 agtttattta atacttaaat ccaactgtta taatagcaaa tacaactaac acaaacaggt    15840
tggttataca caggaattca attaatccag tgggagtaga agagttacag gactgccaga    15900 gagcccctg gctgtgggcg gcagcagtgt gttttactgc gggaacagag agcggcctgt    15960
gctccgacaa atcactagtg agagttggtt gagtgcttct gttctcttgt gtatgtaaac    16020
atttaatatt ttgaacctat aatttgttta gatctaatat gaaacacat tctgggcttc    16080 aagagagtaa ttcccagaaa gagttgacgt caactgtgtg tctggttttt tcatcttaaa    16140
aacacacagc ttcggccggg cgcagtggcc cacgcctgta atcccaacac tttgggaggc    16200
cgaggtggga agatcacgag gtcaggagat cgagaccatc ctggctaaca gagtgaaacc    16260
ctgtctctac taaaaataca aaaattagc cgggcatggt gtcgggtgcc tgtagtccca    16320
gttactctgg aggctgaggc aggagaatga cgtgaaccca ggaggggag cttgcactga    16380 gccaagatct cgccactgca ctccaacctg gggacagagc aagattccgt ctcaaaaaaa    16440 aaagaaaaa aaaaaaccac acagcttcat ttaaagtga aaaccaaga tcctgttttt    16500 tctttctttt ttaaggattc tgatattcat ctcaaacaac cttgctgatt aatatagttc    16560
atttggttgt cttagccata gtgtagcttt gaatactgtt aataattttt ttttaacttg    16620
gcaatttaaa ccatggctct gactgtctgt ttttggattg tgtgtttctg agagagatcc    16680
```

-continued

```
tattgattga ctcacatttc cttagatttt agatgctgtg agcctagagg agcggttcaa    16740
gatgactata ccactgcttg tcagacaaat tgaaggcctg aaattgcttc aaaaaaccag    16800 aaacccaag caagatgatg ataagagggt aaatatttat tttaacccat ttcagttttg     16860
aaaaaaaaat aaggagaata aagagaggaa caaagaagaa aagtttattg tctcctacca    16920
ctcgcactac tgataaaatt taggtgtttc cctctcatcc ttttctttgc ctggattttt    16980
ttttaaagca tgtaagcatt tttctcactt tgttttggtt atcatccaaa aggataattt    17040
actgagccat ttcccctttt gtgttgtttc caatgttttg tgtattgtaa acactaacaa    17100
ataactatga tgggtgtctt tgagtataac attttttttac tgcatgtaat actaagaaac    17160
taatacaaaa ctctttctta aaaggactat atgttgtgtc aaaatttggc tgttttcaac    17220
ttataataag tttccatttt tatttagtca aactcttgat ctttttttgt tttctaagct    17280
taagtcctct aaccttcagt ggcttgataa atattcactt tcctttcagt ttaattttag    17340
ttgatttttt aaaagtatt taattcttta acccatatat tattttgaag acagcagttg      17400 tattttccc tcaaatagct ttttgtttga ctcaacacca ctaattaaat aatccttccc      17460
atccccatta tcatctatta catttatatg tatgatggga tctgtttgaa gtctaccttg    17520
atctgctgat tttactattt ttatgtctgg acagagttta tattaggaag atatatttga    17580
tgtggacagg atgtgaaaat ggcatttctc tgaaggtgtt gagatgcagc gctctgactt    17640
aagttgaggc gttgagaatt atgttagcaa tttgacgttc atcagcgcag aagtcttgtc    17700
atcaaagaga atacattgta gagaaagcgg agcagaaggg aagaactcct ccccggtggg    17760
actagagaag gggcagtcaa gtaggctgag gagagagata ggaacagtga tgatcatgct    17820
ggcgattagt actccaggac accatgctgt ttaaaacatg cagaaagctg gattatttct    17880
ggcttgagat caggtcaggg actcaattac tcattttgta tagagagaca aatccactgg    17940
gagttgcaga aaactgcaac ttactctcag taaagtttgc catcacttaa aatgaaagtt    18000
tttcaaaagt gctccagaaa ataagcaaga gacagttatt taaaaagtag gaattaggat    18060
aatatttgga gttaacctaa aactctctcc ttttgttcc cctaagagtt gaaaagcact     18120
gttttagcag tcaggaagga aaatgcatt aaaaagtgct tttgtcttaa caatgaaatc     18180
actgatatgc ttataaaaat ctcacttttta aaaatatat aatatgttca gttttttatt   18240
tataatattt tatctgctga tgacttatgt aagaataaaa gcatatattt agtacttgtg    18300
tttttataaa attaaatttt tatttactgc tttatgtttt aaacattttt atatttgaat    18360
gtattaaata gataaatttt ccaggttaaa aaataagttc tgggctgaat gcagtggctc    18420
atgcctgtaa tcccagcact tgggaggcc aaggaaggag aattgcttga ggccaggagt     18480
tcaagaccag gctgggcaac atagtgagac ctcatcttta caaaaaaaat ttaaaaaatt    18540
agccagcatg ctggtgtgtg tctgtagtcc cagctattta ggaagctgag gtggaaggat    18600
tacttgagcc agggaggttg aggctgcagt aagcagtgtt catgccattg cacttcagcc    18660
tggattacaa agcttgacct tgtctcaaaa ataaaatgt tctgggggct tttaaattaa      18720
atgctagtat ataattttgc tccagtagtg gttgtttatt catgaatttc aaggagcata    18780
taaggtagtt ttaacatatg atagagagat catagagaat acaaaggcca tttgactttg    18840
cacagaatat gttttttaga tttgaaagaa caatttggc aggatgggaa cagatgccga     18900
aggctcactg aagtaattga tgaggtaggg gatctggtgg ttatagccac ttgctggaga    18960
agcagaactt cacaagaaag gaagtaaata gtgcgatagt taactagaag aaactagagg    19020
```

```
taagaaaaaa atattttgaa agcaggaaag ctttgaagac aaaatagagc cagtggtgga    19080
aaggttgaag atgctaggaa gaaattttgt aatgtaggag ataaaatgga attttttca    19140 gtcaccaaat ggtaagaagt aatgtatttc aagaaaatag tggctgcaat agtagctcaa    19200
agaaaggtaa ttcctagatg gtttaattat ttctagtatc cagttccttg aaatttgttt    19260
tctcatgcaa gtattattgt aagcatatac caaagaatca tgtctacctt acgttggtct    19320
acttctgcaa ttctgctgcc tctctgtata caactgcctt ttgattatca ttctgaactt    19380
cacttcctaa agatagagac tgtagtcata aaaatattta ttcagcacca gtcataatct    19440
tatgtgtacc tgggtacttc gtttccaatt tattttgaca tacggtttta cttttctgct    19500
ttctatgtta ggttatagca atacgcccta ttaggagaat tacacatatc tcaggtactt    19560
tagaagatga agatgaagat gaagataatg atgacattgt catgctagag aaaaaaatac    19620
gaacatctag tatgccagag caggcccata agtctgtgt caaagagata aagaggtaaa     19680
ttataaaagg catttgttca ttattgtttt cattcttggt actcctgatt aacaccactt    19740
tcactactct tttctccaat actgaggata cataatacaa atcttccacc tgcagtgtgc    19800
tgtcaggcaa tataactctt gcagctgcct ttttgttgtc tgaaagaaca gaccatgctt    19860
ctttgtttat acgtaatgtt tgttcagtta gcatcatatt cttcacatgt gacttttctt    19920
ctctagatta taaactctca agggcaagga ctgtccattt ctctttgtac aagacaaagt    19980
acagggaaac cttgataaca gaataggata tatgggttga ttacattttc tggatatccc    20040
cagtgttaaa ctgaaagcca ttttttcctt gcatactttt aactttataa ctcttattac    20100
atttttcttt attagtgaat tgtagtgagc ctgcttgaat gcttagtgac ttaatatttg    20160
actttctgag gcttacagtt aagaacatta gtaattgtag ttgatgggta ttttatattg    20220
cctctgacat tagttaatat atgtagaaca tttattatgt gcagaacact tgctaagca    20280 ttgcatatat tatggaagta gcatttgtta ttaaatatat gatattagct tgcttttatg    20340
agcagacctc actcatctct gatacaaaaa aaatgtatt gtattatgca tagttaggca    20400
cttacatctt attgtgataa gtaaaccaat ggatatatgt cacttgacta tccctgtgag    20460
cttaaaaggg acacacacta gtaaggccat atttccaggt tagaattaga tataatgttt    20520
tctcctgcag tttgcaggta tctgccttat tttgttttgt aagtacctta agtacttaga    20580
aaatatgaga atactttgta gagaaagcag agcagaaggg aagaacccct ccctggtggg    20640
actccagaag gggcagttaa gtaggctggg gagagagata ggagtggtga tcattacatt    20700
acaaaacaaa ataaacgttt tattatctgg atactttaaa acttttttcag atttgtttaa    20760 acatgcatga tatatctaac caagaaagag agctgtgttt gattttctg ttatggaatt     20820 tttctgtgtt cttgaacatg tttgctgtgt attctttctc cacagactca aaaaaatgcc    20880
tcagtcaatg ccagaatatg ctctgactag aaattatttg gaacttatgg tagaacttcc    20940
ttggaacaaa agtacaactg gtaagccaaa aaataacacc tgttttgcag tctaattgtc    21000
actcagaaag ctcatgcaat ttttcatttc aaatttactc cactgattgt cgtactgtta    21060
aattattttt gttttcaatt tttttgaaac cattttattg aagtgtgatt gtcgtacaaa    21120
aagctgtata taattaatga atacatctca gtgagtttca gaataagtat acacccatga    21180
aaccatcaca atcttcatag ccataaacat atccgtcacc tccaaagttt cctcctacct    21240
cttttgtgat tattattatc atcattatta ttggcttttt tcttttggtg ctggtggtaa    21300
gaacattgaa cataaggtct aatgttaaat taacaatatt gttagcgata ggcacttttc    21360
tttatagtag atctctagaa cttatttatc ttgcataagt gaaactttgt tccctttaac    21420
```

```
catcacctcc catttccttc tcctctcatc ctgtggcaac tactagtcta ctctccattt    21480
ctatgagttt cactatttta gattccacat gcattaaata ggtgaaatca tacagtactt    21540
gtctttctgt gtctggctta tttcacttag catgatgccc tctaacctag aggtccatcc    21600
atgttgtcac agatggcaag atttccttct tttttaaggt gcataatatt ccattgtgtg    21660
tctataccac attttcttta ttcacttatg tgtcagtaga catttcagtt atttccgtat    21720
cttggctatt gtaagtaata ctgcagtgaa tacggaagtg cagataactc tttgagatcc    21780
tgatttcagt tcctttggct gtttacccag aggtggcatt gctggatcat atgtaagttg    21840
tatttgaact tttttagtaa cttccatact gttttcataa tggctgttat cgggggacct    21900
gccccaataa tcatgtaggt tcttttctat tttcctaagc attggctggc ttgagaaata    21960
aagagacaga gtacaaaaga gagaaatttt aaagctgggt gtctggggga gacatcacac    22020
gttggtagga tccgtgatgc cccacaagcc acaaaaacca gcaagttttt attagggatt    22080
ttcaaaaggg gagggagtgt gcgaataggt gtgggtgaca gacatcaagt acttaacagg    22140
gtaatagaat atcacaaggc aaatggaggc agggcgagat cacaggacca cagctccgag    22200
gcgaaattaa aattgctaat gaagtttcgg gcaccattgt cactgataac atcttatcag    22260
gagacggggt tttgagataa cggatctgac caaaatttat tagatgggaa tttcctcttc    22320
ctaataagcc tgggagcgct atgggagact ggagtctatc tcacctctgc aatctcgacc    22380
ataagagaca ggtacgcccc ggggggggcca gttcagagac ctacccctag gtgcgcattc    22440
tgtttctcag ggacattcca tgctgagaaa aaagaattca gcgatatttc ttccatttgc    22500
ttttgaaaga agagaaatat ggctctgttc tgcccggctc accagcggtc agagtttaag    22560
gttatctctc ttattccctg aacaattgct gttatcctgt tcttttttcca cggtgctcag    22620 atttcatatt gcacaaacac acatgctgta caatttgtgc agttaacgca attatcacat    22680
agtcctgagg ccacatacat cctccttggc tgacaggatt aagagattaa agtaaagaca    22740
ggcataggaa atcacaagag tattgattga ggaagtgata agtgtccatg aaatctttac    22800
gatttatgtt tagagattgc agtaaagaca ggcataagaa attacaaaag tattaatttg    22860
gggaactaat aaaatgtccat aaaatcttca caatccacgt tcttctgcca tggcttcagc    22920
cggtccctcc gtttggggtc cctgacttcc cgcaacacgc tgtaccaatt tacattccga    22980
acaacagtgt acaagggtgc ccttttctcc atatcctcac cttcactgat gatggttttt    23040
ttgtttgttt gtttgttttt ttaaataatg gccatcctaa caggcataaa gtgctttctc    23100
attgtggttt tgatttgcat ttccctgatg attagtcatg ataagcacct atttgatttt    23160
ttgccgttaa gtttcatgag ttccttgtgt attttggata ttaacccctt atcagaaaata    23220 tggtttgcac atatttctg ctgttacata ggttgccttc tcattttgct gaacttttttt    23280 tattctgtac agaagctttt cagtttgata taatttcact tgttcatttt tgcttttgtt    23340
gccttgactt tggtgtcaat atccaaaaat accatgccca gaccaatgtc aaggagcttt    23400
taaaatatat tttgttctag gagttttaca gtttcaggcc ttacatttaa gtctttaatc    23460
cattttgaat taatgtttgt acatggtgtc atataagggt tcaagtgcat tcttctgcct    23520
gtgggtatct ggttttccca caacattttc ttgaagagac tgccctttcc ctattgtata    23580
ttcttggtgc ccttgttgaa aattggttga ccttctaggt aactttatag gtttatttct    23640
gggccctcta ttctattcca ttggtccgtg tgtctgtttt tgtgccagaa tcatactctc    23700
tgattactgt agcttcgtaa tataacttga agtcagaaag tctggtgcct ccacgttttgt    23760
```

```
tcttgctcaa gattggtttg gctattcagg gtcttttgta atttcttatt aatttttagga    23820
tttttaaatc tattttttgtg aaaaatgtca ttggaatttt aatagggatt acattgaact    23880
tgtaaattgc tttgagtggt atagacattt taacaacatt cttctagtct acgaacatgt    23940
aatatctttc catttatttg tgtctgactt atttcatcag tgttttataa ttttagtgt     24000
acagacattt tacctccttg gttaagtttg tacttaagta tttcattctt tctgaaacta    24060
ttgtaaatga gattgtttcc ttaatttcta tttatttatt tatttttttg acaggagttt    24120
cactcttgtc gcccaggctg gagtgcagtg gcatgatctt ggctcactgc aacctctgcc    24180
tcccaagttc aagcgattct cctgcctcag cctcacgagt agccttaaat acaggcacct    24240
gccatgacac ccggctaatt ttttgtattt ttagcagaga cggggtttca ccatgttgga    24300
caggctagtc tcgaactctt gacctcaagt gatccacctg cctcggcctc ccaaagtgct    24360
gggattacaa acgtgagcca ctgcgtctgg cccttaattt ctctttggag aaaggttttt    24420
tttttttttg agctttattg aagtgtaatt gacgtacagt aaacttcaca aatgtagtat    24480
gtacattttg atgagttttg acttacatat acatctgtaa taccatcacc ataattaaga    24540
taatgagcat aaccctcacc tccaaaagtt tcttcatgct ctttgataat cccttccttc    24600
ttccccgccc ctttcctcct tgcctcctaa tccccaagca accactaaag attaatctgt    24660
attttctaaa atttcatata aatggaatca tagagtatga gcccttttt ctggcttctt     24720
taattcagca tgattatttt gaggttcatc catgttgctg tatataacag taatttgttt    24780
ctttttattg ctggagttgt attctgttgt atggatatac catcatttgt ttatcaattc    24840
atctgttgat agacatttgg gttgttttca gttttttggc tattaaaaat aaagctgtct    24900
gggcacagtg gctcatacct gtaatcctag cactttgaga gaccaaagtg gacagatcat    24960
ttgagcccag gagtttgaga ccagcatgag taacacagga agaccccaac tctatttaaa    25020
aaaataaaat aataaatgaa ataaaaatat ttaataaaat atcaaaaaat aaagctactg    25080
tgaactgtgg tagtaaattt attttttaaat ttatgtaatg tttgcatgtc gtgacaaaat    25140
actgcctttt agttgaaagg aaacattttct tggtactctg agatgccatg tgtgtcagca    25200
ctagagatgt gtagcagcca tgtatccatc atgaaaataa ttccattgtt tagcattgca    25260
catagcacaa agaactgaag atgaataaat tatggtataa aaggagtcat gttaagctcc    25320
taaaccatta ctacacagga ttatgtctag ataattgtga gtgtggttat aaaaccatga    25380
aaatgccatt catatatata tttttgagat ggagtctcgc tctgtcaccc agtctggagt    25440
gcagtggtgt gatcttgact cactgcagcc tccgcctcct gggttcaagc aattctcctg    25500
cctcagcctc tcaagtagct gggattacag gcgcttgcaa ccacacccaa ctcattttg     25560
tattttagt agagacaggg tttcactaca ttggccaggc tggtctcgaa cttctggcct    25620
caagtgatct gcctgctttg tcctccaaaa gtgctgggat tacagacctg agccactgtg    25680
tccagcctaa atatctttgt ttgtttgttt gttcgttttt tgagatggtg tcttgccctg    25740
tcggccaggc tgtagtgcag tggtgtgatc tcagctcact gcaacccctg cctcctgtgt    25800
tcaagtgact ctcctgccct agtctactga gtagcaggga ttacaggcgc ctgccaccat    25860
gcccagctaa ttttttgtgtt tttagtagag atggggtttc accatgttgg ccaggctggt    25920
ctcgaactcc tgacctcaag tgatcctccc acctcggcct cccaaagtgt tgggattaca    25980
ggtgtgagcc accgagcctg gccccccatt cataatttct gaaagagaag tttacctacc    26040
aagtagagat ctcagatagt aaccgaaaac aaaaaggaaa gcagagagga aagagttgta    26100
ggaaatatgt ttgcagattt tcccagctta gaggagtcag tagataccat ttcaatcttc    26160
```

```
taattataaa taaggaaatt tatattgaaa tttgaaaaat tttttacatg taatcacatg    26220
ttattcaaaa caggaagcat gctttctgaa tcattaaaga gaataattag aaaaatatat    26280
cctgtataga aaagatagaa aataatttat acagcatgga aatcacctt actttaaaaga    26340 ttgaaagaac ttttaaaatt gtctttactt ggcatatttc ttgcaagaaa tttcttcaca    26400
gtgttttcag tcttttctaa attatcttga cttttattct taccttactg aatgtgttaa    26460
tcatgaatgg ataacgcatt ataacaagta cctttttagg tacaagatga tattttgatg    26520
gaaacttact cttcttgaac atgatgacat tgatgaccta acactgaacc atgtttgcat    26580
aactaaaata aatcccactg ggacttagta tattattctt tatagatttg atttactagc    26640
attttaatat ttacagctat ataaaaagat ttgtctgagg ttttctttta tgtttactgt    26700
ggtaggtttt agtgtcaggg ctagcactgt gaaacaattg agaaactctc tatctttcac    26760
ttcttcatat attcattggt tgggttctgg agccaggaaa gggggaagaa attttagttg    26820
ttcttctcct acttcactca cctaggactc tgactaaaat caatagtact ataattaaat    26880
tatatagttt actgcttagc taggttttt gggggactag cttgggaacc aaattaccat    26940
ctcaggccat ttttttcctt tatgaaatat ccttagcaaa ttctaaataa ttaattaaaa    27000
gatatgtatt aattaattaa aagatttctg tgtatttctc tctcccatct tcttctttca    27060
ctgccagcat gatcaggtgg ctgtgtatta taccctggca gccacccagc tagtgaattc    27120
attttggctt ctgttacctg gtgtttaatc tgagtatttt aaatgctaaa tcttattagt    27180
aaacctgttg aaagcttggc tctagaaaca aagcctaact catacacttc tggtgagact    27240
ttgatacaac tttctgtgtg gcaattaggc aattctttac atcatctgtt ttttttttt    27300 tttttgaccc agcacttctg ttcatagaag ataagctgaa agaaatcatt gcagatatat    27360
gggaagattt agttccagtg atgcacagtt gaagcatctt ttataaatgt aaagatgtgt    27420
aaacaacttg aatgctcagc agtagggaat tagttaaatg aatatagata atttagtaat    27480
ggaacattaa gtaaccatag aatgttactg ataaatatat gtgtgacagt gaaagttgtc    27540
tgtcatatat taagtgaaaa aaacattta caaaacttaa aggccccata aaatcccatt    27600
ttgaaaaata ggtttgtaaa tgcacgcaca cagcctggaa ttacatatac tgaagtaaag    27660
gtagtggtga tctcttgggg gcatgagatt atgggtaact gttttcttct tttctgttag    27720
tgttatcagg ttttctggaa tgaacatatg ttactactga aataaggaaa aaaatcaccc    27780 tttttttaa aaacaaatg ccagcacaca tacaatatgt agaaattaag aagtaatgca    27840
taactagaaa atcattccaa ataaaatgat atgaacattg agtttttaat tgtgtagtgc    27900
ctactatctc tgggacact aagtcttaag cagagaaacc aaaccaaatg cagatctcct    27960
agaatcctca tctagaaaga tccaagtctg ttcttatcac atctattttc aaaaaaata    28020 ttttgccctc gtcatgcttg aaaggagttc tttaacttaa aaattttatg tgttctaatt    28080
atttctgttg ggttatttga cagaccgcct ggacattagg gcagcccgga ttcttctgga    28140
taatgaccat tacgccatgg aaaaattgaa gaaaagagta ctggaatact tggctgtcag    28200
acagctcaaa aataacctga agggcccaat cctatgcttt gttggccctc ctggagttgg    28260
taaaacaagt gtgggaagat cagtggccaa gactctaggt cgagagttcc acaggattgc    28320
acttggagga gtatgtgatc agtctgacat tcgaggacac aggtagaaca cttctctcag    28380
tttaatctct gattcctctt tcttttttaat tgactagagc tccctaaaag cttaggcata    28440
gcatacatct attttcctta aagggctatg tgtggtacct tgaatgaaaa ggacatttac    28500
```

-continued

```
aagaagtatc agctagccta gagcctctaa gcgtaatgat aaacccaaac taaccttgat   28560
ttgtatgaca gtggatacta ctctgtgcct caacttcct ggaatctcat ttgaatgtaa   28620
ttataagtta tttatgattg gatattatta tgtctttaca ctcttttcaa cccagtagca   28680
tgccataaat aatgatccct aactctcaga gttaaaaaaa gtaactgcaa tagggagggc   28740
caataggagg aggtgagaag tctttgataa caaacttgtt ctgattgcag tctaaacttc   28800
ctcttatgaa ggttggtttg tattatgaat atgagtaata aggataaatg ttagcataat   28860
tattaaggct tattcttgca ttttggactc actttctata aaaaaacaat aaactgtaag   28920
aactgtccct ctaggctggg cacagtggct catgcctgta atcctaacac tttgggaggc   28980
tgaggtgggt ggattgtttg agcctaacag tttgagacca gccggggcaa catagggaaa   29040
cacttttgtc tctacaaaat ttatatttaa attttttaat tttaaatttt aattttgtc    29100 tccacaaaaa ttaaaaaatt atgcaggcac agtggcatgc acctgtggtc ccagctactc   29160
aggaggctga gatgggagaa tcatttaggc cnnnnnnnnn nnnnnnnnn nnnnnnnnn     29220 nnnnnnnnn nnnnnnnnn naaccaagcg gcaaataagg aaactttgtc ttacacaagt    29280
aaatttactt cttcatttac attaaatttg gttccacaaa aatataaaat taagctaggc   29340
acaatggcag gccttgtgtt cccagctctt agaaggtcta aatggagtat cattacgtct   29400
tgaaagttcc agtttgcagt aacccatatt gtccctcgc acgccagcct ggagacagag    29460
acattatctc aaacaaacaa acaaacaaac aacaacaaaa ctgtttctga ttaatctgac   29520
attattagaa tcagatttgc atgttgcatt cattgttctc actggtctct ttgttgatct   29580
gatggaaatt gccttgggaa agcatgaatt tacatttcgt ggtttaaggg attcatagca   29640
attgtaagtt gtgagaaaac atacctatag tgtatgtgtt aaagaacatg tttaaatgta   29700
ggaaccatga actgcttata aagaatatg atgcttttt aatatcttgt tttctatttg     29760
ccttattcaa agggatccct atccatagac agggatggga aactgtttca gaaacttttc   29820
tataagaaat ggttatttt attctctttt atttgctcac ttaaaattct tacgcattta    29880
aaaagtatca ttactggcct tgtgtagtag ctcatgcctg taatcccagc actttgggag   29940
gccaaggcag gcagttgctt gagctcagga gttcaagaac agcctgggca acttggtgac   30000
accccatctc taaaaaaata ataataataa attttaaaaa agactcatca caagatttta   30060
gtaaataaac aatgaggcgt gcagatcaga gtagagaatt gatttgggtg atttcttctg   30120
gcaatttcaa aagatatttt tgttgcctag acttcttatt cttgcatgta ccactagagg   30180
ctatagtttg ctttcgtaaa ggaattggca tttctcttgg accaaactca agaagctgc    30240 gtctagggcc taaatcttct aattttagct acagagtaag tatttgatgg catttagaga   30300
gtgagttcgt ggaattaatg ctatgtgaaa ttgacatcat aagcacgtga catgtaggta   30360
atttgttctt atttcttttc acattggtat tgattatttg ataaggcttg gaaagcactt   30420
attcaatacc tgacacacag tgagcattca ctaaaaatta gctttaacca ttatttaaat   30480
tctattaata aattctcagg aggacaaatt tagatttaca agcttcagta tgagtttta    30540 taaatttcaa tctgattttt taattgcctt ctaaaatatt tatcctattc tcagcattat   30600
tacttaattt atacggcaga attatgggaa aatgcatttt tctgttgcct actaatggac   30660
agtgtatagt gtcatggttc tcaccactta caaacatcac tggattaaaa taaatctcta   30720
ttttaaatcc ttactgacat ataaaatttg ttctttttt caagtgaata tgcttttgtg    30780
tatgtgactg tattaagaaa attgagtctg aagaaaataa gaattgactt tatgggtctt   30840
ttgtaaaagg aggttgtgtt acaatcacca ttgcctaaaa tatttgtaaa tataaccttt   30900
```

-continued

```
ttagaaacgt atatatggag gctgtgattg ttgccgagta aaaagtataa ggatttgttt    30960
tgtgaatcat tctattcagc ctgattttag atacaccttg ctggtaagtg ttacttagcc    31020
atcagtgtac cagatgtttg attaactact atagcaacct gcccttgtgc tgttggggac    31080
atattaccca tctaccccgt gaattattaa agcctggtga aaaattttat ttcaaaccct    31140
gtttggaagc acgtggagag tagtgggtt cagttgttga ggaaagggtg agggcagagc    31200
atgcacttag gtcagttatg aattgaaggt gaataggagg aggagagaaa gaacaaccga    31260
caattccagc acaaccatgg gtgtgcctgg gggaacatgt ggttccatgt gacagttgag    31320
gcatttggga gacaacccag gtcttgacgt ttgagtaccg gtcacatgct cacagttaga    31380
gttcatgaaa agttttgttt ttcctcagcc tttgagtagg caccactgtt ccgcagcctt    31440
agaatagcca aggaaaaaga aagccaggga aaaagaaagc tgctttgtta ttgtccttgc    31500
ttatcctctc gattttgcca ctcactctcc ctgttttccc atgtgtggaa cactttcctt    31560
ttgctaaaag tacctgcgta tgagaagaag gatgccgata agttggggat tgattttaaa    31620
aacaagcaaa gatatgtttt ttatggttaa atgataatga ggtgggagat ggggaagcaa    31680
aagagaggct tgccttaata tttaatctta aacttggaaa ataatagtga tctgactaaa    31740
cattgcctca ttttttgtctg tattgttttg agtagcttaa aggaagaata atgtttatgc    31800
tacgtattaa ctcattcagt ttttcagtct tttcgatatt tctcatttgg atttatctcc    31860
attgtgattt ttctgtccac tttgtaagcc acaaaatact cattcccttc tatcagtttt    31920
aacaacttaa atttttatat ttaagtatta catttaaata atttaagtca attcacacaa    31980
atataaggta actaacttct tttaagatga agttttatga aataatgttt gcataattgt    32040
ttttcatttg ttctttggta aaaagaaata atatattatt gttatgatat atcttaaatc    32100
actgtggata ttaactccta gaaatacttt accagctgtt tacttagata ataaaattat    32160
attattgcaa gaaatccttg tctcaacttt caaacaagat gagaagaaaa atgaacttgt    32220
gatttccaca ttgatacatt ttcatatgca acctgaaatg gtaaagttat aaataaaacta    32280
tttcattatt agtttctaca agggaaaaat aactgaagca gcaagcttct aatgtatttt    32340
tttagcatag tgtaccagat atattatggt ttgcccacta tcctttcaac ttacatttgc    32400
atgtagctct tctttgcctc tccaaaactt aggtttattt taaggcctca acccaaggct    32460
tcctccatta atgtaagtgc agtcagttat gatttcactc ttctctaaac tgaccaccta    32520
ttgtgctcct ttatcgaata cgggcctctg gcatttctac catacaactg tggagatgaa    32580
acataaatac gttataaaa agtacaagct ttctcaggca ggggatttat cgtctatctc    32640
ctttatgtac cccatgatgc ttatttaaca tggtgctaaa tgtggtgagc gctctctggg    32700
tgttttgtga attcatgtaa gattaaaaca taatattttg gaagttatgc aacccttag    32760
acgagtacac ccatacaaat tagtctataa aaagatttag gaatgactac cagaagaata    32820
attgcatttg tttagacatg ctattataca ttaaaatccc agtttcttaa agactgtttt    32880
tcttttttgag atcattagga tcttttttaa actgattcct ttttccagtt tgagatacac    32940
acacacaccc acacacccac ccacacccac acccacacat ccacacaccc ttggtagaaa    33000
atgtgaaaaa taaggggaaa aaatcctcat gttttttctac cgtacaaaga taatcactgt    33060
taacatttgt tttgttctgc cagacttatc attggatttt aagtaacaga attgtaatcc    33120
tgtcattttc acttaacatt gtaacactta aactctttc tattccaaat tctttgtaaa    33180
ttttatttta acagtttgca ttatagcctg cgggagccga gccctttaat tgaataggta    33240
```

```
ggaagagtgg atggtgaaat gcctatattt ttctctcttg tctgctataa aagacatttg   33300
caaaagttgc ttccatgagg cagaaattga atgggactc aaattcaggt gtactgaatt    33360
ctgctcttgt gcttttcca ggaaaccaga agtaaacttt aagtagctgt tgctaataat    33420
gatgagcatc actggaaagc tcactgtgtg ccagggaccg tgctgtgtgc tttgcctgtg   33480
ttctctcatg atccttatat taatataacc caccaggttg acactatttt ccccatctta   33540
taggtgagga aactgaggct taggtcaagt aatttgccca aaatagtatt cagaggcttg   33600
tactgtgtta cctttagagt gctgatggaa agatgctttg agtgctggca cggtggatct   33660
ggtggggaac aatcttacag ctctatatct agcctctact ctgtggtaag accccgtctc   33720
tgtcataaaa gtgctcactg gctctataga ggaggttatt atacccatga ataaaaacta   33780
ggttgtaagt aaccatcaga tgagttatgg ggccagtaag tgctgtagac attgcattat   33840
tagagcgatc cctttgtgag aggtagtcag aaaaagtttc ttagaattgt tgggattac    33900
gtagcaggaa gaggagtatt aagggcagga aggcaccata ttttaagaa aggtaaaaat    33960
ttttaagggg cgtaatagta tcttgattgt ggttgaagca agaaagtaat ggcagcaagt   34020
tgggaagatg aatgggagct ggattgtgaa aagcctcgaa ctccagacaa aggaatttga   34080
accttattct gtaggctctg ggaagcaatg gaaagtgtaa gaggaattgc ttatatacag   34140
tgtgagtaga atctaggatt ccaattttt tagaaagggt gcctacctag aatattattt    34200
tctctctgtg acttcaggtg tagaattgtc agtacttgtt tttgaagttt actcatcaaa   34260
aaaggaaagg caaataaata actgcagcaa aaaatgaccc attagagcct ttgagattct   34320
ttaaaaaaat tcccttccct accactctta aaaatcagag taatggcaaa tctgtaagtt   34380
ctctagaaaa ataattggaa agaatttata aattctgagt ctcgtctttc ctgtatctga   34440
ttctgaaatc ttgaatgtgc taattcctta tattaacagg acaatgttta ttgccttgc    34500
ttccctgtgc cttagtcacc tttcccggat gaaaggcatt cccatgatat ttttaaggct   34560
tgcttgcctt ttcaaagttc actctgttta ttctgtccta ctttataccca gtcatgtggc  34620
agaaatcagg cctgctctgt gaatcggctt tgtgcagatc atgaggtaac tgtggctgtt   34680
ccacttgtca ttgatcattt tcttctcggc agtcaggctt ttatgccttt tcagagacag   34740
catttgcttt gcacaacata gacagcaggg ttataattaa aattagtaaa ttgctgcttt   34800
aagttttgct ggctttgtaa aaaagacacc tttttggtt tgataaactt atgtgttttt    34860
atttcatgcc acactctaca tctgtcataa ttatgtgggt gattcttgtc caaatacaat   34920
aaagcaggct ctcacatttt aacgttcaac aaaatacctg gctggctgaa cgtggttatt   34980
gccaattagt gcatatggga tgaatacagt tttgttcaaa aggacagaat aatgaattc    35040
tgatataaat actgttgacc ccagatcctt atactataat taatagatta tttcctctga   35100
aaataaaaga gattggagtt tttctttttt gttgttgttt ttggtctgca ttctgagtgg   35160
ctgtttgaac tgattttaat ttccttcatg aagatgatga tgttttagct ggcccagggg   35220
cagccatttc agtgtgcata aaggtggttg cgttgggtag ggggatgctc agaaaaatca   35280
tggaaagcat gggaattcat agggtacttt ggacattttg gaatcttgaa gagtaagaac   35340
cgtaactggt gacttaagtg tcgtgttct tcatttcacc aaaatggcaaa atgtgataca   35400
gttcttccaa tatcatgggc aacttgtagc cagaattaag tagaagataa gattagaatt   35460
gaatataata acttttgatt tatcatagtg cctttaaat acatagtacc tctttgctat    35520
attatagtga tagctaaatg atcttttcac attcctaagt tttgatttct gaatggcgtc   35580
gctcctgcct cctgacatct cacactgtga atgtgctact tgctttctct aggcgcacct   35640
```

-continued

```
atgttggcag catgcctggt cgcatcatca acggcttgaa gactgtggga gtgaacaacc    35700
cagtgttcct attagatgag gttgacaaac tgggaaaaag tctacagggt gatccagcag    35760
cagctctgct tgaggtaaga tttggaaaat tccctgtctg tcttcatact ggaagagtat    35820
ggaggagggt tgataatcat attcaagtga tatacacagt ggtgtagctt tagttatggg    35880
aaaaacagtt tgataccggc tgaggtctga gcaatttggc acttaaatta aaatgttttt    35940
gagatttctt tcactaagtc ccctttttt ttattttcct tttgtatttt aatcagatag    36000
tttaacaaag ttttgtgcac acttattatc tagaggccaa caattctaca cagttatggc    36060
aaaaaaaaca gcaagcaagt ctccttctcc ctggggtccc ccatgccttc ttctgcactt    36120
tgacctcttc agcttttagt tgattaaccc tattttcaaa atagcatggc tatcttgcac    36180
ttcctgattt ttttttttt tagttttgt cattttctat agatgccccc caacaggagg    36240
tgaagatttt accttttttc ttccgttgtc cccactgtat cattttata ccttagatct    36300 cgcaataaga attttttct tgttttttg ttgttttttt cttgtgaata ctaatacatc    36360
catattagta tttacattat tatgattatg taaatgcttt tcacagcagg agccacatgg    36420
taaactgtga tcacttttcc tgttcctatt tttgttttc tctactttt aagaatattt    36480 tcagagttag ctgtcttgtt tcttttgttt acttttcac caatcgtcta attctgtcaa    36540
gaccttcaga cactttaggt gttctatcca ttttatcttc ttaagcgtcc ggtctgaact    36600
ggttgttttt gacatccggt tttatggctt ccttcctagg ttctccctc acctctcacc    36660 atgttggatt tcctgtctcc tgtattccat tcttgctct ttcttggtcc attccctcat    36720
ttttgtggtg ttaactccct gatagtttcc tgagaaagct tgcatgagtg gtaaatgttt    36780
tagactttgc atatctgaaa atgtctttat gtttccctca tacttgatta gtaatttgag    36840
taaagaattc tggttggaaa taatttttct atagaattgt actttgcctc cattttactt    36900
cactttccca tttccagtgt tgctgttggt aaaactgatt ccattcagtt cctatccttg    36960
cagacctgct ttaccctgaa aactttcagg ttcttccctt tatcctggga ttctgaaatt    37020
tcctaataat ctgccttggc atgggtttct tttcatgcat ttttgctcat tctttctttg    37080
aattcttcct gttctttggt tctaaaattt ttcttaaatt ctttattga tgacttttcc    37140 cctttatttt ttggaactcc catgacttgg atattatgtt tcagacttat cttttctctc    37200
ctattagtct ccacttttat gttttgctct actttctgtg cagactttct cagatttatc    37260
ttttaaaaac cctctgaatt tattatttca aaaactttct ctgcatgttc ttttatagta    37320
tcctgttctt gttacatagt tgtaatatat cttatctcca tgagaaagat acttatagat    37380 atatttttaaa atttttacttc tctgaccact tggtatatta aaaagaaaaa gaaaaaatt    37440 acttctcttt aagctgcttt tatctgttta ttatatattt cttttagtct cttttatatt    37500
agagtctttc attagatatc tggacatttt tgtttgtgtg tttatattta atagtaaggg    37560
acaaaaaggc tgattggagg ctatgagcat aggagtgggg cttatcaaca gtgagttcca    37620
caatagagtc agctggctgt gctgtttggt tgaggaatct tctactcaat agctttaagt    37680
cttccttctt aggatggtca gattcctcag agaagacttc ctgtctcttg ccttgagaat    37740
gaaggcctgg ctgccatcat tctgggaacc aagcagggga agaatgattg gggtcggggg    37800
tatcactgca ttcagcatcc gtgtatatgc attcacctga gctcttgttt tcagcatagt    37860
atatgttctt atcagctgtg cccagggtcc cctgtgcaga gaaccactgt tttatgttct    37920
taagaaaata aacttccagt gttttgctgg ggtgggggag gggatctggg atctgactgc    37980
```

-continued

```
ttcctaaatt tatttcagcc agtcctcctt attttagcac atcagcccct cctcccttttt   38040 acccttgctt aaaatattat taatgcaaat tgatttgtaa aattgaggaa aacttacttt   38100
gtgaaagttt ttatttttttt cttgtttatt tctgtgcttt gagctgcctc gtgcttcctg   38160 tttttttttct gttttttgtga tcttagaaca ggatggcctg ggacatgtgt cttattaagc   38220
aggagaccat acattctggt ttgcttggca cattcccagt ttatgcctaa tattaattgc   38280 actcttttttt agtctcagaa gtgggttttg tttggacgat aaaaaagtac agttaccttta   38340 cttaaaagcc ctggtatttg gaggtaaggg tttgatttgg ttcagttttg ctacttttta   38400
ttgtaagatc attaccttct ggctccataa ctggttcttt ttactatgaa gagtaaaata   38460
gtgaacatta tttaagattt tagtagtttc ttatataata tctttagact ttcagtttaa   38520
tttatattgg gacatttttt caggttatct gacagattct cccattagac acttacagtt   38580
atcctgttga aaataatttt agagtattcc cctgacactt aaatttttttc aacaactgtt   38640 ttgaagcaag ttcaccaaag acagctttac aagtagtagt agatgattaa gtcccctgtt   38700
tatttgttca gttgataaac aatatgtttt aggtcttcac ctatatatac tttgtaatga   38760
ttcaataata tttgttaaat tgatctttga taacaagcag ctagcataat gatattttct   38820
tgtctgatgt agaccttggt actcactttt ttggcagtcg atttattagc attcaaaaaa   38880
aaggtatgaa aacctcaaat gatatctcag agtaaatgcc ccctgggccc acgtactaat   38940
cactgtagtt tagttatgaa tagcattggt tccttacaga ctgtaaatgc tataaaatga   39000
agcaagacat acatatggag gaactgagta tcttggtagc tgacagcctc ttcctccctg   39060
cttgcccaag tcctgggtaa aaacctcaga cctcacagat tgttgaaaca attaaataac   39120
agtacatatt aaagcactct ataaatggta aagtactgta cagatgttaa tttaatatcc   39180
actgatattt cttctgtgtc catttttgaaa gccacttgct gcttccattg ccagtaggtt   39240
cacttaaatt taaaaaaaga acaaactcaa ttacacaaca cgttacattt aaagtgaata   39300
ttcctgagag tttggagacc caagtatagt tttattatct ttctacatag aaaacctgct   39360
tttaaaaaat gatatctaga tattatttgt aaaatgtata agattatttt atgtttaagc   39420
taattatatt attaaggtaa tatagcccag atgtgaagaa tgtaatagta gatgtaaata   39480
tacactagag tgcttactct gaataaagaa taaactttttt ctgctgtgta ttcttctttt   39540
tatttatgta ggatatgccc gtttccttga cctaccatgt aattgttgct tatgtaaaac   39600
agaatgtatt tcaagttatt acttaatatt gtccaaaaaa ggagaattca aaatttagat   39660
gatctctttt gaaaatttat tggaagacta taaaaatagg tccaactact taattaataa   39720
atggtggtag gcagtagaat ttgggcaagt ctataactga gtagcactaa aatattagat   39780
ataaggaaag taagggcttg tatgtaatta atagacttga aagaaaatta cagaattatt   39840
ttcttaccag atatatgtta tatttataac tggcacatgt ccagacttta ttgttaaata   39900
tgaatgcata tctcaaatac atttttgtgt gagtgggcaa ataaaatgca tggatacaat   39960
aattaattgt ctttataggc aataatattt acagttcgaa aaacatatat tccccaaaat   40020
agagaagtca ctagtctaga tatagtaaac ttcctttaaa actgaagttc ttacttaatt   40080
cgaattagat ccagttagta attagaccaa tagtatattt actacttaga tacagtagac   40140
atgatctttt gatttgagct atacaattat tgtcaaagaa tgtcagaaga gagggactta   40200
gacatcatct aatccagctt catgctctta aggataaaaa gcttaaggcc taagatatta   40260 ttttaattttc ttatttcact acatgctata ttaatgatat aatttccaaa tatcgaatgg   40320
agttaaaaaa tgccttaaat aaggcatacc ttgttttatt gtgttgtgct tcattgtact   40380
```

-continued

```
tcacagactg tgttttttta acaaattaaa tgtttatggn nnnnnnnnnn nnnnnnnnnn    40440
nnnnnnnnnn nnnnnnnnnn nnnnnnnnnn nnnnnnnnnn nnnngggcac ccgtgtatcc    40500
ccagcccctc ggaagcttga gccaataaca ataccttgac ccggggaggc agagtttgcg    40560
gtcaccggag ggggggggg ggcgtcgcaa cctgggttac aaaccaatac tctttctccc     40620
gtccccgaca aaaaaagaa agaaagtgtt tatggcaacc ccgtgtcaag caagtctgtt    40680
gacaccattt ttccaacatc ttacttcatg tctgtatgtc acattttggt agttattgca    40740
atatttttaa cttttcatt attatatcct attatgatga tctgttatca gtgatctttg     40800
gtattgctat tgtgattgtt ttggggcacc acaaactgca cccatataag acagcaaact    40860
taatcaataa atgttgagta tgtactaact gctcaactgg ccaggcattc ccctttctct    40920
ctccctctcc tctggctcct attccctgag acacagcaat attgaaatta ggccaagtaa    40980
taaccctgca gtggcttcta agtgttgaag tgaaggaag agtcacacat ctcattgtaa     41040
atcgaaagct aaaaataatt aagcttagtg aggaaggcat gttgaaagct aggcctcttg    41100
tgccagatag ccaagttgtg agttcagagg aaaaattctc aaaggaaatt agaaatgcta    41160
ttccagtgaa cacaccaatg ataagaaagt gaaatggcct tattgctgat atgaagaaag    41220
ttttagtggt ctggataaaa gattaagcca actacaacat tcccttaagc cgaaacctag    41280
tccagagcaa ggccctaagg ctcttcagtt ctatgaaagc tgagagaggt gagaaagctg    41340
cagaagaaaa atttgaagct aacagaagtt ggttcatgag atttaaggca agaagccatt    41400
tctacaacat aaagtgcaaa gggaagcagc aagtactgat gtattgtaga agctgcatca    41460
tgttatctat ccagaacatc tagctaacat cattgataaa ggtggctaca ctaaaaaaca    41520
gattttctat gtagatgaaa cagccttatt ttgtattgga agaagtgtca tttaggactt    41580
tcatggctag agaagtcagt acctggcttc aaagcttcaa agggcaggct aactcttgtt    41640
agggctaat gcagctggtg actttaagat gaagccagtg ctcattgacc attctgaaaa     41700
ccctaaggcc cttaagaatg atgcaaaatc tactctgcct tgttctgta aatgaacaa      41760
caaagcctag gtgacaatgc atctgtttat agcatggttt tactaagtac tttaagccca    41820
ctgttgaaac ttaccgttca aaaaaaatag attcttttga aaatattact gctcgttgtc    41880
aatgcttctg gtcacccaag agctgtgatg gagatgtaca aggagattaa tactgttttc    41940
attccttata aaacaacatc cattctgcag cccatggatc aaggagttat tttaactttc    42000
aagtcttatt atttaagaaa cacattttt aaggctattg ctcccataga ttatgattcg     42060
tcccatgcat cagggcgaag tacattgaaa accctagaa aagattcacc attctagatg     42120
ccattaagaa cattcatgat tcacgggagg aggtcaaaat atcaacatga acaggagttc    42180
aggaagagtt gattccagcc ctcatggatg actttgaggg gttcagactt cagtggagga    42240
agttaccgca gttgtggtag aaatagcaag agaactagaa ttagacccca agatgtgac    42300
tgaaatactg caatctcatg gtaaaacttg aacagatgag gagttgcttc ttacagatga    42360
gcaaagaaag cgggtttctt gaaatggaat ctagtcctgg tgaggatgct atgaaccttg    42420
ttgaaatgac aaccttgatg ttgtgaacct tgttgaaatt ctaaacaaga tttagaatat    42480
tacataaaca tagttgataa aggcagcaac agggtttgaa aggattgact tcaattttga    42540
aagaaattct acggtgggca aaatgctatc gaatagcaat gcaggctata agaaattgtt    42600
tcatgaaagg aagagtcaat agatgaagca aattttactg ttgccttatt ttaagaaatc    42660
gccacagcca ccctaacttt cagcagccac cacctgatca gtcatcaacc attaatattg    42720
```

```
agacaagaca ctccaccagc aaaatgacaa caactaacac tgaagactca ggtgattagc    42780
attttatagc aagaaagtat ttgttaatta aggcatgtac attgttttt agacataatg    42840 ctattgcaca cttaatagac tatagtatat tgtgtaaaca taacttttat atgcactggg    42900
aaacaaaaaa aaacatacat gtgactcact ctgttgcaaa atttgcttta ttgcagtggt    42960
ctggaactga acccacagtg tctctgaggt atacctgtat tgaggagggg ttgcaaattt    43020
tagcacatag gcaaatttgc aaatatggaa taataaggat caactgtaat tactgcttta    43080
tgccattatc ttttaaatca gataagaaaa agttacgtca acaatatatt tacactgcct    43140
tttatgtttg caatgtaatc acttctgcca gtgcgctcta tttctttgtg tggatactgt    43200
ctagtgtcct taaacttcag tctttcatat ttcttgtctc atctcctggt gacatattct    43260
cagtttttgt ttttctggga atgtcttaat ttctccttca tttttgaagt aattttgttg    43320
gtatagaatt tgggttgaca attgtttgct ttcagccctt tcgcatgtcc tctcaccact    43380
ttctggtctc tgtggtttct gctgtgaagc cagctgttaa gcttgtggcg gatctcttat    43440
gcctaatgag ggcagcattt ttctctcata gttttcagta ttctctcttt gtctttcatt    43500
tctgacagat tgactgtgtt tatgtgtgat cctctgagtt tacttagttc tttttgagct    43560
tcttggatgt gtaggtaaat gttttttcatc aaatttgaga agtatgtggc cagtatttct    43620
tcaaatattc tttatgcccc tttctttttc ctctccttct gaaactcgta ttatggtgtg    43680
ttggtaatct ttgtggagtc ccgtaggtct ctaaagtgct gttcactttt tttaaagcct    43740
tttttctttc tattcttcag acaggatcat ctcagttgac ctgtcttcaa gttcattgat    43800
tctttcttct gccagctgaa attgtcattc agcccctcta gtgaatttt cattcaaatt    43860 actgtagttt tcaactccaa aatttctatt ttaaaattt tattatttat ctttgtttat    43920
attctctatt tgtcaagaca tcattctcat actttcctgt aattgtttag acatgatttc    43980
ctttagtttt tttaaatgtt agtaaatata acagaaaaag tcccattttt accactttta    44040
tgtgtacagt tcagtaatgt taagcacatt cgcattgttg tgcagccaat ctccagaact    44100
ttttcatctt gttaaagtga aggtgtatac tcattacaca gcaattccct gtttctttct    44160
ccctccctca gtccctggca gctaccattc tcttttctgt ttctatgagt gactactcta    44220
tatacctcat ataagtgcat catacggtac ttatctttt ataattgact gacttcactt    44280
agtttcctca aagttcatca atgttgggc attagttttt taagcatatt tatagtagct    44340
gatttgtaat cttttttttt ttttttttga gacggagtct caccatgttg cccaggctgg    44400
agtgcagtgg cgggatcttg gctcactgca agctccgcct cccaggttca ccattctc    44460 ccgcctcagc ctcccaagta gctgggacta caggtgcctg ccaccaggtc tggctaattt    44520
tttgtatttt tagtagagat ggggtttcac catgttagcc aggatggtct cgatctcctg    44580
accttgtgat ctgcccgcct tggcctccca aagtgctgag attacagtcg tgagccaccg    44640
tgcctggccg ctgatttgta atctttatct aataaatcca acatgtcttc cttagggatg    44700
gtttccattg acttctcttt ttctttttg agacagggtc tcgctctgtc acccagactg    44760
gagtgcagtg gcgcactcat ggctcatggc agccttgacc ttacccaggc tcaagtgacc    44820
cacccacctc agcctcccga gtagctggga ctacaggcac acaccagcat gcctggccaa    44880
ttttttgtag agacagggtt tcgccatgtt gcccaggctg gtctcgaact cctgagctca    44940
agcaatttgc tcaccttggc ctcccagagt actgggatta caggcatgag ccactgaacc    45000
cagctgactt ctcttttttt tttttactct ttagggccgt acttttgtat ttctttgtgt    45060
gtgtctcata attttttttg ttgaaactga atatttagag tgttatattt atattaaata    45120
```

```
cagtcagata tataattgaa taatataacc ttaagggttt tttgtttgtg ctgttgttgt   45180
tgctgtttgt ttagtgactt tctggtttca ttctgtaaag tctgttttat tcattaatgt   45240
gtgaccactg aagttgctca gtttgtttag tggtcagcta gtgaccggac agagatttcc   45300
ttaagtacct ggacagtagc tctcccactc cttgcccaag gggctcttat gtgtgtattg   45360
aagtgggcct ttcacacttt ggcagatggt ttacaactct gccttagcct tcacttcctg   45420
cttttgcaga gcctcagtgt ctgccaaaga tgagcttata gggccttctc aggtctttcc   45480
tggatatact tagagcctgc acattcacat gaaattttgg attctcaggc atatgtcaag   45540
gcttttcaaa gtccccatga atatctcatt tcccagtttt tccatttaag ttttttggtc   45600
agcctcttgt tagtcccaac tagtttcatt gcctcaggca gctgcagtgc taaaacagtt   45660
gccactggtt gtttttggca aatgtcctaa ggataaaact gttctcacag agtgttctct   45720
gagttaagtc aaataaggat atggagctct tctaaggaac tgccagagtc aaacagggac   45780
agttctctgg ggatggggct tttgaaggat tgtaatcctt ttctaccccc taacaggatt   45840
gctaggctac tggttttcac agctactggg gttatgaggc tgttgatttt gctaccatga   45900
acttgagaga aagggatgag tgtaaagcaa gttaaaatat cacaaagctc gttctgttta   45960
ttgagattca gctgtttttc ttgaataagc actcctcaaa ttgttgcaag ttagtatgta   46020
gcattctgaa aaagttgatt ttgacaattt ttgctagtgc tctcattgct tttctggagg   46080
agcagatttt cagagtttct tactctacca ttatataata gaagtgcttc ctcccccatt   46140 tcatttttgat tctgtgcttg aatgatttca ctgcatgctt ctgatacttg tattttggtt   46200
tatcacttgt tcagatgaaa tatatcttca ggttacttca ttcaaagatt tgtgtgtgag   46260 ttgtatttg aatctcttct atatttgaga aggcttcttt gttgtctgca ccagtagtaa   46320
tatatatgta aataaaataa gaatgtatta gtcttcttct tttttttttt tttttttttt   46380
gagacggagt cttgccctgt cacccaggct ggagtgcaat agtgcaatct ggctcactg   46440 caacctctgc ctcccaggtt caagcgattc tcctgcctca gtctcctgag tagctgagat   46500
tacaggcacg tgccaccacg cctgactaat ttttgtatc tttagtagag atgggctttc   46560
accatgttgg ttaggctggt ctcgaactcc tgacctcgtg atccatccgc ctcggcctcc   46620
caaagtgctg gtattacagg catgagccac cgcgcccagt cagaatgtat tagaatgtat   46680
ttcttaagac tgccataaca aaataccaca gactgggtag ctttgaagac caaacagaaa   46740
tttatttcct tatggttttg gaggctagaa ttccaagacc aaggtgttta taggtttgat   46800
ttctcctaag gcctctctcc ttggcttaca gacaaccgac ttgtggctgt gtcctcggga   46860
gacctgtgtg catgcatccc tggggtctcc tctttcctct tataagggta ccaattgtat   46920
tagactaggg gcccactctt accttcattt aaccttaatt accttcttaa acaccctgtc   46980
tccaaataca gtcttcaccc tgactgccct tgagacagag cggagggggt tagggattct   47040
gtcaattttg aggggcaca attcagtcca taacaaagga catatataat agatacataa   47100
tatatatgta ccagtgtgcc catatcatgt actttatgta aaacgaaatc agttttaaaa   47160
ggtaattata ttttcaatga aagcactgtg ttctaattag ataattgttt ttacttcata   47220
atatgtctat cctagcttat tatataaata aaagtgtcaa ctctgttatt ttcttgtggt   47280
tcataccttt gcctataccc tttttaatga tactttgcag gaatcttttt aaaccactca   47340 acccattgt aatattaggc tctgtgaacc cggaaaattt gagacaggtc tcagttaatt   47400
taggaagtat atttggccaa ggttgaggac gcgcgcccat gacacagcct caggaggtcc   47460
```

```
tgacgacacg tgcccaaggt ggtcagagca cagcttgatt ttatacattt tagggaagca    47520
tgagacgtca atcagcatat gtaaggtgaa cattggtttg gtctggaaag gcaggacagc    47580
tctctggaga gggcttccag gtcacaggta gataagagac aaaccttgt gttcttttga     47640 gtttctgatt agcctttcca aaggggcaa tcaggtttac ctcagtgagc agagggtga     47700 ctttgaatag aatgggaggc aggtttgccc taagcgttcc cagcttgatt tttccctcta    47760
gtctggtgat tttggggggcc aaatatattt tcttttcaca gcacacatgg acagcaatgt   47820
gctgtaatta tagttaaggc agataagtga ggacaccaca ggcagccttc gaccttatgg    47880
aacttcttct aagtgaagac atcaattcca ttttggatat taaatattta caagctattt    47940
ttttctggta tttataaata aaaagataa atacaaatac taatattttc tacttgcact     48000
ttggtgggtc atttccact tttgtgacca ctggtctaaa tagataaaca aatgtcttca     48060
caaatgggta gtaggttcac aggtgttcat tttgttatta tgcatcatat cttatatata    48120
ttacatatat ttgatgtatt caagattgta aaatatttta aactagtgat aattttgctt    48180
gaaaattctg taggtgttat tctaatgaca ttctcatttt tattgcacag gaggaggaat    48240
ctaaatcttt tcaatctata gtgtcaaggt cttctagaat attttcgttt ctttaatccc    48300 tatttaatt tactgagacc tcttctttag ttatattaac cagttatgaa ttgtatctct    48360 taattttttcc cgtatttatc ccctacatgt ctctaaagcc ctttttcttc tatgtcctga   48420
acacttttct caagtttgtc tttatcacag atttaatttc catagttgag gatatagagg    48480
aaaagtaaac tcagtttctc ctactgcact ctcacaacac agaacacctc tgaccaaatg    48540
cacgggtttt ttctccatat gccaagcaag cagttcttca gcaaccgacc acagctgggt    48600
gtcctctaat tcaattctga caaagtgtat cagatcctac ggggttgagca ctgagtccca   48660 caagactgcc tcccccttca gatgccagtc gtgagttgac ttccagaacg tgtgaccaac    48720
cagttataaa ttggagtacc cacaagcccc cctcctcagg tttgcttaat ttgctagagt    48780
agctcacaga actcagggaa acaatttact tgcatttact ggtttattaa aagaatattt    48840
taaagaatac aaacaaacag cacaggagct tccatcccag tgaagtcagg gtccaccagt    48900
cttcttgcac ctgggtgtgc tcaaattcac cttcctggaa gcttcctgac ctcagtcctt    48960
tcgggttttt aatggaggcc ttgtcacata ggcctgattg attaaatcac tggccattgg    49020
tgatcaactc aactcttagc tcttctcccc tcccaagaga ttgggctggg gaactgacaa    49080
gtcctcagcc ctctaatcat gccttggtct ttcctgtgac cagcccacat cctgaagctg    49140
tggagggact gccagccacc agtcaatcac taacatacaa aatgatactt atcactttgg    49200
tgattccaag gattttagga gttgcatgtc aggaaacaaa gagatgaagg ccaaatatat    49260
attttacagt atcataatag tattaattgt gtgtggcttt cagagctgat tttagttatg    49320
ttattttatc tttattttct gttgtggaaa atttcaacca tagcaaaagc agagaagata    49380
gtataatgaa ttctgtggac tcatcaccca gctttaatat cttgtttcat ctattgcttc    49440
ccattctccc ctacccaacc tctgattatt ttgaagcaga ttccagacat catctttca    49500 taaatgtttc agtagctatc gacaaaagat atacacttttt aaaaagcata atcatactat   49560
atcacaccta aagatgacag ttacctagtc ttgtgtaatg aactctatgt aatctattcc    49620
tggattgcct acagacatct atagttcttc tcttgtcaga aattattatt gaagaataat    49680
tctcagtgta cattcctccc acggttcatc ccattgtgac ttcacattcc taggaataat    49740
gcgtcatatc acagctattt ccattcccag tcatacttttg taggtaggaa ttatagtcct   49800
aggattgata cagaaaatct tttagttggg gagaataaag gagaaacagc cctaattatt    49860
```

```
tttgaaagtg gccctggatg tgggcagtag aatccctgct ctgaagttag ggtaagaaga    49920
tgaggtttga tagctacaaa gctcttaatt gtaattttcg tccttccatg gactcaccag    49980
tttgcctcgg agcttcatct gagtagtgat taccagaaat tattttctgc cagaatattg    50040
atcagtattt ctgatgctgt ttaaattcta tatgtctttt tatgcttttg aaaaccagaa    50100
agtatctgag acaggtctca accagtttag aagtttattt tggcaacgtt ctccagagat    50160
gattgtgagg gcttcagtat ttaaagggga atgggcagat attggggaaa gaggaagaaa    50220
ttttaaaagg tatgagtaga caagagacaa acggttgcat tcttttgagt ctttgatcag    50280
ccattcacct gtgagagggg agcagaggaa tagtcactga cgcattcatc tagcttagtg    50340
aatctgcatt tctacataag ataaaataaa tatagcgtac aggaagccat cagatatgca    50400
tttgtctcag gtgagcagag ggatgacttt gagttctgtc ctttgtcctg tatgtgtaaa    50460
gaataagcta tcaatttaca tggttggggt gaaattcaac agaactgtta caggttaaag    50520
atcttgggc ctacaaggaa tttctcagtg gggggattgt gagggagata tgtagctttt    50580
tttgtctttg tagctatctt atttggaaac aaaatgggag gcaggtttgt gtgacgcagt    50640
tcccagcttg tctcttccct tttgcttagt gatttggggg tcctgagatt tactttcctt    50700
tcacactctt cctgagtaaa agaggaaggc aggcaaattg ggcacaaatt tagcctaagt    50760
ctgcctcctt acatattaat attttaagtt tggcctaaag gtttcccctt acaaagtaaa    50820
ctgcagccta actagctgtg taaacacact attcttaaca ccaatcacag attttcagca    50880
agtcacagga agtcagctgt taacaaactt taaataaagc aaacaccaag ctgtaagcaa    50940
tcccgctgtt tctgtacact cttttgtttt tgcatgtcgc tttcctttt ctgtccataa     51000
atattatcaa accatatgcc agagtttctc tgaacctatt ctgtttctgg gagctgccca    51060
atttgagact tgttctttgc tcaattaaac tgttaattta tctagagttt ttcttttaac    51120
aagcatcact aattttttct ccttataatc taggtattct gtcacactgt tttaaaaacc    51180
tccttcataa ttcagaaaca ttgctttatt aattttccta cttttaaaa acgctagtgt    51240
cttaaaattt taagagaaaa aaattacttg ttcaagtctg acagccattt ctaaaacata    51300
tccagcatat atgaattaca tatgcttaga gccattaaag aatagaattt tttccggcca    51360
ggcatggtgg ctcatgcctg taatcccagc actttgggag gccgaggtgg gcagatcacg    51420
aggtcaggag atcgagacca tcctggctaa catggtgaaa ccccatctct actaaaaata    51480
caaaaaagta gccgtgcatg gtggcgggcg cctgtagtcc cagctactcg ggaggctgag    51540
gcaggagaat ggcgtgagcc cgggaggcgg agcttgcagt gagccgagat cgcgccactg    51600
cactctagcc tgggcgaaag aacgagactg tctcaaaaaa aaaaagaat agatttttt     51660
ccttagctag tgttaaaaaa ttactcatga cgcttattaa aggtggtaag gattacttta    51720
ttcaaggtgg gagactacgt ataagaaaca ctgcaatggg gttttgcagt gacaggagga    51780
gagtgaatgg ggaatcagta gagggaaaca ttctaagagg aagaattggg gttacgggg    51840
attctcacta gaaggacaca acagaactct tgctgaaggg aggccagggt gaaagatac    51900
tgggttagaa gtgagaacag atacgtatgg gtatgggtca ttttttgctaa cctgacttag    51960
caggattctt gctcaaattg gattttacaa agacagaggg aaggctgaca ttggcctagt    52020
tgagcagagg actcagagga gcctgactca agtttgcgtc aaaagaagag cgttttttgtc   52080
actagatgat agttttaact attttccata cataaacatt ttccgtacct aaacagtttg    52140
tttgttcatt tgtttgttag tttgtgttgg attttcactc tgtcgcccac gctggagtgc    52200
```

```
agtggcgtga tctcagccca cggcaacttc tgcctccaaa gttcaagcaa ttctcatgcc   52260
tcagcctccc gagtagctgg agctacaggc atgtgccacc ataccaggct aattttttgta  52320 ttttttttta gtagagacag agtttcacca tgttggctag gctggtctca acacctgac   52380 ctcaactgat ctgcctgctt cggcctccca agtacttgg attacaggtg tgagccaccg   52440
tgcccggcct gtgaacagtt tttagatgat tagtagatag taagaccact cttaaccaat   52500
tcaatactga acataattag ttttccttga ttacttgaaa gtacttgttt tttaatgata   52560
ttaaacatta ttaagtcttg tgaaaatgtg aaattagagc tttctgggaa ttctagatag   52620
agtttccagt aataattaat gtttaacaaa attcagaatt atgtatgagg cctagaatta   52680
agactagctt ggggctgggc gtggtagcgc acgtctgtaa tccctgcact tgggaggcc   52740 aaggcaggtg gattgcttga ggccaggagt ttgagaccaa tctggccaac atggtgaaac   52800
cccatctcta ctaaaattgc aaaaattagc caggtggggg tggtacgcac ctgtaatccc   52860
agctactcag gaggcaaaga ttgtagtgag ctggagacca tgccactgca cctcaacctt   52920
ggtgacaaaa tgagactctg tctcaaacaa aacaaaacaa aacaaaacaa aaaactaact   52980
ttggatagtt ttgaaaataa gtaaaacttc agaaagaatc agaaggtagg aaaaactgct   53040
tatatagtta aattgtggtt ggtgagtata ttagtcattt tattgccttt ttgaatatgt   53100
atggcaaccc tatttatagt aattgggcgt aagtgagagt gttaatatgt ttaaggtttg   53160
gaacatgtag aagctgttgg tgccttatga aagttctgca ccagcccctt agcaacaagt   53220
gcctgtgact tgaagctctt taatgtacag ttgcacattt taagaatcca agttgactga   53280
taaattatct aatgtatcta attcaaatat ttttaagagc tattgtaatc ccagtacttt   53340
gggagactga ggcaggcgga tcacttgagg tcaagaattt gagaccagcc tggccaacat   53400
ggtgaaaccc catctctact aaaaatacaa aagttagcca ggcatggtgg cgcacacctg   53460
tagtcccagc tactcaggag gctgaggcag gagaatcgct ggaacccggg aggcggaggt   53520
tgcagtgagc tgagattgtg ccactgcact ccaacctggg caacagagta agactctgtc   53580
tcaagaaaaa aagagttatt gatgttttgc ttattataag cagcaatgtt ttgtagtaag   53640
ccatttttaa atagtgaatt ttttgctgta tcagaatata gtagcatagt aattttttact   53700 cttatttaac tcatagcaaa ggttactctt atttggaatt ctccttttcag ttaaataatt   53760 tataccagac tttctgaaaa tgtttgagga ggattatatg ggttcttatt tactggttct   53820
ttgagaattt caaaatactt tacacatttg ctttatattc ccatagcagt ttagataggg   53880
tgtgttacca agatggaaac tggttctgca ggactggtaa cttatgatgg ccaaacaatg   53940
agtcattaat aaaatagattt ttgaacaaag cttgaaactg taatttctgc tgctttgtgc   54000 tattacatttt tcagaaattt tgacactgaa cgtattttat tttttaaaaa gtatgtagaa   54060
tgtagagaat gcaaataata atgctcagat gttagttttg tctgtttctt aaattcttct   54120
gagcagaaat accaaccttg ccagtacatc atgtgtgttt tcacttatat acagccttct   54180
gttggcacta ctaaagtttt taaaatgttt tttgttctcc cctaggtgtt ggatcctgaa   54240
caaaaccata acttcacaga tcattatcta aatgtggcct tgacctttc tcaagttctt   54300 tttatagcta ctgccaacac cactgctacc attccagctg ccttgttgga cagaatggag   54360
atcattcagg ttccaggtac ctgactctta aatcattatg atacatcttg cctttctgac   54420
cataacttta aaattagtta tgctatggag ttttgactaa agaagttca tttgccaaca   54480 tacaatcttc agaagttctg aggaatgtat ataaatcagt ttctatgtag cttcaaagtc   54540
tggaagagca aaacagcaaa cgttgacaac aacaatttca gatttaatta gcatgaaaga   54600
```

```
atgataattt tatgacaaat aagacattct tctttagtat aatttctaaa atggcaggct    54660
gtgtgtggtg gctcacacct gtcatcccag cacttttggg aggctgaggc aggtggatca    54720
cttgaggtca ggaattcgag accagcctgg ccaacgtggt gaaacaccat ctcaataaaa    54780
atacaaaaat tagcctggca tggtggcggg cgcctgtagt cccacctact cgggaggctg    54840
aggcgggaga attccttga acctgggaa ggggaggttg cagtgagcct cacgccactg    54900
cactccagcc tgggtgacag agtgaaactc catttcaaaa aaaaaaaaa aaaagagta    54960 actgaacttt ctcataaaat ctggcctcac ttttatatta aagtgcatgc cgcttttaaa    55020
ttcctcttga atctgtcaaa tagttaaatt ttttaaatgt cttccctgtc actggagcgt    55080
gcaaaatgta ttccttcagt tactaacact agataagtta tagcattttc accttatttt    55140
aattgctcag aattgttttt ccctggaaga gatcaaatat cactgagttt ttttttaatg    55200
tagagtagaa tctaaatgtc tttatttatt taattattta gagacagagt ctagcttgtt    55260
gcccaggctg gagtgcagtg gcacgatctc ggctcactgc agcctccgcc tcgaagttc    55320 aagtgagtct cgtgtgtcag cctcccaagt agctgagatt acaggcactc gtgaccacgc    55380
ccaggtaatt tttgtatttt tagtagagac catgttggcc agtctggcct cgaactcctg    55440
gcctcaagta atctgcctgc cttggcctcc aaaagtataa ggattacaga cgtgagccac    55500
catgtccagc ctaaatgtct tttacttatt ttttcttttt ttgagatgga gtctcactct    55560
gtcacccagg ctgaatgca gtggcacaat cttggctcac tgcaacctct gcctcctggt    55620
tcaagcgatt cttgtgcctc agcctcctga gtagctggga ctacaggtgt gcaccatcac    55680
acctggctaa ttttttgcatt gttagtaggg acagggtttc gccatattgg ccaggctggt    55740
cttgaactcc tgaccttagg tgattcaccc gcctcagcct ccaaagtgct gggattacag    55800
gcgtgaaccg ccacactcgg ccctaaatgt ctttagattc taaatgtaat ctaaatgtat    55860
ttttcatatt aatctgaaat atatttttac tactaagtga attataattg gatttctgtt    55920 tgttttttt ttgagatgga gtctcactct gtcaccaggc tggagtgcag tggcacgatc    55980
tcagctcact gcaacctcta tgtcccaggt tcaaacaatt ctcttgcctc agcctcacaa    56040
gtagctggga ctacaggcgt gcaccaccac gcccagctaa ttttttgtatt tttagtagag    56100 atgggatttc accatgttgg ccaggaaggt ctcaatgtct tgacctcatg atccaccac    56160 cttggcctcc caataaact ggatttctta attatctgtg agcattgcag gttcctgtat    56220
ttagttttaa aatatggtag agtaaaaagt taattgtgtg tatttaaagt ctaaagtaaa    56280
taagtaatga attccctgga aactccaagt tatggcagaa aattcattag atacactaaa    56340
gtaaagtgaa agaatcagga cagctgctgc agaggggagc atatgatgcc accttcttcc    56400
tttggcagat ttagctgtcc gatcttctag cttttcctggt gtttactaac ctctttccat    56460
tcaaaaggtg ccttatcaat tcatattttt aattttttgct tgttaaatgg aaagggacat    56520
tagttggaat tttgtcttac gggatttaga gacaaaggaa atctatattt attcaggcta    56580
ttaaataaga acattatgtg ttctaaatat actatatata gaaaaaatac atatatacat    56640
acataaatac atatgcacac atatataaat acatacacac acacacacac atatatatat    56700
ataccatcat gtggaggaaa aaacctttta tatggacatc ttaggttttc ttttgctgct    56760
acaatttatt ttatagtcat agttctggaa acagtatctt tagagccctt cccttggaac    56820
ccactgctta tttaattgag gtgtgtgtgt gtgtgtgtgt gtgtgtgtgt gtgtgtgtgt    56880
gtgtgtgttt caagtataga tcaaattagg ctaaaaagat gcatttattc ttctatttga    56940
```

-continued

```
aatttcagag gatttgagga taaagagata attgtctcta agatttgagg tgttttcctc   57000
tttgggaaat atatcattta atcagaaaac tttcaagcac tgtgcttagt aaatgcttgt   57060
tttgtttgtg aaaacgttgg aaattttaac aattattgac ttagatcaaa tttctttttc   57120
tttttttttt tggaggcagt ctctgttgcc caggctggag tgcagtggtg caatctcaac   57180
tcattgcaac ctccacctcc ccagctgaag caattctcgt gcctcagcct ccagagtaac   57240
caggactaca gacatgcgca accatgctca gctaattttt tgtgttttta gtagagacag   57300
ggtttcgcca tgttgcccag gctggtctca aactcttaag ttcaagtgat ccgcccgcct   57360
cagcctccca aagtgctagg attacaggtg tgagctaacg tgcctggcca gaataaattt   57420
cttcattgta attatagtct catttgaaat aatacttaaa tttgttctaa atctaagatc   57480
catttaatgc tacatttgat tcattaaaaa agcatggcac tggctgggag cagtgactca   57540
tgcctataat cctcagcact tgggaggct gaggnnnnnn nnnnnnnnnn nnnnnnnnnn   57600
nnnnnnnnnn nnnnnnnnnn nnnctataa tctcagcact tgggaggct gaggctggtg   57660 gatcacttga ggccaggagt ttgagaccag cctggccaac ttggcaaagc cctgtctact   57720
gaaaatacaa aaatcagcca gcgtggttgt gcatgcctgt aatcccagct gctcgggagg   57780
gtgaggcagg agaatcactt gaacctgaga ggtggaggtt gtagtgagcc gagatcacgc   57840
cactgcactg cagcctgggc gacagagcaa gactctgtct ctaaaaaaaa aaacaaaaaa   57900
caaagcatgg cattatggga gccatgtaaa taattacaaa acaagatctc ttcttttcca   57960
ggttatacac aggaggagaa gatagagatt gcccataggc acttgatccc caagcagctg   58020
gaacaacatg ggctgactcc acagcagatt cagatacccc aggtcaccac tcttgacatc   58080
atcaccaggt tagttagcca tcctgaggct tcattaactc caggcaactt ttgagtattt   58140
actgagttac caaacaggac atagagtatc aatatttgag ttttttcatct tttgagataa   58200 gccacagtct cctgaaaagg agattagttt attggcatcc catagcatcc atttctcttt   58260
cttcaacaac ttccagcaag tgttatcata actattgatt tacaccgttc tctacactag   58320
gcagaagttt acagagaaac catttggaat attgttatag ctaaagctga aatttatgct   58380
ttgccacaat agcaatataa ggggttaatt tgatcattta aaaccaaat acatggcaaa   58440 tatagagaca cttttatgc ccaggatctt gaaagttgtt gaattctctt aagaggtgat   58500
atgctacttt cagataatct gatttaagtt actcactttt cttttcttct ctttggctga   58560 gagatttta aaatccttag aattttgatc ttcagaatta acactggaac aatagagaag   58620
gtgccttccc aagtttacta ccaaatgctt aagcctgtag caagcagtgt gtaaattatc   58680
tgaatagagt attgcttagt ctaatttaca gattccctgt ttgaatggaa aatatactct   58740
gttgagaatt tatatccacc acagcctctt acagttttcc tagctcagta ttacagatcc   58800
attgcatcat ccagcaagtc atgtcaggct gccaagctct cctcttgcgg ccctttcta   58860 gtaactactg tttttaagag atttgaagta tctctctatt ttgaactttg acttagagtt   58920
tggccagact gtcttttgat ctatgccttc ttatggatct atttagattt atatacaaag   58980
cagtaagact aagtcttacc tgggggttcc ttttcttaat ttgtcttgtg atttatggtg   59040
tagataatgc caggagaaat aaattaagtg acttatatgt ctgagtcttc caacaatatc   59100
attattccag ataacaccca tgatgccttt gggtaacttt caataagtca tttaacatttt   59160 ttgatagctt ccccatctgt aaaatatgag ggatggagaa aaatccgagag tttatctgaa   59220 taataatgat tctgaagagt gatcattatt tatatttccc agttgttacc tagagaactg   59280
tttctttttt tatgtatact tgttaactca aaatatcaga tcttaaaagc tgtggacata   59340
```

-continued

```
aggaaatatc tggagcagtt ttgttagttt tgatattgtt tttaaaaaca gcacaagtat    59400
gtactattcc aggcacagtt tttggatatt tagtgagtta ccaaacttag gacatagagt    59460
atcaatattt gagtttttca tcttttgtga taagtcacag tcatagaccc taatgttcta    59520
gtctttctta tctccaagta taactcacct gcttgaatac ttccagtccc agtatgctta    59580
attctagcga ataactacct tttcatgggt aattctaact gtaacaaaga tattctttt    59640 atttatttat ttattttta agacaggttt tcatgctgtt actcaggctg gagtgcagtg    59700
gcatgatctt gggtcactgg agcctctgcc tcctaggctc aagccatctt gccatctcag    59760
ctcccaagta gctgggacca caggtgcatg ccgggcgtgg tggtgtgtgc ctgtaatccc    59820
agctactcgg gaggctgagg caggggaatt gcttgaacca gggaggtgga ggttgcggtg    59880
agttgagatc gtgccactgc actccagcct gggcaacaga gtgagactcc gtctcaaaaa    59940
aaaaaaaata gagatgggt tctcaccatc ttggccaggc tggcctggaa ctcctgagct    60000
caagtgataa ttgttacaaa gatactcttt ctattcactt ttctataatt ttcttcttct    60060
gccttatagg agcacctgga atctaagtgt aattcctcct tgtacagccc ttctgacatt    60120
aagataaaat actatcaggt gctgcacact aagtgttctc ttcttcaagc taaccattcc    60180
tctcctctgt accattcctc ttgatgtagt ttcaagactt ctcaccctcc tgattagtct    60240
tcttctgaaa gaatcctgta tatcaatgtg tcttttaaaa ttaaacaccc agaattgaac    60300
acagtgtttc agatagagtc taaacagttc atggtatagg aagcccatgc ttttcttatt    60360
ctgactatat tattttatga ctgtatctct agattcttag cttttaaag attattctct    60420 tccctttttc agtgaatttc gctaagcttg gcatatccca ttttgtattt ataaagctga    60480 atttttaaa gcccaaatgt agaagttgtt aagatgcctc cctgttttct cccttattga    60540
aattatacgt agttgcataa ataggctttt atatccttct atacctttga ctgaaatgag    60600
tattagagtg tttagctaag agcttttttat ctgtctttc tcagaacttt taaaatctgc    60660
tttcctaaag tctacagtgt atgtctgact taatcaaatg tatggctttg tcaaatccaa    60720
ttcttcagat aaaactgcat tctccacctg atcctgtcca ttcaggtcca tccaaagctg    60780
agtggccaaa agtggtttca ctatataatg gtctgtggaa tgacttaacg gagtttgatt    60840
ctaatgtaca tgtgtttaaa gcagctctgc ttaaaccaca catagcatct ttttcacaaa    60900
gtcctcaaag tcagtgctgt catcacttag catacctcct tcctttagaa atcttcacaa    60960
tgaaaataca ctgaagaaag gtggttagca aagtgcctag tgaaaaccag atttctgtct    61020
cagatttgtt tttgttttag ttccacaaag agcacaattt ctcttattct ttcagtagta    61080
tttcaaatac aatgaattta tctagaattt tcctaaattg acaaattttg tttaagaaaa    61140
ctcttcaaca aattaccgag gagtaaatgg tttttatat gctgccaagt ttactttggc    61200
aatgtaaatt gaactagaac tagggttcat ttttaagtgt aggattataa ttcaagataa    61260
tctgtataaa ggaaattgtt gtagctgaaa atagatcaaa gtattgaaga ataacaata    61320 atgaggagtt ttaagtgtgg aaaagttagt actcaagaaa gggtaatgaa cttttaaatg    61380
tacactgttt taccaaaaat gttaatcaca ttacctctct atttttttaa gtggtatata    61440
gtcaaaaata aaatatttt gtttgatgac aggtatacca gagaggcagg ggttcgttct    61500
ctggatagaa aacttggggc catttgccga gctgtggccg tgaaggtggc agaaggacag    61560
cataaggaag ccaagttgga ccgttctgat gtgactgaga gagaaggttg gtgaccttgt    61620
tctggcattc tcaggcctgg tggctaggag tgagtgacag aagaaggttg ggtatggagg    61680
```

```
ggaaggtgtt gggtagtcct tggagcagtg gcacacatga ctccactgtt aaatgcatcc      61740
agtaagtaat accttaatgt ttcaacatat ttcatccaga ggattgtctt ttacaaatag      61800
cacagtttta actggaataa taatatgaat gctttgagga tataggaact gtattagggt      61860
tcactagagg gacaagacta ataggataga tgtgtatatg aagaagagtt taaggagtat      61920
taactcacac aatcacatgg tgaagtccca aataggcca tctgcaggcc gaggagcaag       61980
gaagccagtc caagttccaa aatctcaaaa gtagggaagc cgacagtaca gccttcagtc      62040
tgtggccgaa gccccaagag cccccagcaa accactggcg tacgttcaag agtccaaaag      62100
ttgaagaact tcgagtccaa tattcgaggg caagaagcat ccagcacggg agaaagctga      62160
aggccagaag attcagcaag tctgatcctt ccagcttctt ttctctgctt tattctagcc      62220
atgctggaag ctgattagat ggtgcccact cagattgagg gtgggtctgc ctctcctagt      62280
ccgctgactc aaatgttaat ctcctttgac tatatcctca cagacacact ggaacaatac      62340
tttgcatcct tcaatccaaa gttgaaactc actattaacc atcacagtaa ctttctccag      62400
atgtataatg atggtgtacg ttatgtatgg gttctggtgt tatcttattt ctttctgacc      62460
cagacagtta agtctttaaa taatttataa cataaaaagt ttttacaaca taagacaatc      62520
catgctgttc aggtactgca aggacagacc tttgtactct ggaatagctc catgtgtaat      62580
aatttttcac acattttctt ttatggataa acaactaaat gtaatttaaa ttattcttta      62640
aaaaattatt gtgaaggtgt tctattactg gaattaatca aatgtggatg ttcctttggt      62700
atctacttaa aatgttttaa ctggccaggc acagtggctc atgcctttga tcccagcact      62760
ttggaaggtt gaggcaggca gatgacttga ggtcaggagt ttgagaccag cctagccaac      62820
acggtgaaac cccgtctcta ctaaaaatac aaaaattagc caggcgtggt gttgggcgcc      62880
tgtagtcccc gctactctgg aggttgaggc aggagaatcg cttgagccca aaagtcagag      62940
gttgcagtga gcaaaggtca tgcccactgc actccatctg ggcaacggag cgagactcca      63000
tctcaaaaaa ataaataagt aaataaaata aaatgtttta atttcttgcc ccaaaactgt      63060 aagggtctc agttcatcat atcatgctgt tatgcagttt gccaaaactt gctttaacaa       63120
acatgagttg tagggaattg acaatttctt tcatagtaaa gagatttatt agattttct       63180 atcatttcca tagctgtttc cagaaaggag ttggatgact gtgattaaag aaccataatt      63240
tatggtggac ccagttgaac agacacagcc aaatgtcttt cttgttttc catcagtcgc       63300 tgaacacagt gcattttaca gcagtagcat cagagtcagc tttcacagaa tccttctgtg      63360
gccagtacag tgcttcaccc ctgcctcccc acgcctggaa cctcactggt tcattttctc      63420
cagagagcga agctccctatc ttctgttgga ttggagggag gcagtgcctt cattatgtgg    63480
agtaggagta gaggtagtga gttctaattg tattttatcc agactttaaa acttgtgctt      63540 tattttatt attttatt tatttactt tttgagatgg agtctcgctc tgtcgtccag         63600
gctggactgc ggtggcacaa tcttggctca ctgcaacctc cgtctccgag gttcaagtga     63660
ttctcctgcc tcagcctccc cagtagctgg tactgtagac ggatgccacc acgcccggct    63720 aattttttgta tttttagtag agacagggtt tcaccatgtt ggccaggctg gtcttcaact   63780
gctaacctca ggtgatctgc ccaccttagc ctgccaaagt gctgggatta caggtgtgag    63840
ccactgcgcc tggctttatt tttatttttt attttactc tgccttggga gaatctagaa      63900
aacttttgcc ttttgtccca ctcttcatcc atgctttcag ggctaccttg aattctttag    63960
cttttgtaga cttttaggac ccacatcaac ttgttgttct ctatctctag ccccacaaat    64020
gttgaggttt ctgctttctc tagcctgtta agtgttggtt acttttttgtc catgtacttt  64080
```

```
ttgtttccca aaattttgtc agcatctctt gtcagctgat gtcctctttg tcattatttt    64140
tgttcttgtg ggtttatata ttttttattt cttaattgtc attttaatac tattcagaca    64200
ggaagtaaaa acgcatgctc agactaccat ttatagaaat ttgaatttaa aaaaaatgtc    64260
ctaggtgagg gagtacctat caagggtgga aatcacttgt gtagatgaca gtgacagtgg    64320
agaactgaag tctataaaag ttaagaccta gatctagatg ctcctgaatt tcccttttt    64380 attcttaaca acacttcctt tgtgctgtga tctcaagcaa ctgagcctag gtcttttat    64440 tcttgtctga tataacagaa ggtagaggat gaaataaatg agtttattag gtaacacatt    64500
ttgaaaattg tgtttaagat ttagatgata tattttagaa cttctaataa attcagagga    64560
attcaatgtc aaaggaaact tttgtatagt tatacattgc ttaatgttta tacatacatc    64620
catgtagcat acttctaata atatctttaa ttatactagt tattttaaaa taacccacaa    64680
atactcaagg aattgttcag tttgtgaact gtgtgagaac tacagttttt catggtaaca    64740
tttatttgtg tggttttaa aagtgatcac aggacatctc ctaaaagata atatagttaa    64800
gcagatttgc ttagttaaga tattaccaag agcatctaga tgaataatta gaataaatac    64860
ttgtctcttg gagacgattt tgggtgtagt ctttactaga ggcataggta tggactccaa    64920
gttggctcta atattatgag atacccttga gtaaataaca gccattctct agaccttagt    64980
agaatgatta ttaggtgtcc tgaattgttt atgacctcaa ccaaaccaaa agaataattt    65040
ctacaaaaga gtctatgtta ggttttcata gcaccaagtt caaatggagc ttagtaatga    65100
aaattttctc attaagaaat gaattaatta aaattaagag cataaaataa gacagttgtt    65160
ttagaaactt caagtaatac agtgtgggag ttattttaa tgttaaaaat aaagctttcc    65220
taattcaagc acgagagaca gaaaaaaaat aataaggctg aacttggagt tactgccagg    65280
aagaaaagta attttaggcc acaagcttca aaacaggcag aaacctccag tgtatcaaac    65340
aaactttctg gaataggccc agaagcactg atctgtgaac agttgtcttt gtatttgtgg    65400
ggtcttaact ggcagttaaa gagactaaat aatagcaggg agtttaaaaa gcaggtgaga    65460
tttagaattg atcgatctgt gttagcggag gaacatttat ggtttcagtc acttacctat    65520
aaagtatgag aattgtttct ttaaaagaat gctgcctctg ttttttctgca tgttgttagt    65580 attttctgaa ttgccgtttt cctttctagg gtatttgttg ggttgagaga ttagttggat    65640
tacatgacta cagtttttatt ctgctttttg cctgccttt gccaagaaag acacaaatgt    65700
cccatgtatt taattttgca cacttcagtg tttctaaaca gggtaaatgt tcatttgttt    65760
aagtacccat gtatcatata ttcaattat atctagcaag attttttcctc aaaaattatc    65820 ctaagcaaag aaggatttat attataatca gtccttataa agtttctcat aatacactgc    65880
attctcaatt actttatttt tgaagaacat agtatttgag gaagttacat taaacagaaa    65940
gaacctgggt agatactagt ttctgattat tttcatagaa gtcacctgaa aaattggtta    66000
gaaaaaaaag acaaaattaa tacaaattta acagttattt gtgaaatatg taaatgttgt    66060
gttattccat tttgctgtgc tacaaaggaa tacttgaggc tgggtaattt ataaagaaaa    66120
gagatttgtt tgggtcagag ttctgcaggc tctataacag gcacagtgct agcttataag    66180
gtgagacctt aggtagctta taatcatgat ggaggacaat gggagagcag gcatgtcaca    66240
tggtgagaga gggagcaagg aaagagccag ggacctttta acaaccagct gtcatgtgaa    66300
ctcattacca tggggaaggc accaagccat ttatcaggga tctgccccctg tgacccaaac    66360 atctcccagt aggtccctcc tccaacattg ggaaacaaag ctatagtaac caaaacagca    66420
```

-continued

```
tggtactggt ataaaaatag acacatagat caatggaaca gaatgcagaa actagaaata    66480
aagccacaaa tctacagcca actgatcttt ggcaaagtag acaaaaacgt acactgggaa    66540
aggacaacct attcagtaaa tggtgctgag aaaattggat agccatctgc agaaagaatg    66600
aaactgaacc actctctctc ttattttata taaaaatcaa ctcgaggtta ggctaggtgg    66660
ctcacacctg taatctcagc actttgggag gctgaggtgg gtggatcact tgaggtcagg    66720
agtctgagac caacctggcc aaaatggtga acccccgtct ctactaaaaa tacaaaaatt    66780
agctgggcgt gctggtgcat gcctatagtc ccagctactc gggaggctga cacaggagaa    66840
tcacttgaac ccaggaggcg gatggtgcag tgagcccgag atcgcgccat tgcactccag    66900 tgtagggggta tcgcagcgag actctgtctc aaaaaaaaa aaaaaaaagt caactcaaga    66960
tagattaaag actttaaatg taaaatccaa aactaaaaca tactagaaga aaatctagaa    67020
aaaattcttc tagacgttgc cataaacaaa gagttcatga ctaagacctc agaagcaaaa    67080
gcaacaaaac caaaagtaga cagatgagac ttaattaaac taaaaagctt tttatacagc    67140
aaaagaaaca acagagtaaa cagacagctt gcagaataag caaaaatatt tgcaaaatac    67200
atatgcaaaa gaccaatacc cagaatctac aaggtaactc aagcaactca acaacaacaa    67260
aagaacccca ataacccca ttaaaaagta ggcaaaggag atgaaagaca ttttttcaaaa    67320 gaagacatac aagtggccag gaagcatttg aaaaaatgct caatatcact aatcatcaga    67380
gaaatgaaaa atctatgaga taccatctta taccagtcaa aatggctatt tttagaaagt    67440
caaaagtaac agatgttggt gaggatgtgg agaaaaggga gtgcttatat agtgctggga    67500
gaaatgtaaa ttagtaccac ctctatggaa aacatatgga gagttctcaa agaacaaaaa    67560
atagaaccgt catttgatcc agcaatccca ctactgggta tataccagaa ggaaaagaat    67620
tcattatgtc aaaagatac ctgcacacat atgttcgttt tatctgatat aaaaagtctg    67680
ttttatctgg tataaaaaga atggaatcat gccttttgca gcaatatgga tgaaactgaa    67740
ggctgtgaca ataactcaga aattcaaata ctgaatattc tcatttataa gtggaagcca    67800
aataatgtgg acatatgaac atagagtgtg gaataataga cacaagcatg agctatcatg    67860
cccagcctca aaaatttaa ttccctctt aattttgtca ttgacccaaa ggttgtccag    67920
gagcatgttg tttaatttac atgtgtttgt atattttga gagttttctct tcagattgat    67980 ttttagtttt attccattgt gtgaagatac ttgatatgat tttgattttt ttttaaattt    68040
attgagactt gttttgtggc ctgacgtttg gtctgtcttg gagaatgtcc catgtgctaa    68100
tgagaaaaat gtatctttt ggttgttgg gtagaatgtt ctgtaaatgt ctgttaggtc    68160
catttggttt taagttcagt gtttctttgt tgactttgtc tgtctcagtg ttgaagtccc    68220
acattttgta ttgctatctg tctctttct taggcctagt agtatttgtt ttattaatct    68280
ggtactccag ttttgggagt atatacttag gattgttata tcttcttgtt gaattgatcc    68340
ctatgtcatt atatactggc ctttaaaaaa aaaaaaacta ttgttgattt aaagtctgtt    68400
ttatctaata taagtatagt tactcttgct tgcttttggt ttccttttgc atggaacatt    68460
tttccacccc tttaccttca gtctgtgtgt ctttaacagt aaggcaaatt tcttgtaagc    68520
agcatgtagt tgttgttttt taatccattg caccaattta tatctttgaa gtggtgcatt    68580
caaggttaat actgatgcat gaggttttgt tccagtcata atgttaattg ctatctagtt    68640
gctttgtaga ttttttttt tcttttaagc aagagtcttg agtcttgctc tgtcacccag    68700
tctggagtgc aatggcgcga tcttggctca ctacaacctc cacctcccaa gttcaagcga    68760
ttcccttgct tcagcctccc aagtagctgg aattacaggt gcatgccacc atgcctggct    68820
```

```
aatttttgta ttttagtac agacgggatt ttgtcacgtt ggccaggctg gtctcgaact   68880
cctgacctca ggtgatcctc ccgccttggc ctcccaaagt gctgggatta caggcgtgaa   68940
ccaccgcaac cagccagctt tgtagattct ttgtttgttt tttgttcccg ctttgtggtc   69000
ttctggagtt ctgtcatgtt gccctttat ttctttcttt tccttatttg tataattgtt   69060
tcataaaact tgtgagtttc atgtgttttt atgatagagt atcaccttt gttcccatgt   69120
ttagaacttc tttaaatatt tctcatagga ccaatcaagt ggtgatgaat tccctcattt   69180
gcttatctgg gaaacacttt atttctcctt catttgtgaa gcttacacta gcaggataca   69240
aaattcgagt tgaccatttt tctttaagca ctttgaaaat agaatcccg tctcttctgg   69300
cttctgaagt ttctgctgag aagtccactg ttagtttgat gaagtttcct gtataagtga   69360
ctagacactt ttactgtatt tagggatttt cccttcacat tgaccttaga cagcctgatg   69420
actagatgcc atggtgagat cctctctcgca atgtatttgg ctggagtttg ttgagcgtct   69480
tgtatctgga tgtctagatc ctttgctaga ctagggaagg ttttctcaat tattttctca   69540
aataggtttt ctgaaatttt tgcttttct tctcctctag gaatacctat gattcatagg   69600
ttccaatgtc ttatgtaatc ccttacttt cagaggctct actcattttt taaaattctt   69660
ttttctttt tttttttgtc tgactggatt aattgaaaaa acctatctta aagttctgag   69720
gttctttctt ctgcttggtc tagtctgttg ttgaagcttt caaatgtatt ttataattcc   69780
ttcaatgaat tttttatttc caggagttct gtttggtttt ctttttaaaa tacctatctc   69840
tttggtaaat ttctcattca tttcctgaac tgattttctg acttctttgt attagttttc   69900
agatttctct tgtatcttgt tgagctactt ttttctttt aatttaattt tattttgaaa   69960
cagggtctcg ctctgttgcc ttgtctggag tgcagtgatg cagtcatagc tcattgtaag   70020
cccaagcagt cctctgcctc actgtcctaa gtagctacaa attcaggcac ataccaccac   70080
acctagctta tttttttatt ttttgtagag atggagggtt atactgtgtt gcccaggcta   70140
gtcttgaact cctggcctta agtgatcctc cttcctcttg ccttggcttc ctaaactatt   70200
gggattgcag gcatgagtca ctgtgccctg ccctgacag cttcttcttt ttttttttt   70260
ctgagacaga gttttaccct gtcacccagg ctagagtgca gtggcacgat ctcggctcac   70320
tgcagcctcc acctcctggg ttcaagtgat tcttgtgcct cagcctcctg agtagctggg   70380
attacaagcg tgcgttacca tgcctggcta atttttgtat tttttagta gagatgcggt   70440
ttcaccttgt tggccaggca ggtcttgaac tcctggcctc aagtgatcca tccaccttgg   70500
cttcctaaag tgctaggatt acaggtgtga gccactgtat ccagccctg atagcttctc   70560
taaatcagtg ttttgaattc tttatctggc attttgaaga tttgtttttt agttaggatc   70620
cattgctaga gaattactgt gtttctctgg gggtgtcata gcacctttt ttttttcatat   70680
ttccaatatt actgtgctga ttcatttgta tctgggataa cagttgcttc ttattatttt   70740
ttagtttact tttgttgggg caggactttc ttttcccttga ggatgtatct attatgtatg   70800
ttgagtaggg tcatttggct ttgcttcagg gtgcattcag tgacatagac actgtatgat   70860
agccttggtt ataaagtagt cttagtatgg tggctttctc aaatgccagt gacagtagta   70920
atgtacgggg tgggtgattg ggctcaaggc ctcctgccta gctggggtgg atgatggtgg   70980
cagcagaggt cgtgcaaaac ttgctttctt ccaaggcact atgcagttgt atcaatagat   71040
gttgtaatgg gtggtgcagg ttgacttccc agctaggagg tggtgcctgc agatgagcgt   71100
cagctgcaat agtggcagta gggtgattaa cctttgtaat tcaagaatta ttcaggtatc   71160
```

-continued

```
tcaggtaccg agctgggccg tgaaactctc agggtcctg gtcttgtgct gtgcttccag    71220
ggtagattgt ggggtgaagc caggcaggct ggaccagcca agctcatgtt tgagccccct    71280
gaatgggtac ttagggcctg ggataaaatt tccagaggct gcctcataca ttgtttcaag    71340
aattacttta tcttagataa tcttggtatc tggtagtgta agtcttccag ctttgttctt    71400
cttcagaatt gggttggcta ttgtaggtcc ttcaaatatc catgtaaatt ttaaagtcag    71460
tttgtcattt tctaccaaca agtaaataaa taaaaactcc tggggcattt ttattatgat    71520
tccgttgaat ctgtaaatct agttggggag aattgacaat ttgtattatc aagtcttcta    71580
attcatgacc agcttcattt atttaagtct tcttacataa gttttttttc ttcagctttt    71640
aagttccagg gtacatgtgc aggatgtaca agtttattat gtaggtaaac atgtgccatg    71700
gtggtttgct gcacagataa tccatcaccc aggtattaag cccagcatcc attagctatt    71760
cttcctgatg ctctccctcc cctcactccc acccacaaca ggcccagtg tgtattttc     71820
cctgccatgt gtccatgtgt tgtcattgtt cagctcccac ttataagtga gaacatgcag    71880
tgtttggttt tctgatcctg cattagtttg ttgaggataa tggcttctag tttcatccat    71940
gtccctgcag aggacatgct ctcgttcctt tttatggctg catagtattt catggtgtac    72000
atgtaccaca ttttctttat ccagtctgtc attgatgcgc atttggttg attccatgtc     72060
tttgctattg tgaatagtgc tgcaatgaat atatataaat cattctgttt ctttggctat    72120
atacccagta gtgggattgc tggatcaaat ggtatttctg cttctagatc tttgaggaat    72180
caccacactg tcttccacaa tggttgaact aattaaactc ccaccaacag tgtaaaagca    72240
ttccttattc ttcacaacct cgccagcatc tgttgtttct tgacttttta ataattgtca    72300
ttctgactgg cgtgagatgg tatctcattg tagtttttat ttgcatttct ctaatgatca    72360
gtgatgttga gctctttgtc ctatgtttgt tggcaacata atgtcttctt ttgagaagtg    72420
tctgttcatg tcccttgccc actttttaat ggggttgttt ttttttttcc ttgtaaattt    72480
gtgttcctgg tagactctag atactagact tttgtcgggt ggatagattg aaaaattctt    72540
ttcccattct gtaggttgtc tgttcactct gatgatactt tcttttgctg tgcagaagct    72600
cttagtttta attagatccc atttgtcaat ttttgcttt gttgctattg cttttgtcat      72660
tttcttcatg aaatctttgc ccgtgcctat gtcctgaatg gtattgccta gatttttttc    72720
taaggttttt atagttttgg gttttacatt taagtcttta attcatcttg agttattaaa    72780
taatttttgt ataaggtgta aggaagggt ccagtttctg ttttctgcat atggctagcc     72840
agttttccca gcaccattta ttaaatagag aatcctttct tcattggtta ctagtacaaa    72900
aacagacaca tagaccaata gaatagaatg gagaactcag aaataagacc acacatctac    72960
aaccatctga tcttcttaaa taagttttt aagagttttg atcattttct gtggcacact      73020
tttacataat ttttctttag atatcttcct aggtatttga tctttatgtg tatattattg    73080
taaataacgt tcttaaaatt ttgttttcta atttttttgtt ggtagtgtat gacaatgcaa    73140
tattggcctc ctgttcaaca aacttgccac attcacttat taatcataat tgtttgtgga    73200
atcttttgga ttttctgcat ctaccatcct gtaatcacaa atgcagatgt cagttttac      73260
ttcttccttt ccaacgttat accttttatt taatttcttc cctaatatgt tggctaggac    73320
ctcctgggaa atgctgaata gaaataatga taatagacaa agtaagcagg ataaaagcct    73380
atgaagaaat taccaactga cataggcttt gctttgtagc tttaggtcac ccctcatcac    73440
ctaatattat aaaatgacaa ttcggtagga ttctcagaaa ctgtccagtt tgaccctgat    73500
ttaattctca acattctcca gtaaacacta tgccttgcct gtttgacttt gttaacagac    73560
```

```
atgtcagaca atcatgtggt gaagtgtgat tttacttgtt tattcaacct gagatttgct    73620
gacagttcgt tctgtgttgc tgtaacagaa taccacagac tgggtaattt taaatgagca    73680
gaaatgtatt ggttcacagt tctggaggct gaagagtcca atgtcaaggt gccagcttct    73740
gacaggaacc ttcttgctgc atcttcacat ggcagaaggg caaagaaaga aaggggggcc    73800
tgaactcact cttttataag gatatcagtc tcacccataa gggcagaatc ttcaggaacc    73860
taagagcaac ttgttacttc atggcctact gacctcttaa aagtctcact acttaatatt    73920
gttacaatgg cagttaaatt tcaacatgaa ttttgaaggg gacaaacatt taaaccatag    73980
cactgacttt cttgaatttg tatactcttt tattggtttt ggaaagattt tggccattat    74040
cttttcaaat attcttccca ttttttttact cttccttctg ggattctgag aagagagccc    74100
ttcactgtct cttatcctcc tttctatttt ttttttgttt gttaattttt ctctctcatt    74160
cagtttagat atttttctgtt gccctgtatt ccagtttgtt attgctttct tctatttttt    74220
tgtggtctgc tattaagcct atgaagttct taattaccat attgtaattt ttttttttttt    74280 ttttttttac tttagaatg ccactggat atttttttttt tctttctttta agacagagtc    74340 tcactctgtc acccaggcta aagtgcagtg gcacgatttt ggcttactgc aacctttgcc    74400
tcctggattc aagcgattct gatgtctcag cctcctgagt agctgggatt acaggcgtgt    74460
accaccatac ccagctaatt ttgtattttt agtagagacg gggtttcacc gtgttggcca    74520
ggctggtctc gaactcctta ccttaggtga tctgccctcc tctgcctgcc aaagtgcaaa    74580
gtgctgggat tacaggcatg agccaccgcg cccagcccat tggattcttt tttttttttt    74640 tttttttga gacggagtct cgccctgttg ctcaggctgg catgcagtgg cgtgaccttg    74700
gctaactgca accttcacct cccaggttca agtgattctc ttgcttcagc ctcccgagta    74760
gctgggatta caggcgcccg ccaccacacc cgaccaattt ttgtattttt agtagagacg    74820
gggtttcacc atgttggcca ggctggtctt gaactcctga cctcaagtga tccacccacc    74880
ttggcctccc aaagtgctgg gattacaggc atgggccacc acaccggcc aggattcttt    74940 gtatatatat ggactccaat agattctcca ttgatatttt ctatcttttt atctatttaa    75000
tccctccttt tccctatttt cttggacatg ctagtcatta ttttgaaaat ctctacctta    75060
acactccatt atctgattca gttatgtttg gtgtttgttt tgtttgtatt accttttttt    75120
cccccttgat ttctagtttt ttgttctgtt ttttagcatt tcttgtattt ttttactgga    75180
tgccagacat tggatgaaaa atacaagggc tgtaactatt atcctctgaa aagtgttaca    75240
ttttcttctg attggtaact acagtaccaa cctgtcactc tgtcctgtca aggctgagtt    75300
ttaggctttg tcaggactcg tcaatttcag tttgggtctt attactggga tacagtcttt    75360 attttttatta tgtggtactc ccaggatgta gttcttattc cttcgtgggt gacccttact    75420
tctagagcat gatctttctg agttctcaca tgaaaatcca atcaggtctt tagcatcctg    75480
gcttctcctt tctcctgggt ttctaaaaga ctcaccctga atacattcaa cttaggagtt    75540
agtcaacagc ttgaggggga tttaagtgca gattttgag atccttcttt ttggtttctt    75600
cctttattgg gattttgcca atgaagtccc agttgctttg acaacctcta attttcagaa    75660
ttacttttga ctaaatgttt tatgattcta aacataccat ctactctgtc aattctgaat    75720
tatggtgata ctcaattcta cctcaaatcc caaagaaaag agggggaaaa aacaacaaaa    75780
ctaagaagaa acattgcttt tgttttgtag ctttaggctt ctacctatat aattgactat    75840
tataaaatct catttgagta ggatctttag tagccaccta ctttgactgt gatttgattt    75900
```

```
ataaatccct tcacaacatt cctcagtaaa caccatgctt tgcctgtttg acttggttaa    75960
cagacatgtc tttataaact tggctatcca ttttccagtc tgtaggaaaa gagaagctgt    76020
aagttggaga aaaggctagt ggttgggtgg tgagtcataa gcaataagat ttgatgtcag    76080
tgatgacagg cctgtcctct tatgatagat tccttgagcc ccctgctgac cacaaagctt    76140
tggctggcta gaccacaagt ctgtctccct caatgacaat ttttgtagct caatatggat    76200
cctatttttgt gtgagttgca tttggagatt tattgtttat ctgctgtatt tgccttaggt    76260
gggacagtga aatcaaccta atgtagtgga aggaagtagg tattacatcc ttaattcctt    76320
gatatacatc cttttattat gtggtactcc cgggatgtgg ttttttcagat ttggagaaga    76380
atagttaaaa aaaaaaaatg cagaaaggat caaaagcact tgattctctc gcagggacag    76440
cttcctgttt tggttgagga aggagctgca cttaaaataa ctagcataaa gcatgcttag    76500
ggcttgcttt ccagacaacc tcaatttaaa atgcatcaaa agccaggtgt ggtggctaac    76560
atctgtaatc ccagcacttt gggaggctga agagggcaga tcacttgagg tcaggagttt    76620
gagaccagcc tggccaacat ggtgaaaccc catctcttct aaaaatacaa aaattagctg    76680
ggcgtggtgg cacacacctg tagtcccagc tacttgggag gctgagatgg gaggatcatt    76740
tgaacctggg aggcggggat tgcagtgagc cgagatcaca ccacagcact ctagcctggg    76800
caacagagca agactctgcc tcaaaaaaag aaagaaaata aaattcatca aaataaaata    76860
tttgaatttt acagcactag ttcttttcat tcattgactt tcattctccc actttaccac    76920
acctttaact attggcaaga atgtggtgag tgggagaaag cgtatcctgc cacgtaagca    76980
agtataccta gagccaaggg gtcagagtgt cacagaggag agccacatgc tgatgggctt    77040
gtgttcgttc ccactcactg actatgcaag cgcctcttct cttagccttt ctcaggatgc    77100
agttctccag ggaggaatca gccttctgtt gggctgcttt cagagctctt tgttgtggct    77160
tcctgccatt gactttgcaa gccctaagca tgctttatgc tagttatttt aagtgcagct    77220
ccttcctcaa ccaaaacagg aagctggctc tgcaagagaa tcaagtgctt ttgatccttt    77280
cagcttttttt ttttttgac tattcttctc caaatctgaa acatatccat tctcgtctac    77340
ggccatgagt gcatttatgt aacagaaaaa tgctaaattt aatgtttaga aagtaacctc    77400
tgtggccaga catggtgact aatgcctgta atcctggcac tttgggaggc cgaggcaggc    77460
agatcacttg aggccaggag ttcgagacca gcctggccaa cacagtgaaa ccctgtctct    77520
actaaaaata gaaaaaatta gttgggcatg gtggtgggtg cctgtaatct cagctacttg    77580
ggagggtgag gcaggagaat cacttgagcc caagaggtgg aggtcgcagt gagccaaaaa    77640
tcaagccact gcactctagc ctggatgaca gagcaagact ctctcaaaaa aaataaaaag    77700
taacctctgt gctttgtgta acttttttgct aaattcctgt cttttgtcttc ttggaacagt    77760
cttctacttg ttacaggatc ttcctatctt ttggatttta tattagtttt aatataaaat    77820
taatatagtt ttatattata tagcccactg acatggctgt tagctgacct cagttccttg    77880
ctgacttggc cagagccttc agtttcttat ctctggtaag aggtaatgtg tctctcccta    77940
gggcaaggct gtgacagctg cttctccca gagggaatga tgtgtgagag aagcagggag    78000
agtaagaatc aagacaaaac tgcagtcttt tatacccatc actattgcca tattctcttg    78060
gtcacacagc ccaaccctgg tatgatatgg gaggcactaa ctccatgggg atgggatatc    78120
tgggcaccat cttgaaggct agctgacaca gattattttt tgtgcgtgtg cctgtaagaa    78180
tttttttggcc aggcgtggtg gctcacgcct ttaatcccag cactttggga gggcgaggtg    78240
ggtgggtcac gaggtcagga gttcaagacc agcctggcca agatggtgaa accccatctc    78300
```

```
tactgaaata caaaaattag ccaggcatgg tggcaggggc ctgtaatctc aactactcgg   78360
gaggctgagg caggagaatc gcttgaactt gggggggcgga ggttgcagtg agccgagatc   78420
acgccactgc actctagcct gggcagcaga gtaagactct gtctcaaaaa aaaaaaaaaa   78480
aaaaagaatt tttctaagcc cgcattgaag tttatactgt agaatatcca tcaaacttga   78540
gctgatttct tatcaaagac ccaggttgca cagatagggg ttagaagttt ggattcggtt   78600
ttgcattttc agtatttaaa gtcttgtttc atcttgttca ttcttacctt tcctttgatt   78660
gtattagtag ctcaggacaa ataagaattt ataattttcc aaggaactaa ggttgctgtt   78720
gaggaatatg ggtttcagag acaagagttt aggcactggc tcattggtac taagcttcag   78780
gggtttgtag tgttgttaga gctaattgga ttttacaaat aagccaagat tattaaaaaa   78840
aaaaaataga tctagagagt aacactttct gtgctaaatc cattgcattt gatgggatac   78900
taggcagtat gctatgtcca aacttctaaa atcaggcggt ggtctaacgt tgaggtgaaa   78960
atatcatgtt gggtatatac tgccaatatc atgaagatat actaaatatt attttctgag   79020
tctgacattt acactgattt actgatttat ccctcatcaa tattggcctg gtttaagaga   79080
gacttgtttg cctgtacaga ccgggaggaa gcttcaatga aggcaaaaat ctaactataa   79140
taggagccaa acatttgtta tttgaattcc aattggggac aggaaaataa aatattatca   79200
aataattata aagtcatcat tctgttaaat gaatcatata ggaaaatgca ttgaccttaa   79260
aacagagtct ggctctgtta cccggactgg agtggagtgg cctggtttca acttgctgca   79320
acctccacct cacgggctta agctgtcctc ccacctcagt ccctagagta gctgggacca   79380
caggttttgc catgttgctc aggctgttct caaactcctg agctcaagaa atccacctgt   79440
ctcagcctcc tgaagtgctg ggattacagg cgtgagccac cgcgcccggc ctgcagtgac   79500 cttggttgt cattgttata cattatcaaa acaaactcaa gttacaagag tattaaagca   79560
atacttaatg gttttaaaaa aaatattaca aaaggtctct gcattttaac tactcatcta   79620
aataattgtc taggaatatt ttctgaatct ctaatacagg aaatgagatt tattaataca   79680
taaaacccac tgaaaacagg ggtgcaaact ttcttgtctg gtactaaaga tggattccta   79740
tgttttgggc ccttgtttat accagtttat tcaatcagtg agtcagctag catttactga   79800
atagtcatat gcgttgctta atgatgggga taatgttctg agaagtgcat ccctgggaaa   79860
ttttgtcatt gtggaaacat catagagtgt acttacacaa acctagatgg tatagctttc   79920
tacacaccta ggctatatgg tatagcctgt taatcctagg ctataaactt ctacagcatg   79980
tgactatact gaatactgta ggcaattata acagagtggt atttgtatat ctaaacaaca   80040
gatgaacaat aaagaaaaaa taacaacaa ataaaagctg gtacttctgt ataaaggcac   80100
ttaccatgaa tggagttgca ggactggaag tagctctgcg tgagtcagca agtgagtggg   80160
agtgaatgtg aaagcctagg acattactgt gtatatacta ctatagactt attaacactg   80220
tacacttagc ctgtattttt taattttttt cttttttttt ttttacttct ttttcttttt   80280
ttgagacagg ctgtgttgct caggctggtc ttgaactctt gggctcaagt gatccttcta   80340
cctcatcctc ctaagtagct gggattacag gtgtgtgcca ccacacccag ctttttaaaa   80400
cttttcaaat cttttataat aacactcagc ttaaaacaca aatacactgt atagctatac   80460
aaaaaatatt tttaccccat ttatgcctag tgctccatta ttggaacact aagcttgtgg   80520
gagttattta tatcctactg ctcaaggtca ttgccaaggt ctgattttc acaaaaaaaa   80580 attcacaact tctggcataa atgggttaat atccttactg tatataagct tttttaaaaa   80640
```

```
ttgtttttact tttttaaactt ctttgttaaa agcaaagaca cagacacaca ttagcccagt    80700
cctgaactag gtcaggatct tcagtttcac tgtcttccac ttccacatct tggcccactg    80760
gaaggtcttc agaggcagta acatgcatgg ataacagtgc cttctacctt ctgaaggacc    80820
tgcctgaggc tgttttacag ttaacttctt ttttacagaa gggagtacac tctaaaataa    80880
tgatgaaaag catagtatag tccaggcacg atagtgtgtg cctgtagtcc cagctactca    80940
ggaggctgag gcaggaagat tgcttgaacc catgagttca agaccagtct gggcaacata    81000
gcgagactcc acctctaaaa atatatataa gaataaaaaa ttttttttaa atgaagcata    81060
gtaagtacat aaaccaataa catagtcact cactatgact atgaagtatt atgtactgta    81120
tgtaattgta cgtgctgtgc atttatacag ctggcagcac aataggtttg tgtacaccaa    81180
gcatcaccac aaagatttgg gtaatgcatt ccattgccct aacgggcta caacatcact    81240 aggcaatagg aatctttcag gtccgttgtt gtcttctggg acttctgtca tatatgtggt    81300
ctgcctttga ccaaaatgtt gttatgcagt gcgtgactat acccactata tgttcaagtt    81360
ctaaattgga ttctgggaag ctgattaaag agaaaataat gtgtagtcta ttggaagagg    81420
tagataaaca atttttaagt gaaataattg ctaattttta acctctgtgg aggcactgaa    81480
ctgatcattg aaagctctat tttacttact aaagatatgg tagcttataa aaattactta    81540
tagtaaatgg acatgaaaag gtcatttgct tacatctcta aattcatttt gatggaaaaa    81600
tagtggaaaa atgttttgcag ataccctttt gtttgtttgt ttttttcata atagataatt    81660
gccactaaaa ttgaagaatg gccaggtccg ttggctcatg cctgtaatcc cagcactttg    81720
ggaggccaag gcgggtggat tacttaagct caggagttca agattaacct ggccaacatg    81780
gcaaaacccc gtctctacta aaaatacaaa aaattagcca ggtgtggtgg tgcacacgcc    81840
tgttgtccca gctacttggg tgactgaggc atgagaatca catgagcctg ggaggcggag    81900
gttgcagtga gctgagattg tgccactgca ctccagcctg ggcaacaggt gagactctgt    81960
ctccaaaaaa aaaaaaaaac aactaaaatt gaaaaatacc tcacagtcat aacttccatc    82020
tgtatctcag tggttattat gtagaaatgt tcagtaggta aacttgaaag aaaatgtatt    82080
tggtaatcgt aaggttgtgt tgccacccc aaaataatga agaaaatacc aacagaaaga    82140
aaaaggattt attgctggcc tgaaggttct tctgggcatt tgatctacag atttctccat    82200
tatagctagt tcctttaaaa aaataaaaaa cattgaaaat atgcagaccc aaatgccttg    82260
gcagccctgg tcagtaactt gaatctcagt tgcacttagc acaattcctc tggctgggaa    82320
gatgttgttt tggaaaagat taacctgaaa tgacagcacg aattatacag ttggaaatac    82380
tcaggttttt ctgatttttt tcaaaagata ctttgctttt cctttctgc cttaccatgg    82440 gaaggtcctt agatgcatca tatccttgtc agtttagcct tgtgacacat atttctgcaa    82500
ttttgtgcaa taagaaagcc actcgaaatc tcagcatttc atgtcacttt taaagtaggc    82560
tcagttaaaa caaaccact tgattgtttg tataaccaca accatatgtg tctttctctc    82620
catgcttaaa caaggtctga aatcgtgtgt caaacagttg agatgtaaac atctcctcct    82680
cacacataac ccctctgcca tgttgttatt tatatcccca gtaacacact tcttgtccct    82740
gacacaagta cagccgtctc cacattccat tttgctccta ctccatcagc ttgcaagaaa    82800
aattttaatc attcaaaaat aattgttaca taattacttt tcactgatta aaaatatttg    82860
tttacttgac aaaattagca ttaaaaacag taattctttg gcagattaat aagtattttg    82920
atgatttgtc atttttcaca gatgttgata aaatttaaga attacatagc cgaaatttgg    82980
tctaattcaa caaaccacaa ttgactcttt tggtaaggcc ctatgacgaa tggtatggga    83040
```

```
gagtggagtt tatccaatct gactttcatt ttattgatac ggaaactggg gccccatttg    83100
ttcttttttt taattgctac ataatataca tatttatggg gtatagtgtg atgtttcagt    83160
acatgtatac attgtgtaaa aatcaaatca ggctgtttag catatctgtc acctcatata    83220
tttatcattt ctttgtggta agtatattta aaattctcta ttctagctat tttgaaatat    83280
acaatactgt taaccatagt cactgtgcaa tagaacagtg gtccccaacc ttttttggcac   83340 cagggaccaa tttcatggga gacagttttt ccacggacct gtggggtggt ggtttcagga    83400
taaaactctt ccacctcgga tcatcagcat tagattctca taaggagcac ccaccctaca    83460
tccctcacat gcacagttca taattcacaa tagagtttga gctcctatga gaatctaatg    83520
ccgctgctga tctgaccgga ggcggtgctc aggccgtaat gcttgcccac ccgctgctca    83580
cctcctcctg acaggccatg gactggtact gaccagtcca cagcctaggg tttggggacc    83640
cctgcagtag aacaccagaa cttattcctc ctatttatct gcaattttgt acccattgac    83700
caatctctcc ccatccccac tatctctccc cttgccagtc tcttgtaacc actgttctac    83760
tctctgtttc tgtaagatca acttctttag attccacata taagtgagat catgcagtat    83820
ttgtcttttg gtgcctggct aatttcactt aatataatgt cctccaggtt caaccatgtt    83880
gccacatgtg acaggatttt attcttttttg tggctgaata atattccatt gtttatatat    83940
gtcacatttt ctttatccat tcatccgttg atggatgctt acgttgattc catatattag    84000
ctattgtgaa tagtgctgca acaaacatgg aagtgcagat accctttga catattcatt    84060 tcctttggat aaatgcccat ttgtgggatt gctggatcat atgatagttc aacttttaga    84120
ttttgagaaa cctccatact gttttccata atggctgtac taatttacat tccagccacc    84180
agtgtgtaag agttctcctt tctccacatc cacaccaact acaggtggct tttctagact    84240
ggactttagg ttgggacaaa aagtgtcttt gagagtcagt agtcctaata ctgtactgtg    84300
aatgctgtgg acttaggcag tttgtttaag cttgtttaaa ctgggtctct ctttccttag    84360
atataaatgg agggttagac tggatcttta agcttctgcc cagcatttaa tgttctgttt    84420
attgtggttc tagcctgtgc ttcttgaatt cctgattctt cctgaattct gctaagcatc    84480
agaatgcagt ctatacattc tcaacagctt cccaaagaca tgatattagt ataacagaaa    84540
cagtagtagt cctttcttgg aaaattatcc ccatttctgg accctatttt attgctggct    84600
gcaattaaca ggttcttgta tgtcccatcc ttccctcctc ctccctaacc cacaggcatt    84660
aaaaacctgc tgtttgtgaa aatgaacact tctttgataa tctggaagaa ggggttcctg    84720
ttaccagaaa atttagctct tgaactcctg ggactgggct tgaaagcata gtactattat    84780
gcttcagatt aagcagggta tagagaataa ggagtgatca caaaaattct gtcttgaata    84840
aagatgatga tagatatccc agggccctct gtggttagat agtctccatt tctaccacat    84900
tctgaggaat tgtgggtgtt gcgctttta tgtttctggc ctccctgcta cttgccattg    84960
gttggatcac tggccaagag ctaccgagaa ctaccatttt gcttcaagat ttttcaaac    85020 agcaaggaac ttttttattt tttaacagag agctactgaa gtttcctgag ttattacaac    85080 cccttatcc ttcctcctta cttcccctttt caataattcc cttcctccc tcttcccaca    85140 gcagttcttt ggctattggg cctgttttca ttgaaatcat cttcctgtgg cagagggaaa    85200
atgaatagag aagaacagtt gactgtgtcc aagtgatagc tgcttgctta ggaaaagcct    85260
ggtccttccc cagaggagtc tgtccctata ggacttccct ccataatagc tgtgcttcca    85320
tcagctctag aggatggctt agccccttc gggggtacac cgcatttcac tctcacttgg    85380
```

```
ctcacagcca tcaccacagt ccatgctgtg agtgcattgc tggttctgcc cccgtgctgt    85440
gtgcatctct gctgctttaa tgctgggaaa ctccgtggtt atgccccaac tatcttggca    85500
atgttctgaa tcagacatag ataataccta ttaaaggtat taataggcca ataataccta    85560
gtaaagaaga gctgggatat acctctgcat agattaaatc aactagaaaa cactagcccc    85620
ctcccatttt cagaccgatt ttatttcttt taagtgggaa aatagtcgaa gtgggatgaa    85680
gcagagctag cttattctac tcattttata tttctgtggc cttttcaacc tctgtttaac    85740
agcactttat tacttagttt ttttgttttg ttttgttttt ttgggatgga atctcacgtt    85800
gtcgcccagg ttggagtgca gtggcatgat ctcggctcac tgcaacctcc acttcccggg    85860
ttcaagcgat tctcatgtgt tagcctctca agtagctggg attacaggca cctgccacca    85920
ggtccggcta atttttgtgt tttcattaga gatggggttt caccatgttg gccaggctgg    85980
tctcgaactc ctcacctcag gtgatctgcc cgcctcagcc tcccaaagtg ctgggattat    86040
aggtgtgaac caccacgccc agcctcactt tattacttt aagaatatgc ttcaaaatag    86100
tttgtaaaga agattttaat agggagcact tatatgaaat ataatagtga tatatagtat    86160
agcatagagc agagtcttca gtctttgtat ctttttcttt ttttcttatg catatttaat    86220
gtatgtgatt cccaaccgtt gtgtgattgt ggtcagagcc ctgtctgtgg gatgctgggt    86280
agaatgagat tgtagagagc actttgtttt cttgtaattg aagggtttgg ggtgagaata    86340
tgtgagtcat agaaatctgt atagtaaata ttactctaaa aagggagcca tcaggatctg    86400
ggagaatttg ctaaaggaaa actaagaatg aaaaaaggc caggtacagt ggctcactcc    86460
tgtaatccca cactttgag aggccaaggc aggaggacct gaggccagga gttcaagacc    86520
aacctggcca acatagtgaa accccgtctc tactaaaaat acaaaaattg ggccgggcgc    86580
ggtggttcac acctgtaatc ccagcacttt gagaggctgt ggcgggtgaa tcacgatatc    86640
aggagttcga gactagcctg accaacatgg tgaaacccg tctctactaa aaatacaaaa    86700
attgggccgg gcgcagtggc tcacacctgt aatcccagca ctttgagagg ccgtggcggg    86760
tggatcacga tatcaggagt tcgagactag cctgaccaac atggtgaaac cccgtctcta    86820
ctaaaaatac aaaaattagc caggcatggt gacgtgtgcc tgtaatctca gcttctcagg    86880
aggctgaggc aggagaatca cttgaaccca ggaggtggaa gttgcagtga ccgagatca    86940 caccattgcc ctctagcctg ggtgacacgg ggactccgtc tcaaaaaaa aaaaaaaaa    87000 aattggccag gtgtggtggt acacacctgt aatcccagct acttgggagg ctgaggcatg    87060
agaatcgcat gaacacagac ggcagaggtt gcagtgagct gagatcacac cactacgctc    87120
cagcctctgt ctcaaaaaaa aaggggggg agggcggtg ggggagcgg gagccagtat    87180 ataattcagt atctctcatc tatacatatt aaggcttttg accattacca aattctccca    87240
gcagctctct gagagtactg taattctggt tttgctgatt agaaaccag atacaaagag    87300 gtaaagtcac cttgttctag gccactaggt ggtaatctga gtcaggactg gagacaatga    87360 tttatttta atatctcatg taatgttaat ctcataactc agggcataac tcttttacca    87420
ttttggacta tatcatttca ttcatatgat aaagacactg tagcttcccc ctcacctgca    87480
gcttcacttt ctgcagtttt agttacctgt ggtcaaccat cgtccaaaaa tattaactgg    87540
aaaattctag aaataatcca ctcgtaagtt ttaaattgtg cactattctg ggcagtgtga    87600
tgaaatgtcg agccatcctg ctctgtgtga ccctggacag gaagcctctc tttgtccagc    87660
atatccatgc tgtatgactc ccgccccttt agccactcag cagccatctc acttaccaga    87720
tcaactgtct tggtttcagg gtgtttgtgt tcaagtaacc cttcctttac ttaataatgg    87780
```

-continued

```
acccaaagcc aagagcagtg atgctggcat tctgggttta ttttattagt attgttgtaa   87840
atctcttact ttgcttaatt tataaattaa acatgatcat aagtacatat ctatagggaa   87900
aaaatggtat atatagggtt ctgaaccatc ctgcatttca ggtatccacc gtgggtctgg   87960
aaatgtatcg cctgtggaga aggggtgact actgtgtatg taaaaatcac cctgtgtgaa   88020
atgttatatc ctccccttc ctcagtttaa cgttgttttg aaagaattt ctcacattac    88080
ttgaaaacac ttaggaaacc attttagtg actgtagtat tttaccagtt agatatgcca    88140
tggtttactt aaccatgttc ctaatgttgg gtacttatat tggatctaag ttttgctgtt   88200
atttgtagtg ctgcgatggg tgactgtgca caaaccttg cctgtactt tgtgtatttc     88260
cctaaggata gattgctgca aaaagaacc actgagtgtg agactgtaaa tatttggaag    88320
gctttcagtc tatttccata ttgctttcct gaaagattga accagtttat acttctgtaa   88380
gcaacagtgt ttgagaagat ctctttactt tttttaacat tgacctttgt catttcttaa   88440
actttactag ttattttggt aaccggcttg ttttatat ttgaatttct ttgcttctca     88500
gtgaaataat agtttctttt ataggagtat taaccatttg ttaagaacca ctattttagt   88560
ccaaaagaaa ggtatataag aagaaaactg cacaattcca gtgggaagga cttggggtca   88620
gggtccctga tatgttggaa ggttgaactt tttgttgttg gttttccc ttgccttaaa     88680
aagtccatat tgcttgaatg ttgcaatctt gggcaaggcc agcaattaat ccaagggatg   88740
atgccactgt cttctcctgg tgctggtcct ttctgacaga gaacatggta ctagggctga   88800
gtgcttgaat gcttgcacat aggacccaga aggtgcacat ataaccgggg gttcgttcct   88860
tgagtgatat ctttgtgaga tgacattttg cttgttggtt gtttgttta taatgaggaa    88920
tcaaagtggg tattctagga agatccagtg tttccctact cacactttgc attacacaca   88980
gtccaggggg tgactcagaa tccagtgctg tcctgcctct cccagttggc tgacaccatt   89040
ttcttgactg gagccttagt tttctaggca tatattctaa tgatggaaca ttttgaaatg   89100
cagattattt ttgaggttac tgaatttttt aataacacag ctgctgtccc taaattgcca   89160
tcttttataa ggtctagttg cattagaaat agctctccca accccactcc cccagtgctc   89220
agaacgctga accccgtact acacttggaa aaggattgga tgtcctaaag cattggttat   89280
gtaattgtgg gttggctttc acccactgag ctttacttcc tcctgtgatc gtgaaataca   89340
agctggcaac agtaattaga tctcagaaaa gcttgtcaca aagcaccaca gactagagaa   89400
acttgtaagc tcttttgca ctggctgaag ttttgagta ccactacctt ccatctatag     89460
tgtagtaacc ttagacaggt agtgcttttc ttctgtgcat taatttaat taagcaatga    89520
cacctacttt cttttccact ctgagatctg catgtagcta aacttatcag gtgagtgctt   89580
tcccatcttt gatcattgat actgcttgga atataccgga aaaagagcag caagcagaaa   89640
atctcccatt tccacaagct gctgactaac tcagaattgc tagattttgt gaagcaaatg   89700
aatgctataa aagaagtcag aaagatcagg gaagctgtcc ctaggacttg gtcaggccaa   89760
accttgaaat atcaagtgat gttacagagg tacaattatg agaatatata taactcaaga   89820
cttacatatg tgataaatag tgcattgctc tttgccgtct ccaaaggatt ttcttttttt   89880
tttttttttg agacggagtc tcactgtgtc gcccaggctg gagtgcagtg gcgcgatctc   89940
cgctcactgc aagctctgcc tccgggttc acgccattct cctgcctcag cctcccgagt   90000
agctgggact acaggcaccc accaccacgc ccagctaatt ttttgtattt ttagtagaga   90060
cggggtttca ctgtgttagc caggatggtc tcgatctcct gacctcgtga tccacgcgcc   90120
```

-continued

```
tcggcctccc aaagtgctgg gattacaggc gtgagccacc acgcctggcc aggattttat    90180
ttttaattct cacagcaatt ctgcagagag aggtagtgag aggtttaatg ctttgttcaa    90240
cataatttgc tgttaaatag ccattcattg gcagaaaatc tgaactgttg tgttttcctt    90300
cctgtgtcat tcatggtttc agtcctgaag aggagcccac tagagcccaa caggagagga    90360
gagtgggaga atccctcacc cagaagttca cagtggtatc atttagtgac actcaggatg    90420
tctccagtta ttgttagaat ttaaagttag gttcatccct gtgaggtcca agaaaatata    90480
aaaataaaat aagggtctac tagtattaaa catactctgt aatcactttt gaaggaaag    90540 gagttagtgg aaaaaatgga agaaccatag cgaaactaaa ataaatatat gtagatatat    90600
tgctggacgt ggtggctcac acctgtaatc ccaacactat gggaagctga ggcagccaga    90660
tcacttgagg tcaggagttc aagaccagcc tggtcaacat ggtgaaaccc cgtctctact    90720
aaaaatacaa acattaggcc aggctcagtg gctcacacct gtaatcccag cagtttggga    90780
ggctgaggtg ggcggatcac ctgaggtcag gagttcgaga ccagcctggc caacatgctg    90840
aaaccccatc tctactaaaa atgcaaaatt tagctgggca tggtggcaca tgcctgtagt    90900
cccagctaca gggaggttga gccaggagaa tcgcttgaac ccaggaggtg gaggttgcag    90960
tgagccatga ttgtggcact acacgcccgc ctgggtgaca cagcgagact ccatctcaaa    91020
aaaaaaaaaa ttacatatat atacacatac acacacacac aaacattagc cgggcatggt    91080
gttgtgcacc agtaatccca gctactctgg aggctgaggc aggagaatcg cttgaaccca    91140
ggaggcagag gttgcagtga gccgagattg caccactgca ctgcagcttg ggtgacagag    91200
cgagactctg tctcaaaaaa tatagataga tagacaatgt tagataactg cataattatt    91260
atatgtgtgt attaatatac gaagcaatca cttcagaag gaatagtgtg ttaaaaaag    91320 gtaatgaaag atttaaaac aaaacacttc atgagacaag aagttagaac aattacggca    91380
aactaaaaga aaaagctagg aatgagatcg aatacagcca agtatttcct gcagttttaa    91440
aacctctact ccccattttg ggtttctggc cacagattac gtaatatttt tcgttacttg    91500
aactggaatt acaagattg atacagaaga tggtccgata agtcaattgg gtcctgctcc    91560
ttgtatgtct aggtccaaac caaaatgagt caatatttgg acaagatatc agccatccag    91620
ggcttatagg caggtaaagg agatggccca ttattacagg gatttcaaac caggctttgt    91680
attctcttac cctggcactg ccaattatat ttatttattg gaaaatgata accttagagt    91740
taagctatat gcttataaaa gaggcactgc ttatatgggt tctatcatgt ccaggtttac    91800
attgcccgtt agaaaacagg acacctggct gggtgcagca actcatgcct gtaatcccag    91860
cactttggga ggccaagcga gtgaggatcg cttgagccca ggaggtcaag gcagcagtga    91920
gctgtgttca caccagtgca ctagacacca tctcaaaaaa aaaaaaagt gttgggggga    91980 gagagagaaa gagagagaga gagagaagag gaggggaggg gagggatac ctgatcagac    92040 tcctctgaag agggaattga aaagtttgtc acaagccctg agttatgctg atataacaga    92100
gaattgttag atcagagaat ccaaagtaac ctactgcgct tagcccttca gtctttgtcc    92160
tagctatagg ccataaagtt gaatagtgcc gggaattgtt cttgacttaa aatataatg    92220 gtcaaaaagg acaggcaaag ttgtttccct tctggaactt acactttaat ggggagata    92280 gacaataagc aagtaaaagt aattgaacaa ggcaattgca aataccaccc tcggtgagct    92340
cttgaaacac aaattatttc acctgcattc cacagataca caggtgaatg tttgccttga    92400
taaatgcata aaagtgactg aacttttgag gtccactggg ctttttgtttg atatttactg    92460 ctagtgaatt ttccagcctg caaatctctt agaacttcta aatacatttt tttttctttt    92520
```

-continued

```
aggttgcaga gaacacatct tagaagatga aaaacctgaa tctatcagtg acactactga    92580
cttggctcta ccacctgaaa tgccgatttt gattgatttc catgctctga aagacatcct    92640
tgggcccccg atgtatgaaa tggaggtgat tcattctttt tatttctttt tgctccagtc    92700
aatgaaagga acactttatt gaggccccag ggccgtaggg cctggcaggg aggctgccct    92760
ttggggaagg aatagcctta ttcgaccttc tttttgggac gcaggttgtt ggtgtggccg    92820
cacttcttgc agcagttgac tgcatggggg cgcaggcgag cacagctctt gtggcacatc    92880
atcttcttgc agttgtattt ctgggcaagg tggcagaggg aaggctccgt aatgccacct    92940
cacaggcaca gcatcaggcg cagggtggac tctttctgga tgttgtagtc taagagtgtg    93000
tggccatcct tcagctgttt gccctcaaat atcagacact gctggtcagg taagatgccc    93060
tacctgtctt gaattttggc tttgacattc tcagtggcat cactgggctc gacctcaagg    93120
gtgatggtct ggcctgtgag ggtcttcaca aagatccaca tctcagcgtc tgcagcttgg    93180
ccagtctcac tccattctca ttttttttgtt ggtactcact ggtgtactca ggtggttgct    93240
taacagagaa gtaaaattgg atgtttccag aggctgaatt ttgccttaag atggaaactt    93300
tatttctata tggtattgtg ttttagtgct tattgtgata atatgacttg ccaggagcca    93360
gagatcccag ccatatcctc ttttagaacc ccagtctcat tttattctct accattcagt    93420
tccattttaa ggacaatgcc tctgactctt cttcttagaa aaattacata ttcttatgtg    93480
tactttaagg agggatttct ttgtgctatc aagggcttgg gggaagaggc ggggaatcaa    93540
cctgatacag gtctgaaaac atgagcatag cttagcttca gactgtgcta gtgcagaccc    93600
agatgacatc tttcaggaac ctattgttcc attgttaata gttcctttag ggttaaaccc    93660
acatgcaggt ctagccctat tttcatcttt ctctcctaac tgtacctcac agcagaaggc    93720
ctgggtgcca agaccgagtt gaagcagctg atggaaatag atgttagact ataactgcta    93780
agggcattgt gaaataattt ataggtgctt agatgagctt tcataggttg gttactataa    93840
aaatgtttgt attatactac tgaatttagc tttatcatca cctccttatc agtttaagga    93900
aaaaatattt tcagaaaata aatctgataa actatgtaga agataatctc tccatctaac    93960
atttgaaatc attaccagta gatatggttt tcctcaagtt cttacaactg agcagatgag    94020
aaatagcccc caagcctgtc ttgtttatcc atttaaactc taaactggtc attaaagcta    94080
atgagcctct ctacagagct ctcagttaca agaatagaac ttgtttactc ttgacagtaa    94140
atctggactt gaacaataga atcagaagca ttgttttgat tatttgaatt cttaagatat    94200
catggatttg aattttgaag tgttgaaaga acttgagcaa acattgttg attgagaaag    94260 tgaacaaaac ctgctttctc gttctgggag gatccagtga cattgtgagt gaagacgcaa    94320
acaggttttg actcctgcat ggccgatgac cttttttctgt aggcttacca gaaaagtaca    94380
ttccaacagt tctttgagga tttaaactag agcagcaaat aaagacaaaa gattaatgca    94440
tgtctctgtt gcatataccc ctctctccca gccatttctg ctgatgttaa gtttggaagc    94500
attgctgaca ttcctggagc attagcaaag aaagagccaa gagaacagaa atgagaaatt    94560
ttataaacac tgcttaccag ttatccttgt tagcatggga gaaccttatt ttccttgtag    94620
catgtgagct ttaacatagt aacactttta ccaacatgag tctgcagaaa gactccagta    94680
gccattttgt cttttataga tagcatctta gaatggaaga tgtggtgtgt cacatgcgtg    94740
cgtgcggaga gaccaccaaa caggctttgt gtgagcaaca aggctgttat ttcacctggg    94800
tacaggtgag ctgagtccga aaagagagtc agcaaaggga gataggggtg gggccgtttc    94860
```

```
ataggatttg ggtgggtagt ggaaaattac agtcaaaggg ggttgttctc ttgctggcag    94920 gggcggggt cacaaggtgc tcagttgggg agcttctgag ccaggagaag gaatttcact    94980
aggttaatcg ctcagttaag gtgggacaga acaaatcac aatggtggaa tgtcatcagt    95040
taaggcagga accaaccatt ttcacttctt ttgtgattct tcacttgctt caggccatct    95100
ggatgtatac atgcaggtca caggggatat gatggcttag cttgggctca gaggcctgac    95160
atcgtgtttt gagtgttggg aacattgtgt tcatttttt catacttgaa agtgagaact    95220 cacctgtag ccgggtgtct ctacctgtag tggtctgatg accaccagcc ccaaattact    95280
taaccacaca gtctacctct gcttttgcat ctataaaatt aagatttatg gaacatttct    95340
ttcttgtccg tgagggctgt cactgtgcta ggagtgtaat tccattttac atacaaggga    95400
aaaagtttga agagattaaa tgaattgtac aaattcacgt aagtggcagt tggtagagtt    95460
aggattcaga ctcagatcag cttattccaa gtccattatt ctttctacct ttctacagta    95520
ccctgtcagg ccaaaataat tcctgccctt gtctgctaga agagagtggc agtgatgtat    95580
gagagttttt taaaaaggca tctgctctac atcagattct cattcatatt cttaccaact    95640
ctgttgctct gttttggaat gggagaggct gggctcaact tgttgaccac tcccatttt    95700 gtatctcttg gctatcaggc actgtgtaag gccctccaca gtgatcattt aatcctcagt    95760
catggttgtc tttccaataa cagttgagga aacaggctta gagtatttaa ataacttgag    95820
agaagacaca acttatgcca gaaatgagat ttggttctag acctgaccaa ctccaaacct    95880
agtgctgttt attactctag aaaaacatca caggcaacct gagcagggcc tctgttcatt    95940
gcagagagct cacaggtgga cctgagcagg gcgtctgttc tttgcacctc acaagtggcc    96000
agtcttattt ctctacttct ttgtgctttc ctaggcaaag aatctgaaga gagaggttat    96060
actaggaata ctggaataca tgttgaggtg ttcccaagat gttataagat acctttcatt    96120
tgtttgtttt tactttttga gatgaggtct cactctgtca cctaggctgg attgcagtgg    96180
catgatcata gctcactgca acctccacct cctgggctcc cacttcagcc tcctgagtag    96240
ctgggaccac aggcgtgtgc taccataccc agctaatttt ctctgtattt ttttgtagag    96300
atggggtttc accatgttgt cccagactgg tctcaaactt cctgagctca agccatccac    96360
ctgcctcagc cttcccaaag tgctggaatt ataggcatga gccaccaaac ccagccgata    96420
cctttttttt gtctaaatgc ctgtattctc ccttagggta aattacagtc tagggtctgt    96480
ggtttcttct agaaagagtt tgattcattt aataaatacc tattaaggac ctaacatgtg    96540
cttctggcaa cacagtagta aacaagcaag gtatgatgtc tgccttcatg gatcccactt    96600
taatgcagga aaacaataga caagtaaaca aataatcaca aattgaagtt gatgctatag    96660
agaaaacaaa caggggtggta ctgagataga cagtaactac tctagctata tctgaggtct    96720
gttttagagg tagaagtaga catgctgatg ggaaacattt ggggaatgaa ggaaacagtt    96780 atcaaaggg acttacaggt ttctggccag agtgacaggg catgtgtagt agtgctgttt    96840
actgagatgg ggaagacttg gggagggaga tgaggagaga gtgttgcaaa gaaaactgag    96900
agctcttttg aacacattac agttgaaata tccaggctgg gcgcggtggc tcatgcctgt    96960
aatcccagca ctttgggagg ctgaggcagg tggattgctt gagtctggga gttcaagacc    97020
agcctgggcg acacggcaaa atcccttctc tacaaaaaat acaaaaatta gctgggtgtg    97080
gtggcttatg cctgtagtca caactacttg ggaggctgag gtgggaggat cacttgagcc    97140
tgggagacgg aggttgcaat gagccaagat cacgccactg cattccagcc tgggtgacag    97200
aacaagaccc tgtctcaaaa aaataaaata aagttagaa atatctgtga ggcatagaag    97260
```

```
tagagacatt tggacattca gatctattgc tcagaggaaa tacccaagat ggagatttta    97320
gaattattag aaaatagagg atatttagag ccccagatat tgaggctttc acatcaccta    97380
agaaaaaagg atacatttt aaaaagcagg tagtctagaa gcaagccctg aagaacagca     97440
ttatttaggg atcatataga gagaagagga gccaacaaag aagtcgggaa aaacagaaag    97500
ggactgggaa ggaacaagcc ttcagggaag aggaaaacca ggatgttgtg ctgccataga   97560
gacagaagag gagagtattt caagaaagag gggacatcaa aatgtgttta ctgttttgaga  97620 gatcaaaaga agatcaaggt cagaacaaat gtgtattgga tttgatggca tgaaggttgt   97680
tggtgacctt gaaagagatt tcacaaggaa ggagtggtgg ggatggtaga aattggagta   97740
tgttgaagag agaatgggag gcgaggaagt agaattagtg tgtaggcagc tctttagaag   97800
tttggctgta aacaattgca gagaaatgag gcagctagaa gagaatatgg atgtcaaagg   97860
gagaatgttt tcaaaatagt agctgctgct gagagtaatc cagtagagag cacagactga   97920
tgttgcagga cagagcagtg gtacgataga aacaaagtct ccaggaaagt gagaggggt    97980 gggacccaaa gcaccagtga ggaaatggct tttgttggga gaagggatac cttttgcagg   98040
atattatgta gaaagggaca agaatattga gttatttata aggaaaagat tataatgatg   98100
gggctaacgt gtgtgagctg cacaagagag gagtgaagtt agggcagagc tgctgtatga   98160
tgggaatgtg ctggagttca tggcttgagt acaggcgagc tagaaggata agaaatgatg   98220
gtcaggggtt tcagaggtag catggttct gttggtgata agtacctgga agagggtggc    98280
tgagttcagg aggcatttaa agaactgaga agccaggttc tgggagagca tcatgccttc   98340
actgaagaca cccagggtga tagcaggggc tggggcagaa aggaaggagc agagtttaga   98400
atcttcctga atgtcagaga cagtgaagag agagtcagga tggtaaagcc agctgccata   98460
agcaggggct cagaagggta gaagaataag gcctgaaagt tgcaaggcag cctcttactg   98520
actaaatttt aaacttagtc tctttgagct tgatgtcttc ctctgataaa tggtggtaag   98580
catgtgcacg ttatcacaga gttcaaattt ggtgagtcag tgtacccact gcattgccca   98640
gtaatactaa aaagaaaaa acaaatacta atttctgcaa ctaccatact ccctaaaaac    98700
agagacctac ccccaatcac caaaaaatcc ccattgtttt tctaatccaa atttgtaca    98760 tatttaataa ccttatacca ccacttacta tttttttact ttcatcgaag atgaatctac   98820
aaaaatatat taatgtcaaa aaatattact gacctagcaa actggcagtt gggaagtaag   98880
gtaagaaggc acacttttat taattaataa tatcttttgt attccctaaa cagattgaaa   98940
aatgatggat tagttcattc ttgcattcct ataaagaaat acctgaaacc aggcacagtg   99000
gctcacgcct gtaaatccca gcgctttggg aggccaaggt gggcggatcg cttgagttcg   99060
agaccaacct gggcagcaaa gtgagacctg gtctctacaa aaaatacaaa atattacccg   99120
gaaggctgag gtgggatcca cctgagccca gaaggttgag gctgcagtga gctgtgatca   99180
caccattgca ctctagccta agtgacagag tgaaactct gtctcaaaaa aacaaagaa     99240 ccacctgaga ctgggtaatt tataaagaaa agaggtttaa ttggctcacg gttctgaagg   99300
ttctaaagga agcatagctc cagcattagg ccaggtgcat tggctcacac ctgtaatccc   99360
agcactttgg gaggccaagg gcaggcggat catgaggtca ggatttcgag accagcctgg   99420
ccaatatggt gaaaccctgt ctctactaaa aatacaaaat tagctgggcg tggtggcgca   99480
cacctgtagt ctcagctact cgagaggccg aggcagaaga atcacttgaa cccaggaggc   99540
ggaggttgca atgagctgag atcgtgccac tgcactccag cttgggacac agagtgagac   99600
```

```
tccatctcaa aaataaataa ataaataaat aaataaatag ctccagcatc agcttctggg   99660
gaggcctcag gaaacttaca gccttggcag aaagtgaagg gggagccggc atgtcatgtg   99720
gccagagcag gagcaagagt gcaggagggg aggtggccac atgcttttaa acaacccacc   99780
tcccacaaga actcactcac tattgcgagg acgacagtac caagggggatg gggctaaacc   99840 attcatgaga aatttccctc cgtgatccag tcacctccca ccaggcccca cctccagcac   99900
tgaggattat agttcaacat gagatttggt ggagacacag atccaaacca tatcaaatgg   99960
gttctaggaa cttagcctag atttcagatt taggaacagt atcataggtc acctttttcaa  100020 aatacataaa gtttcctaca gaaacaatat caattaagtg catgttttaa aaataaaaat   100080
aaaggttact acaaaaaaag tggggaggag caggagtggg tgcaggtgtc cccaggaagc   100140
ctaggcatag ctcacactgc atgtgctatc acggcgagac tcagaactgc cccgaatccg   100200
aggaggggcc atgcgagtag gtgggcctag gcacctcctc agtcactggc tgtgcccttt   100260
cactctgtca ctgggagaca gaatcctgag ttttctgctt cagggagcct gcatggaaag   100320
agtaggtcac tgccggaaat caggctagtt ttagcaaaag gaacggacat taggcacctc   100380
caaagggaca aaggaccaat atacctggtt ggggacagga ttctgtcatt tgattattcc   100440
tgactcatgt tttcatgagg tagtccccca cctcatataa aagcctcagt gttggcttct   100500
gaccatggtg tatgaaaagc ccttgtctaa aggttactgc cctgagaaaa taataaagga   100560
agaagaggat agacatgaag acactttaaa gcctcctgaa tagaatgcat ccagaagcga   100620
attccaggag attctgtcat catgcttgcc tttcaagcaa acaaaattag ctgctagaac   100680
tgagaaagag tgtaaacacc aactaaatgc ctcaaagaat catggtagta aattacttct   100740
ccatgttgct ccatataaac ctgctgtgcc acctgttgaa ggcagcactg atgctgcatg   100800
ttcagtctgg tccaaggccc caacaggaat ccgttgtgcc aagaaaaggc cctactggaa   100860
ggattggaga gcagctggtt tcagcaatg caagcatcag gccaggctgg ggctgcttaa   100920
tgctgcttaa gagatgacag tggtggaccc caacacctct ccaagggatg tagaatctgc   100980
ttttcccatt tctgaatgct actgaaacaa atctacaact agaaaaatca atatattcatg  101040 aattcaagac ttgggatctc agtactaaga ctttaaagaa gttgccagat ggatcgcttc   101100
tgtggtgaca gccctggcag gagcattcaa gtgctctatg agctacaaaa gaaaccagtt   101160
gatggtgtga acaccactac agagcaacct gcacaccaca gcaatttgac agctcaggtt   101220
ctgtgtctca tgtggcaccg tgcttgtcct tggaaagaag gcctacaaaa ttcttcatat   101280
ctccattcct tgacatctgc tggcaaactc ccactcatat tttaagactc agcctctcct   101340
gtgacacctg tgtcttctct ccaaacaggg agggacgctt gcctcttcag agctccccac   101400
actggagtat aactgctcct gtgtctgatg ccccttagtct cagtgccagg aggtattcat   101460
gcttatgtcc ccatggcctg taacagagcc tgcatcagga tgcttggtaa aggactgttg   101520
aatgaatgtc aaatatgggt ccctctgatg ggtctatacg tgttgatcta ggattggaag   101580
ggtcacaaag agttgtgcat gcttacaatt tcaatcaaat atcactattt ttagttaaga   101640
gggaagagta gtgtgaaatt ggcaataatt agatactcca aatgttcttt aaaaactaat   101700
agcattgatg tattaagaat gcaatcagcc gggcacagca gctcacacct gtaatcccag   101760
cactttggga ggctgaggca ggtggatcat gaggtcagga gttcgagacc agcctggcca   101820
agattgtgaa accccgtctc tactaaaaaa tacaaaaatt agccgggcat ggtgacgcac   101880
acctgtagtc ccagctactt gggaggctga ggcaggagaa ttgcttgaac ccaggaggtg   101940
gaggttgcag tgagcccaga tcgtgccatt gcactccagc ctgggtgacg agcgaaactc   102000
```

```
agtctaaaaa aaaaaagaat gcaatcatac attagaagac acattctgtt ttagattttt 102060
acttaaatat tttaaatact tccttaatct gcatatttac cttattgata gatttcagaa 102120
gaaattgatc atttcatgga acaagattta ttagacacat aaggaaagtg aatcataaca 102180
actgtacagg tgggaaattg aacaacaaaa atgaccctga gatacccaca ttctactttg 102240
gcatatagtg ggaaaaacat tctagacttc aagtctaggc ctatcttggc taatgtaacc 102300
gatgacttca caaccatttt atgggactag aagctgaaag gaaagtactg gtggataaac 102360
atcatattga aattatgttg agtcacttat ttgctataaa acacaaattg ttttgtgtaa 102420
aggggttaag atggctggaa aactgtctcc actcaagagc aagaaagcag catgtgtctt 102480
accctgtacc ttcattttta cttgtacttc ataatttctg agggagaaat acgtggaaac 102540
cagatgcttg atatagtttc agaacacgtc cttaagaat atgactccaa gtctaagaat 102600
tgtaggtcct ttgcttctta gataactact gttagccttg atcacagaga ttccaggttt 102660
aataacttca gttctcccca ctgtgtatat agatgttaag ttacacagat ttggcattat 102720
tcccattttc aggttaatat cagaacactt gttatcaagt caggatagta attgtgagcc 102780
tagatgctct aggtttggcc atacgtggtt atctacacca ccaactgttc caattaacaa 102840
tttaccagtt gcttctaccc aaagtaccaa gactccagca aatggggaat attggaaact 102900
ggcttggctt cttgaagcaa catggtaatc aataagaatc ttggctgggc atggtggctc 102960
atgcctgcag tcccagcact taggaggcc aagatgaaa gatgggaaga tcgctcaagc 103020
ccaggagttc aagaccagcc tgggcgacat cgtgaaaccc catctctaca aaaaaataca 103080
aaaattagct gggtatggtc gtgggtgcct gtagtcccag ctgctgggga gctgaggtgg 103140
gagatcacct gagcccagga ggcagttgca gtgagccaag attgcaccac tgcactccag 103200
cctgggtgac agagtgagac tctgtctcaa aacaaacaaa acaacaatct ggctgggcgc 103260
ggtcgctaat gtctgtaatc ccaacacttt gggaggctga ggaggcagat cacttgaggt 103320
caggaattcg agaccagcct ggccaacatg gtgaaacccg tctctattaa aaatacaaaa 103380
attagccggg catggtggca cacctgta atcccagcta cttgggaggc tgaggcaaga 103440
gaattgcttg aaccaggagg cagaggttgc agtgagctga gatcatgcct ctgcactcca 103500
gcctgagcta cagagcgaga ctctgtctca aaaaaacaaa aaacaaaaac aagaagaatc 103560
ttactactgc ttcttcgggg atacttttgg tattattttg acaaatgaat tgtgaggatt 103620
caaatataag aaagggatta ttcttggtag agttaacaaa attgtaccaa atgacttttt 103680
gtgttaaaca cgattcattc acccaaccct agaaaggagc ctgaatgaag tctaatttgg 103740
gtgacagatt cccacacaaa ttagatgtat gtcattcagg tatagagaat tgattttata 103800
ttagaaaaaa caaaccttgt aaacagtttt ataaataact gtttcatgat tttccttaag 103860
tagtactgat ctcttacata tagatcgttt gtgtctttcg cctcaagtta gtatagaaca 103920
gggcaagtgg caaagctcga ggaaagtgtg acctgaggta catgctgtca gcttgatgct 103980
ggagtttggc ctctcaaatc tctaacctgt taaatgaagt taattaggat taatttttt 104040 taatgtatgt ttactactga aaataagtgc tcggccagac gcagaggctc acgcctgtaa 104100
tcccagcact tgggaggcc gaggctggca gatcacctga agtcagggag tttgagacca 104160
gcctggccaa catggcgaaa cactgtctct attaaaaata caaaaattag ctgggtgtgg 104220
tgatacatgc ctgtaatccc agctactcgg agcctgaggc aggagaactg cttgaaccca 104280
ggaggcggag gttgcattga gccaagattg tgccattgca ctccagccca ggcgacagag 104340
```

```
tgagactcat gtctcaaaaa aaaaaaaaaa aaaaagagga aaagaagtgc ccaatagctt 104400
caatggatgc cacataattt tggaataatt tttacaatca ggaatttcat tgtccaagcc 104460
ccttagaaaa agaagcaacc cagccccata cccagaaagt caagctgtat agtgctgttc 104520
cttagtgagg acggtcaact ctcagtagaa aaatctcctg tttggattag tgcttagttg 104580
acctattgtg ttcagttcct ctaacatgag taacttctat tggataggaa attttgaagc 104640
tcaaagggtg taatgagagt taacattact gattttccac tgttactttt tagtgttttc 104700
ataacttgga tgtgttaacc tatggcccat caactatgct cctagtctca ggtgacaaca 104760
tgttcaattt aagatggcag gcagtacagt ggacctctct catcccatgg gaaggaaccc 104820
aggatgttta ttatgtagta ttgtatagtc tctgcagcag taatagagaa agttaaaggt 104880
aagcggtgga gaagtaaaat ctagagtttc taatataacc cttctcactt ttcttttcaa 104940
aaaaaataag agggtctcac catgttgccc acactggtct ctatcgaact cctgggctca 105000
agcgatcctg tcgtctcagc ctcccaaagt gctaggatta caggcatgag ccactctgca 105060
tggccaagct cactcttctt aaaggtctgc tagtaagagg gttctactt tttgaaacaa 105120 attcatgatt acctaaaatg aagctaggtt atgaagtata tataaatatg cagcccaata 105180
ggctgggtgt ggtggctcac acctgtaatc ccagcacttt gggaggctga ggcaggcaga 105240
tcacttgagg tcaggagttt gagaccagtc tggccaacat ggtgagacca catctctaca 105300
aaaaatacaa aaattagcgg gtgtggtggc ctgtgtgcgc ccatagtacc agccacttgg 105360
gaggcagagg caggagaatc acttgaagcc aggaggcaga gttttcagtg agctgaaatt 105420
gtgtcactgt acttcaagcc tgggcaatgg agtgagactg tctcaaaata tatatatatt 105480
tgcagcccaa taaagatact tagataaaac tattgggttt attccttgaa aactaggca 105540 tgtgtagcta gatctggctc ataaaaagca aagttattta catatatttt aaggtaaaat 105600
tgcctctgat aaatgtcaaa gaggaagttt aggtctttct tctggcagaa agccagagag 105660
taagtgctga atgtgacgca gaatcatgtt aggtaacaag gactttgagg taagtggctg 105720
aagtcttctg tggagtcagc cgactcttgc aggattgtgt ggtatcagtc acctttagca 105780
tttgccaacc caactctgat cattcttctt cttcaaggt atctcagcgt ttgagtcagc 105840
caggagtagc aataggttg gcttggactc ccttaggtgg agaaatcatg ttcgtggagg 105900
cgagtcgaat ggatggcgag ggccagttaa ctctgaccgg ccagctcggg gacgtgatga 105960
aggagtccgc ccacctcgct atcagctggc tccgcagcaa cgcaaagaag taccagctga 106020
ccaatggtag gagcctgcac ccggccaggc aggcgtgacc caggaggcgg taccttccat 106080
ggcggagact ggcatgagct cgagactgcc agttacacat ctagcaaagt acacaccgtt 106140
ttgaacccct gtggaaatcc tagttcccat ttcaggacta tttgactagt gcctgaacta 106200
gaaactaatt caaaaggttt attttgtttt aatacgactt agagtagaat ggaactgttc 106260
ttccacaccc tcacccaaat tgtactgtcc accaatattt tgaagaattc atttacccaa 106320
aacattcatt tttgtttgtg acttttttt taggagaaaa agaaacagg tttaattttt 106380 ctacattaaa gtccctttt cctttttaaa gcttttggaa gttttgatct tcttgacaac 106440
acagacatcc atctgcactt cccagctgga gctgtcacaa aagatggacc atctgctgga 106500
gttaccatag taacctgtct cgcctcactt tttagtgggc ggctggtacg ttcagatgta 106560
gccatgactg gagaaattac actgagaggt cttgttcttc cagtaagtat gaaaaaacaa 106620
tttatatggt tattttttat ttaatttttg aaaattaata ttattttaa atacgggttt 106680 gccttctttc tatgaaaacc ttggttttaa gtatatatta tatttttatg cctgtaacta 106740
```

```
attcatattt taaaattttg atcaaataaa agaaaaactg acaatttttc acattttcct    106800
tttttttttt tttttttttt tgaaatagac aggtctcact ctgttgccca ggctggagtg    106860
cagtggtgtg actgtagctc actatagcca ccaagtcctg ggctcaagcg atcctcctgt    106920
ctgtctcccg aatagctggg actataggag cacgccacca tgctcagcta atttatttta    106980
ttttgcgtag agacagggtc tctctgtgtt gtccaggctt gtctcaaact ccaggtctca    107040
tgcagtcctc tcatctccac ctcccaaagt gctgggatta caggcgtgag ccaccacatt    107100
cagcccacgt ttcccattct aagatttgct aagggaaaaa aatattagtg tggtcatcag    107160
aaatattggc agttacatga aaatttgagg ccttgttcta cttgacaaat tgttaaagat    107220
atagcacatg tgcaaaatgg gatagtagtt gttttttaagc tttaagccca tttcttaaat    107280
ttgaagtttc tttgagacct cctgtccccc tgcagaaaac tttgctagta tagaatggaa    107340
actctaataa agattaacca tatctaatga ctacattttg aaaaggttct atacatgtgg    107400
ggtcttgagg ctccagatcc taaactgctt ataaaatag tgtgataaaa tgtacagaac    107460
ttgagagtat ttaaagttgt tagttgagta ttagtctaca acagactaga ctacaatttt    107520
agtccacaac aagattttgg caggttcata gcaagatgag gaaaaaaaaa aagaaatagt    107580
ctttttttct tttttctatc gagatggagt ccggctctct tacccaggtt ggagtacagt    107640
ggcacaatct ggctcactg caacctctgc ctcccaagtt gaagtgattc tcctgcctca    107700
gtctctcaac tagctgggat tacaagcatg cgccaccacg cccggataat ttttctatt    107760
tttagaacct ccatagaaca aatgggtttt ctacttggtc ccctctcaga gcaaatcgta    107820
gcccaagtaa aggcttctgc agcctcagga gagacagcca cagcggcctg gggtacacct    107880
tcagctccag accattacaa gaggcaggat ggaaagcagc agcacttgaa agaaaggcct    107940
gtgaaagctg gagaaaacct cctttgagaa cagaggacaa gacggggctt tgggatttga    108000
aagtggtcaa agaattattc aggaaaaaac tatagtgaaa aacaatttgt tgttagaact    108060
ccaacatcta aaaggagttc taacaaacag gaaaatggaa tggaacaaat tatccaagaa    108120
ataactgaac atttcctaga agttaaggca tcttgagatc gaaaggacca ttactaacca    108180
ggaaaaacat ttcatcccct tgacttttca gattactgag gataaagcgg cctcagcact    108240
gacactggat gtgcagtacc ttcaaaacta tgagggaaaa tgggccaggc gtggcagctg    108300
acgtctgtaa tcccagcact ttgggaggct aaacaggagg atagctcaag tccaggagtt    108360
caagaccagc ctgggaaata tatctctaca aaaattgttt taaaaatagt aaggaggctg    108420
ggtgtggtgg ctcacgcctg taactccaac actttgggag gccaaggtgg gcgtatcact    108480
tgaggttagg agtttgagac cagcctggcc aacatggtga aaccctgtct ctactaaaaa    108540
tacaaaaaaa ttatccggat gtggtggcgc atgcctgtaa tcccagctac tcaggaggct    108600
gaggcaggag aatcgcttga acctgggagg cagaaagttg cagtgagcca agattgtgcc    108660
actgcaactc tagcttgggt gacagagtaa gactgtctca aaaaaaaaa aaatagtaat    108720
gaaagctgtg agggaaaatg ttttacatct agtcttgtat acatggcctt agtatcaatc    108780
aagtgtgaaa gtaaaatatt ttcaaacatg caaggaatca gttcatctta cactcttttg    108840
aagaaggtac tttgaaggag tacttcagca gcatgaacaa aaccttgaaa gagatgcca    108900
gtggggcggg aaggcctgga gcagccagcc agtcttaatt ggagcagatg caacacatta    108960
ccccaaagca agaatactcc atactcttca agttcctgtg ggccaggaat tcaggagagg    109020
ctgagctggg ttcttgtggc ccagggtctc tggccttaca gtctaggttc cagccaggct    109080
```

-continued

```
gcagtcacat gaaggctgac aggctggaga aactgcttcc atggtggttg actcatgtga 109140
ctggcaaatt ggtcccatct agtggcagga ggccccagtt cctcacctga tggacttgcc 109200
cataggctgc ttgagtgacc tcagacatta tgactggcca cctccagggc aggtgatcaa 109260
gagagattca ggcagcagct ctcgtttttt gtgactcagc cgtggagatc atacagcatc 109320
actcccacca cactctgttt cttaccgagt cacaaagcct ggcccacatt caagcagggg 109380
gaccattgta gacatgtttg aaagccacca taggagccta gtttagggat acattttctt 109440
cattaaccag catggaggtt ctggctttaa acctgtagag agggaagtaa ccccagcaca 109500
cagctaagct ctgcaggagc ggcgctcatg gtcagaatca cgtgctgctt tttcagatca 109560
acctaaagac tagacggttg tgattacacc tgaatgccaa tttactttga cagcatttat 109620
aaaaacaatc attgacagaa gaggaactca tacctatcaa caatttagaa tccccctcat 109680
cagagtcttt aatataacac caattgaaac attaaaaaaa ggttactact tatccttttt 109740
cctggctttc ctagctcatg ctataacaaa acggaagatg atttggatgt tttaaaatag 109800
tagtggttaa attcagtgaa agaaagctgg gtcagggttt cttcagctt gagggtgatc 109860
attaacccta aaaacttttt tctctccttag caggtgggtg gaattaaaga caaagtgctg 109920
gcggcacaca gagcgggact gaagcaagtc attattcctc ggagaaatga aaagacctt 109980
gagggaatcc caggcaacgt acgacaggat ttaagttttg tcacagcaag ctgcctggat 110040
gaggttctta atgcagcttt tgatggtggc tttactgtca agaccagacc tggtctgtta 110100
aatagcaaac tgtaggtcca aatctcaatt ttttagaatt ttaagttatg aagtgctcaa 110160
aggtactgac acagttgatt ttattcacac cattaggggt atgcaagatg tccctgtttt 110220
ataaacataa tcacaacagt aataaacctc aagtagtggc tagtgtttag tatagaaata 110280
taagatgttg atttagtaaa ctgataaaaa tcgaattctt gtcttttttag tgggatcctt 110340
actgtccctg gaaagatata gcatagtggt tctcagcaca gtctccagaa cagaagcatc 110400
tgtagtacct ggtaacttgt tagaaatgta cattctcagg ctccacagca ggccgcctga 110460
atcaaatcct gggaggtggg gacagaaatc tgtgttttaa gaagccttcc aggtaattct 110520
gctgcacact caagttcagg aaccaccggt atagaccatt accttagtgg attacctgt 110580
agagtttatt ggatcctgaa accaatcaat tacttagaac taggcaaaga tgaaagtata 110640
gccaactatt cttggctata tatatatatt caagtgggcc gggcgtgatg gctcacacct 110700
gtaattccag cactttggga ggtcgaggta ggcagatcac cgagcccaag agttcaagac 110760
aatcctggcc aacggcgaaa ctctgtctct acaaaaaata tacaggcgtg ttagcatgtg 110820
cctgtaatcc cagcttcttg ggaagctgag gcacaagaat tgcctgaacc caggaggtgg 110880
aggttgcagt gagctgggat cgcgccattg cactccagcc tggctgacag agcgagactg 110940
tctctaaaaa aaaagactc aagtggaccc tacaatgaag cctacacatc caatagaag 111000
cccttctta tgctgaggga agcagccctc agaacatgat agcttgtatc cagcagagtg 111060
gcacgtgctg gcacacctca cagaagcacc ctggccctgg atgcctgcaa cctcagaaga 111120
gtgcagctcc cagagggagg cagccatcca tctgggatgg tcctaagcat ggaatcctaa 111180
ctcctgattc cgtctcctat ttcttgcttg gctacgccag ttcccaaatc tggtagatgt 111240
ccatgcccat gtgctcctgc tgggactcaa ttcaggctat gtatgactat gaagtcaggc 111300
tcatctgctt actggctgtg tgaactttt gtatcttggt tttcttcatc catgaaatcc 111360
aagtaatact acctaattgt tactgtggag attaagttca aatgcaatgt atagtaatat 111420
taagcaattt ctagttatta ttctagccag taatggactt cagaatcttt tattacacaa 111480
```

```
tataagaata tgtatgtaaa gacattttgg aatttcctgg atgagaagga agtctgggct   111540
gggcatggtg gctcacgcct gtaaccctag cactttagga aatcgaggcg agtggatcac   111600
ttaagctcag gagttcaagg ccagcctggg caacatggca aaaccccatt tctacaaaaa   111660
atacaaaaat tagctgggca tggtggcacc cgcctgtagt ccagctactt gaggctgaga   111720
tgggaggatg agggaggtcg gggctgcagt gagccaagat cacgccactg cactccagca   111780
ccctgggcga cagagtgaga ccctgtctca aaaaaaaaa aaaaaaaag attgggccaa     111840
aatactgtga taaatagca ggcctgctga taaagttta tctgaatgca ttgagaggaa     111900
aagtccagac ctaggactag ttatggcagt tggagagaaa gaacatcggg atgtttgaaa   111960
atatgccatt gactatctta actactgtaa ttttatcatt tccaacgtca tctaactggg   112020
gactagaaca aactgtgaat tcactttcag caaccagagg gcgctaatcc acacccacat   112080
cgctctgccc tgttccaccc agcaggggca acaaggatat aacttggggt tc           112132
```

<210> SEQ ID NO 4
<211> LENGTH: 884
<212> TYPE: PRT
<213> ORGANISM: Homo sapien

<400> SEQUENCE: 4

```
Ser Asp Ser Pro Val Glu Leu Pro Ser Arg Leu Ala Val Leu Pro Phe
 1               5                  10                  15

Arg Asn Lys Val Leu Leu Pro Gly Ala Ile Val Arg Ile Arg Cys Thr
            20                  25                  30

Asn Pro Ser Ser Val Lys Leu Val Glu Gln Glu Leu Trp Gln Lys Glu
        35                  40                  45

Glu Lys Gly Leu Ile Gly Val Leu Pro Val Arg Asp Ser Glu Ala Thr
    50                  55                  60

Ala Val Gly Ser Leu Leu Ser Pro Gly Val Gly Ser Asp Ser Gly Glu
65                  70                  75                  80

Gly Gly Ser Lys Val Gly Gly Ser Ala Val Glu Ser Ser Lys Gln Asp
                85                  90                  95

Thr Lys Asn Gly Lys Glu Pro Ile His Trp His Ser Lys Gly Val Ala
            100                 105                 110

Ala Arg Ala Leu His Leu Ser Arg Gly Val Glu Lys Pro Ser Gly Arg
        115                 120                 125

Val Thr Tyr Ile Val Val Leu Glu Gly Leu Cys Arg Phe Ser Val Gln
    130                 135                 140

Glu Leu Ser Ala Arg Gly Pro Tyr His Val Ala Arg Val Ser Arg Leu
145                 150                 155                 160

Asp Met Thr Lys Thr Glu Leu Glu Gln Ala Glu Gln Asp Pro Asp Leu
                165                 170                 175

Ile Ala Leu Ser Arg Gln Phe Lys Ala Thr Ala Met Glu Leu Ile Ser
            180                 185                 190

Val Leu Glu Gln Lys Gln Lys Thr Val Gly Arg Thr Lys Val Leu Leu
        195                 200                 205

Asp Thr Val Pro Val Tyr Arg Leu Ala Asp Ile Phe Val Ala Ser Phe
    210                 215                 220

Glu Ile Ser Phe Glu Glu Gln Leu Ser Met Leu Asp Ser Val His Leu
225                 230                 235                 240

Lys Val Arg Leu Ser Lys Ala Thr Glu Leu Val Asp Arg His Leu Gln
                245                 250                 255
```

-continued

```
Ser Ile Leu Val Ala Glu Lys Ile Thr Gln Lys Val Glu Gly Gln Leu
                260                 265                 270

Ser Lys Ser Gln Lys Glu Phe Leu Leu Arg Gln Gln Met Arg Ala Ile
            275                 280                 285

Lys Glu Glu Leu Gly Asp Asn Asp Asp Asp Glu Asp Asp Val Ala Ala
        290                 295                 300

Leu Glu Arg Lys Met Gln Asn Ala Gly Met Pro Ala Asn Ile Trp Lys
305                 310                 315                 320

His Ala Gln Arg Glu Met Arg Arg Leu Arg Lys Met Gln Pro Gln Gln
                325                 330                 335

Pro Gly Tyr Ser Ser Arg Ala Tyr Leu Glu Leu Leu Ala Asp Leu
                340                 345                 350

Pro Trp Gln Lys Val Ser Glu Arg Glu Leu Asp Leu Arg Val Ala
            355                 360                 365

Lys Glu Ser Leu Asp Gln Asp His Tyr Gly Leu Thr Lys Val Lys Gln
        370                 375                 380

Arg Ile Glu Tyr Leu Ala Val Arg Lys Leu Lys Pro Asp Ala Arg
385                 390                 395                 400

Gly Pro Val Leu Cys Phe Val Gly Pro Pro Gly Val Gly Lys Thr Ser
                405                 410                 415

Leu Ala Ser Ser Ile Ala Lys Ala Leu Asn Arg Lys Phe Ile Arg Ile
            420                 425                 430

Ser Leu Gly Gly Val Lys Asp Glu Ala Asp Ile Arg Gly His Arg Arg
        435                 440                 445

Thr Tyr Ile Gly Ser Met Pro Gly Arg Leu Ile Asp Gly Leu Lys Arg
450                 455                 460

Val Ser Val Ser Asn Pro Val Met Leu Leu Asp Glu Ile Asp Lys Thr
465                 470                 475                 480

Gly Ser Asp Val Arg Gly Asp Pro Ala Ser Ala Leu Leu Glu Val Leu
                485                 490                 495

Asp Pro Glu Gln Asn Lys Ala Phe Asn Asp His Tyr Leu Asn Val Pro
            500                 505                 510

Phe Asp Leu Ser Lys Val Ile Phe Val Ala Thr Ala Asn Arg Met Gln
        515                 520                 525

Pro Ile Pro Pro Leu Leu Asp Arg Met Glu Ile Ile Glu Leu Pro
530                 535                 540

Gly Tyr Thr Pro Glu Glu Lys Leu Lys Ile Ala Met Lys His Leu Ile
545                 550                 555                 560

Pro Arg Val Leu Glu Gln His Gly Leu Ser Thr Thr Asn Leu Gln Ile
                565                 570                 575

Pro Glu Ala Met Val Lys Leu Val Ile Glu Arg Tyr Thr Arg Glu Ala
            580                 585                 590

Gly Val Arg Asn Leu Glu Arg Asn Leu Ala Ala Leu Ala Arg Ala Ala
        595                 600                 605

Ala Val Lys Val Ala Glu Gln Val Lys Thr Leu Arg Leu Gly Lys Glu
            610                 615                 620

Ile Gln Pro Ile Thr Thr Thr Leu Leu Asp Ser Arg Leu Ala Asp Gly
625                 630                 635                 640

Gly Glu Val Glu Met Glu Val Ile Pro Met Glu His Asp Ile Ser Asn
                645                 650                 655

Thr Tyr Glu Asn Pro Ser Pro Met Ile Val Asp Glu Ala Met Leu Glu
            660                 665                 670

Lys Val Leu Gly Pro Pro Arg Phe Asp Asp Arg Glu Ala Ala Asp Arg
```

-continued

```
                675                 680                 685
Val Ala Ser Pro Gly Val Ser Val Gly Leu Val Trp Thr Ser Val Gly
    690                 695                 700

Gly Glu Val Gln Phe Val Glu Ala Thr Ala Met Val Gly Lys Gly Asp
705                 710                 715                 720

Leu His Leu Thr Gly Gln Leu Gly Asp Val Ile Lys Glu Ser Ala Gln
                725                 730                 735

Leu Ala Leu Thr Trp Val Arg Ala Arg Ala Ala Asp Leu Asn Leu Ser
                740                 745                 750

Pro Thr Ser Asp Ile Asn Leu Leu Glu Ser Arg Asp Ile His Ile His
                755                 760                 765

Phe Pro Ala Gly Ala Val Pro Lys Asp Gly Pro Ser Ala Gly Val Thr
    770                 775                 780

Leu Val Thr Ala Leu Val Ser Leu Phe Ser Asn Arg Lys Val Arg Ala
785                 790                 795                 800

Asp Thr Ala Met Thr Gly Glu Met Thr Leu Arg Gly Leu Val Leu Pro
                805                 810                 815

Val Gly Gly Val Lys Asp Lys Val Leu Ala Ala His Arg Tyr Gly Ile
                820                 825                 830

Lys Arg Val Ile Leu Pro Glu Arg Asn Leu Lys Asp Leu Ser Glu Val
                835                 840                 845

Pro Leu Pro Ile Leu Ser Asp Met Glu Ile Leu Leu Val Lys Arg Ile
    850                 855                 860

Glu Glu Val Leu Asp His Ala Phe Glu Gly Arg Cys Pro Leu Arg Ser
865                 870                 875                 880

Arg Ser Lys Leu
```